US012765840B2

(12) United States Patent
Campbell et al.

(10) Patent No.: US 12,765,840 B2
(45) Date of Patent: Oct. 20, 2026

(54) CONTINUOUS ANALYTE MONITORING SYSTEM WITH MICRONEEDLE ARRAY

(71) Applicant: Biolinq Incorporated, San Diego, CA (US)

(72) Inventors: Alan Campbell, La Mesa, CA (US); Sirilak Sattayasamitsathit, San Diego, CA (US); Jared Rylan Tangney, Encinitas, CA (US); Thomas Arnold Peyser, Menlo Park, CA (US); Joshua Ray Windmiller, San Diego, CA (US)

(73) Assignee: Biolinq Incorporated, San Diego, CA (US)

( * ) Notice: Subject to any disclaimer, the term of this patent is extended or adjusted under 35 U.S.C. 154(b) by 0 days.

(21) Appl. No.: 19/347,553

(22) Filed: Oct. 1, 2025

(65) Prior Publication Data

US 2026/0026749 A1 Jan. 29, 2026

Related U.S. Application Data

(63) Continuation of application No. 18/630,936, filed on Apr. 9, 2024, now Pat. No. 12,453,516, which is a (Continued)

(51) Int. Cl.

*A61B 5/00* (2006.01)
*A61B 5/145* (2006.01)

(Continued)

(52) U.S. Cl.

CPC ............ *A61B 5/685* (2013.01); *A61B 5/0022* (2013.01); *A61B 5/14514* (2013.01);

(Continued)

(58) Field of Classification Search

None

See application file for complete search history.

(56) References Cited

U.S. PATENT DOCUMENTS 3,964,482 A 6/1976 Gerstel et al.
4,305,401 A 12/1981 Reissmueller et al.

(Continued)

FOREIGN PATENT DOCUMENTS

AU 2004200303 A1 2/2004
AU 2011202767 A1 6/2011

(Continued)

OTHER PUBLICATIONS

G. Cui, et al., "Effect of pre-treatment on the surface and electrochemical properties of screen-printed carbon paste electrodes", Analyst, 126(8): p. 1399-1403, Jul. 2001.*

(Continued)

*Primary Examiner* — J. Christopher Ball
(74) *Attorney, Agent, or Firm* — Cooley LLP

(57) ABSTRACT

Described herein are variations of an analyte monitoring system, including an analyte monitoring device. For example, an analyte monitoring device may include an implantable microneedle array for use in measuring one or more analytes (e.g., glucose), such as in a continuous manner. The microneedle array may include, for example, at least one microneedle including a tapered distal portion having an insulated distal apex, and an electrode on a surface of the tapered distal portion located proximal to the insulated distal apex. At least some of the microneedles may be electrically isolated such that one or more electrodes is individually addressable.

23 Claims, 56 Drawing Sheets

Related U.S. Application Data continuation of application No. 18/086,543, filed on Dec. 21, 2022, now Pat. No. 12,011,294, which is a continuation of application No. PCT/US2021/043786, filed on Jul. 29, 2021.

(60) Provisional application No. 63/058,275, filed on Jul. 29, 2020.

(51) Int. Cl.
*A61B 5/1486* (2006.01)
*G01N 27/327* (2006.01)

(52) U.S. Cl.
CPC ...... *A61B 5/14532* (2013.01); *A61B 5/14546* (2013.01); *A61B 5/14865* (2013.01); *A61B 5/6833* (2013.01); *A61B 5/742* (2013.01); *G01N 27/327* (2013.01)

(56) References Cited

U.S. PATENT DOCUMENTS

| | | | |
|---|---|---|---|
| 4,323,996 | A | 4/1982 | Ganter |
| 4,407,295 | A | 10/1983 | Steuer et al. |
| 4,450,842 | A | 5/1984 | Zick et al. |
| 4,908,117 | A | 3/1990 | Kinlen et al. |
| 4,919,770 | A | 4/1990 | Preidel et al. |
| 4,969,468 | A | 11/1990 | Byers et al. |
| 5,035,711 | A | 7/1991 | Aoki et al. |
| 5,131,390 | A | 7/1992 | Sakaguchi et al. |
| 5,215,088 | A | 6/1993 | Normann et al. |
| 5,279,543 | A | 1/1994 | Glikfeld et al. |
| 5,286,364 | A | 2/1994 | Yacynych et al. |
| 5,540,828 | A | 7/1996 | Yacynych |
| 5,730,714 | A | 3/1998 | Guy et al. |
| 5,766,132 | A | 6/1998 | Yasukawa et al. |
| 5,832,410 | A | 11/1998 | Lin et al. |
| 5,869,078 | A | 2/1999 | Baudino |
| 5,953,306 | A | 9/1999 | Yi |
| 6,036,055 | A | 3/2000 | Mogadam et al. |
| 6,048,337 | A | 4/2000 | Svedman |
| 6,091,975 | A | 7/2000 | Daddona et al. |
| 6,104,940 | A | 8/2000 | Watanabe et al. |
| 6,132,449 | A | 10/2000 | Lum et al. |
| 6,132,499 | A | 10/2000 | Wong et al. |
| 6,132,755 | A | 10/2000 | Eicher et al. |
| 6,139,718 | A | 10/2000 | Kurnik et al. |
| 6,175,752 | B1 | 1/2001 | Say et al. |
| 6,269,053 | B1 | 7/2001 | Kawata et al. |
| 6,284,126 | B1 | 9/2001 | Kurnik et al. |
| 6,312,612 | B1 | 11/2001 | Sherman et al. |
| 6,319,374 | B1 | 11/2001 | Nordling |
| 6,364,890 | B1 | 4/2002 | Lum et al. |
| 6,413,396 | B1 | 7/2002 | Yang et al. |
| 6,432,723 | B1 | 8/2002 | Plaxco et al. |
| 6,465,091 | B1 | 10/2002 | Ou-Yang |
| 6,471,903 | B2 | 10/2002 | Sherman et al. |
| 6,527,762 | B1 | 3/2003 | Santini, Jr. et al. |
| 6,551,849 | B1 | 4/2003 | Kenney |
| 6,587,705 | B1 | 7/2003 | Kim et al. |
| 6,599,408 | B1 | 7/2003 | Chan et al. |
| 6,603,987 | B2 | 8/2003 | Whitson |
| 6,611,707 | B1 | 8/2003 | Prausnitz et al. |
| 6,793,789 | B2 | 9/2004 | Choi et al. |
| 6,801,041 | B2 | 10/2004 | Karinka et al. |
| 6,814,845 | B2 | 11/2004 | Wilson et al. |
| 6,862,466 | B2 | 3/2005 | Ackerman |
| 6,908,453 | B2 | 6/2005 | Fleming et al. |
| 7,081,195 | B2 | 7/2006 | Simpson et al. |
| 7,097,776 | B2 | 8/2006 | Govinda Raju |
| 7,132,054 | B1 | 11/2006 | Kravitz et al. |
| 7,183,068 | B2 | 2/2007 | Burson et al. |
| 7,262,068 | B2 | 8/2007 | Roy et al. |
| 7,343,188 | B2 | 3/2008 | Sohrab |
| 7,344,499 | B1 | 3/2008 | Prausnitz et al. |
| 7,366,556 | B2 | 4/2008 | Brister et al. |
| 7,415,299 | B2 | 8/2008 | Zimmermann et al. |
| 7,429,333 | B2 | 9/2008 | Chiou et al. |
| 7,456,112 | B2 | 11/2008 | Lee |
| 7,471,972 | B2 | 12/2008 | Rhodes et al. |
| 7,473,244 | B2 | 1/2009 | Frazier et al. |
| 7,493,232 | B1 | 2/2009 | Surina |
| 7,534,330 | B2 | 5/2009 | Yu et al. |
| 7,583,990 | B2 | 9/2009 | Goode, Jr. et al. |
| 7,599,726 | B2 | 10/2009 | Goode, Jr. et al. |
| 7,613,491 | B2 | 11/2009 | Boock et al. |
| 7,645,263 | B2 | 1/2010 | Angel et al. |
| 7,715,893 | B2 | 5/2010 | Kamath et al. |
| 7,725,148 | B2 | 5/2010 | Shah et al. |
| 7,768,408 | B2 | 8/2010 | Reggiardo et al. |
| 7,778,680 | B2 | 8/2010 | Goode, Jr. et al. |
| 7,785,301 | B2 | 8/2010 | Yuzhakov |
| 7,797,028 | B2 | 9/2010 | Goode, Jr. et al. |
| 7,811,231 | B2 | 10/2010 | Jin et al. |
| 7,837,654 | B2 | 11/2010 | Shumate et al. |
| 7,885,697 | B2 | 2/2011 | Brister et al. |
| 7,905,833 | B2 | 3/2011 | Brister et al. |
| 7,917,186 | B2 | 3/2011 | Kamath et al. |
| 7,949,382 | B2 | 5/2011 | Jina |
| 7,959,569 | B2 | 6/2011 | Goode et al. |
| 8,005,526 | B2 | 8/2011 | Martin et al. |
| 8,010,174 | B2 | 8/2011 | Goode, Jr. et al. |
| 8,022,292 | B2 | 9/2011 | Arianpour et al. |
| 8,064,977 | B2 | 11/2011 | Boock et al. |
| 8,088,321 | B2 | 1/2012 | Ferguson et al. |
| 8,094,009 | B2 | 1/2012 | Allen et al. |
| 8,108,023 | B2 | 1/2012 | Mir et al. |
| 8,110,079 | B2 | 2/2012 | Gooding et al. |
| 8,125,331 | B2 | 2/2012 | Allen et al. |
| 8,130,095 | B2 | 3/2012 | Allen et al. |
| 8,160,665 | B2 | 4/2012 | Mischler et al. |
| 8,160,671 | B2 | 4/2012 | Kamath et al. |
| 8,160,834 | B2 | 4/2012 | Liang et al. |
| 8,162,901 | B2 | 4/2012 | Gonnelli et al. |
| RE43,399 | E | 5/2012 | Simpson et al. |
| 8,216,138 | B1 | 7/2012 | McGarraugh |
| 8,236,368 | B2 | 8/2012 | Jung et al. |
| 8,249,684 | B2 | 8/2012 | Kamath et al. |
| 8,257,324 | B2 | 9/2012 | Prausnitz et al. |
| 8,280,475 | B2 | 10/2012 | Brister et al. |
| 8,280,476 | B2 | 10/2012 | Jina |
| 8,284,046 | B2 | 10/2012 | Allen et al. |
| 8,287,453 | B2 | 10/2012 | Li et al. |
| 8,308,960 | B2 | 11/2012 | Kälvesten et al. |
| 8,346,335 | B2 | 1/2013 | Harper et al. |
| 8,376,945 | B2 | 2/2013 | Hayter et al. |
| 8,386,004 | B2 | 2/2013 | Kamath et al. |
| 8,423,114 | B2 | 4/2013 | Simpson et al. |
| 8,428,678 | B2 | 4/2013 | Kamath et al. |
| 8,452,369 | B2 | 5/2013 | Huys et al. |
| 8,463,350 | B2 | 6/2013 | Kamath et al. |
| 8,483,793 | B2 | 7/2013 | Simpson et al. |
| 8,506,529 | B1 | 8/2013 | Yang |
| 8,548,553 | B2 | 10/2013 | Kamath et al. |
| 8,565,848 | B2 | 10/2013 | Brister et al. |
| 8,574,165 | B2 | 11/2013 | Marsh |
| 8,588,884 | B2 | 11/2013 | Hegde et al. |
| 8,617,069 | B2 | 12/2013 | Bernstein et al. |
| RE44,695 | E | 1/2014 | Simpson et al. |
| 8,626,257 | B2 | 1/2014 | Li et al. |
| 8,637,351 | B2 | 1/2014 | Kälvesten et al. |
| 8,660,628 | B2 | 2/2014 | Wang et al. |
| 8,700,114 | B2 | 4/2014 | Gottlieb et al. |
| 8,708,966 | B2 | 4/2014 | Allen et al. |
| 8,798,799 | B2 | 8/2014 | Deo et al. |
| 8,815,070 | B2 | 8/2014 | Wang et al. |
| 8,870,763 | B2 | 10/2014 | Yang et al. |
| 8,882,665 | B2 | 11/2014 | Yang et al. |
| 8,986,256 | B2 | 3/2015 | Scholten et al. |
| 9,008,743 | B2 | 4/2015 | Hayter et al. |
| 9,008,745 | B2 | 4/2015 | Pushpala et al. |
| 9,055,901 | B2 | 6/2015 | Brister et al. |
| 9,125,625 | B2 | 9/2015 | Wang et al. |
| 9,182,368 | B2 | 11/2015 | Pushpala et al. |

(56) References Cited

U.S. PATENT DOCUMENTS

| | | | |
|---|---|---|---|
| 9,234,872 | B2 | 1/2016 | Homyk et al. |
| 9,248,273 | B2 | 2/2016 | Guvanasen et al. |
| 9,332,934 | B2 | 5/2016 | Hayter et al. |
| 9,336,423 | B2 | 5/2016 | Goodnow |
| 9,357,951 | B2 | 6/2016 | Simpson et al. |
| 9,386,954 | B2 | 7/2016 | Saini et al. |
| 9,387,000 | B2 | 7/2016 | Corrie et al. |
| 9,414,778 | B2 | 8/2016 | Mao et al. |
| 9,420,965 | B2 | 8/2016 | Brauker et al. |
| 9,498,155 | B2 | 11/2016 | Brauker et al. |
| 9,532,741 | B2 | 1/2017 | Brauker et al. |
| 9,551,698 | B2 | 1/2017 | Huys et al. |
| 9,580,828 | B2 | 2/2017 | Moffat et al. |
| 9,662,056 | B2 | 5/2017 | Budiman et al. |
| 9,669,156 | B2 | 6/2017 | Jennewine |
| 9,737,247 | B2 | 8/2017 | Wang et al. |
| 9,743,870 | B2 | 8/2017 | Wang et al. |
| 9,743,871 | B2 | 8/2017 | Simpson et al. |
| 9,757,061 | B2 | 9/2017 | Shults et al. |
| 9,770,211 | B2 | 9/2017 | Hayter et al. |
| 9,804,114 | B2 | 10/2017 | Rhodes et al. |
| 9,933,387 | B1 | 4/2018 | Mccanna et al. |
| 9,958,409 | B2 | 5/2018 | Gerber et al. |
| 10,022,076 | B2 | 7/2018 | Hoss et al. |
| 10,034,636 | B2 | 7/2018 | Huang |
| 10,039,480 | B2 | 8/2018 | Brauker et al. |
| 10,046,114 | B1 | 8/2018 | Biederman et al. |
| 10,052,055 | B2 | 8/2018 | Li et al. |
| 10,092,207 | B1 | 10/2018 | Windmiller |
| 10,136,846 | B2 | 11/2018 | Wang et al. |
| 10,173,042 | B2 | 1/2019 | Pushpala et al. |
| 10,182,748 | B2 | 1/2019 | Catt et al. |
| 10,188,333 | B2 | 1/2019 | Kamath et al. |
| 10,228,341 | B2 | 3/2019 | Katsuki et al. |
| 10,299,712 | B2 | 5/2019 | Brister et al. |
| 10,327,678 | B2 | 6/2019 | Gottlieb et al. |
| 10,492,708 | B1 | 12/2019 | Windmiller |
| 10,524,730 | B2 | 1/2020 | Reitz et al. |
| D875,254 | S | 2/2020 | Cooke et al. |
| 10,549,080 | B2 | 2/2020 | Pushpala et al. |
| 10,610,103 | B2 | 4/2020 | Brister et al. |
| 10,612,153 | B2 | 4/2020 | Ivanovskaya et al. |
| 10,709,332 | B2 | 7/2020 | Brister et al. |
| 10,743,800 | B2 | 8/2020 | Larvenz et al. |
| 10,780,222 | B2 | 9/2020 | Ward et al. |
| 10,820,860 | B2 | 11/2020 | Pushpala et al. |
| 10,835,163 | B2 | 11/2020 | Haghgooie et al. |
| 10,881,334 | B2 | 1/2021 | Facchinetti et al. |
| 10,932,700 | B2 | 3/2021 | Simpson et al. |
| 10,983,083 | B2 | 4/2021 | Harding et al. |
| 11,020,026 | B2 | 6/2021 | Boock et al. |
| 11,035,872 | B2 | 6/2021 | Boutelle et al. |
| 11,045,142 | B1 | 6/2021 | Windmiller et al. |
| 11,051,724 | B2 | 7/2021 | Pace et al. |
| 11,123,532 | B2 | 9/2021 | Pushpala et al. |
| 11,172,851 | B2 | 11/2021 | Pushpala et al. |
| 11,179,068 | B2 | 11/2021 | Pace et al. |
| 11,197,985 | B2 | 12/2021 | Pushpala et al. |
| 11,272,866 | B2 | 3/2022 | Pushpala et al. |
| 11,272,885 | B2 | 3/2022 | Pushpala et al. |
| 11,291,390 | B2 | 4/2022 | Pushpala et al. |
| 11,331,022 | B2 | 5/2022 | Halac et al. |
| 11,359,300 | B1 | 6/2022 | Beer et al. |
| 11,406,818 | B2 | 8/2022 | Windmiller |
| 11,432,747 | B2 | 9/2022 | Cho et al. |
| 11,478,194 | B2 | 10/2022 | Windmiller et al. |
| 11,596,332 | B2 | 3/2023 | Shults et al. |
| 11,654,270 | B2 | 5/2023 | Mansfield, III et al. |
| D988,160 | S | 6/2023 | Morelock |
| 11,672,965 | B2 | 6/2023 | Mansfield, III et al. |
| 11,697,007 | B2 | 7/2023 | Gu et al. |
| D996,999 | S | 8/2023 | Morelock |
| 11,819,650 | B2 | 11/2023 | Pushpala et al. |
| D1,012,744 | S | 1/2024 | Morelock |
| 11,857,344 | B2 | 1/2024 | Windmiller et al. |
| 11,865,289 | B2 | 1/2024 | Pushpala et al. |
| 11,872,055 | B2 | 1/2024 | Tangney et al. |
| D1,013,544 | S | 2/2024 | Morelock |
| 11,896,792 | B2 | 2/2024 | Pushpala et al. |
| 11,896,793 | B2 | 2/2024 | Pushpala et al. |
| 11,903,738 | B2 | 2/2024 | Pushpala et al. |
| 11,904,127 | B2 | 2/2024 | Mansfield et al. |
| 11,963,796 | B1 | 4/2024 | Windmiller et al. |
| 11,986,614 | B2 | 5/2024 | Mansfield et al. |
| 11,992,314 | B2 | 5/2024 | Hahn et al. |
| 12,011,294 | B2 | 6/2024 | Campbell et al. |
| D1,033,641 | S | 7/2024 | Morelock |
| D1,035,004 | S | 7/2024 | Morelock |
| 12,048,558 | B2 | 7/2024 | Kendall et al. |
| D1,038,794 | S | 8/2024 | Morelock |
| 12,070,307 | B2 | 8/2024 | Ebejer et al. |
| 12,070,313 | B2 | 8/2024 | Fuchs et al. |
| 12,109,032 | B1 | 10/2024 | Windmiller et al. |
| D1,051,745 | S | 11/2024 | Morelock |
| D1,057,153 | S | 1/2025 | Morelock |
| D1,068,516 | S | 4/2025 | Morelock |
| 12,279,888 | B2 | 4/2025 | Campbell et al. |
| 12,285,271 | B2 | 4/2025 | Campbell et al. |
| 12,336,816 | B2 | 6/2025 | Campbell et al. |
| D1,083,640 | S | 7/2025 | Morelock |
| D1,083,977 | S | 7/2025 | Morelock |
| 12,369,830 | B2 | 7/2025 | Windmiller et al. |
| 12,453,516 | B2 | 10/2025 | Tangney et al. |
| 12,507,921 | B2 | 12/2025 | Alonso-Soski et al. |
| 12,582,337 | B2 | 3/2026 | Campbell et al. |
| 12,599,337 | B1 | 4/2026 | Windmiller et al. |
| 12,605,100 | B2 | 4/2026 | Windmiller et al. |
| 12,629,060 | B2 | 5/2026 | Campbell et al. |
| 2002/0004640 | A1 | 1/2002 | Conn et al. |
| 2002/0020688 | A1 | 2/2002 | Sherman et al. |
| 2002/0055704 | A1 | 5/2002 | Scott et al. |
| 2002/0072784 | A1 | 6/2002 | Sheppard et al. |
| 2002/0105080 | A1 | 8/2002 | Speakman |
| 2002/0120186 | A1 | 8/2002 | Keimel |
| 2002/0169393 | A1 | 11/2002 | Cunningham et al. |
| 2002/0187556 | A1 | 12/2002 | Shartle et al. |
| 2003/0068666 | A1 | 4/2003 | Zweig |
| 2003/0078549 | A1 | 4/2003 | Stupar et al. |
| 2003/0088166 | A1 | 5/2003 | Say et al. |
| 2003/0095582 | A1 | 5/2003 | Ackley |
| 2003/0100040 | A1 | 5/2003 | Bonnecaze et al. |
| 2003/0104119 | A1 | 6/2003 | Wilson et al. |
| 2003/0135158 | A1 | 7/2003 | Gonnelli |
| 2003/0135161 | A1 * | 7/2003 | Fleming ............ A61M 37/0015 606/186 |
| 2003/0199788 | A1 | 10/2003 | Erickson et al. |
| 2003/0208167 | A1 | 11/2003 | Prausnitz et al. |
| 2003/0225360 | A1 | 12/2003 | Eppstein et al. |
| 2003/0235817 | A1 | 12/2003 | Bartkowiak et al. |
| 2004/0065158 | A1 | 4/2004 | Schrepfer et al. |
| 2004/0082875 | A1 | 4/2004 | Donoghue et al. |
| 2004/0111017 | A1 | 6/2004 | Say et al. |
| 2004/0138543 | A1 | 7/2004 | Russell et al. |
| 2004/0146611 | A1 | 7/2004 | Arias et al. |
| 2004/0189311 | A1 | 9/2004 | Glezer et al. |
| 2004/0220625 | A1 | 11/2004 | Silvestri et al. |
| 2005/0013753 | A1 | 1/2005 | Eaton et al. |
| 2005/0036020 | A1 | 2/2005 | Li et al. |
| 2005/0101841 | A9 | 5/2005 | Kaylor et al. |
| 2005/0137536 | A1 | 6/2005 | Gonnelli |
| 2005/0209565 | A1 | 9/2005 | Yuzhakov et al. |
| 2005/0267440 | A1 | 12/2005 | Herman et al. |
| 2005/0272989 | A1 | 12/2005 | Shah et al. |
| 2006/0015061 | A1 | 1/2006 | Kuo et al. |
| 2006/0016700 | A1 | 1/2006 | Brister et al. |
| 2006/0173259 | A1 | 8/2006 | Flaherty et al. |
| 2006/0264716 | A1 | 11/2006 | Zander |
| 2006/0281121 | A1 | 12/2006 | Unger et al. |
| 2007/0020641 | A1 | 1/2007 | Heeger et al. |
| 2007/0060815 | A1 | 3/2007 | Martin et al. |
| 2007/0078445 | A1 | 4/2007 | Malloy |
| 2007/0105404 | A1 | 5/2007 | Lee et al. |
| 2007/0151868 | A1 | 7/2007 | Staib et al. |
| 2007/0169533 | A1 | 7/2007 | Shah et al. |

(56) References Cited

U.S. PATENT DOCUMENTS

2007/0170054 A2 7/2007 Wilsey
2007/0191700 A1 8/2007 Say et al.
2007/0191733 A1 8/2007 Gianchandani et al.
2007/0213044 A1 9/2007 Steingart et al.
2007/0227907 A1 10/2007 Shah et al.
2007/0282246 A1 12/2007 Henley
2008/0009800 A1 1/2008 Nickel
2008/0009801 A1 1/2008 Nickel
2008/0027369 A1 1/2008 Carter et al.
2008/0027426 A1 1/2008 Kelly et al.
2008/0033269 A1 2/2008 Zhang
2008/0097280 A1 4/2008 Martin et al.
2008/0097352 A1 4/2008 Beck et al.
2008/0119707 A1 5/2008 Stafford
2008/0154107 A1 6/2008 Jina
2008/0156661 A1 7/2008 Cooper et al.
2008/0161654 A1 7/2008 Teller et al.
2008/0213461 A1 9/2008 Gill et al.
2008/0221408 A1 9/2008 Hoarau et al.
2008/0234562 A1 9/2008 Jina
2008/0255434 A1 10/2008 Hayter et al.
2008/0275327 A1 11/2008 Faarbaek et al.
2008/0288026 A1 11/2008 Cross et al.
2008/0319298 A1 12/2008 Huys et al.
2009/0043250 A1 2/2009 Gonnelli
2009/0057148 A1 3/2009 Wieder et al.
2009/0062752 A1 3/2009 Gonnelli
2009/0066348 A1 3/2009 Shin et al.
2009/0069650 A1 3/2009 Jennewine
2009/0069651 A1 3/2009 Zimmermann et al.
2009/0069697 A1 3/2009 Frazier et al.
2009/0084678 A1 4/2009 Joshi et al.
2009/0088652 A1 4/2009 Tremblay
2009/0090623 A1 4/2009 Chuang et al.
2009/0099427 A1 4/2009 Jina et al.
2009/0101498 A1 4/2009 Papadimitrakopoulo et al.
2009/0118672 A1 5/2009 Gonnelli et al.
2009/0131778 A1 5/2009 Jina et al.
2009/0143761 A1 6/2009 Cantor et al.
2009/0152598 A1 6/2009 Baek et al.
2009/0157330 A1 6/2009 Rinne et al.
2009/0191616 A1 7/2009 Lu et al.
2009/0198118 A1 8/2009 Hayter et al.
2009/0218239 A1 9/2009 Gooding et al.
2009/0234202 A1 9/2009 Goix et al.
2009/0259118 A1 10/2009 Feldman et al.
2009/0294306 A1 12/2009 Feldman et al.
2009/0301994 A1 12/2009 Bhandari et al.
2010/0006451 A1 1/2010 Gordon et al.
2010/0021637 A1 1/2010 Revol Cavalier et al.
2010/0022416 A1 1/2010 Flemming et al.
2010/0025238 A1 2/2010 Gottlieb et al.
2010/0030045 A1 2/2010 Gottlieb et al.
2010/0049021 A1 2/2010 Jina et al.
2010/0052892 A1 3/2010 Allen et al.
2010/0052897 A1 3/2010 Allen et al.
2010/0052898 A1 3/2010 Allen et al.
2010/0052915 A1 3/2010 Allen et al.
2010/0056873 A1 3/2010 Allen et al.
2010/0108509 A1 5/2010 Curry et al.
2010/0137779 A1 6/2010 Seitz
2010/0160756 A1 6/2010 Petisce et al.
2010/0200538 A1 8/2010 Petisce et al.
2010/0213079 A1 8/2010 Willis
2010/0268043 A1 10/2010 Yodfat et al.
2010/0279377 A1 11/2010 Shah et al.
2010/0286803 A1 11/2010 Tillotson et al.
2011/0027127 A1 2/2011 Simpson et al.
2011/0042241 A1 2/2011 Kotsis et al.
2011/0077490 A1 3/2011 Simpson et al.
2011/0105871 A1 5/2011 Zimmermann et al.
2011/0140703 A1 6/2011 Chiao et al.
2011/0196216 A1 8/2011 Quarder et al.
2011/0210017 A1 9/2011 Lai et al.
2011/0224515 A1 9/2011 Mir et al.
2011/0230736 A1 9/2011 Tepper et al.
2011/0237925 A1 9/2011 Yue et al.
2011/0247934 A1 10/2011 Wang et al.
2011/0275918 A1 11/2011 Yamashita et al.
2011/0306853 A1 12/2011 Black et al.
2011/0319787 A1 12/2011 Lamoise et al.
2012/0018302 A1 1/2012 Shiraki et al.
2012/0037515 A1 2/2012 Solanki
2012/0067734 A1 3/2012 Wang et al.
2012/0078071 A1 3/2012 Bohm et al.
2012/0123232 A1 5/2012 Najarian et al.
2012/0172692 A1 7/2012 Tamada et al.
2012/0209244 A1 8/2012 Gray
2012/0277629 A1 11/2012 Bernstein et al.
2012/0323097 A9 12/2012 Chowdhury
2013/0053660 A1 2/2013 Shieh
2013/0065257 A1 3/2013 Wang et al.
2013/0135158 A1 5/2013 Faraone et al.
2013/0144131 A1 6/2013 Wang et al.
2013/0158376 A1 6/2013 Hayter et al.
2013/0197338 A1 8/2013 Yu et al.
2013/0225956 A1 8/2013 Huang et al.
2013/0281808 A1 10/2013 Shieh
2013/0324820 A1 12/2013 Petillo et al.
2013/0338632 A1 12/2013 Kaplan et al.
2013/0338746 A1 12/2013 Guvanasen et al.
2013/0345597 A1 12/2013 Hagino et al.
2014/0135679 A1 5/2014 Mann et al.
2014/0259652 A1 9/2014 Pushpala et al.
2014/0275897 A1 9/2014 Pushpala et al.
2014/0275899 A1 9/2014 Gottlieb et al.
2014/0275907 A1 9/2014 Feldman et al.
2014/0303471 A1 10/2014 Rajaraman et al.
2014/0336487 A1 11/2014 Wang et al.
2014/0378804 A1 12/2014 Kalvesten et al.
2015/0073238 A1 3/2015 Matsumoto et al.
2015/0126834 A1 5/2015 Wang et al.
2015/0186609 A1 7/2015 Utter, II
2015/0208970 A1 7/2015 Huang
2015/0208985 A1 7/2015 Huang
2015/0243851 A1 8/2015 Lee et al.
2015/0250421 A1 9/2015 Arumugam et al.
2015/0276758 A1 10/2015 Addisu
2015/0313527 A1 11/2015 Renlund
2015/0351670 A1 12/2015 Vanslyke et al.
2016/0022187 A1 1/2016 Pushpala et al.
2016/0029937 A1 2/2016 Sia et al.
2016/0029966 A1 2/2016 Salas-Boni et al.
2016/0058342 A1 3/2016 Maiz-Aguinaga et al.
2016/0095541 A1 4/2016 Wang et al.
2016/0095547 A1 4/2016 Wang et al.
2016/0139069 A1 5/2016 Wang
2016/0157764 A1 6/2016 Di Palma et al.
2016/0158514 A1 6/2016 Stoeber et al.
2016/0162662 A1 6/2016 Monirabbasi et al.
2016/0166184 A1 6/2016 Teng et al.
2016/0166186 A1 6/2016 Ferguson et al.
2016/0213908 A1 7/2016 McAllister et al.
2016/0258945 A1 9/2016 Malima et al.
2016/0270704 A1 9/2016 DeTurk
2016/0296149 A1 10/2016 Polsky et al.
2016/0302687 A1 10/2016 Lee et al.
2016/0324442 A1 11/2016 Zdeblick
2016/0370377 A1 12/2016 Ahmad
2017/0003766 A1 1/2017 Budiman
2017/0007813 A1 1/2017 Negi et al.
2017/0035331 A1 2/2017 Paranjape et al.
2017/0055835 A1 3/2017 Scherer et al.
2017/0086713 A1 3/2017 Pushpala et al.
2017/0095652 A1 4/2017 Pushpala et al.
2017/0108459 A1 4/2017 Katsuki et al.
2017/0127989 A1 5/2017 Feldman et al.
2017/0128009 A1 5/2017 Pushpala et al.
2017/0164881 A1 6/2017 Fujita et al.
2017/0172475 A1 6/2017 Pushpala et al.
2017/0238851 A1 8/2017 Duhamel et al.
2017/0251958 A1 9/2017 Pushpala et al.
2017/0251959 A1 9/2017 Feldman et al.
2017/0251960 A1 9/2017 Crouther et al.

(56) References Cited

U.S. PATENT DOCUMENTS

| | | | |
|---|---|---|---|
| 2017/0311852 | A1 | 11/2017 | Morgan |
| 2017/0347925 | A1 | 12/2017 | Wang et al. |
| 2017/0347926 | A1 | 12/2017 | Farooqui |
| 2018/0014787 | A1 | 1/2018 | Ganton et al. |
| 2018/0116572 | A1 | 5/2018 | Simpson et al. |
| 2018/0140235 | A1 | 5/2018 | Pushpala et al. |
| 2018/0256086 | A1 | 9/2018 | Polsky et al. |
| 2018/0279929 | A1 | 10/2018 | Huang et al. |
| 2018/0317820 | A1 | 11/2018 | Pace et al. |
| 2018/0338712 | A1 | 11/2018 | Cass et al. |
| 2018/0338713 | A1 | 11/2018 | Polsky et al. |
| 2018/0340203 | A1 | 11/2018 | Holmes et al. |
| 2019/0001108 | A1 | 1/2019 | Ono |
| 2019/0008425 | A1 | 1/2019 | Srinivasan et al. |
| 2019/0008433 | A1 | 1/2019 | Peyser et al. |
| 2019/0022365 | A1 | 1/2019 | Chowdhury et al. |
| 2019/0029577 | A1 | 1/2019 | Koelker et al. |
| 2019/0076075 | A1 | 3/2019 | Miller et al. |
| 2019/0090811 | A1 | 3/2019 | Reitz et al. |
| 2019/0091455 | A1 | 3/2019 | Reitz et al. |
| 2019/0094169 | A1 | 3/2019 | Shah et al. |
| 2019/0101551 | A1 | 4/2019 | Plaxco et al. |
| 2019/0110724 | A1 | 4/2019 | Kamath et al. |
| 2019/0125223 | A1 | 5/2019 | Wang et al. |
| 2019/0167167 | A1 | 6/2019 | Mitchell et al. |
| 2019/0170739 | A1 | 6/2019 | Garner et al. |
| 2019/0201675 | A1 | 7/2019 | Miller et al. |
| 2019/0209095 | A1 | 7/2019 | Kamath et al. |
| 2019/0223795 | A1 | 7/2019 | Patolsky et al. |
| 2019/0224712 | A1 | 7/2019 | Petisce et al. |
| 2019/0231263 | A1 | 8/2019 | Ribet et al. |
| 2019/0240469 | A1 | 8/2019 | McAllister et al. |
| 2019/0241926 | A1 | 8/2019 | McKinlay et al. |
| 2019/0261907 | A1 | 8/2019 | Brister et al. |
| 2019/0274599 | A1 | 9/2019 | Polsky et al. |
| 2019/0274600 | A1 | 9/2019 | Pesantez et al. |
| 2019/0298210 | A1 | 10/2019 | Bennet et al. |
| 2019/0307379 | A1 | 10/2019 | Boock et al. |
| 2019/0309433 | A1 | 10/2019 | Sattayasamitsathit et al. |
| 2019/0310219 | A1 | 10/2019 | Boock |
| 2019/0320947 | A1 | 10/2019 | Chen et al. |
| 2019/0328938 | A1 | 10/2019 | Son |
| 2019/0357827 | A1 | 11/2019 | Li et al. |
| 2019/0358441 | A1 | 11/2019 | Zvezdin et al. |
| 2020/0000387 | A1 | 1/2020 | Gerhardt et al. |
| 2020/0029876 | A1 | 1/2020 | Brister et al. |
| 2020/0037938 | A1 | 2/2020 | Rong et al. |
| 2020/0046272 | A1 | 2/2020 | Brister et al. |
| 2020/0101286 | A1 | 4/2020 | Windmiller et al. |
| 2020/0121902 | A1 | 4/2020 | Pushpala et al. |
| 2020/0138343 | A1 | 5/2020 | Gerasopoulos et al. |
| 2020/0178853 | A1 | 6/2020 | Pushpala et al. |
| 2020/0187778 | A1 | 6/2020 | Brister et al. |
| 2020/0214566 | A1 | 7/2020 | Allen et al. |
| 2020/0237296 | A1 | 7/2020 | Schiff et al. |
| 2020/0254240 | A1 | 8/2020 | Windmiller et al. |
| 2020/0297997 | A1 | 9/2020 | Windmiller et al. |
| 2020/0305771 | A1 | 10/2020 | Feldman et al. |
| 2020/0330007 | A1 | 10/2020 | Garai et al. |
| 2020/0359949 | A1 | 11/2020 | Brauker et al. |
| 2020/0390395 | A1 | 12/2020 | Pushpala et al. |
| 2020/0405234 | A1 | 12/2020 | Pushpala et al. |
| 2021/0045663 | A1 | 2/2021 | Simpson et al. |
| 2021/0045665 | A1 | 2/2021 | Simpson et al. |
| 2021/0045666 | A1 | 2/2021 | Simpson et al. |
| 2021/0060322 | A1 | 3/2021 | Burton |
| 2021/0100452 | A1 | 4/2021 | Brister et al. |
| 2021/0100504 | A1 | 4/2021 | Pushpala et al. |
| 2021/0100505 | A1 | 4/2021 | Pushpala et al. |
| 2021/0183508 | A1 | 6/2021 | Parker et al. |
| 2021/0187286 | A1 | 6/2021 | Windmiller et al. |
| 2021/0190719 | A1 | 6/2021 | LaTour et al. |
| 2021/0236057 | A1 | 8/2021 | Pushpala et al. |
| 2021/0321942 | A1 | 10/2021 | Pushpala et al. |
| 2021/0345916 | A1 | 11/2021 | Boock et al. |
| 2021/0353229 | A1 | 11/2021 | Pierart et al. |
| 2021/0379370 | A1 | 12/2021 | Windmiller et al. |
| 2021/0386338 | A1 | 12/2021 | Zhang et al. |
| 2021/0393201 | A1 | 12/2021 | Morelock et al. |
| 2022/0031244 | A1 | 2/2022 | Windmiller et al. |
| 2022/0047190 | A1 | 2/2022 | Taylor et al. |
| 2022/0054813 | A1 | 2/2022 | Pushpala et al. |
| 2022/0054814 | A1 | 2/2022 | Pushpala et al. |
| 2022/0087610 | A1 | 3/2022 | Pushpala et al. |
| 2022/0104773 | A1 | 4/2022 | Lee et al. |
| 2022/0151516 | A1 | 5/2022 | Wang et al. |
| 2022/0151518 | A1 | 5/2022 | Pushpala et al. |
| 2022/0151519 | A1 | 5/2022 | Pushpala et al. |
| 2022/0151558 | A1 | 5/2022 | Pushpala et al. |
| 2022/0175278 | A1 | 6/2022 | Campbell et al. |
| 2022/0175279 | A1 | 6/2022 | Pushpala et al. |
| 2022/0175282 | A1 | 6/2022 | Hoss et al. |
| 2022/0192548 | A1 | 6/2022 | Liu et al. |
| 2022/0214300 | A1 | 7/2022 | Wang et al. |
| 2022/0225901 | A1 | 7/2022 | Chapman et al. |
| 2022/0233107 | A1 | 7/2022 | Pushpala et al. |
| 2022/0241569 | A1 | 8/2022 | Quan et al. |
| 2022/0249189 | A1 | 8/2022 | Choi et al. |
| 2022/0257181 | A1 | 8/2022 | Wang et al. |
| 2022/0298291 | A1 | 9/2022 | Shin et al. |
| 2022/0322975 | A1 | 10/2022 | Baker et al. |
| 2022/0322977 | A1 | 10/2022 | Simpson et al. |
| 2022/0361776 | A1 | 11/2022 | Wang et al. |
| 2022/0370011 | A1 | 11/2022 | Windmiller et al. |
| 2023/0003725 | A1 | 1/2023 | Wang et al. |
| 2023/0012662 | A1 | 1/2023 | Tehrani et al. |
| 2023/0074798 | A1 | 3/2023 | Tangney et al. |
| 2023/0094419 | A1 | 3/2023 | Mansfield, III et al. |
| 2023/0099617 | A1 | 3/2023 | Mansfield, III et al. |
| 2023/0137258 | A1 | 5/2023 | Windmiller |
| 2023/0190147 | A1 | 6/2023 | Campbell et al. |
| 2023/0256220 | A1 | 8/2023 | Mansfield, III et al. |
| 2023/0301552 | A1 | 9/2023 | Mallires et al. |
| 2023/0310823 | A1 | 10/2023 | Mansfield, III et al. |
| 2023/0414102 | A1 | 12/2023 | Allen et al. |
| 2024/0008777 | A1 | 1/2024 | Fuchs et al. |
| 2024/0081740 | A1 | 3/2024 | Windmiller et al. |
| 2024/0164719 | A1 | 5/2024 | Campbell et al. |
| 2024/0252115 | A1 | 8/2024 | Tangney et al. |
| 2024/0272113 | A1 | 8/2024 | Ouyang et al. |
| 2024/0315614 | A1 | 9/2024 | Campbell et al. |
| 2024/0337620 | A1 | 10/2024 | Iketani et al. |
| 2024/0341636 | A1 | 10/2024 | Yang et al. |
| 2024/0366125 | A1 | 11/2024 | Alonso-Soski et al. |
| 2024/0366149 | A1 | 11/2024 | Kendall et al. |
| 2024/0382157 | A1 | 11/2024 | Windmiller et al. |
| 2024/0408366 | A1 | 12/2024 | Mansfield et al. |
| 2024/0423511 | A1 | 12/2024 | Di et al. |
| 2024/0423526 | A1 | 12/2024 | Windmiller et al. |
| 2025/0000395 | A1 | 1/2025 | Brister et al. |
| 2025/0009301 | A1 | 1/2025 | Gross et al. |
| 2025/0049397 | A1 | 2/2025 | Campbell et al. |
| 2025/0213859 | A1 | 7/2025 | Windmiller et al. |
| 2025/0281080 | A1 | 9/2025 | Campbell et al. |
| 2025/0311950 | A1 | 10/2025 | Poudineh et al. |
| 2025/0331758 | A1 | 10/2025 | Windmiller et al. |
| 2026/0013755 | A1 | 1/2026 | Harris et al. |

FOREIGN PATENT DOCUMENTS

| | | | |
|---|---|---|---|
| AU | 2012326664 | A1 | 4/2014 |
| CN | 101068591 | A | 11/2007 |
| CN | 108404286 | A | 8/2018 |
| CN | 108652618 | A | 10/2018 |
| CN | 108845012 | A | 11/2018 |
| CN | 211357412 | U | 8/2020 |
| CN | 112617822 | A | 4/2021 |
| CN | 113352654 | A | 9/2021 |
| CN | 113648529 | A | 11/2021 |
| CN | 113717955 | A | 11/2021 |
| CN | 114010934 | A | 2/2022 |
| CN | 114129503 | A | 3/2022 |
| CN | 115404534 | A | 11/2022 |
| CN | 118516717 | A | 8/2024 |

(56) References Cited

FOREIGN PATENT DOCUMENTS

| | | | |
|---|---|---|---|
| DE | 102008048984 | A1 | 4/2010 |
| DE | 102015209669 | A1 | 12/2016 |
| EP | 1377338 | A2 | 1/2004 |
| EP | 1006868 | B1 | 6/2004 |
| EP | 1372602 | B1 | 4/2007 |
| EP | 1377338 | B1 | 8/2008 |
| EP | 1792565 | B1 | 10/2008 |
| EP | 1187653 | B1 | 3/2010 |
| EP | 2359885 | A1 | 8/2011 |
| EP | 3135796 | A1 | 3/2017 |
| EP | 2898821 | B1 | 12/2017 |
| EP | 3285851 | A1 | 2/2018 |
| EP | 3364183 | A1 | 8/2018 |
| EP | 3381370 | A1 | 10/2018 |
| EP | 4212095 | A1 | 7/2023 |
| EP | 3829418 | B1 | 11/2024 |
| EP | 3829437 | B1 | 11/2024 |
| EP | 4009865 | B1 | 11/2024 |
| EP | 4482372 | A1 | 1/2025 |
| FR | 3099696 | A1 | 2/2021 |
| JP | H0222552 | A | 1/1990 |
| JP | H0231741 | A | 2/1990 |
| JP | H05215712 | A | 8/1993 |
| JP | H067324 | A | 1/1994 |
| JP | H07275227 | A | 10/1995 |
| JP | 2003038464 | A | 2/2003 |
| JP | 2003038465 | A | 2/2003 |
| JP | 2003111742 | A | 4/2003 |
| JP | 2004180773 | A | 7/2004 |
| JP | 2005087613 | A | 4/2005 |
| JP | 2005525141 | A | 8/2005 |
| JP | 2005322591 | A | 11/2005 |
| JP | 2006510467 | A | 3/2006 |
| JP | 2008506468 | A | 3/2008 |
| JP | 2008512162 | A | 4/2008 |
| JP | 2008540013 | A | 11/2008 |
| JP | 2008544763 | A | 12/2008 |
| JP | 2009544409 | A | 12/2009 |
| JP | 2010523167 | A | 7/2010 |
| JP | 5053330 | B2 | 10/2012 |
| JP | 2013506847 | A | 2/2013 |
| JP | 2013521942 | A | 6/2013 |
| JP | 2014533523 | A | 12/2014 |
| JP | 2017512118 | A | 5/2017 |
| JP | 2017108763 | A | 6/2017 |
| JP | 2018019826 | A | 2/2018 |
| JP | 2019506910 | A | 3/2019 |
| JP | 2019107040 | A | 7/2019 |
| JP | 2019526332 | A | 9/2019 |
| JP | 2019205852 | A | 12/2019 |
| JP | 2020527063 | A | 9/2020 |
| JP | 2020170011 | A | 10/2020 |
| JP | 2022501100 | A | 1/2022 |
| JP | 2022508575 | A | 1/2022 |
| KR | 100793615 | B1 | 1/2008 |
| KR | 101621945 | B1 | 5/2016 |
| KR | 20160108111 | A | 9/2016 |
| KR | 20170041375 | A | 4/2017 |
| KR | 20180127729 | A | 11/2018 |
| WO | WO-2000074763 | A2 | 12/2000 |
| WO | WO-2006060106 | A1 | 6/2006 |
| WO | WO-2006093422 | A1 | 9/2006 |
| WO | WO-2006116242 | A2 | 11/2006 |
| WO | WO-2007040938 | A1 | 4/2007 |
| WO | WO-2009034313 | A2 | 3/2009 |
| WO | WO-2009064164 | A2 | 5/2009 |
| WO | WO-2009124095 | A1 | 10/2009 |
| WO | WO-2010014959 | A2 | 2/2010 |
| WO | WO-2010022252 | A2 | 2/2010 |
| WO | WO-2010045247 | A1 | 4/2010 |
| WO | WO-2010059276 | A1 | 5/2010 |
| WO | WO-2010120364 | A2 | 10/2010 |
| WO | WO-2011056095 | A1 | 5/2011 |
| WO | WO-2012020332 | A2 | 2/2012 |
| WO | WO-2012142625 | A2 | 10/2012 |
| WO | WO-2013058879 | A2 | 4/2013 |
| WO | WO-2014120114 | A1 | 8/2014 |
| WO | WO-2015073459 | A1 | 5/2015 |
| WO | WO-2016009228 | A1 | 1/2016 |
| WO | WO-2016189301 | A1 | 12/2016 |
| WO | WO-2017129980 | A1 | 8/2017 |
| WO | WO-2017189707 | A1 | 11/2017 |
| WO | WO-2018017196 | A1 | 1/2018 |
| WO | WO-2018071265 | A1 | 4/2018 |
| WO | WO-2018164886 | A1 | 9/2018 |
| WO | WO-2018170363 | A1 | 9/2018 |
| WO | WO-2019046333 | A1 | 3/2019 |
| WO | WO-2019156934 | A1 | 8/2019 |
| WO | WO-2019222615 | A1 | 11/2019 |
| WO | WO-2019239258 | A1 | 12/2019 |
| WO | WO-2020023804 | A1 | 1/2020 |
| WO | WO-2020069565 | A1 | 4/2020 |
| WO | WO-2020069567 | A1 | 4/2020 |
| WO | WO-2020069570 | A1 | 4/2020 |
| WO | WO-2020117918 | A1 | 6/2020 |
| WO | WO-2020186118 | A1 | 9/2020 |
| WO | WO-2021007344 | A1 | 1/2021 |
| WO | WO-2021015389 | A1 | 1/2021 |
| WO | WO-2021025260 | A1 | 2/2021 |
| WO | WO-2021062475 | A1 | 4/2021 |
| WO | WO-2021081456 | A1 | 4/2021 |
| WO | WO-2021086690 | A1 | 5/2021 |
| WO | WO-2021118124 | A1 | 6/2021 |
| WO | WO-2021118431 | A1 | 6/2021 |
| WO | WO-2021119546 | A1 | 6/2021 |
| WO | WO-2021216186 | A2 | 10/2021 |
| WO | WO-2021216186 | A9 | 12/2021 |
| WO | WO-2022026764 | A1 | 2/2022 |
| WO | WO-2022066985 | A1 | 3/2022 |
| WO | WO-2022066992 | A1 | 3/2022 |
| WO | WO-2022090741 | A1 | 5/2022 |
| WO | WO-2022136785 | A1 | 6/2022 |
| WO | WO-2022170283 | A1 | 8/2022 |
| WO | WO-2022240700 | A1 | 11/2022 |
| WO | WO-2023055755 | A1 | 4/2023 |
| WO | WO-2023064877 | A1 | 4/2023 |
| WO | WO-2023133468 | A1 | 7/2023 |
| WO | WO-2023229662 | A2 | 11/2023 |
| WO | WO-2024000015 | A1 | 1/2024 |
| WO | WO-2024010827 | A1 | 1/2024 |
| WO | WO-2024163950 | A2 | 8/2024 |
| WO | WO-2024238798 | A1 | 11/2024 |
| WO | WO-2025144429 | A2 | 7/2025 |
| WO | WO-2025231565 | A1 | 11/2025 |

OTHER PUBLICATIONS

Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. 8 pages.

Allen et al., "Continuous glucose monitoring counseling improves physical activity behaviors of individuals with type 2 diabetes: A randomized clinical trial" Diabetes Res Clin Pract. Jun. 2008 80(3): 371-379. doi:10.1016/j.diabres.2008.01.006.

American Diabetes Association, "Diabetes and Emotional Health: A Practical Guide for Health Professionals Supporting Adults with Type 1 and Type 2 Diabetes" U.S. Edition (2021), 214 pages.

American Diabetes Association® Press Release (2020). "American Diabetes Association® Applauds policymakers' Focus on Addressing High Costs of Insulin for Seven Million Americans," 4 pages.

American Diabetes Association Professional Practice Committee, "6. Glycemic Goals and Hypoglycemia: Standards of Care in Diabetes—2024" Diabetes Care Jan. 1, 2024; 47(Suppl 1):S111-S125.

American Diabetes Association Professional Practice Committee, "7. Diabetes Technology: Standards of Medical Care in Diabetes—2022" Diabetes Care Jan. 1, 2022; 45(Suppl 1):S97-S112.

Bantle, J.P. et al. (1997). "Glucose measurement in patients with diabetes mellitus with dermal interstitial fluid," J. Lab. Clin. Med. 130:436-441.

(56) References Cited

OTHER PUBLICATIONS

Barrett et al., "Risk for Newly Diagnosed Diabetes 30 Days After SARS-CoV-2 Infection Among Persons Aged 18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.
Battelino et al., "Continuous glucose monitoring and metrics for clinical trials: an international consensus statement" Lancet Diabetes Endocrinol (2023) 11:42-57.
Beckles, G.L. et al. (2016). "Disparities in the prevalence of diagnosed diabetes—United States, 1999-2002 and 2011-2014," MMWR 65:1265-1269.
Brown, "Design of Electronics for Wearable Electrochemical Sensors" University of California, San Diego, Master's Thesis (2019) 48 pages.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Centers for Disease Control, "National Diabetes Statistics Report 2020 Estimates of Diabetes and Its Burden in the United States" (2020) 32 pages.
Centers for Disease Control, "National Diabetes Statistics Report" May 2024, 16 pages.
Chang, H. et al. (2017). "A swellable microneedle patch to rapidly extract skin interstitial fluid for timely metabolic analysis," Adv. Mater. 29:1702243. 8 pages.
Chen et al., "Electrochemically Mediated Electrodeposition/Electropolymerization to Yield a Glucose Microbiosensor with Improved Characteristics" Anal. Chem. (2002) 74:368-372.
Clutter et al., "Epinephrine plasma metabolic clearance rates and physiologic thresholds for metabolic and hemodynamic actions in man" J Clin Invest. (1980) 66(1):94-101.
Czupryniak et al., "Ambulatory Glucose Profile (AGP) Report in Daily Care of Patients with Diabetes: Practical Tips and Recommendations" Diabetes Ther (2022) 13:811-821.
Diabetes Care (2021). "7. Diabetes Technology: Standards of Medical Care in Diabetes—2021," Diabetes Care 44(Supplement 1):S85-S99.
Diabetes Control and Complications Trial Research Group, "The effect of intensive treatment of diabetes on the development and progression of long-term complications in insulin-dependent diabetes mellitus" N Engl J Med Sep. 30, 1993; 329(14):977-986.
Donnelly et al., "Microneedle Arrays Allow Lower Microbial Penetration Than Hypodermic Needles In Vitro" Pharmaceutical Research (2009) 26(11):2513-2522.
Donnelly, R.F. et al. (2007). "Microstructured Devices for Transdermal Drug Delivery and Minimally-Invasive Patient Monitoring," Recent Patents on Drug Delivery & Formulation 1:195-200.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Eddy et al., "The modification of enzyme electrode properties with non-conducting electropolymerised films" Biosensors & Bioelectronics (1995) 10:831-839.
Ehrhardt et al, "Behavior Modification in Prediabetes and Diabetes: Potential Use of Real-Time Continuous Glucose Monitoring" Journal of Diabetes Science and Technology Mar. 2019; 13(2):271-275.
Ehrhardt et al., "Continuous Glucose Monitoring as a Behavior Modification Tool" Clin Diabetes. Apr. 2020; 38(2):126-131. doi: 10.2337/cd19-0037.
Ehrhardt et al, "The Effect of Real-Time Continuous Glucose Monitoring on Glycemic Control in Patients with Type 2 Diabetes Mellitus" Journal of Diabetes Science and Technology May 2011; 5(3):668-675.
Elsayed et al., "2. Classification and Diagnosis of Diabetes: Standards of Care in Diabetes—2023" Diabetes Care Jan. 1, 2023; 46(Suppl 1):S19-S40.
Extended European Search Report for European Application No. 23218205.5 dated Jun. 11, 2024, 7 pages.
Extended European search report for European Application No. 25151041.8 mailed May 27, 2025, 7 pages.
Extended European Search Report for European Application No. EP20898007.8 dated Nov. 29, 2023, 9 pages.
Extended European Search Report for European Application No. EP21837561.6 dated Jun. 21, 2024, 7 pages.
Extended European Search Report mailed on Mar. 30, 2023, for European Application No. EP20881425.1, 8 pages.
Extended European Search Report mailed on May 8, 2015, for EP Application No. 12842020.5, filed on Aug. 31, 2012, 7 pages.
Extended European Search Report mailed on Oct. 27, 2022, for EP Application No. 21850331.6, filed on Jul. 29, 2021, 8 pages.
Fang, M. et al. (2021). "Trends in Diabetes Treatment and Control in U.S. Adults, 1999-2018," N. Engl. J. Med. 384:2219-2228.
Fayfman et al., "Management of Hyperglycemic Crises: Diabetic ketoacidosis and hyperglycemic hyperosmolar state" Med Clin North Am. May 2017; 101(3):587-606.
Final Office Action for U.S. Appl. No. 17/073,331 mailed Dec. 17, 2024, 13 pages.
Final Office Action for U.S. Appl. No. 17/389,156 mailed Oct. 21, 2025, 18 pages.
Final Office Action for U.S. Appl. No. 17/650,056 mailed on Feb. 14, 2025, 34 pages.
Final Office Action for U.S. Appl. No. 18/527,128 mailed Sep. 6, 2024, 19 pages.
Final Office Action for U.S. Appl. No. 18/630,936 mailed Sep. 20, 2024, 16 pages.
Final Office Action mailed on Aug. 15, 2022, for U.S. Appl. No. 16/051,398, filed Jul. 31, 2018, 15 pages.
Final Office Action mailed on Aug. 19, 2016, for U.S. Appl. No. 14/965,755, filed Dec. 10, 2015, 17 pages.
Final Office Action mailed on Aug. 29, 2023, for U.S. Appl. No. 18/086,543, filed Dec. 21, 2022, 17 pages.
Final Office Action mailed on Dec. 7, 2020, for U.S. Appl. No. 15/961,793, filed Apr. 24, 2018, 13 pages.
Final Office Action mailed on Feb. 1, 2024, for U.S. Appl. No. 17/073,331, filed Oct. 17, 2020, 12 pages.
Final Office Action mailed on Feb. 8, 2024, for U.S. Appl. No. 16/051,398, filed Jul. 31, 2018, 15 pages.
Final Office Action mailed on Jul. 15, 2022, for U.S. Appl. No. 17/650,056, filed Feb. 4, 2022, 25 pages.
Final Office Action mailed on Jun. 9, 2021, for U.S. Appl. No. 16/169,939, filed Oct. 24, 2018, 24 pages.
Final Office Action mailed on Mar. 15, 2024, for U.S. Appl. No. 17/367,274, filed Jul. 2, 2021, 33 pages.
Final Office Action mailed on May 18, 2018, for U.S. Appl. No. 15/687,145, filed Aug. 25, 2017, 23 pages.
Final Office Action mailed on May 21, 2021, for U.S. Appl. No. 16/051,398, filed Jul. 31, 2018, 11 pages.
Final Office Action mailed on May 9, 2022, for U.S. Appl. No. 17/389,153, filed Jul. 29, 2021, 17 pages.
Final Office Action mailed on Nov. 27, 2023, for U.S. Appl. No. 17/389,156, filed Jul. 29, 2021, 29 pages.
Final Office Action mailed on Nov. 28, 2016, for U.S. Appl. No. 14/342,536, filed Jul. 30, 2014, 34 pages.
Final Office Action mailed on Oct. 27, 2022, for U.S. Appl. No. 15/913,709, filed Mar. 6, 2018, 21 pages.
Final Office Action mailed on Sep. 23, 2021, for U.S. Appl. No. 15/913,709, filed Mar. 6, 2018, 17 pages.
Final Office Action mailed on Sep. 7, 2023, for U.S. Appl. No. 17/650,056, filed Feb. 4, 2022, 29 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gao et al., "Simultaneous detection of glucose, uric acid and cholesterol using flexible microneedle electrode array-based bio-

(56) References Cited

OTHER PUBLICATIONS sensor and multi-channel portable electrochemical analyzer" Sensors and Actuators B: Chemical (2019) 287:102-110.
Ghimire et al., "Ketoacidosis" StatPearls Publishing, Jan. 2024, NCBI Bookshelf, 8 pages.
Gittard, S.D. et al. (2009). "Fabrication of Polymer Microneedles Using a Two-Photon Polymerization and Micromolding Process," J. Diabetes Sci. Technol. 3:304-311.
Grady, M. et al. (2017). "Examining the Impact of a Novel Blood Glucose Monitor with Color Range Indicator on Decision-Making in Patients With Type 1 and Type 2 Diabetes and its Association With Patient Numeracy Level," JMIR Diabetes 2:e24. 11 pages.
Grady, M. et al. (2018). "Use of Blood Glucose Meters Featuring Color Range Indicators Improves Glycemic Control in Patients with Diabetes in Comparison to Blood Glucose Meters Without Color (Accents Study)," J. Diab. Sci. Tech. 12:1211-1219.
Groenendaal, W. et al. (2008). "Modeling Glucose and Water Dynamics in Human Skin," Diab. Tech. Therap. 10:283-293.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
Heinemann, "Interferences With CGM Systems: Practical Relevance?" Journal of Diabetes Science and Technology (2022) vol. 16(2) 271-274.
Henry et al. "Microfabricated microneedles: a novel approach to transdermal drug delivery." Journal of pharmaceutical sciences. Aug. 1998;87(8):922-925.
International Search Report and Written Opinion for Application No. PCT/US2022/028196, mailed on Aug. 29, 2022, 8 pages.
International Search Report and Written Opinion for PCT Application No. PCT/US2020/064700, mail date Mar. 9, 2021, 11 pages.
International Search Report and Written Opinion for PCT Application No. PCT/US2024/014324 mailed Sep. 20, 2024, 22 pages.
International Search Report and Written Opinion mailed on Feb. 6, 2024, for International Application No. PCT/US2022/078819, filed on Oct. 27, 2022, 13 pages.
International Search Report mailed on Dec. 30, 2021, for PCT Application No. PCT/US2021/043786, filed on Jul. 29, 2021, 7 pages.
International Search Report mailed on Feb. 4, 2021, for PCT Application No. PCT/US2020/056517, filed on Oct. 20, 2020, 2 pages.
International Search Report mailed on Jun. 27, 2013, for PCT Application No. PCT/US2012/053544, filed on Aug. 31, 2012, 4 pages.
International Search Report mailed on Sep. 10, 2020, for PCT Application No. PCT/US2020/037379, filed on Jun. 12, 2020, 2 pages.
International Search Report mailed on Sep. 30, 2021, for PCT Application No. PCT/US2021/040385, filed on Jul. 2, 2021, 2 pages.
Invitation to pay additional fees for International Application No. PCT/US2024/014324, dated Jul. 30, 2024, 16 pages.
Jeon, G. et al. (2011). "Electrically Actuatable Smart Nanoporous Membrane for Pulsatile Drug Release," Nano Lett. 11:1284-1288.
Jina, A et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring With Glycemic Control and Acute Metabolic Events Among Patients With Insulin-Treated Diabetes," JAMA 325:2273-2284.
Lhernould, M.S. et al. (2015). "Review of Patents for Microneedle Application Devices Allowing Fluid Injections Through the Skin," Recent Patents on Drug Delivery & Formulation 9:146-157.
Maahs et al., "Effect of Acetaminophen on CGM Glucose in an Outpatient Setting" Diabetes Care (2015) 38:e158-e159.
Malitesta et al. (1990). "Glucose fast-response amperometric sensor based on glucose oxidase immobilized in an electropolymerized poly(o-phenylenediamine) film," Anal. Chem. 62:2735-2740.
Martens, T. et al. (2021). "Effect of Continuous Glucose Monitoring on Glycemic Control in Patients with Type 2 Diabetes Treated with Basal Insulin a Randomized Clinical Trial," JAMA 325:2262-2272.
Mcclatchey, P.M. et al. (2019). "Fibrotic Encapsulation Is the Dominant Source of Continuous Glucose Monitor Delays," Diabetes 68:1892-1901.
Mendes-Soares et al., "Assessment of a Personalized Approach to Predicting Postprandial Glycemic Responses to Food Among Individuals Without Diabetes" JAMA Network Open Feb. 1, 2019; 2(2):e188102. 13 pages.
Miller et al., "Hypoglycemia in patients with type 2 diabetes mellitus" Arch Intern Med Jul. 9, 2001; 161(13):1653-1659.
Miller, P.R. et al. (2011). "Integrated carbon fiber electrodes within hollow polymer microneedles for transdermal electrochemical sensing," BioMicrofluidics 5(1):013415. 14 pages.
Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Newton et al., "Diabetic ketoacidosis in type 1 and type 2 diabetes mellitus: clinical and biochemical differences" Arch Intern Med Sep. 27, 2004; 164(17):1925-1931.
Nguyen et al., "Human studies with microneedles for evaluation of their efficacy and safety" Expert Opinion on Drug Delivery (2018) 15:3, 235-245.
Non-Final Office Action for U.S. Appl. No. 16/051,398 mailed Feb. 20, 2025, 13 pages.
Non-Final Office Action for U.S. Appl. No. 17/073,331 mailed Aug. 28, 2024, 13 pages.
Non-Final Office Action for U.S. Appl. No. 17/073,331 mailed Jul. 16, 2025, 21 pages.
Non-Final Office Action for U.S. Appl. No. 17/389,156 dated Apr. 16, 2024, 28 pages.
Non-Final Office Action for U.S. Appl. No. 17/389,156 mailed Jan. 22, 2025, 17 pages.
Non-Final Office Action for U.S. Appl. No. 17/757,216 mailed on Mar. 26, 2025, 14 pages.
Non-Final Office Action for U.S. Appl. No. 18/050,450 mailed on Aug. 13, 2025, 9 pages.
Non-Final Office Action for U.S. Appl. No. 18/431,808 mailed Nov. 27, 2024, 16 pages.
Non-Final Office Action for U.S. Appl. No. 18/630,936 mailed Jun. 13, 2024, 19 pages.
Non-Final Office Action for U.S. Appl. No. 18/630,936 mailed on Dec. 12, 2024, 18 pages.
Non-Final Office Action for U.S. Appl. No. 18/824,598 mailed Nov. 4, 2024, 14 pages.
Non-Final Office Action for U.S. Appl. No. 18/824,598 mailed on Dec. 23, 2024, 27 pages.
Non-Final Office Action for U.S. Appl. No. 18/926,029 mailed on Dec. 12, 2024, 10 pages.
Non-Final Office Action for U.S. Appl. No. 19/213,907 mailed Aug. 8, 2025, 12 pages.
Non-Final Office Action for U.S. Appl. No. 19/258,472 mailed on Aug. 12, 2025, 29 pages.
Non-Final Office Action mailed on Apr. 13, 2020, for U.S. Appl. No. 15/961,793, filed Apr. 24, 2018, 13 pages.
Non-Final Office Action mailed on Apr. 6, 2017, for U.S. Appl. No. 14/342,536, filed Jul. 30, 2014, 32 pages.
Non-Final Office Action mailed on Apr. 8, 2022, for U.S. Appl. No. 17/650,056, filed Feb. 4, 2022, 14 pages.

(56) References Cited

OTHER PUBLICATIONS

Non-Final Office Action mailed on Dec. 13, 2023, for U.S. Appl. No. 18/086,543, filed Dec. 21, 2022, 16 pages.
Non-Final Office Action mailed on Dec. 21, 2022, for U.S. Appl. No. 16/051,398, filed Jul. 31, 2018, 12 pages.
Non-Final Office Action mailed on Feb. 16, 2023 for U.S. Appl. No. 17/738,990, 9 pages.
Non-Final Office Action mailed on Jan. 19, 2018, for U.S. Appl. No. 14/843,926, filed Sep. 2, 2015, 11 pages.
Non-Final Office Action mailed on Jan. 26, 2024, for U.S. Appl. No. 15/913,709, filed Mar. 6, 2018, 20 pages.
Non-Final Office Action mailed on Jan. 27, 2023, for U.S. Appl. No. 17/971,415, filed Oct. 21, 2022, 15 pages.
Non-Final Office Action mailed on Jul. 30, 2024, for U.S. Appl. No. 17/650,056, filed Feb. 4, 2022, 32 pages.
Non-Final Office Action mailed on Jun. 2, 2023, for U.S. Appl. No. 17/367,274, filed Jul. 2, 2021, 27 pages.
Non-Final Office Action mailed on Jun. 20, 2023, for U.S. Appl. No. 17/073,331, filed Oct. 17, 2020, 10 pages.
Non-Final Office Action mailed on Mar. 10, 2016, for U.S. Appl. No. 14/965,755, filed Dec. 10, 2015, 15 pages.
Non-Final Office Action mailed on Mar. 29, 2023, for U.S. Appl. No. 17/650,056, filed Feb. 4, 2022, 27 pages.
Non-Final Office Action mailed on Mar. 30, 2016, for U.S. Appl. No. 14/342,536, filed Jul. 30, 2014, 31 pages.
Non-Final Office Action mailed on Mar. 9, 2017, for U.S. Appl. No. 14/965,755, filed Dec. 10, 2015, 17 pages.
Non-Final Office Action mailed on Mar. 9, 2023 for U.S. Appl. No. 17/389,156, filed Jul. 29, 2021, 24 pages.
Non-Final Office Action mailed on May 13, 2022, for U.S. Appl. No. 15/913,709, filed Mar. 6, 2018, 20 pages.
Non-Final Office Action mailed on May 2, 2023, for U.S. Appl. No. 15/913,709, filed Mar. 6, 2018, 18 pages.
Non-Final Office Action mailed on May 24, 2023, for U.S. Appl. No. 18/086,543, filed Dec. 21, 2022, 19 pages.
Non-Final Office Action mailed on May 24, 2024, for U.S. Appl. No. 18/527,128, filed Dec. 1, 2023, 17 pages.
Non-Final Office Action mailed on Nov. 1, 2017, for U.S. Appl. No. 15/687,145, filed Aug. 25, 2017, 19 pages.
Non-Final Office Action mailed on Nov. 26, 2021, for U.S. Appl. No. 16/051,398, filed Jul. 31, 2018, 15 pages.
Non-Final Office Action mailed on Nov. 29, 2021, for U.S. Appl. No. 17/389,153, filed Jul. 29, 2021, 14 pages.
Non-Final Office Action mailed on Nov. 4, 2021, for U.S. Appl. No. 16/169,939, filed Oct. 24, 2018, 20 pages.
Non-Final Office Action mailed on Oct. 16, 2020, for U.S. Appl. No. 16/051,398, filed Jul. 31, 2018, 13 pages.
Non-Final Office Action mailed on Sep. 15, 2023, for U.S. Appl. No. 16/051,398, filed Jul. 31, 2018, 12 pages.
Non-Final Office Action mailed on Sep. 16, 2020, for U.S. Appl. No. 15/913,709, filed Mar. 6, 2018, 15 pages.
Non-Final Office Action mailed on Sep. 3, 2020, for U.S. Appl. No. 16/169,939, filed Oct. 24, 2018, 19 pages.
Notice of Allowance (Corrected) mailed on Apr. 19, 2024, for U.S. Appl. No. 18/086,543, filed Dec. 21, 2022, 4 pages.
Notice of Allowance (Corrected) mailed on Jan. 25, 2024, for U.S. Appl. No. 17/349,234, filed Jun. 16, 2021, 4 pages.
Notice of Allowance (Corrected) mailed on Mar. 18, 2024, for U.S. Appl. No. 17/349,234, filed Jun. 16, 2021, 9 pages.
Notice of Allowance for U.S. Appl. No. 17/389,156 mailed Dec. 27, 2024, 6 pages.
Notice of Allowance for U.S. Appl. No. 17/389,156 mailed Nov. 20, 2024, 5 pages.
Notice of Allowance for U.S. Appl. No. 17/389,156 mailed Sep. 25, 2024, 12 pages.
Notice of Allowance for U.S. Appl. No. 18/431,808 mailed Feb. 20, 2025, 7 pages.
Notice of Allowance for U.S. Appl. No. 18/527,128 mailed Feb. 26, 2025, 9 pages.
Notice of Allowance for U.S. Appl. No. 18/630,936 mailed Jul. 1, 2025, 8 pages.
Notice of Allowance for U.S. Appl. No. 18/824,598 mailed Apr. 4, 2025, 9 pages.
Notice of Allowance for U.S. Appl. No. 18/926,029 mailed Mar. 5, 2025, 8 pages.
Notice of Allowance mailed on Apr. 10, 2024, for U.S. Appl. No. 18/086,543, filed Dec. 21, 2022, 10 pages.
Notice of Allowance mailed on Aug. 24, 2018, for U.S. Appl. No. 15/687,145, filed Aug. 25, 2017, 7 pages.
Notice of Allowance mailed on Dec. 20, 2023, for U.S. Appl. No. 17/349,234, filed Jun. 16, 2021, 13 pages.
Notice of Allowance mailed on Feb. 13, 2018, for U.S. Appl. No. 14/843,926, filed Sep. 2, 2015, 8 pages.
Notice of Allowance mailed on Jul. 12, 2017, for U.S. Appl. No. 14/342,536, filed Jul. 30, 2014, 14 pages.
Notice of Allowance mailed on Jul. 6, 2017, for U.S. Appl. No. 14/965,755, filed Dec. 10, 2015, 12 pages.
Notice of Allowance mailed on Jun. 11, 2024, for U.S. Appl. No. 15/913,709, filed Mar. 6, 2018, 9 pages.
Notice of Allowance mailed on Jun. 12, 2023, for U.S. Appl. No. 17/738,990, filed May 6, 2022, 7 pages.
Notice of Allowance mailed on Jun. 12, 2023, for U.S. Appl. No. 17/971,415, filed Oct. 21, 2022, 14 pages.
Notice of Allowance mailed on Mar. 21, 2024, for U.S. Appl. No. 18/086,543, filed Dec. 21, 2022, 6 pages.
Notice of Allowance mailed on Mar. 4, 2024, for U.S. Appl. No. 18/086,543, filed Dec. 21, 2022, 10 pages.
Notice of Allowance mailed on May 25, 2021, for U.S. Appl. No. 15/961,793, filed Apr. 24, 2018, 11 pages.
Notice of Allowance mailed on Sep. 12, 2022, for U.S. Appl. No. 17/389,153, filed Jul. 29, 2021, 8 pages.
Notice of Allowance mailed on Sep. 25, 2023, for U.S. Appl. No. 17/971,415, filed Oct. 21, 2022, 8 pages.
Notice of Allowance mailed on Sep. 26, 2023, for U.S. Appl. No. 17/738,990, filed May 6, 2022, 7 pages.
Office Action and Swedish Search Report mailed on Oct. 17, 2023, for SE Application No. 2251496-2, 8 pages.
Ohashi et al., "Analgesic Effect of Acetaminophen: A Review of Known and Novel Mechanisms of Action" Front Pharmacol. Nov. 30, 2020;11:580289, 6 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Prausnitz, "Engineering Microneedle Patches for Vaccination and Drug Delivery to Skin" Annu. Rev. Chem. Biomol. Eng. (2017) 8:177-200.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Samant et al., "Mechanisms of sampling interstitial fluid from skin using a microneedle patch," Proc. Natl Acad. Sci. U.S.A. (2018) 115(8):4583-4588.
Segel et al., "Hypoglycemia-associated autonomic failure in advanced type 2 diabetes" Diabetes Mar. 2002; 51(3):724-733.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Shivers et al., "Turn it off!: diabetes device alarm fatigue considerations for the present and the future" J Diabetes Sci Technol May 1, 2013; 7(3):789-794.

(56) References Cited

OTHER PUBLICATIONS

Singh, T.R.R. et al. (2010). "Microporation techniques for enhanced delivery of therapeutic agents," Recent Patents on Drug Delivery & Formulation 4:1-17.
Supplementary European Search Report mailed on Oct. 9, 2023, for EP Application No. 22808101.4, 4 pages.
Swedish Search Report mailed on Feb. 3, 2023 for SE Application No. 2350067-1, 7 pages.
Tanenbaum et al., "Diabetes Device Use in Adults With Type 1 Diabetes: Barriers to Uptake and Potential Intervention Targets" Diabetes Care Feb. 2017; 40(2):181-187.
Texas Instruments (Sep. 2007). Data sheet for a LMP2234 quad micropower, 1.6V, precision, operational amplifier with CMOS input, Sep. 2007, revised Mar. 2013. 31 total pages.
Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.
UK Prospective Diabetes Study (UKPDS) Group, "Intensive blood-glucose control with sulphonylureas or insulin compared with conventional treatment and risk of complications in patients with type 2 diabetes (UKPDS 33)" Lancet Sep. 12, 1998; 352(9131):837-853.
Vicente-Perez et al., "Repeat application of microneedles does not alter skin appearance or barrier function and causes no measurable disturbance of serum biomarkers of infection, inflammation or immunity in mice in vivo" European Journal of Pharmaceutics and Biopharmaceutics (2017) 117:400-407.
Vigersky et al., "Short- and Long-Term Effects of Real-Time Continuous Glucose Monitoring in Patients with Type 2 Diabetes" Diabetes Care Jan. 2012; 35:32-38.
Ward et al., "A Wired-Based Dual-Analyte Sensor for Glucose and Lactate: In Vitro and In Vivo Evaluation" Diabetes Technology and Therapeutics Jun. 2004; 6(3):389-401.
Windmiller, J.R. (2012). "Molecular scale biocomputing: An enzyme logic approach," University of California, San Diego, a dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Written Opinion of the International Search Authority mailed on Sep. 10, 2020, for PCT Application No. PCT/US2020/037379, filed on Jun. 12, 2020, 4 pages.
Written Opinion of the International Searching Authority mailed on Dec. 30, 2021, for PCT Application No. PCT/US2021/043786, filed on Jul. 29, 2021, 10 pages.
Written Opinion of the International Searching Authority mailed on Feb. 4, 2021, for PCT Application No. PCT/US2020/056517, filed on Oct. 20, 2020, 5 pages.
Written Opinion of the International Searching Authority mailed on Jun. 27, 2013, for PCT Application No. PCT/US2012/053544, filed on Aug. 31, 2012, 15 pages.
Written Opinion of the International Searching Authority mailed on Sep. 30, 2021, for PCT Application No. PCT/US2021/040385, filed on Jul. 2, 2021, 5 pages.
Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.
Yue et al., "Evaluation of a 12-Hour Sustained-Release Acetaminophen (Paracetamol) Formulation: A Randomized, 3-Way Crossover Pharmacokinetic and Safety Study in Healthy Volunteers" Clinical Pharmacology in Drug Development (2018) 7(1) 95-101.
Babity et al., "Advances in the Design of Transdermal Microneedles for Diagnostic and Monitoring Applications" Advanced Science News (2018) 14:1803186, pp. 1-16.
Bandodkar et al., "Non-invasive wearable electrochemical sensors: a review" Trends in Biotechnology Jul. 1, 2014; 32(7):363-371.
Bollella et al., "Microneedle-Based Biosensor for Minimally-Invasive Lactate Detection" Biosens. Bioelectron. Jan. 2019; 123:152-159.
Bollella et al., "Minimally Invasive Glucose Monitoring Using a Highly Porous Gold Microneedles-Based Biosensor: Characterization and Application in Artificial Interstitial Fluid" Catalysts Jun. 2019; 9:580, pp. 1-14.
Brothers et al., "Achievements and Challenges for Real-Time Sensing of Analytes in Sweat within Wearable Platforms" Acc. Chem. Res. Jan. 2019; 52:297-306.
Burge et al., "Continuous Glucose Monitoring: The Future of Diabetes Management" Diabetes Spectr. (2008) 21:112-119.
Campbell et al., "Wearable Electrochemical Alcohol Biosensors" Curr. Opin. Electrochem. May 2018; 10:126-135.
Chinnadayyala et al., "Review—In Vivo and In Vitro Microneedle Based Enzymatic and Non-Enzymatic Continuous Glucose Monitoring Biosensors" ECS Journal of Solid State Science and Technology Apr. 2018; 7:Q3159-Q3171.
Choi et al., "Bio-Integrated Wearable Systems: A Comprehensive Review" Chem. Rev. Jan. 2019; 119:5461-5533.
Ciui et al., "Wearable Wireless Tyrosinase Bandage and Microneedle Sensors: Toward Melanoma Screening" Adv. Healthcare Mater. (2018) 7:1701264, 9 pages.
Coffey et al., "Rapid and selective sampling of IgG from skin in less than 1 min using a high surface area wearable immunoassay patch" Biomaterials Mar. 2018; 170:49-57.
Darmau et al., "Self-Extracting Dextran-Based Hydrogel Microneedle Arrays with an Interpenetrating Bioelectroenzymatic Sensor for Transdermal Monitoring with Matrix Protection" Adv Healthc Mater. Jan. 2025; 14(2):e2403209, 17 pages.
Dunn et al., "Wearables and the medical revolution" Per. Med. Sep. 2018; 15:429-448.
El-Laboudi et al., "Use of Microneedle Array Devices for Continuous Glucose Monitoring: A Review" Diabetes Technology & Therapeutics (2013) 15(1):101-115.
EP Application No. 25191106.1, Extended European Search Report mailed Nov. 26, 2025; Applicant Biolinq, Inc; 8 pages.
EP Application No. 25221877.1, Extended European Search Report mailed Jan. 20, 2026; Applicant Biolinq Incorporated; 11 pages.
Garcia-Lopez et al., "Study of the fabrication of AISI 316L microneedle arrays" Procedia Manufacturing (2018) 26:117-124.
Goud et al., "Wearable Electrochemical Microneedle Sensor for Continuous Monitoring of Levodopa: Toward Parkinson Management" ACS Sens. Aug. 2019; 4:2196-2204.
Gowers et al., "Development of a Minimally Invasive Microneedle-Based Sensor for Continuous Monitoring of B-Lactam Antibiotic Concentrations in Vivo" ACS Sens. Apr. 2019; 4:1072-1080.
Heikenfeld et al., "Accessing Analytes in Biofluids for Peripheral Biochemical Monitoring" Nat. Biotechnol. Apr. 2019; 37:407-419.
Heikenfeld et al., "Wearable sensors: modalities, challenges, and prospects" Lab Chip Jan. 2018; 18:217-248.
Ingrole et al., "Trends of microneedle technology in the scientific literature, patents, clinical trials and internet activity" Biomaterials (2021) 267:120491, pp. 1-24.
Jacobse et al., "Atomic-Scale Identification of the Electrochemical Roughening of Platinum" ACS Cent. Sci. (Nov. 15, 2019) 5:1920-1928.
Jiang et al., "Microneedle-based skin patch for blood-free rapid diagnostic testing" Microsystems and Nanoengineering (2020) 6:96, pp. 1-11.
Kathuria et al., "Polymeric Microneedle Array Fabrication by Photolithography" Journal of Visualized Experiments Nov. 2015; 105:e52914, pp. 1-8.

(56) References Cited

OTHER PUBLICATIONS

Kim et al., "Continuous glucose monitoring using a microneedle array sensor coupled with a wireless signal transmitter" Sensors & Actuators: B. Chemical (2019) 281:14-21.
Kim et al., "Wearable Biosensors for Healthcare Monitoring" Nat. Biotechnol. Apr. 2019; 37(4):389-406.
Kohler et al., "Fabrication of highly porous platinum electrodes for micro-scale applications by pulsed electrodeposition and dealloying" Journal of Power Sources (Nov. 15, 2013) 242:255-263.
Lee et al., "A Graphene-Based Electrochemical Device with Thermoresponsive Microneedles for Diabetes Monitoring and Therapy" Nat. Nanotechnol. Mar. 2016; 11:566-572.
Lee et al., "A Patch Type Non-Enzymatic Biosensor Based on 3D SUS Micro-Needle Electrode Array for Minimally Invasive Continuous Glucose Monitoring" Sensors Actuators B Chem. (2016) 222:1144-1151.
Lee et al., "Continuous glucose monitoring systems—Current status and future perspectives of the flagship technologies in biosensor research" Biosens. Bioelectron. Feb. 2021; 181:113054, 19 pages.
Leiden University, "The roughening of a platinum electrode" (Jan. 28, 2020) 6 pages.
Liu et al., "Microneedles for transdermal diagnostics: Recent advances and new horizons" Biomaterials (2020) 232:119740, pp. 1-16.
Madden et al., "Biosensing in dermal interstitial fluid using microneedle based electrochemical devices" Sensing and Bio-Sensing Research (2020) 29:100348, 1-17.
Miller et al., "Microneedle-Based Sensors for Medical Diagnosis" J. Mater. Chem. B Feb. 2016; 4:1379-1383.
Miller et al., "Multiplexed microneedle-based biosensor array for characterization of metabolic acidosis" Talanta (2012) 88:739-742.
Min et al., "Wearable electrochemical biosensors in North America" Biosensors and Bioelectronics Jan. 2021; 172:112750, pp. 1-16.
Muller et al., "Surface Modified Microprojection Arrays for the Selective Extraction of the Dengue Virus NS1 Protein as a Marker for Disease" Anal. Chem. Mar. 2012; 84:3262-3268.
Parrilla et al., "Wearable All-Solid-State Potentiometric Microneedle Patch for Intradermal Potassium Detection" Analytical Chemistry Jan. 2019; 91:1578-1586.
Rawson et al., "Microneedle biosensors for real-time, minimally invasive drug monitoring of phenoxymethylpenicillin: a first-in-human evaluation in healthy volunteers" Lancet Digital Health Nov. 2019; 1:e335-e343.
Rawson et al., "Towards a minimally invasive device for beta-lactam monitoring in humans" Electrochem Commun. Sep. 2017; 82:1-12.
Sharma et al., "A pilot study in humans of microneedle sensor arrays for continuous glucose monitoring" Analytical Methods Mar. 2018; 10:2088-2095.
Sharma et al., "Evaluation of a minimally invasive glucose biosensor for continuous tissue monitoring" Anal Bioanal Chem Oct. 2016; 408:8247-8435, 9 pages.
Sharma et al., "Rapid, low cost prototyping of transdermal devices for personal healthcare monitoring" Sens Biosensing Res. Apr. 2017; 13:104-108.
Sulaiman et al., "Hydrogel-Coated Microneedle Arrays for Minimally Invasive Sampling and Sensing of Specific Circulating Nucleic Acids from Skin Interstitial Fluid" ACS Nano Aug. 2019; 13:9620-9628.
Takeuchi et al., "Functionalized microneedles for continuous glucose monitoring" Nano Convergence (2018) 5:28, pp. 1-10.
Tasca et al., "Microneedle-based electrochemical devices for transdermal biosensing: a review" Electrochemistry Apr. 2019; 16:42-49.
Tehrani et al., "An integrated wearable microneedle array for the continuous monitoring of multiple biomarkers in interstitial fluid" Nature Biomedical Engineering Nov. 2022; 6(11):1214-1224.
Teymourian et al., "Electrochemical glucose sensors in diabetes management: an updated review (2010-2020)" Royal Society of Chemistry, Chem. Soc. Rev. (2020) 49:7671-7709.
Teymourian et al., "Lab under the Skin: Microneedle Based Wearable Devices" Adv. Healthc. Mater. (2021) 10:2002255, 19 pages.
Teymourian et al., "Microneedle-Based Detection of Ketone Bodies along with Glucose and Lactate: Toward Real-Time Continuous Interstitial Fluid Monitoring of Diabetic Ketosis and Ketoacidosis" Anal. Chem. (2020) 92:2291-2300.
Teymourian et al., "Wearable Electrochemical Sensors for the Monitoring and Screening of Drugs" ACS Sensors Aug. 2020; 5:2679-2700.
U.S. Appl. No. 16/051,398, Notice of Allowance mailed Dec. 4, 2025; Inventor Windmiller, Joshua et al.; 10 pages.
U.S. Appl. No. 17/073,331, Final Office Action mailed Feb. 6, 2026; Inventor Windmiller, Joshua et al.; 18 pages.
U.S. Appl. No. 17/650,056, Non-Final Office Action mailed Sep. 5, 2025; Inventor Wang, Joseph et al.; 29 pages.
U.S. Appl. No. 17/757,216, Notice of Allowance mailed Nov. 7, 2025; Inventor Wang, Joseph et al.; 13 pages.
U.S. Appl. No. 18/510,544, Non-Final Office Action mailed Feb. 25, 2026; Inventor Windmiller, Joshua Ray et al.; 12 pages.
U.S. Appl. No. 18/610,163, Notice of Allowance mailed Apr. 15, 2026; Inventor Windmiller, Joshua et al.; 10 pages.
U.S. Appl. No. 19/213,907, Notice of Allowance mailed Jan. 21, 2026; Campbell; Alan Steven et al.; 7 pages.
U.S. Appl. No. 19/258,472, Notice of Allowance mailed Dec. 17, 2025; Inventor Windmiller, Joshua et al.; 9 pages.
U.S. Appl. No. 19/422,217, Non-Final Office Action mailed Apr. 6, 2026; Inventor Mckinlay, Robert et al.; 12 pages.
Valdes-Ramirez et al., "Microneedle-Based Self-Powered Glucose Sensor" Electrochem. Commun. Jul. 2014; 47:58-62.
Ventrelli et al., "Microneedles for Transdermal Biosensing: Current Picture and Future Direction" Adv. Healthcare Mater. (2015) 4:2606-2640.
Wang, "Electrochemical Glucose Biosensors" Chemical Reviews (2008) 108:814-825.
Wang et al., "Microneedle patch for the ultrasensitive quantification of protein biomarkers in interstitial fluid" Nature Biomedical Engineering Jan. 2021; 5:64-76.
Wang et al., "Recent Advances in the Design of Polymeric Microneedles for Transdermal Drug Delivery and Biosensing" Lab Chip Mar. 2017; 17:1373-1387.
Wei et al., "Electrochemical surface reshaping of polycrystalline platinum: Morphology and crystallography" Electrochimica Acta (Apr. 20, 2008) 53(11):4051-4058.
Wei et al., "Integrated individually addressable microneedle arrays for robust glucose monitoring and on-demand insulin releasing" Microsyst Nanoeng. Nov. 11, 2025; 11(1):211, 12 pages.
Wiorek et al., "Epidermal Patch with Glucose Biosensor: pH and Temperature Correction toward More Accurate Sweat Analysis during Sport Practice" Anal. Chem. Jun. 2020; 92:10153-10161.
Wolkowicz et al., "A Review of Biomarkers in the Context of Type 1 Diabetes: Biological Sensing for Enhanced Glucose Control" Bioeng. Transl. Med. (2021) 6(2):e10201, 17 pages.
World Economic Forum, "Top 10 Emerging Technologies of 2020" Special Report Nov. 2020, 26 pages.
Xie et al., "Engineering Microneedles for Therapy and Diagnosis: A Survey" Micromachines Mar. 2020; 11:271, pp. 1-28.
Xie et al., "Reduction of measurement noise in a continuous glucose monitor by coating the sensor with a zwitterionic polymer" Nature Biomedical Engineering Dec. 2018; 2:894-906, 15 pages.
Yang et al.,"In Situ Sampling and Monitoring Cell-Free DNA of the Epstein-Barr Virus from Dermal Interstitial Fluid Using Wearable Microneedle Patches" ACS Applied Materials & Interfaces Sep. 2019; 11:38448-38458.
Yetisen et al., "Wearables in Medicine" Adv. Mater. Jun. 2018; 30:1706910, 26 pages.
Zhang et al., "Bio-inspired clamping microneedle arrays from flexible ferrofluid-configured moldings" Science Bulletin Jun. 2019; 64:1110-1117.
Zhang et al., "Encoded Microneedle Arrays for Detection of Skin Interstitial Fluid Biomarkers" Advanced Materials Jul. 2019; 31:1902825, pp. 1-8.

(56) References Cited

OTHER PUBLICATIONS

Zhang et al., "Microneedle-assisted technology for minimally invasive medical sensing" Microchemical Journal (2021) 162:105830, pp. 1-12.

* cited by examiner

1100

1100

MN formed post anisotropic wet etch

Angled (75°-80°) dicing blade cut offset from central z-axis

Resulting asymmetric MN with tip apex intact

CONTINUOUS ANALYTE MONITORING SYSTEM WITH MICRONEEDLE ARRAY

CROSS-REFERENCE TO RELATED APPLICATIONS

This application is a continuation of U.S. patent application Ser. No. 18/630,936, filed Apr. 9, 2024, which is a continuation of U.S. patent application Ser. No. 18/086,543, filed Dec. 21, 2022, now U.S. Pat. No. 12,011,294, which is a continuation of International Patent Application No. PCT/US2021/043786, filed Jul. 29, 2021, which claims priority to U.S. Provisional Patent Application No. 63/058,275, filed Jul. 29, 2020, the contents of each of which are hereby incorporated in their entirety by this reference.

TECHNICAL FIELD

This invention relates generally to the field of analyte monitoring, such as continuous glucose monitoring.

BACKGROUND

Diabetes is a chronic disease in which the body does not produce or properly utilize insulin, a hormone that regulates blood glucose. Insulin may be administered to a diabetic patient to help regulate blood glucose levels, though blood glucose levels must nevertheless be carefully monitored to help ensure that timing and dosage are appropriate. Without proper management of their condition, diabetic patients may suffer from a variety of complications resulting from hyperglycemia (high blood sugar levels) or hypoglycemia (low blood sugar levels).

Blood glucose monitors help diabetic patients manage their condition by measuring blood glucose levels from a sample of blood. For example, a diabetic patient may obtain a blood sample through a fingerstick sampling mechanism, transfer the blood sample to a test strip with suitable reagent(s) that react with the blood sample, and use a blood glucose monitor to analyze the test strip to measure glucose level in that blood sample. However, a patient using this process can typically only measure his or her glucose levels at discrete instances in time, which may fail to capture a hyperglycemia or hypoglycemia condition in a timely manner. Yet a more recent variety of glucose monitor is a continuous glucose monitor (CGM) device, which includes implantable transdermal electrochemical sensors that are used to continuously detect and quantify blood glucose levels by proxy measurement of glucose levels in the subcutaneous interstitial fluid. However, conventional CGM devices also have weaknesses including tissue trauma from insertion and signal latency (e.g., due to the time required for the glucose analyte to diffuse from capillary sources to the sensor). These weaknesses also lead to a number of drawbacks, such as pain experienced by the patient when electrochemical sensors are inserted, and limited accuracy in glucose measurements, particularly when blood glucose levels are changing rapidly. Accordingly, there is a need for a new and improved analyte monitoring system.

SUMMARY

In some variations, a microneedle array for use in sensing an analyte may include a plurality of microneedles (e.g., solid microneedles). Each microneedle may include a tapered distal portion having an insulated distal apex, and an electrode on a surface of the tapered distal portion, where the electrode is located proximal to the insulated distal apex.

In some variations, a method for monitoring a user may include accessing a body fluid of a user with an analyte monitoring device, and quantifying one or more analytes in the body fluid using the analyte monitoring device, where the analyte monitoring device may include a plurality of solid microneedles. In some variations, at least one of the microneedles may include a tapered distal portion having an insulated distal apex, and an electrode on a surface of the tapered distal portion, where the electrode is located proximal to the insulated distal apex.

In some variations, a microneedle array for use in sensing an analyte may include a plurality of solid microneedles, where at least one microneedle includes a tapered distal portion having an insulated distal apex, and an electrode on a surface of the tapered distal portion, where a distal end of the electrode is offset from the distal apex.

In some variations, a method of sterilizing an analyte monitoring device may include exposing the analyte monitoring device to a sterilant gas, where the analyte monitoring device comprises a wearable housing, a microneedle array extending from the housing and comprising an analyte sensor, and an electronics system arranged in the housing and electrically coupled to the microneedle array. The analyte monitoring device may be exposed to the sterilant gas for a dwell time sufficient to sterilize the analyte monitoring device.

In some variations, a microneedle array for an analyte monitoring device may include a plurality of sensing microneedles (e.g., solid microneedles), where each sensing microneedle includes a tapered distal portion comprising a working electrode configured to sense an analyte, and a body portion providing a conductive connection to the working electrode. The body portion of each sensing microneedle may be insulated such that each working electrode is individually addressable and electrically isolated from every other working electrode in the microneedle array.

In some variations, a microneedle array for a body-worn analyte monitoring device may include at least one microneedle including a pyramidal body portion having anon-circular (e.g., octagonal base), and a tapered distal portion extending from the body portion and comprising an electrode, where the distal portion comprises a planar surface that is offset from a distal apex of the at least one microneedle.

In some variations, a method for monitoring a user may include accessing a dermal interstitial fluid of the user at a plurality of sensor locations with an integrated analyte monitoring device comprising a single microneedle array, and quantifying one or more analytes in the dermal interstitial fluid using a plurality of working electrodes in the microneedle array, where each working electrode is individually addressable and electrically isolated from every other working electrode in the analyte monitoring device.

In some variations, a body-worn analyte monitoring device may include a wearable housing and a microneedle array. The microneedle array may extend outwardly from the housing and include at least one microneedle configured to measure one or more analytes in a user wearing the housing, and the housing may include a user interface configured to communicate information indicative of the measurement of the one or more analytes.

In some variations, a method for monitoring a user may include measuring one or more analytes in the user using a body-worn analyte monitoring device comprising a wearable housing and one or more analyte sensors, and communicating information indicative of the measurement of the one or more analytes through a user interface on the housing.

DETAILED DESCRIPTION

Non-limiting examples of various aspects and variations of the invention are described herein and illustrated in the accompanying drawings.

Figure 1:
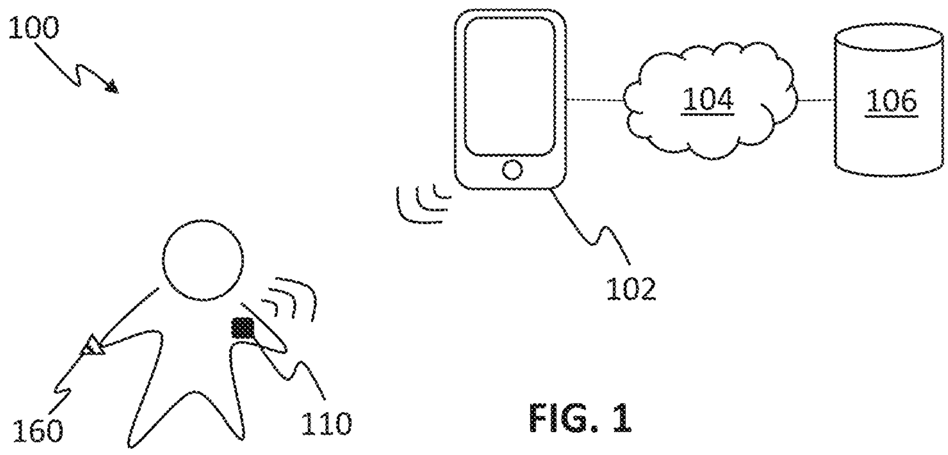
FIG. 1 depicts an illustrative schematic of an analyte monitoring system with a microneedle array.

As generally described herein, an analyte monitoring system may include an analyte monitoring device that is worn by a user and includes one or more sensors for monitoring at least one analyte of a user. The sensors may, for example, include one or more electrodes configured to perform electrochemical detection of at least one analyte. The analyte monitoring device may communicate sensor data to an external computing device for storage, display, and/or analysis of sensor data. For example, as shown in FIG. 1, an analyte monitoring system 100 may include an analyte monitoring device 110 that is worn by a user, and the analyte monitoring device 110 may be a continuous analyte monitoring device (e.g., continuous glucose monitoring device). The analyte monitoring device 110 may include, for example, a microneedle array comprising at least one electrochemical sensor for detecting and/or measuring one or more analytes in body fluid of a user. In some variations, the analyte monitoring device may be applied to the user using suitable applicator 160, or may be applied manually. The analyte monitoring device 110 may include one or more processors for performing analysis on sensor data, and/or a communication module (e.g., wireless communication module) configured to communicate sensor data to a mobile computing device 102 (e.g., smartphone) or other suitable computing device. In some variations, the mobile computing device 102 may include one or more processors executing a mobile application to handle sensor data (e.g., displaying data, analyzing data for trends, etc.) and/or provide suitable alerts or other notifications related to the sensor data and/or analysis thereof. It should be understood that while in some variations the mobile computing device 102 may perform sensor data analysis locally, other computing device(s) may alternatively or additionally remotely analyze sensor data and/or communicate information related to such analysis with the mobile computing device 102 (or other suitable user interface) for display to the user. Furthermore, in some variations the mobile computing device 102 may be configured to communicate sensor data and/or analysis of the sensor data over a network 104 to one or more storage devices 106 (e.g., server) for archiving data and/or other suitable information related to the user of the analyte monitoring device.

The analyte monitoring devices described herein have characteristics that improve a number of properties that are advantageous for a continuous analyte monitoring device such as a continuous glucose monitoring (CGM) device. For example, the analyte monitoring device described herein have improved sensitivity (amount of sensor signal produced per given concentration of target analyte), improved selectivity (rejection of endogenous and exogenous circulating compounds that can interfere with the detection of the target analyte), and improved stability to help minimize change in sensor response over time through storage and operation of the analyte monitoring device. Additionally, compared to conventional continuous analyte monitoring devices, the analyte monitoring devices described herein have a shorter warm-up time that enables the sensor(s) to quickly provide a stable sensor signal following implantation, as well as a short response time that enables the sensors(s) to quickly provide a stable sensor signal following a change in analyte concentration in the user. Furthermore, as described in further detail below, the analyte monitoring devices described herein may be applied to and function in a variety of wear sites, and provide for pain-free sensor insertion for the user. Other properties such as biocompatibility, sterilizability, and mechanical integrity are also optimized in the analyte monitoring devices described herein.

Although the analyte monitoring systems described herein may be described with reference to monitoring of glucose (e.g., in users with Type 2 diabetes, Type 1 diabetes), it should be understood that such systems may additionally or alternatively be configured to sense and monitor other suitable analytes. As described in further detail below, suitable target analytes for detection may, for example, include glucose, ketones, lactate, and cortisol. One target analyte may be monitored, or multiple target analytes may be simultaneously monitored (e.g., in the same analyte monitoring device). For example, monitoring of other target analytes may enable the monitoring of other indications such as stress (e.g., through detection of rising cortisol and glucose) and ketoacidosis (e.g., through detection of rising ketones).

Various aspects of example variations of the analyte monitoring systems, and methods of use thereof, are described in further detail below.

Analyte Monitoring Device

Figure 2A:
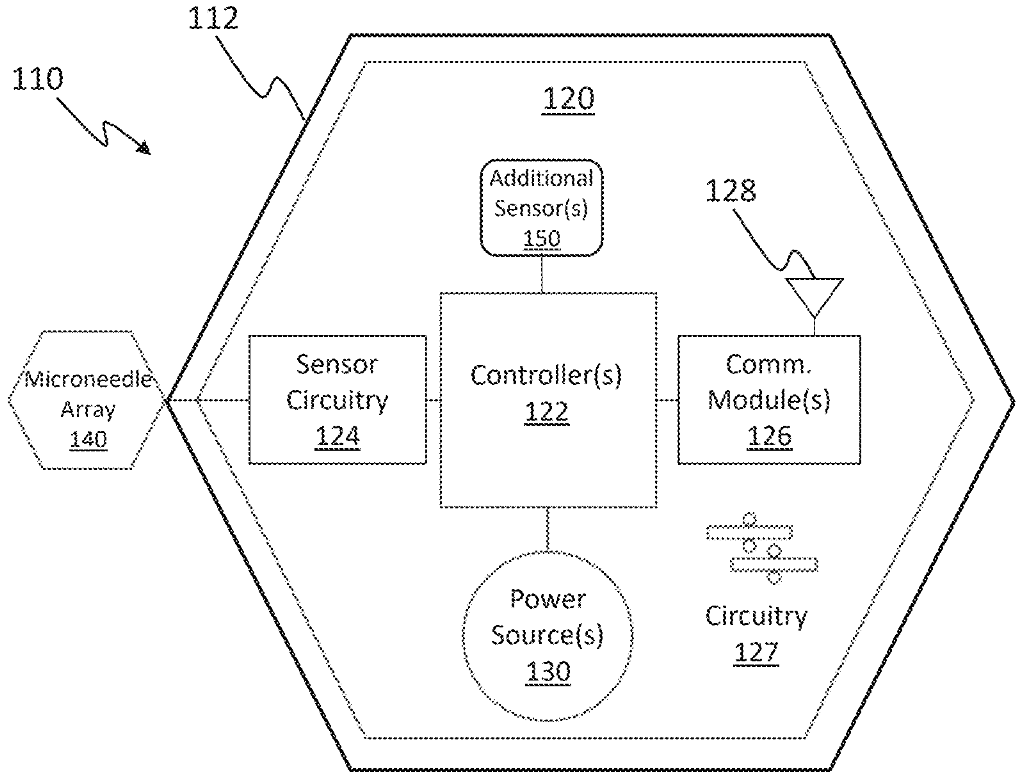
FIG. 2A depicts an illustrative schematic of an analyte monitoring device.

As shown in FIG. 2A, in some variations, an analyte monitoring device 110 may generally include a housing 112 and a microneedle array 140 extending outwardly from the housing. The housing 112, may, for example, be a wearable housing configured to be worn on the skin of a user such that the microneedle array 140 extends at least partially into the skin of the user. For example, the housing 112 may include an adhesive such that the analyte monitoring device 110 is a skin-adhered patch that is simple and straightforward for application to a user. The microneedle array 140 may be configured to puncture the skin of the user and include one or more electrochemical sensors (e.g., electrodes) configured for measuring one or more target analytes that are accessible after the microneedle array 140 punctures the skin of the user. In some variations, the analyte monitoring device 110 may be integrated or self-contained as a single unit, and the unit may be disposable (e.g., used for a period of time and replaced with another instance of the analyte monitoring device 110).

An electronics system 120 may be at least partially arranged in the housing 112 and include various electronic components, such as sensor circuitry 124 configured to perform signal processing (e.g., biasing and readout of electrochemical sensors, converting the analog signals from the electrochemical sensors to digital signals, etc.). The electronics system 120 may also include at least one microcontroller 122 for controlling the analyte monitoring device 110, at least one communication module 126, at least one power source 130, and/or other various suitable passive circuitry 127. The microcontroller 122 may, for example, be configured to interpret digital signals output from the sensor circuitry 124 (e.g., by executing a programmed routine in firmware), perform various suitable algorithms or mathematical transformations (e.g., calibration, etc.), and/or route processed data to and/or from the communication module 124. In some variations, the communication module 126 may include a suitable wireless transceiver (e.g., Bluetooth transceiver or the like) for communicating data with an external computing device 102 via one or more antennas 128. For example, the communication module 126 may be configured to provide uni-directional and/or bi-directional communication of data with an external computing device 102 that is paired with the analyte monitoring device 110. The power source 130 may provide power for the analyte monitoring device 110, such as for the electronics system. The power source 130 may include battery or other suitable source, and may, in some variations, be rechargeable and/or replaceable. Passive circuitry 127 may include various non-powered electrical circuitry (e.g., resistors, capacitors, inductors, etc.) providing interconnections between other electronic components, etc. The passive circuitry 127 may be configured to perform noise reduction, biasing and/or other purposes, for example. In some variations, the electronic components in the electronics system 120 may be arranged on one or more printed circuit boards (PCB), which may be rigid, semi-rigid, or flexible, for example. Additional details of the electronics system 120 are described further below.

In some variations, the analyte monitoring device 110 may further include one or more additional sensors 150 to provide additional information that may be relevant for user monitoring. For example, the analyte monitoring device 110 may further include at least one temperature sensor (e.g., thermistor) configured to measure skin temperature, thereby enabling temperature compensation for the sensor measurements obtained by the microneedle array electrochemical sensors.

Figure 2B:
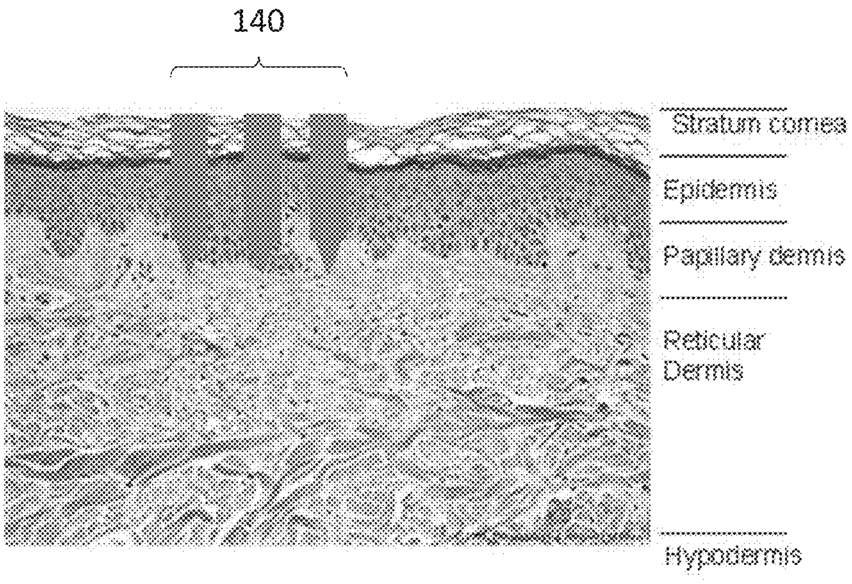
FIG. 2B depicts an illustrative schematic of microneedle insertion depth in an analyte monitoring device.

In some variations, the microneedle array 140 in the analyte monitoring device 110 may be configured to puncture skin of a user. As shown in FIG. 2B, when the device 110 is worn by the user, the microneedle array 140 may extend into the skin of the user such that electrodes on distal regions of the microneedles rest in the dermis. Specifically, in some variations, the microneedles may be designed to penetrate the skin and access the upper dermal region (e.g., papillary dermis and upper reticular dermis layers) of the skin, in order to enable the electrodes to access interstitial fluid that surrounds the cells in these layers. For example, in some variations, the microneedles may have a height generally ranging between at least 350 μm and about 515 μm. In some variations, one or more microneedles may extend from the housing such that a distal end of the electrode on the microneedle is located less than about 5 mm from a skin-interfacing surface of the housing, less than about 4 mm from the housing, less than about 3 mm from the housing, less than about 2 mm from the housing, or less than about 1 mm from the housing.

In contrast to traditional continuous analyte monitoring devices (e.g., CGM devices), which include sensors typically implanted between about 8 mm and about 10 mm beneath the skin surface in the subcutis or adipose layer of the skin, the analyte monitoring device 110 has a shallower microneedle insertion depth of about 0.25 mm (such that electrodes are implanted in the upper dermal region of the skin) that provides numerous benefits. These benefits include access to dermal interstitial fluid including one or more target analytes for detection, which is advantageous at least because at least some types of analyte measurements of dermal interstitial fluid have been found to closely correlate to those of blood. For example, it has been discovered that glucose measurements performed using electrochemical sensors accessing dermal interstitial fluid are advantageously highly linearly correlated with blood glucose measurements. Accordingly, glucose measurements based on dermal interstitial fluid are highly representative of blood glucose measurements.

Additionally, because of the shallower microneedle insertion depth of the analyte monitoring device 110, a reduced time delay in analyte detection is obtained compared to traditional continuous analyte monitoring devices. Such a shallower insertion depth positions the sensor surfaces in close proximity (e.g., within a few hundred micrometers or less) to the dense and well-perfused capillary bed of the reticular dermis, resulting in a negligible diffusional lag from the capillaries to the sensor surface. Diffusion time is related to diffusion distance according to $1=x^2/(2D)$ where/is the diffusion time, x is the diffusion distance, and D is the mass diffusivity of the analyte of interest. Therefore, positioning an analyte sensing element twice as far away from the source of an analyte in a capillary will result in a quadrupling of the diffusional delay time. Accordingly, conventional analyte sensors, which reside in the very poorly vascularized adipose tissue beneath the dermis, result in a significantly greater diffusion distance from the vasculature in the dermis and thus a substantial diffusional latency (e.g., typically 5-20 minutes). In contrast, the shallower microneedle insertion depth of the analyte monitoring device 110 benefits from low diffusional latency from capillaries to the sensor, thereby reducing time delay in analyte detection and providing more accurate results in real-time or near real-time. For example, in some embodiments, diffusional latency may be less than 10 minutes, less than 5 minutes, or less than 3 minutes.

Furthermore, when the microneedle array rests in the upper dermal region, the lower dermis beneath the microneedle array includes very high levels of vascularization and perfusion to support the dermal metabolism, which enables thermoregulation (via vasoconstriction and/or vasodilation) and provides a barrier function to help stabilize the sensing environment around the microneedles. Yet another advantage of the shallower insertion depth is that the upper dermal layers lack pain receptors, thus resulting in a reduced pain sensation when the microneedle array punctures the skin of the user, and providing for a more comfortable, minimally-invasive user experience.

Thus, the analyte monitoring devices and methods described herein enable improved continuous monitoring of one or more target analytes of a user. For example, as described above, the analyte monitoring device may be simple and straightforward to apply, which improves ease-of-use and user compliance. Additionally, analyte measurements of dermal interstitial fluid may provide for highly accurate analyte detection. Furthermore, compared to traditional continuous analyte monitoring devices, insertion of the microneedle array and its sensors may be less invasive and involve less pain for the user. Additional advantages of other aspects of the analyte monitoring devices and methods are further described below.

Housing

As described above, an analyte monitoring device may include a housing. The housing may at least partially surround or enclose other components of the analyte monitoring device (e.g., electronic components), such as for protection of such components. For example, the housing may be configured to help prevent dust and moisture from entering the analyte monitoring device. In some variations, an adhesive layer may attach the housing to a surface (e.g., skin) of a user, while permitting a microneedle array to extend outwardly from the housing and into the skin of the user. Furthermore, in some variations the housing may generally include rounded edges or corners and/or be low-profile so as to be atraumatic and reduce interference with clothing, etc. worn by the user.

For example, as shown in FIGS. 3A-3E, an example variation of an analyte monitoring device 300 may include a housing 310 configured to at least partially surround other various internal components of the device 300, and a microneedle array 330 that extends outwardly from a skin-facing surface (e.g., underside) of the housing 310.

Figure 3A:
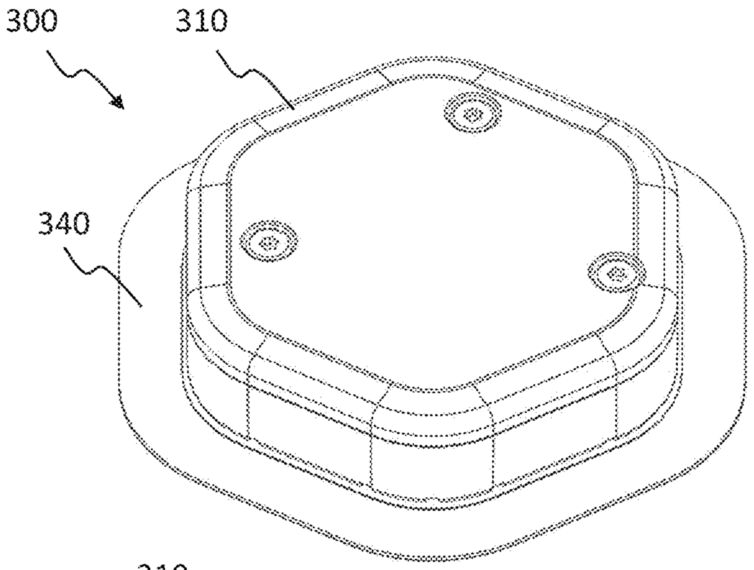
FIGS. 3A-3C depict an upper perspective view, a side view, and a lower perspective view, respectively, of an analyte monitoring device.
Figure 3B:
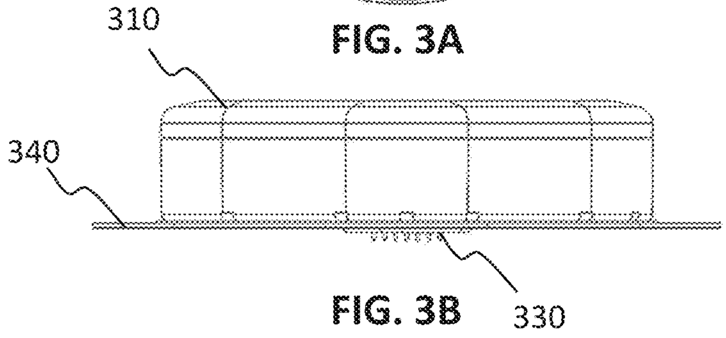
Figure 3C:
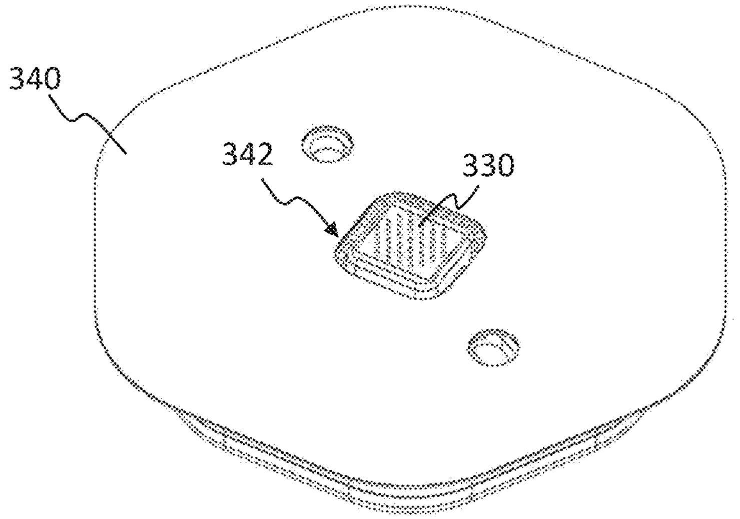
Figure 3D:
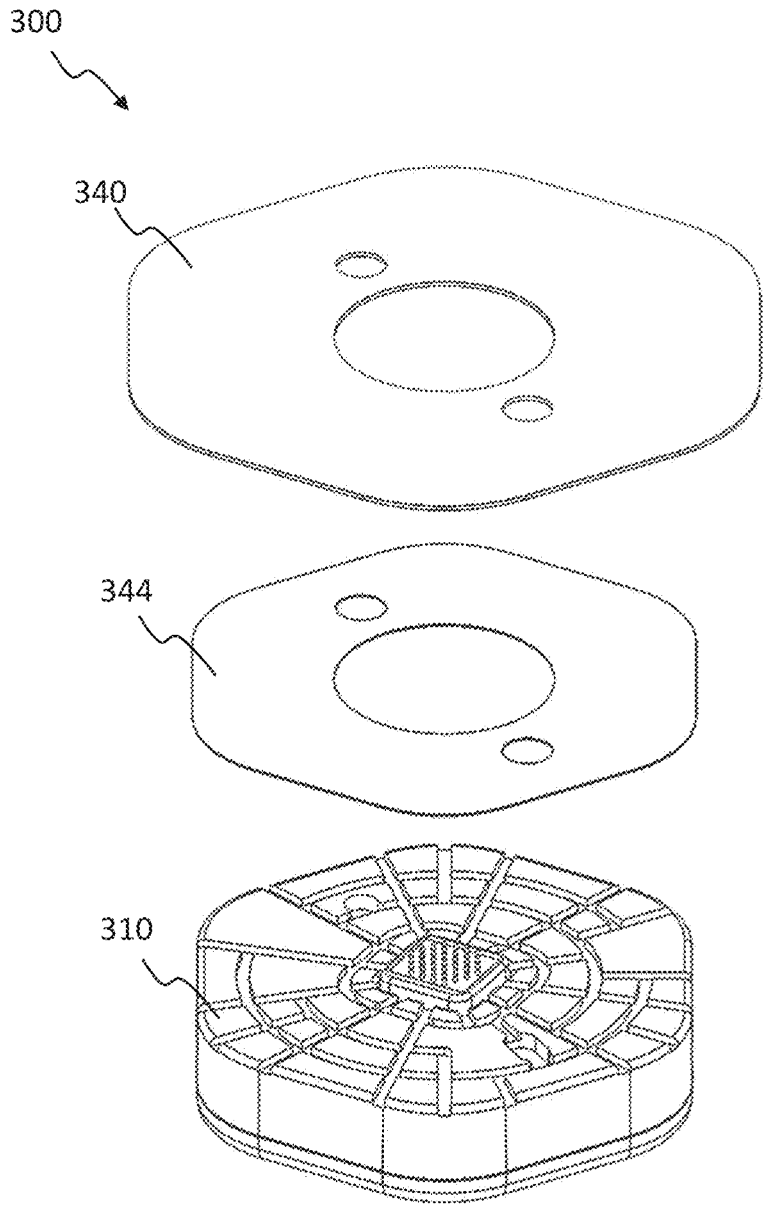
FIG. 3D depicts a partially exploded view of the analyte monitoring device shown in FIG. 3A including an adhesive layer.
Figure 3E:
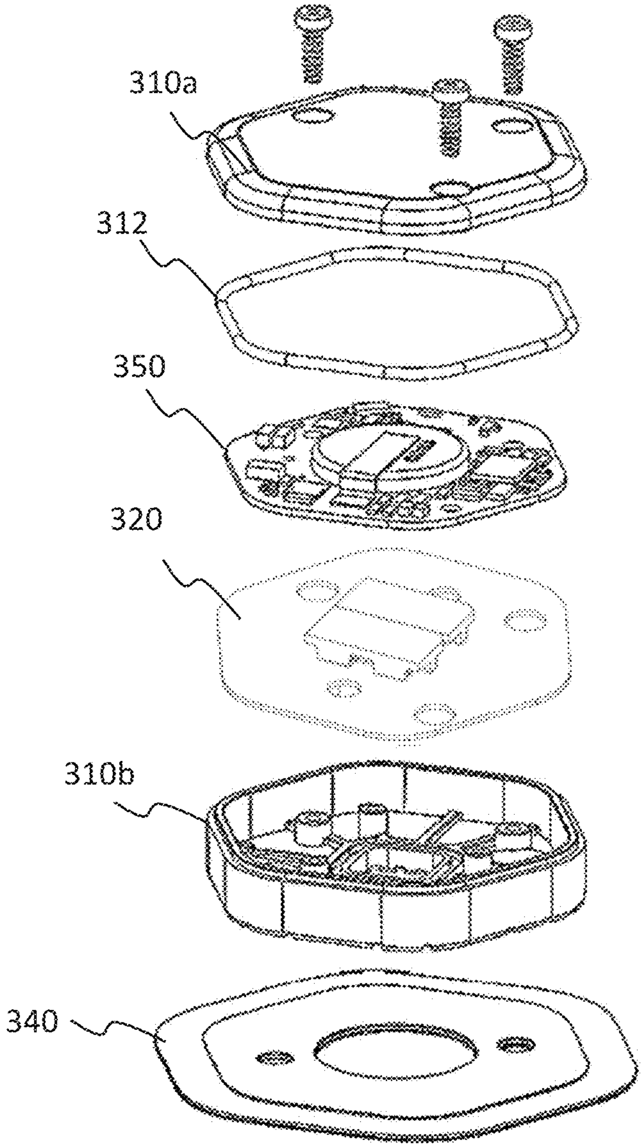
FIG. 3E depicts an exploded view of the analyte monitoring device shown in FIG. 3A.
Figure 3F:
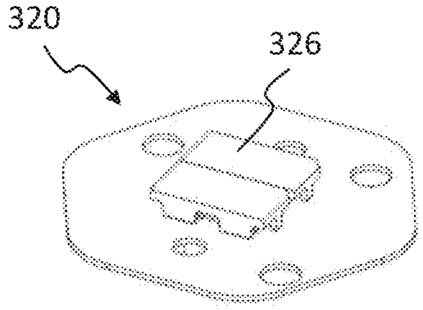
FIGS. 3F-3I depict an upper perspective view, a lower perspective view, a side view, and an exploded view, respectively, of a sensor assembly in an analyte monitoring device.
Figure 3G:
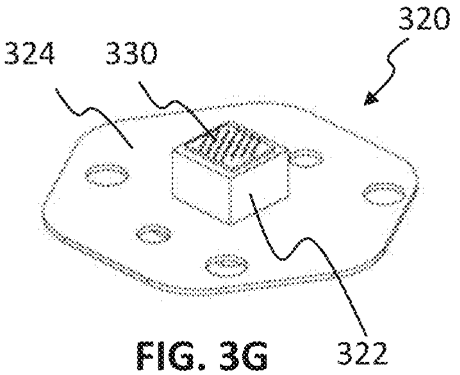

The housing 310 may, for example, include one or more rigid or semi-rigid protective shell components that may couple together via suitable fasteners (e.g., mechanical fasteners), mechanically interlocking or mating features, and/or an engineering fit. For example, as shown in FIG. 3E, the housing may include a housing cover 310*a* and a housing base 310*b*, where the cover 310*a* and the base 310*b* may be secured together with one or more threaded fasteners (e.g., fasteners that engage threaded holes in the upper and/or lower housing portions). The cover 310*a* and the base 310*b* may include radiused edges and corners, and/or other atraumatic features. When coupled together, the cover 310*a* and the base 310*b* may form an internal volume that houses other internal components such as a device printed circuit board 350 (PCB), a sensor assembly 320, and/or other components such as a gasket 312. For example, the internal components arranged in the internal volume may be arranged in a compact, low profile stack-up as shown in FIG. 3E. While FIG. 3E illustrates a housing 310 include multiple housing components, in some variations the housing 310 may include a single component defining the internal volume for housing internal device components. In some embodiments, the housing 310 may be filled with a suitable potting compound (e.g., epoxy) to reduce deleterious environmental effects such as temperature, humidity, pressure, and light.

Furthermore, the analyte monitoring device 300 may include an adhesive layer 340 configured to attach the housing 310 to a surface (e.g., skin) of a user. The adhesive layer 340 may, for example, be attached to a skin-facing side of the housing 310 via a double-sided adhesive liner 344 as shown in in the variation depicted in FIG. 3D. Alternatively, the adhesive layer 340 may be coupled directly to the skin-facing side of the housing 310 with one or more suitable fasteners (e.g., adhesive, mechanical fasteners, etc.). The adhesive layer 340 may be protected by a release liner that the user removes prior to skin application, in order to expose the adhesive. In some variations, the analyte monitoring device may include 3M® 1504XL™ double-sided adhesive and 3M® 4076™ skin-facing adhesive, available from 3M®. These materials are selected for their: breathability, wearability, mean water vapor transmission rate (MWVTR), biocompatibility, compatibility with sensor sterilization method/strategy, appearance, durability, tackiness, and ability to retain said tackiness for the duration of sensor wear.

The adhesive layer 340 may, in some variations, have a perimeter that extends farther than the perimeter or periphery of the housing 310 (e.g., which may increase surface area for attachment and increase stability of retention, or the attachment to the skin of a user). Furthermore, in some variations, the adhesive layer 340 may include an opening 342 that permits passage of the outwardly extending microneedle array 330. The opening 342 may closely circumscribe the shape of the microneedle array 330 as shown in FIG. 3C (e.g., square opening closely corresponding in size and shape to a square microneedle array), or have another suitable size and shape that is larger than the footprint area of the microneedle array (e.g., circular opening larger than a square microneedle array).

Figure 4A:
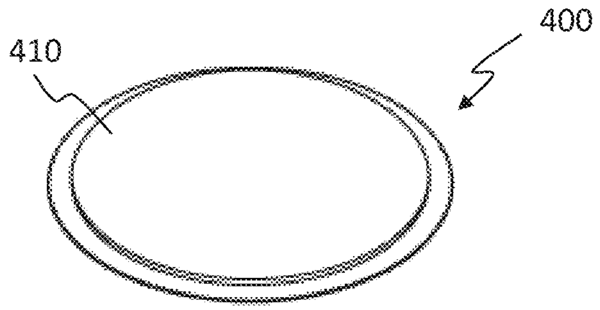
FIGS. 4A-4E depict a perspective view, a side view, a bottom view, a side cross-sectional view, and an upper perspective transparent view, respectively, of an analyte monitoring device.
Figure 4B:
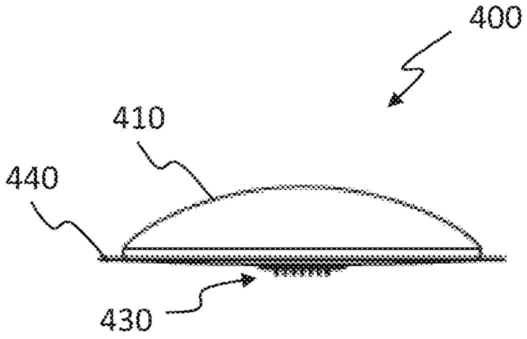
Figure 4C:
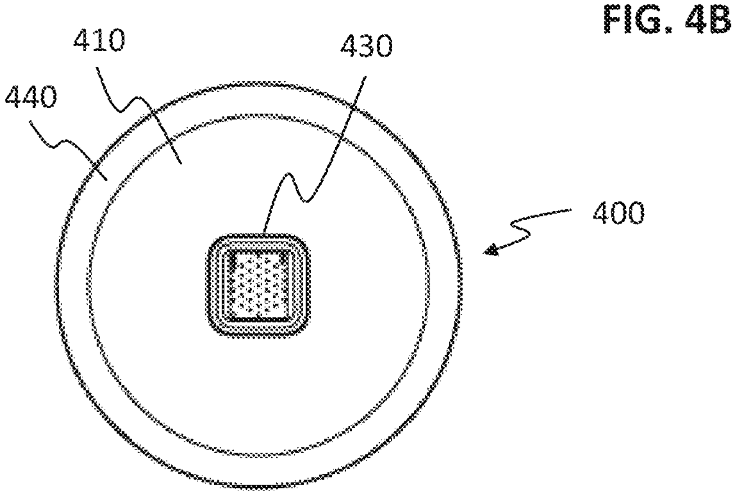

Although the housing 310 depicted in FIGS. 3A-3E is hexagonal shaped and generally prismatic, it should be understood that in other variations, the housing 310 may have any suitable shape. For example, in other variations the housing may be generally prismatic and have a base that has an elliptical (e.g., circular), triangular, rectangular, pentagonal, or other suitable shape. As another example, FIGS. 4A-4C illustrate an example variation of an analyte monitoring device 400 including a dome-shaped housing 410. While the dome-shaped housing 410 depicted in FIGS. 4A-4C is generally circular, in other variations the dome-shaped housing may have a base that has another suitable elliptical shape or polygonal shape.

Figure 4D:
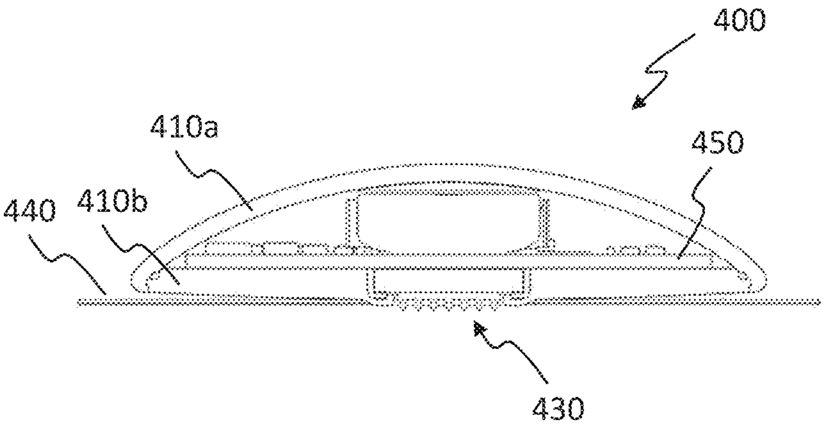
Figure 4E:
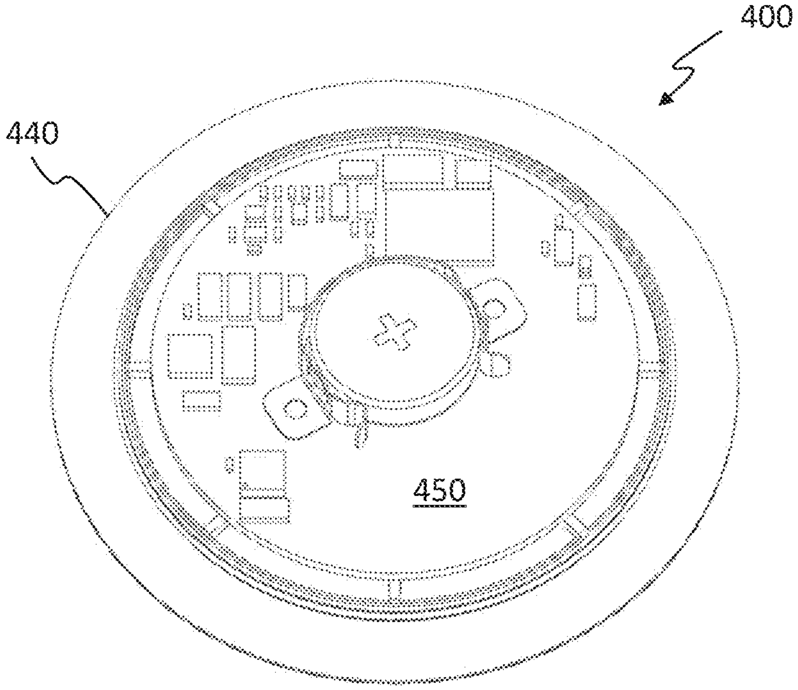

Similar to the housing 310, the housing 410 may include an internal volume configured to at least partially surround other components of the analyte monitoring device 400. For example, as shown in the cross-sectional view of FIG. 4D, the housing 410 may include a domed cover 410*a* coupled to a base 410*b*, so as to form an internal volume within which a device PCB 450 and a sensor assembly with a microneedle array 430 may be arranged. Additionally, the housing 410 may be configured to couple to a surface via an adhesive layer 440, and the microneedle array 430 may extend outwardly from the housing and beyond the adhesive layer 440. Furthermore, as shown in FIGS. 4D and 4E, the adhesive layer 440 may extend beyond the perimeter of the housing 410.

User Interface

In some variations, an analyte monitoring system may provide user status, analyte monitoring device status, and/or other suitable information directly via a user interface (e.g., display, indicator lights, etc. as described below) on the analyte monitoring device. Thus, in contrast to analyte monitoring systems that may solely communicate information to a separate peripheral device (e.g., mobile phone, etc.) that in turn communicates the information to a user, in some variations such information may be directly provided by the analyte monitoring device. Advantageously, in some variations, such a user interface on the analyte monitoring device may reduce the need for a user to constantly maintain a separate peripheral device in order to monitor user status and/or analyte monitoring device status (which may be impractical due to cost, inconvenience, etc.). Additionally, the user interface on the analyte monitoring device may reduce risks associated with loss of communication between the analyte monitoring device and a separate peripheral device, such as a user having an inaccurate understanding of their current analyte levels (e.g., leading the user to assume their analyte levels are high when they are actually low, which could, for example, result in the user self-administering an inaccurate dose of drug or withholding a therapeutic intervention when it is medically necessary).

Additionally, the ability to communicate information to a user via the analyte monitoring device itself, independently of a separate peripheral device, may reduce or eliminate the need to maintain compatibility between the analyte monitoring device and separate peripheral devices as such peripheral devices are upgraded (e.g., replaced with new device models or other hardware, run new versions of operating systems or other software, etc.).

Accordingly, in some variations, the housing may include a user interface, such as an interface to provide information in a visual, audible, and/or tactile manner to provide information regarding user status and/or status of the analyte monitoring device, and/or other suitable information. Examples of user status that may be communicated via the user interface include information representative of analyte measurement in the user (e.g., below a predetermined target analyte measurement threshold or range, within a predetermined target analyte measurement range, above a predetermined target analyte measurement threshold or range, increase or decrease of analyte measurement over time, rate of change of analyte measurement, other information relating to trend of analyte measurements, other suitable alerts associated with analyte measurement, etc.). Examples of analyte monitoring device status that may be communicated via the user interface include device operation mode (e.g., associated with device warm-up state, analyte monitoring state, battery power status such as low battery, etc.), a device error state (e.g., operational error, pressure-induced sensing attenuation, fault, failure mode, etc.), device power status, device life status (e.g., anticipated sensor end-of-life), status of connectivity between device and a mobile computing device, and/or the like.

In some variations, the user interface may by default be in an enabled or "on" state to communicate such information at least whenever the analyte monitoring device is performing analyte measurements) or whenever the analyte monitoring device is powered on, thereby helping to ensure that information is continuously available to the user. For example, user interface elements may communicate through a display or indicator light(s) (e.g., as described below) not only alerts to flag user attention or recommend remedial action, but also when user status and/or device status are normal. Accordingly, in some variations, a user is not required to perform an action to initiate a scan to learn their current analyte measurement level(s), and such information may always readily be available to the user. In some variations, however, a user may perform an action to disable the user interface temporarily (e.g., similar to a "snooze" button) such as for a predetermined amount of time (e.g., 30 minutes, 1 hour, 2 hours, etc.) after which the user interface is automatically reenabled, or until a second action is performed to reenable the user interface.

In some variations, the user interface of the housing may include a display configured to visually communicate information. The display may, for example, include a display screen (e.g., LCD screen, OLED display, electrophoretic display, electrochromic display, etc.) configured to display alphanumeric text (e.g., numbers, letters, etc.), symbols, and/or suitable graphics to communicate information to the user. For example, the display screen may include a numerical information, textual information, and/or a graphics (e.g., sloped line, arrows, etc.) of information such as user status and/or status of the analyte monitoring device. For example, the display screen may include text or graphical representations of analyte measurement levels, trends, and/or recommendations (e.g., physical activity, reduced dietary intake, etc.).

As another example, the display on the housing may include one or more indicator lights (e.g., including LEDs, OLEDs, lasers, electroluminescent material, or other suitable light source, waveguides, etc.) that may be controlled in one or more predetermined illumination modes to communicate different statuses and/or other suitable information. An indicator light may be controlled to illuminate with multiple colors (e.g., red, orange, yellow, green, blue, and/or purple, etc.) or in only one color. For example, an indicator light may include a multi-colored LED. As another example, an indicator light may include a transparent or semi-transparent material (e.g., acrylic) positioned over one or more different-colored light sources (e.g., LED) such that different-colored light sources may be selectively activated to illuminate the indicator light in a selected color. The activation of light sources can either occur simultaneously or in sequence. An indicator light may have any suitable form (e.g., raised, flush, recessed, etc. from housing body) and/or shape (e.g., circle or other polygon, ring, elongated strip, etc.). In some variations, an indicator light may have a pinhole size and/or shape to present the same intensity of the light as a larger light source, but with significantly less power requirements, which may help conserve onboard power in the analyte monitoring device.

Indicator light(s) on the display may be illuminated in one or more various manners to communicate different kinds of information. For example, an indicator light may be selectively illuminated on or off to communicate information (e.g., illumination "on" indicates one status, while illumination "off" indicates another status). Additionally or alternatively, an indicator light may be illuminated in a selected color or intensity to communicate information (e.g., illumination in a first color or intensity indicates a first status, while illumination in a second color or intensity indicates a second status). Additionally or alternatively, an indicator light may be illuminated in a selected temporal pattern to communicate information (e.g., illumination in a first temporal pattern indicates a first status, while illumination in a second temporal pattern indicates a second status). For example, an indicator light may be selectively illuminated in one of a plurality of predetermined temporal patterns that differ in illumination frequency (e.g., repeated illumination at a rapid or slow frequency), regularity (e.g., periodic repeated illumination vs. intermittent illumination), duration of illumination "on" time, duration of illumination "off" time, rate of change in illumination intensity, duty cycle (e.g., ratio of illumination "on" time to illumination "off" time), and/or the like, where each predetermined temporal pattern may indicate a respective status.

Additionally or alternatively, in some variations, a display may include multiple indicator lights that may be collectively illuminated in one or more predetermined illumination modes or sequences in accordance with one or more predetermined spatial and/or temporal patterns. For example, in some variations, some or all of the indicator lights arranged on a display may be illuminated in synchrony or in sequence to indicate a particular status. Accordingly, the selected subset of indicator lights (e.g., the spatial arrangement of the indicator lights that are illuminated) and/or the manner in which they are illuminated (e.g., illumination order, illumination rate, etc.) may indicate a particular status. Additionally or alternatively, a plurality of indicator lights may illuminate simultaneously or in sequence to increase the diversity of the color palette. For example, in some variations, red, green, and blue LEDs may be illuminated in rapid succession to create the impression of white light to a user.

It should furthermore be understood that one or more of the above-described illumination modes may be combined in any suitable manner (e.g., combination of varying color, intensity, brightness, luminosity, contrast, timing, location, etc.) to communicate information. Additionally or alternatively, an ambient light sensor may be incorporated into the device body to enable dynamic adjustment light levels in the indicator light(s) to compensate for environmental light conditions to help conserve power. The ambient light sensor may, in some variations, be used in conjunction with a kinetic sensor (e.g., as described in further detail below) to further determine appropriate periods for the analyte monitoring device to enter into a power saving mode or reduced power state. For example, detection of darkness and no motion of the analyte monitoring device may indicate that the wearer of the analyte monitoring device is asleep, which may trigger the analyte monitoring device to enter into a power saving mode or reduced power state.

Figure 31A:
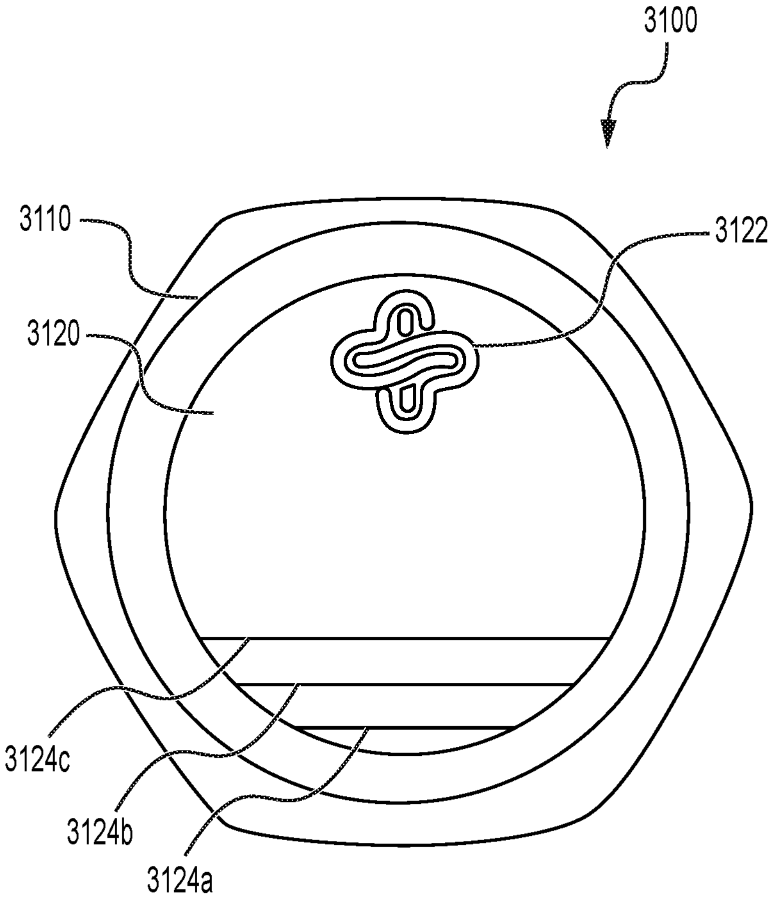
FIGS. 31A and 31B depict illustrative schematics of a housing of an analyte monitoring device including a user interface with indicator light elements.

FIG. 31A illustrates an example variation of an analyte monitoring device 3100 including a housing 3110 and a user interface 3120 with multiple indicator lights (3122, 3124*a*-3124*c*). Indicator light 3122 may, for example, be selectively illuminated to indicate a device state (e.g., operation mode, error state, power status, life status, etc.). Although indicator light 3122 is in the shape of a symbol (e.g., logo), it should be understood that in other variations, the indicator light 3122 may have any suitable shape (e.g., text, other geometric shape, etc.). Indicator lights 3124*a*-3124*c* may be selectively illuminated to indicate a user status (e.g., information representative of analyte measurement). Although indicator lights 3124*a*-3124*c* are linear elements extending across the user interface (e.g., chords across a circular display), it should be understood that in other variations, the indicator lights 3124*a*-3124*c* have other suitable shapes (e.g., wavy lines, circular, etc.). In some variations, a 1-dimensional array of indicator lights of any suitable shape may be arranged on the housing 3110 (e.g., arranged in a row, a column, an arc, etc.). Alternatively, the housing 3110 may include a multi-dimensional array of indicator lights of any suitable shape.

Figure 31B:
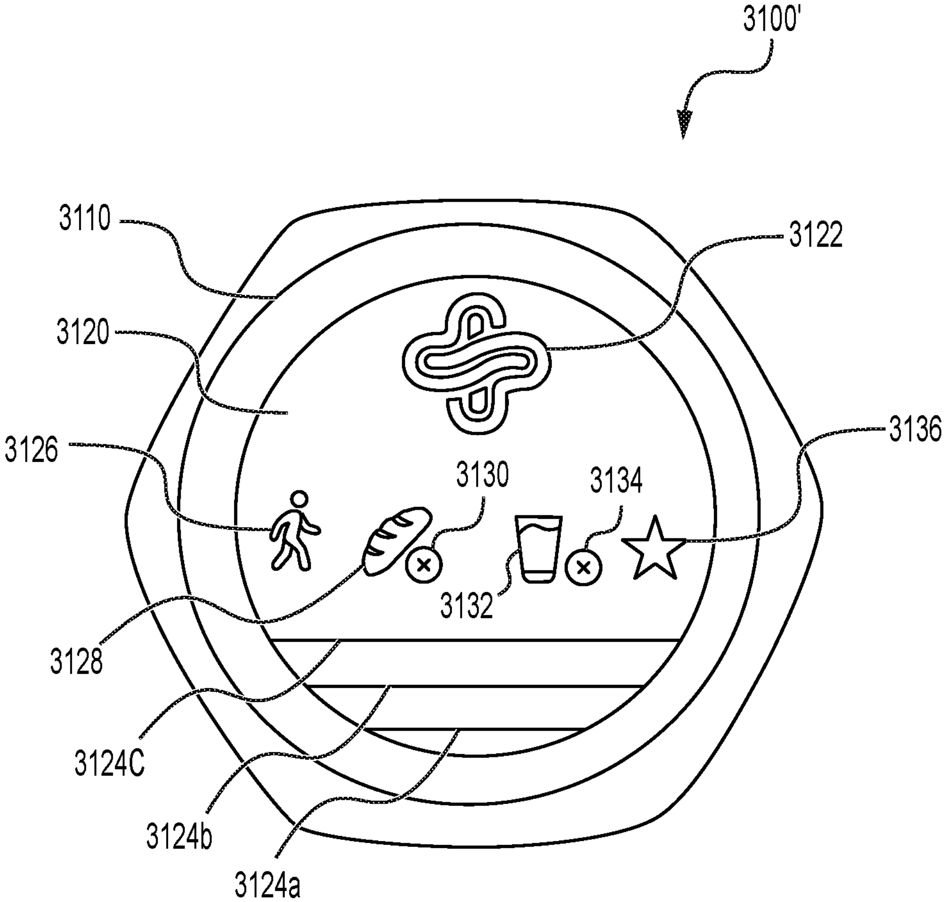

Furthermore, in some variations, an indicator light may include an icon (e.g., symbol) that may be indicative of analyte information (e.g., up arrow to indicate rising analyte measurement level trend, down arrow to indicate falling analyte measurement level trend), analyte monitoring device status (e.g., exclamation point to indicate a device error state), and/or other suitable information. Additionally or alternatively, iconography in the indicator light(s) may be used to communicate recommendations for the user such as behavioral recommendations. Iconography may, for example, have the advantage of communicating recommendations to a user in a more universal or language-agnostic manner (e.g., without the need for language translations to tailor the device to different geographical regions or user preferences, etc.). For example, as shown in FIG. 31B, in some variations, in the context of glucose monitoring, a user interface for an analyte monitoring device 3100' may include a running person icon 3126 to indicate a recommendation that the user engage in physical activity. As another example, a food icon 3128 may indicate a recommendation that the user consume food (or in combination with an "X" icon 3130, to indicate a recommendation that the user restrict food). As another example, a drink icon 3132 may indicate a recommendation that the user consume fluid such as water (or in combination with an "X" icon 3134, to indicate a recommendation that the user restrict fluid). As another example, a star icon 3136 may indicate positive reinforcement (e.g., indicating success in analyte measurement levels staying within a normal or target range for a predetermined period of time). However, it should be understood that behavioral recommendations may vary based on the indication relating to the analyte(s) being monitored. For example, in some variations in which the analyte monitoring device is additionally or alternatively used to monitor cortisol, rising cortisol levels (and/or rising glucose levels) may be correlated to an increase in user stress. Accordingly, in some of these variations the analyte monitoring device may include a suitable icon to indicate a recommendation to the user to reduce exposure to stressors, to meditate, etc. to avoid implicating adverse health effects due to stress.

In the variations shown in FIGS. 31A and 31B, each of the indicator lights 3124*a*-3124*c* may be exclusively illuminated to indicate a different analyte measurement (e.g., in target range, below target range, significantly below target range, above target range, significantly above target range, etc.). Furthermore, the indicator lights 3124*a*-3124*c* may be arranged adjacent to each other, such that they may be selectively illuminated in a progressive sequence to communicate trend information of analyte measurements (e.g., progressive sequence of illumination in a first direction that corresponds to an increase in measured quantity of an analyte, progressive sequence of illumination in a second direction that corresponds to a decrease in measured quantity of an analyte, pace of illumination progression in the first direction or the second direction that corresponds to a rate of increase or decrease in measured quantity of an analyte, etc.). An example of such progressive sequence of illumination is further described below with reference to FIGS. 33A-33D. While one device status indicator light 3120 and three user status indicator lights 3124*a*-3124*c* are shown in FIGS. 31A and 31B, it should be understood that in other variations, an analyte monitoring device may include any suitable number of indicator lights, such as one, two, three, four, five or more device status indicator lights, and one, two, three, four, five or more user status indicator lights. Further details regarding an example operation of the user interface 3120 to communicate device status and/or user status are described below (e.g., with reference to FIGS. 32A-32C, 33A-33D, 34A-34C, and 35A-35B).

Microneedle Array

Figure 5A:
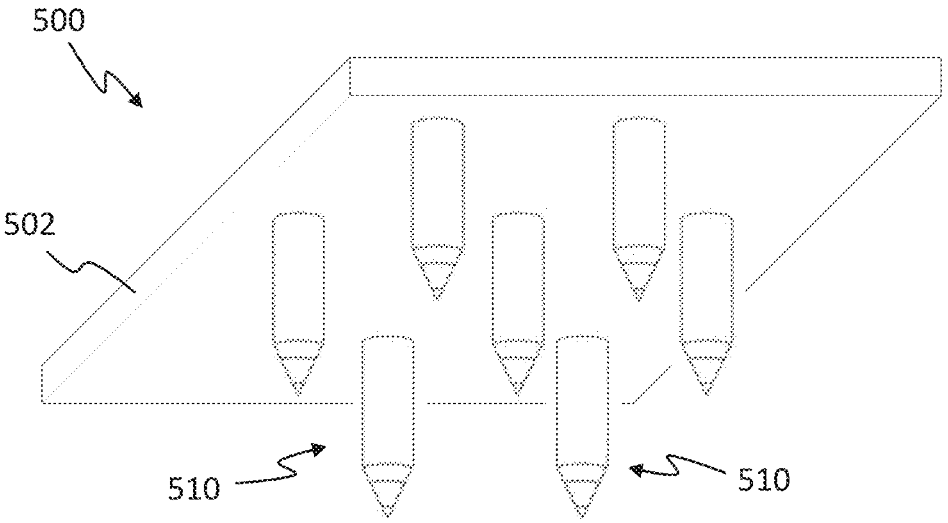
FIG. 5A depicts an illustrative schematic of a microneedle array.
Figure 5B:
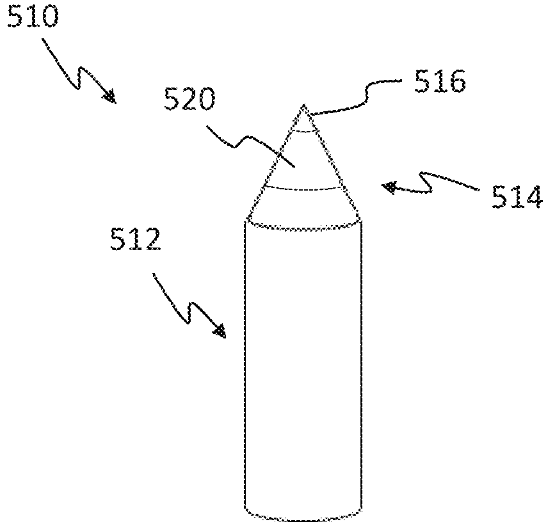
FIG. 5B depicts an illustrative schematic of a microneedle in the microneedle array depicted in FIG. 5A.

As shown in the schematic of FIG. 5A, in some variations, a microneedle array 510 for use in sensing one or more analytes may include one or more microneedles 510 projecting from a substrate surface 502. The substrate surface 502 may, for example, be generally planar and one or more microneedles 510 may project orthogonally from the planar surface. Generally, as shown in FIG. 5B, a microneedle 510 may include a body portion 512 (e.g., shaft) and a tapered distal portion 514 configured to puncture skin of a user. In some variations, the tapered distal portion 514 may terminate in an insulated distal apex 516. The microneedle 510 may further include an electrode 520 on a surface of the tapered distal portion. In some variations, electrode-based measurements may be performed at the interface of the electrode and interstitial fluid located within the body (e.g., on an outer surface of the overall microneedle). In some variations, the microneedle 510 may have a solid core (e.g., solid body portion), though in some variations the microneedle 510 may include one or more lumens, which may be used for drug delivery or sampling of the dermal interstitial fluid, for example. Other microneedle variations, such as those described below, may similarly either include a solid core or one or more lumens.

The microneedle array 500 may be at least partially formed from a semiconductor (e.g., silicon) substrate and include various material layers applied and shaped using various suitable microelectromechanical systems (MEMS) manufacturing techniques (e.g., deposition and etching techniques), as further described below. The microneedle array may be reflow-soldered to a circuit board, similar to a typical integrated circuit. Furthermore, in some variations the microneedle array 500 may include a three electrode setup including a working (sensing) electrode having an electrochemical sensing coating (including a biorecognition element such as an enzyme) that enables detection of a target analyte, a reference electrode, and a counter electrode. In other words, the microneedle array 500 may include at least one microneedle 510 that includes a working electrode, at least one microneedle 510 including a reference electrode, and at least one microneedle 510 including a counter electrode. Additional details of these types of electrodes are described in further detail below.

Figure 6:
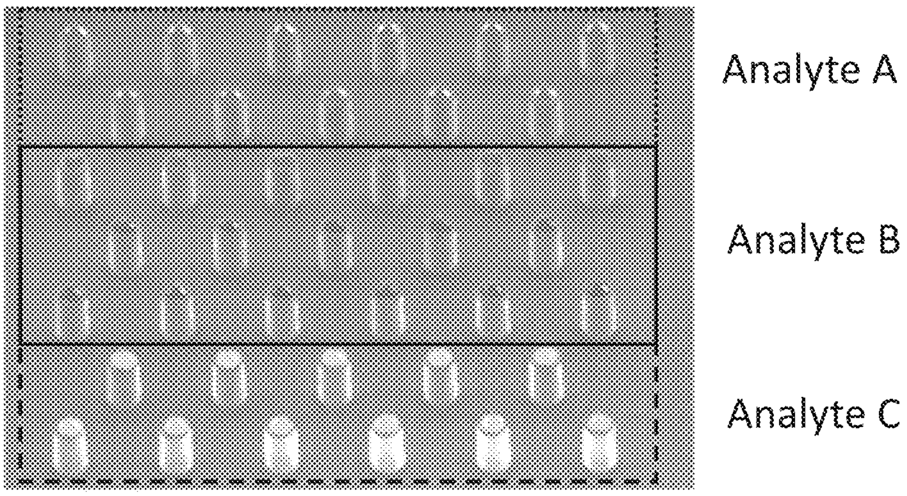
FIG. 6 depicts an illustrative schematic of a microneedle array used for sensing multiple analytes.

In some variations, the microneedle array 500 may include a plurality of microneedles that are insulated such that the electrode on each microneedle in the plurality of microneedles is individually addressable and electrically isolated from every other electrode on the microneedle array. The resulting individual addressability of the microneedle array 500 may enable greater control over each electrode's function, since each electrode may be separately probed. For example, the microneedle array 500 may be used to provide multiple independent measurements of a given target analyte, which improves the device's sensing reliability and accuracy. Furthermore, in some variations the electrodes of multiple microneedles may be electrically connected to produce augmented signal levels. As another example, the same microneedle array 500 may additionally or alternatively be interrogated to simultaneously measure multiple analytes to provide a more comprehensive assessment of physiological status. For example, as shown in the schematic of FIG. 6, a microneedle array may include a portion of microneedles to detect a first Analyte A, a second portion of microneedles to detect a second Analyte B, and a third portion of microneedles to detect a third Analyte C. It should be understood that the microneedle array may be configured to detect any suitable number of analytes (e.g., 1, 2, 3, 4, 5 or more, etc.). Suitable target analytes for detection may, for example, include glucose, ketones, lactate, and cortisol. For example, in some variations, ketones may be detected in a manner similar to that described in U.S. patent application Ser. No. 16/701,784, which is incorporated herein in its entirety by this reference. Thus, individual electrical addressability of the microneedle array 500 provides greater control and flexibility over the sensing function of the analyte monitoring device.

In some variations of microneedles (e.g., microneedles with a working electrode), the electrode 520 may be located proximal to the insulated distal apex 516 of the microneedle. In other words, in some variations the electrode 520 does not cover the apex of the microneedle. Rather, the electrode 520 may be offset from the apex or tip of the microneedle. The electrode 520 being proximal to or offset from the insulated distal apex 516 of the microneedle advantageously provides more accurate sensor measurements. For example, this arrangement prevents concentration of the electric field at the microneedle apex 516 during manufacturing, thereby avoiding non-uniform electro-deposition of sensing chemistry on the electrode surface 520 that would result in faulty sensing.

As another example, placing the electrode 520 offset from the microneedle apex further improves sensing accuracy by reducing undesirable signal artefacts and/or erroneous sensor readings caused by stress upon microneedle insertion. The distal apex of the microneedle is the first region to penetrate into the skin, and thus experiences the most stress caused by the mechanical shear phenomena accompanying the tearing or cutting of the skin. If the electrode 520 were placed on the apex or tip of the microneedle, this mechanical stress may delaminate the electrochemical sensing coating on the electrode surface when the microneedle is inserted, and/or cause a small yet interfering amount of tissue to be transported onto the active sensing portion of the electrode. Thus, placing the electrode 520 sufficiently offset from the microneedle apex may improve sensing accuracy. For example, in some variations, a distal edge of the electrode 520 may be located at least about 10 μm (e.g., between about 20 μm and about 30 μm) from the distal apex or tip of the microneedle, as measured along a longitudinal axis of the microneedle.

The body portion 512 of the microneedle 510 may further include an electrically conductive pathway extending between the electrode 520 and a backside electrode or other electrical contact (e.g., arranged on a backside of the substrate of the microneedle array). The backside electrode may be soldered to a circuit board, enabling electrical communication with the electrode 520 via the conductive pathway. For example, during use, the in-vivo sensing current (inside the dermis) measured at a working electrode is interrogated by the backside electrical contact, and the electrical connection between the backside electrical contact and the working electrode is facilitated by the conductive pathway. In some variations, this conductive pathway may be facilitated by a metal via running through the interior of the microneedle body portion (e.g., shaft) between the microneedle's proximal and distal ends. Alternatively, in some variations the conductive pathway may be provided by the entire body portion being formed of a conductive material (e.g., doped silicon). In some of these variations, the complete substrate on which the microneedle array 500 is built upon may be electrically conductive, and each microneedle 510 in the microneedle array 500 may be electrically isolated from adjacent microneedles 510 as described below. For example, in some variations, each microneedle 510 in the microneedle array 500 may be electrically isolated from adjacent microneedles 510 with an insulative barrier including electrically insulative material (e.g., dielectric material such as silicon dioxide) that surrounds the conductive pathway extending between the electrode 520 and backside electrical contact. For example, body portion 512 may include an insulative material that forms a sheath around the conductive pathway, thereby preventing electrical communication between the conductive pathway and the substrate. Other example variations of structures enabling electrical isolation among microneedles are described in further detail below.

Such electrical isolation among microneedles in the microneedle array permits the sensors to be individually addressable. This individually addressability advantageously enables independent and parallelized measurement among the sensors, as well as dynamic reconfiguration of sensor assignment (e.g., to different analytes). In some variations, the electrodes in the microneedle array can be configured to provide redundant analyte measurements, which is an advantage over conventional analyte monitoring devices. For example, redundancy can improve performance by improving accuracy (e.g., averaging multiple analyte measurement values for the same analyte which reduces the effect of extreme high or low sensor signals on the determination of analyte levels) and/or improving reliability of the device by reducing the likelihood of total failure.

In some variations, as described in further detail below with respective different variations of the microneedle, the microneedle array may be formed at least in part with suitable semiconductor and/or MEMS fabrication techniques and/or mechanical cutting or dicing. Such processes may, for example, be advantageous for enabling large-scale, cost-efficient manufacturing of microneedle arrays. For example, in some variations, the microneedle array may be formed at least in part using techniques described in U.S. patent application Ser. No. 15/913,709, which is incorporated herein in its entirety by this reference.

Microneedle Structures

Described herein are multiple example variations of microneedle structure incorporating one or more of the above-described microneedle features for a microneedle array in an analyte monitoring device.

Figure 7A:
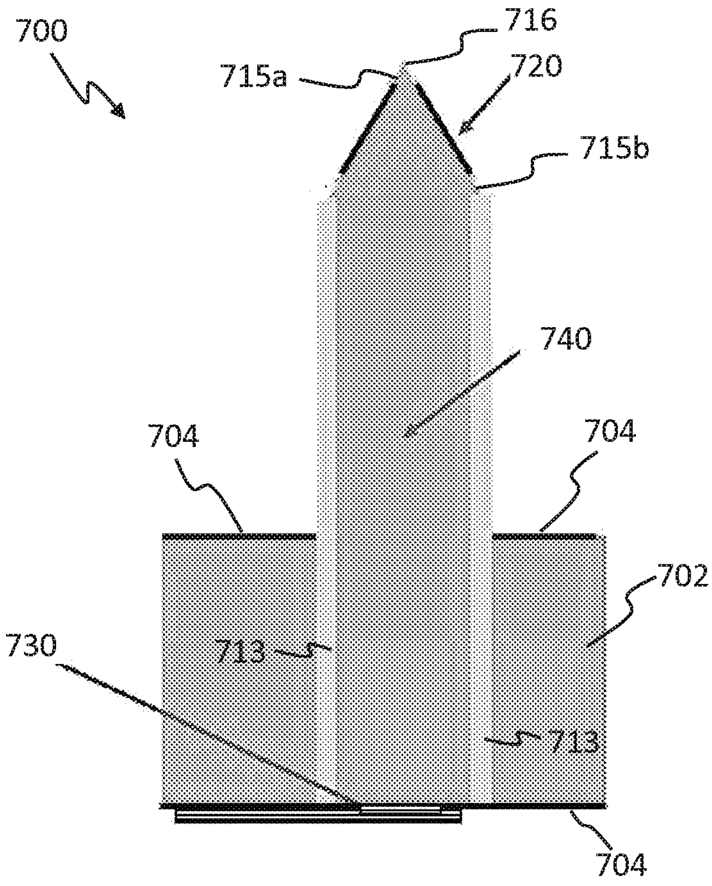
FIG. 7A depicts a cross-sectional side view of a columnar microneedle having a tapered distal end.
Figure 7B:
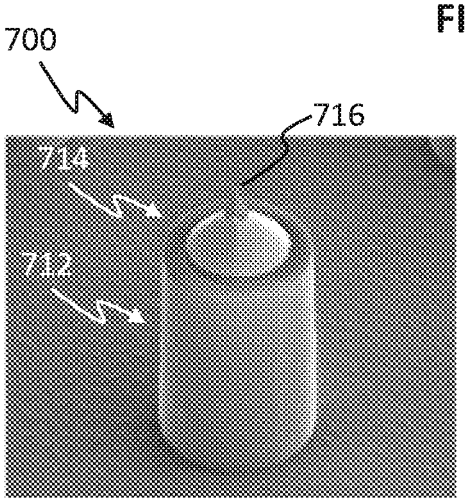
FIGS. 7B and 7C are images depicting perspective and detailed views, respectively, of an embodiment of the microneedle shown in FIG. 7A.
Figure 7C:
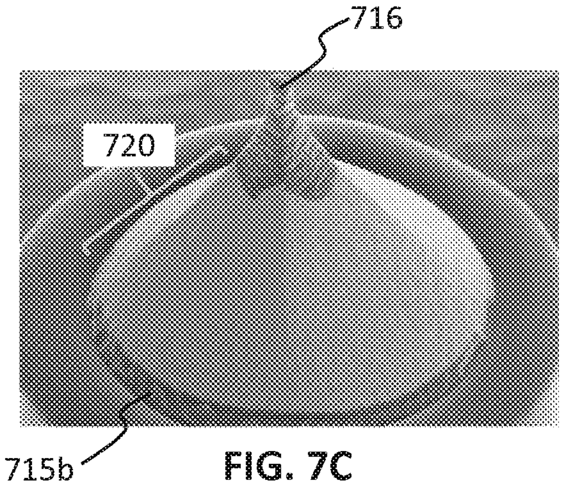

In some variations, a microneedle may have a generally columnar body portion and a tapered distal portion with an electrode. For example, FIGS. 7A-7C illustrate an example variation of a microneedle 700 extending from a substrate 702. FIG. 7A is a side cross-sectional view of a schematic of microneedle 700, while FIG. 7B is a perspective view of the microneedle 700 and FIG. 7C is a detailed perspective view of a distal portion of the microneedle 700. As shown in FIGS. 7B and 7C, the microneedle 700 may include a columnar body portion 712, a tapered distal portion 714 terminating in an insulated distal apex 716, and an annular electrode 720 that includes a conductive material (e.g., Pt, Ir, Au, Ti, Cr, Ni, etc.) and is arranged on the tapered distal portion 714. As shown in FIG. 7A, the annular electrode 720 may be proximal to (or offset or spaced apart from) the distal apex 716. For example, the electrode 720 may be electrically isolated from the distal apex 716 by a distal insulating surface 715*a* including an insulating material (e.g., $SiO_2$). In some variations, the electrode 720 may also be electrically isolated from the columnar body portion 712 by a second distal insulating surface 715*b*. The electrode 720 may be in electrical communication with a conductive core 740 (e.g., conductive pathway) passing along the body portion 712 to a backside electrical contact 730 (e.g., made of Ni/Au alloy) or other electrical pad in or on the substrate 702. For example, the body portion 712 may include a conductive core material (e.g., highly doped silicon). As shown in FIG. 7A, in some variations, an insulating moat 713 including an insulating material (e.g., $SiO_2$) may be arranged around (e.g., around the perimeter) of the body portion 712 and extend at least partially through the substrate 702. Accordingly, the insulating moat 713 may, for example, help prevent electrical contact between the conductive core 740 and the surrounding substrate 702. The insulating moat 713 may further extend over the surface of the body portion 712. Upper and/or lower surfaces of the substrate 702 may also include a layer of substrate insulation 704 (e.g., $SiO_2$). Accordingly, the insulation provided by the insulating moat 713 and/or substrate insulation 704 may contribute at least in part to the electrical isolation of the microneedle 700 that enables individual addressability of the microneedle 700 within a microneedle array. Furthermore, in some variations the insulating moat 713 extending over the surface of the body portion 712 may function to increase the mechanical strength of the microneedle 700 structure.

The microneedle 700 may be formed at least in part by suitable MEMS fabrication techniques such as plasma etching, also called dry etching. For example, in some variations, the insulating moat 713 around the body portion 712 of the microneedle may be made by first forming a trench in a silicon substrate by deep reactive ion etching (DRIE) from the backside of the substrate, then filling that trench with a sandwich structure of $SiO_2$/polycrystalline silicon (poly-Si)/$SiO_2$ by low pressure chemical vapor deposition (LPCVD) or other suitable process. In other words, the insulating moat 713 may passivate the surface of the body portion 712 of the microneedle, and continue as a buried feature in the substrate 702 near the proximal portion of the microneedle. By including largely compounds of silicon, the insulating moat 713 may provide good fill and adhesion to the adjoining silicon walls (e.g., of the conductive core 740, substrate 702, etc.). The sandwich structure of the insulating moat 713 may further help provide excellent matching of coefficient of thermal expansion (CTE) with the adjacent silicon, thereby advantageously reducing faults, cracks, and/or other thermally-induced weaknesses in the insulating structure 713.

The tapered distal portion may be fashioned out by an isotropic dry etch from the frontside of the substrate, and the body portion 712 of the microneedle 700 may be formed from DRIE. The frontside metal electrode 720 may be deposited and patterned on the distal portion by specialized lithography (e.g., electron-beam evaporation) that permits metal deposition in the desired annular region for the electrode 720 without coating the distal apex 716. Furthermore, the backside electrical contact 730 of Ni/Au may be deposited by suitable MEMS manufacturing techniques (e.g., sputtering).

Figure 8:
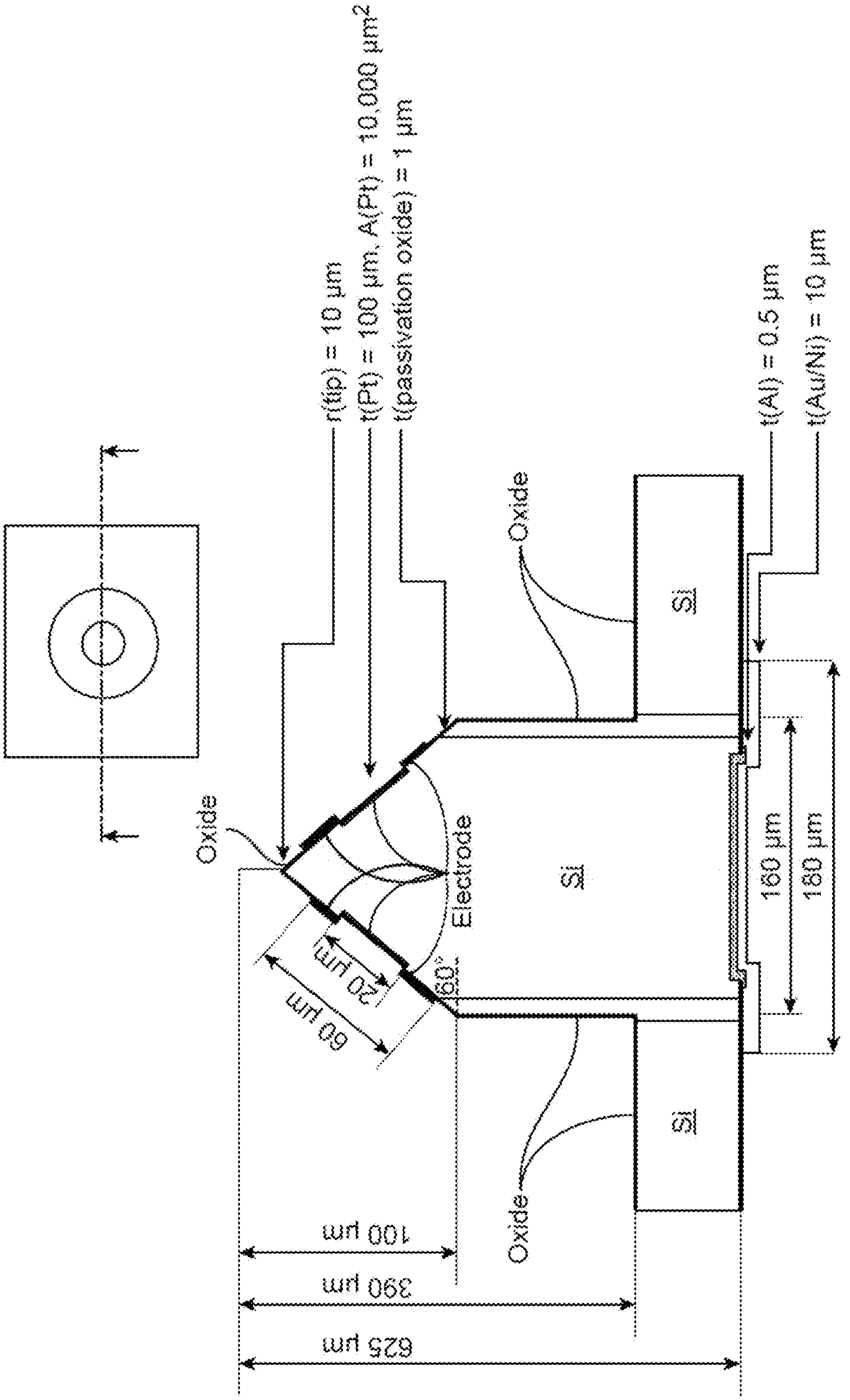
FIG. 8 depicts an illustrative schematic of a columnar microneedle having a tapered distal end.

The microneedle 700 may have any suitable dimensions. By way of illustration, the microneedle 700 may, in some variations, have a height of between about 300 μm and about 500 μm. In some variations, the tapered distal portion 714 may have a tip angle between about 60 degrees and about 80 degrees, and an apex diameter of between about 1 μm and about 15 μm. In some variations, the surface area of the annular electrode 720 may include between about 9,000 $\mu m^2$ and about 11,000 $\mu m^2$, or about 10,000 $\mu m^2$. FIG. 8 illustrates various dimensions of an example variation of a columnar microneedle with a tapered distal portion and annular electrode, similar to microneedle 700 described above.

Figure 9:
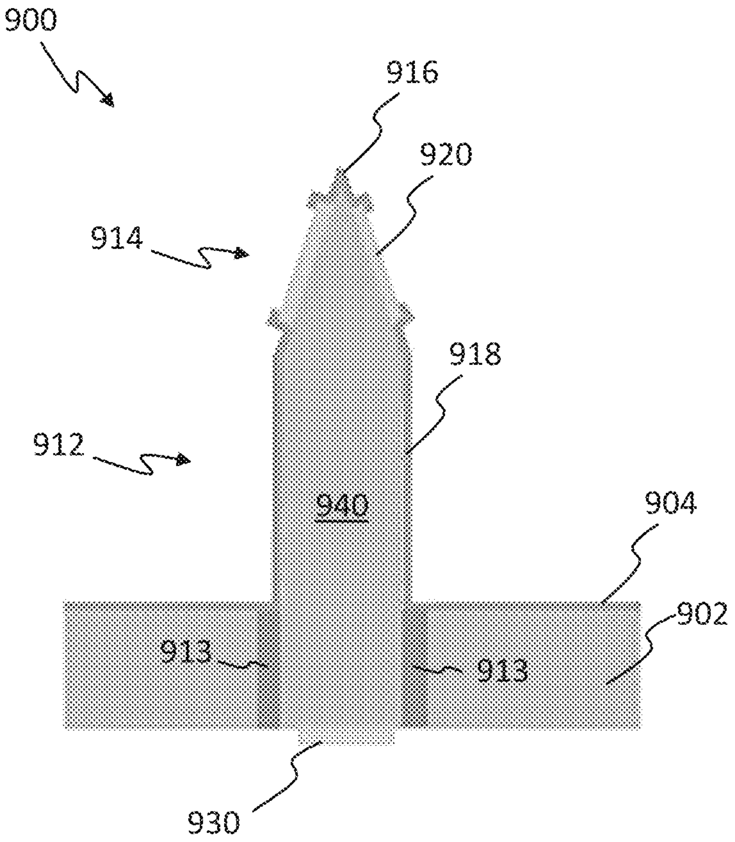
FIG. 9 depicts a cross-sectional side view of a columnar microneedle having a tapered distal end.

FIG. 9 illustrates another example variation of a microneedle 900 having a generally columnar body portion. The microneedle 900 may be similar to microneedle 700 as described above, except as described below. For example, like the microneedle 700, the microneedle 900 may include a columnar body portion 912, and a tapered distal portion 914 terminating in an insulated distal apex 916. The microneedle 900 may further include an annular electrode 920 that includes a conductive material and is arranged on the tapered distal portion 914 at a location proximal to (or offset from or spaced apart from) the distal apex 916. The electrode 920 may be in electrical communication with a conductive core 940 passing along the body portion 912 to a backside electrical contact 930. Other elements of microneedle 900 have numbering similar to corresponding elements of microneedle 700.

However, compared to the microneedle 700, the microneedle 900 may have a sharper tip at the distal apex 916 and a modified insulating moat 913. For example, the distal apex 916 may have a sharper tip angle, such as between about 25 degrees and about 45 degrees, and an apex radius of less than about 100 nm, which provides a sharper microneedle profile that may penetrate skin with greater ease, lower velocity, less energy, and/or less trauma. Furthermore, in contrast to the insulating moat 713 (which extends through the substrate 702 and along the height of the microneedle body portion 712 as shown in FIG. 7A), the modified insulating moat 913 may extend only through the substrate 902 such that the sandwich structure filling the trench (e.g., created by DRIE as described above) forms only the buried feature in the substrate. Although the sidewall of the microneedle 900 is shown in FIG. 9 as extending generally orthogonal to the substrate surface, it should be understood that because the modified insulating moat 913 need not extend the entire height of the microneedle body portion 712, in some variations the sidewall of the microneedle 900 may be angled at non-orthogonal angles relative to the substrate (e.g., the sidewall may have a slight positive taper of between about 1 degree to about 10 degrees, or between about 5 degrees and about 10 degrees).

In some variations, the rest of the microneedle surface 900 (aside from the annular electrode 920) may include an insulating material extending from substrate insulation 904. For example, a layer of an insulating material (e.g., $SiO_2$) may extend from a frontside surface of the substrate 902 to provide a body portion insulation 918, and may further extend up over a proximal edge of the electrode 920 as shown in FIG. 9. Another region of insulating material may similarly cover a distal edge of the electrode 920 and insulate the distal apex 916. Such region of insulating material and/or modified insulating moat 913 may help prevent electrical contact between the conductive core 940 and the surrounding substrate 902. Accordingly, like the microneedle 700, the microneedle 900 may maintain electrical isolation for individual addressability within a microneedle array. In some variations, the process to form microneedle 900 may result in higher yield and/or provide lower production cost compared to the process to form microneedle 700.

Figure 10:
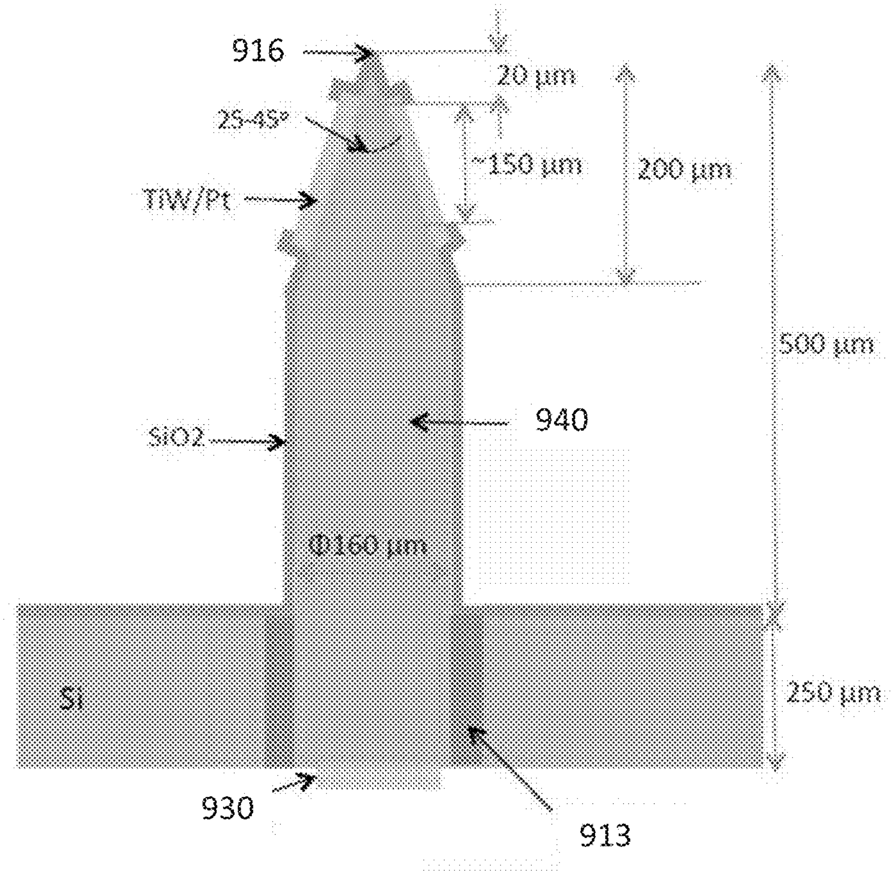
FIG. 10 depicts an illustrative schematic of a columnar microneedle having a tapered distal end.

The microneedle 900 may have any suitable dimensions. By way of illustration, the microneedle 900 may, in some variations, include a height of between about 400 μm and about 600 μm, or about 500 μm. In some variations, the tapered distal portion 914 may have a tip angle of between about 25 degrees and about 45 degrees, with a tip radius of less than about 100 nm. Furthermore, the microneedle may have a shaft diameter of between about 160 μm and about 200 μm. FIG. 10 illustrates additional various dimensions of an example variation of a columnar microneedle with a tapered distal portion and annular electrode, similar to microneedle 900 described above.

Figure 27A:
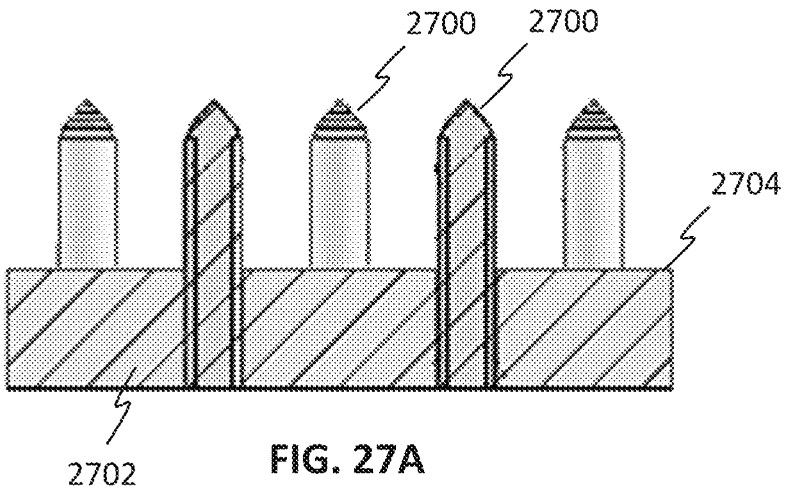
FIGS. 27A and 27B depict illustrative schematics of a microneedle array and a microneedle, respectively.
Figure 27B:
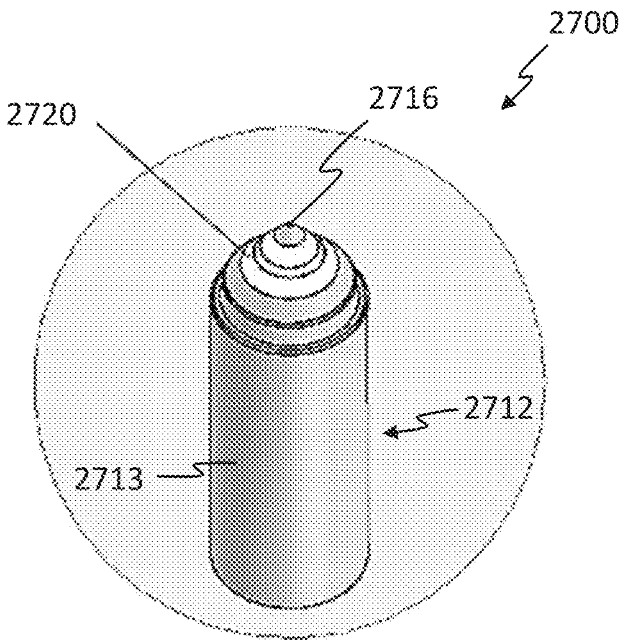
Figure 27F:
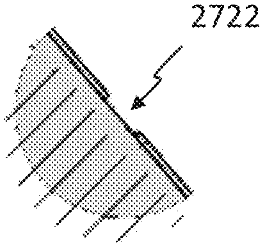
FIGS. 27C-27F depict detailed partial views of an illustrative variation of a microneedle.
Figure 27C:
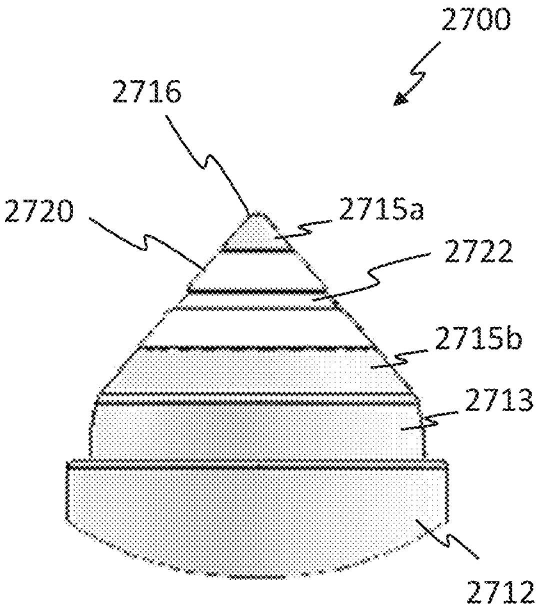
Figure 27E:
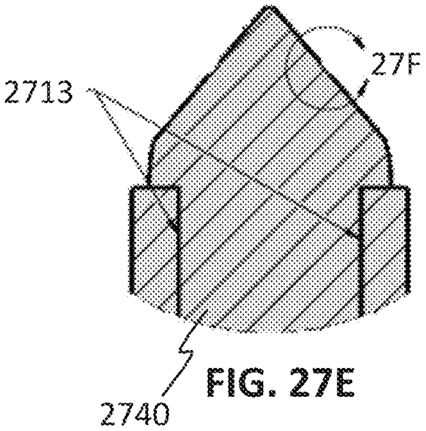
Figure 27D:
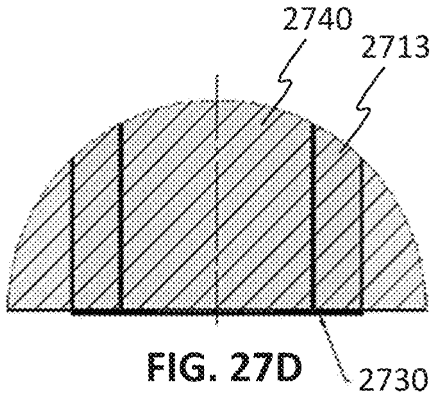

FIGS. 27A-27F illustrate another example variation of a microneedle 2700 having a generally columnar body portion. The microneedle 2700 may be similar to microneedle 700 as described above, except as described below. For example, as shown in FIG. 27A, like the microneedle 700, the microneedle 2700 extends from a substrate 2702. An upper surface of the substrate 2702 may include a layer of substrate insulation 2704. As shown in FIG. 27B, like the microneedle 700, the microneedle 2700 may include a columnar body portion 2712, and a tapered distal portion arranged on a cylinder 2713 and terminating in an insulated distal apex 2716. The cylinder 2713 may be insulated and have a smaller diameter than the columnar body portion 2712. The microneedle 2700 may further include an annular electrode 2720 that includes a conductive material and is arranged on the tapered distal portion at a location proximal to (or offset or spaced apart from) the distal apex 2716. As shown in FIG. 27C, the electrode 2720 may be electrically isolated from the distal apex 2716 by a distal insulating surface 2715*a* including an insulating material (e.g., $SiO_2$). In some variations, the electrode 2720 may also be electrically isolated from the columnar body portion 2712 by a second distal insulating surface 2715*b*. The electrode 2720 may be in electrical communication with a conductive core 2740 passing along the body portion 2712 to a backside electrical contact 2730. Other elements of microneedle 2700 as shown in FIGS. 27A-27F have numbering similar to corresponding elements of microneedle 700.

However, the electrode 2720 on the microneedle 2700 may include a tip contact trench 2722. This contact trench may be configured to help establish ohmic contact between the electrode 2720 and the underlying conductive core 2740 of the microneedle. In some variations, the shape of the tip contact trench 2722 may include an annular recess formed in the surface of the conductive core 2740 (e.g., into the body portion of the microneedle, or otherwise in contact with a conductive pathway in the body portion) such that when the electrode 2720 material is deposited onto the conductive core 2740, the electrode 2720 with the tip contact trench 2722 may have a stepped profile when viewed from the side. The tip contact trench 2722 may advantageously help provide a margin of error to ensure contact between the electrode 2720 and the underlying conductive core 2740. Any of the other microneedle variations described herein may also have a similar tip contact trench to help ensure contact between the electrode (which may be, for example, a working electrode, reference electrode, counter electrode, etc.) with a conductive pathway within the microneedle.

Figure 28B:
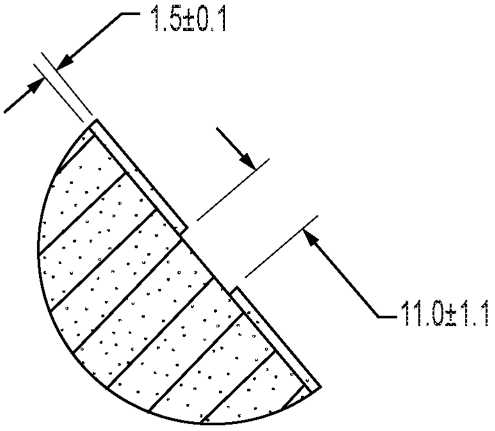
FIGS. 28A and 28B depict an illustrative variation of a microneedle.
Figure 28A:
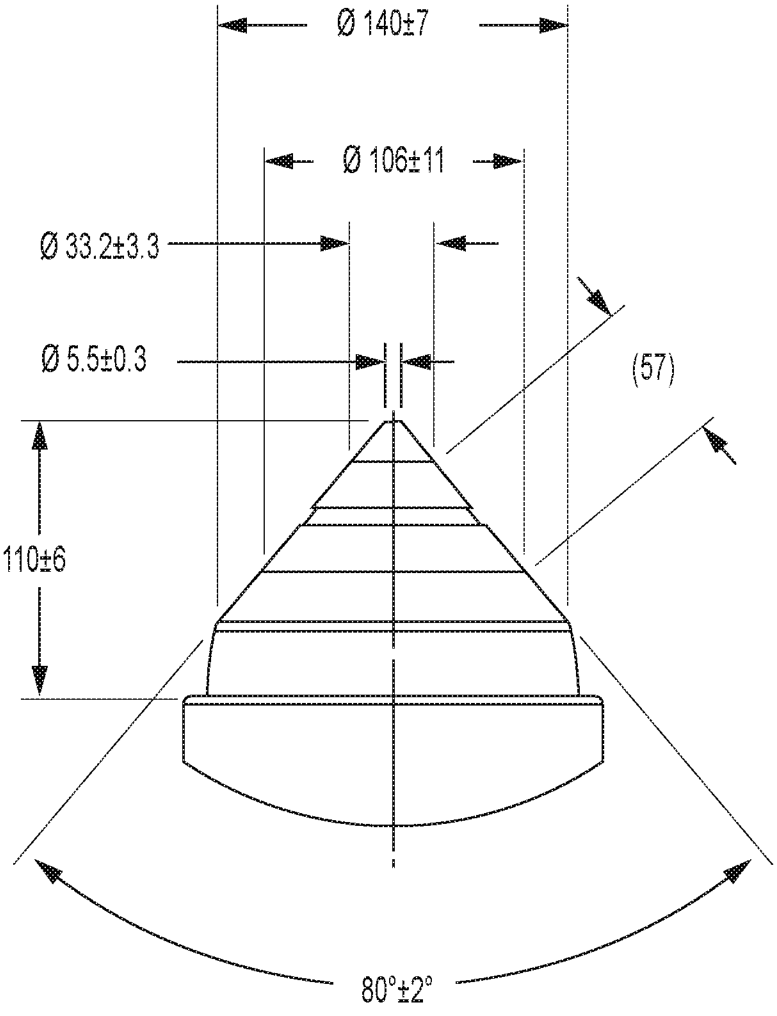

FIGS. 28A and 28B illustrate additional various dimensions of an example variation of a columnar microneedle with a tapered distal portion and annular electrode, similar to microneedle 2700 described above. For example, the variation of the microneedle shown in FIGS. 28A and 28B may have a tapered distal portion generally having a taper angle of about 80 degrees (or between about 78 degrees and about 82 degrees, or between about 75 degrees and about 85 degrees), and a cone diameter of about 140 μm (or between about 133 μm and about 147 μm, or between about 130 μm and about 150 μm). The cone of the tapered distal portion may be arranged on a cylinder such that the overall combined height of the cone and cylinder is about 110 μm (or between about 99 μm and about 116 μm, or between about 95 μm and about 120 μm). The annular electrode on the tapered distal portion may have an outer or base diameter of about 106 μm (or between about 95 μm and about 117 μm, or between about 90 μm and about 120 μm), and an inner diameter of about 33.2 μm (or between about 30 μm and about 36 μm, or between about 25 μm and about 40 μm). The length of the annular electrode, as measured along the slope of the tapered distal portion, may be about 57 μm (or between about 55 μm and about 65 μm), and the overall surface area of the electrode may be about 12,700 $μm^2$ (or between about 12,500 $μm^2$ and about 12,900 $μm^2$, or between about 12,000 $μm^2$ and about 13,000 $μm^2$). As shown in FIG. 28B, the electrode may furthermore have a tip contact trench extending around a central region of the cone of the tapered distal portion, where the contact may have a width of about 11 μm (or between about 5 μm and about 50 μm, between about 10 μm and about 12 μm, or between about 8 μm and about 14 μm) as measured along the slope of the tapered distal portion, and a trench depth of about 1.5 μm (or between about 0.1 μm and about 5 μm, or between about 0.5 μm and about 1.5 μm, or between about 1.4 μm and about 1.6 μm, or between about 1 μm and about 2 μm). The microneedle has an insulated distal apex having a diameter of about 5.5 μm (or between about 5.3 μm and about 5.8 μm, or between about 5 μm and about 6 μm).

Figure 11A:
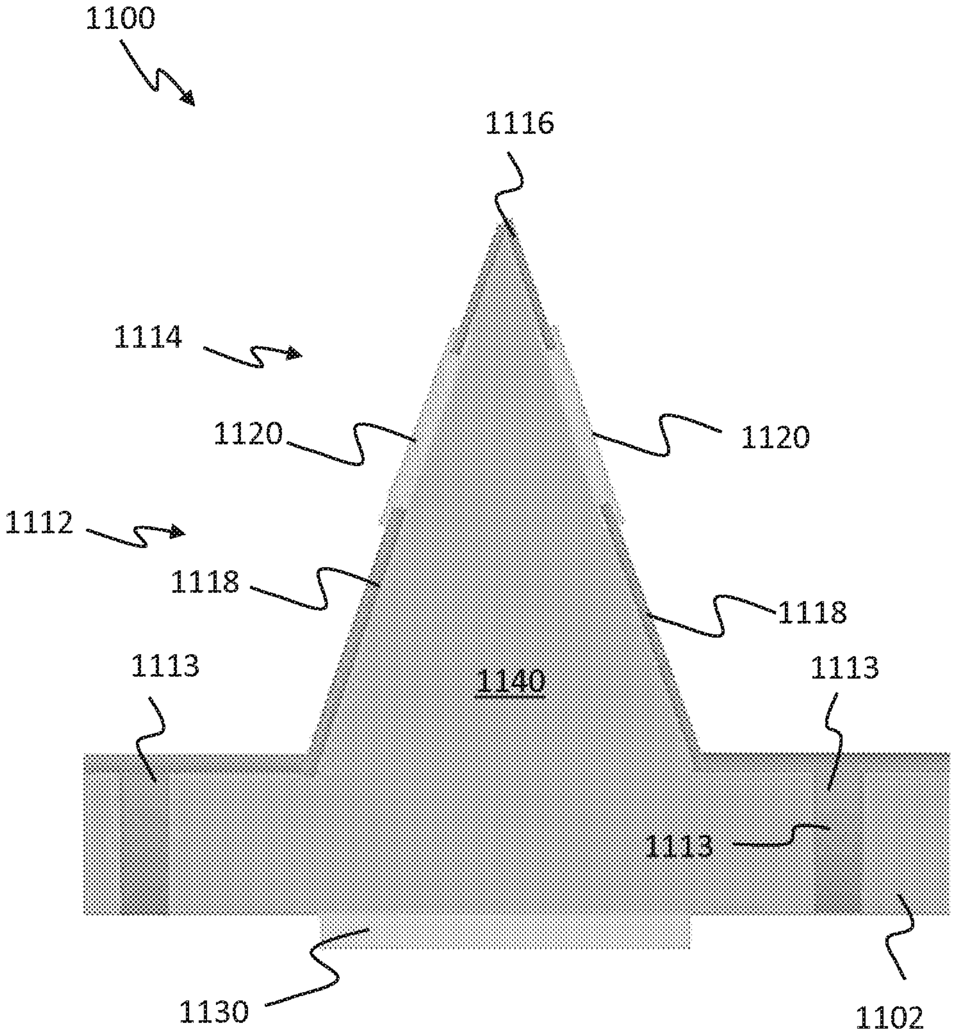
FIG. 11A depicts a cross-sectional side view of a pyramidal microneedle having a tapered distal end.

In some variations, a microneedle may have a generally pyramidal body portion and a tapered distal portion with an electrode. For example, FIG. 11A illustrates an example variation of a microneedle 1100 having a generally pyramidal body portion 1112 and a tapered distal portion 1114 extending from the body portion 1112. The microneedle 1100 may also include an annular electrode 1120 arranged on the tapered distal portion 1114 and proximal to an insulated distal apex 1116. The electrode 1120 may be conductively coupled via a conductive pathway through the conductive core 1140 of the microneedle to a backside electrical contact 1130. Like the microneedle 900 described above with respect to FIG. 9, the microneedle 1100 may include an insulating moat 1113 that is arranged around the base of the body portion 1112 and extends through the substrate 1102 to provide electrical insulation around the microneedle 1100 (e.g., for individual addressability) and help prevent electrical contact between the conductive core 1140 and the surrounding substrate 1102. However, in contrast to the insulating moat 913 shown in FIG. 9, the insulating moat 1113 may be offset from the base of the microneedle 1100. The moat may, for example, be offset between about 10 μm and about 400 μm, between about 10 μm and about 300 μm, between about 10 μm and about 200 μm, or between about 10 μm and about 100 μm from where the base of the microneedle 1100 meets the substrate 1102 to which it is attached. In some variations, the insulating moat may include a filler material including parylene, $Si_3N_4$, and $SiO_2$, which may provide for low thermal stress and an insulating material that is chemical- and water-resistant. Additional body portion insulation 1118 may extend from a frontside surface of the substrate 1102 up to the proximal edge of the electrode 1120. Another region of insulating material may extend from the distal edge of the electrode 1120 and insulate the distal apex 1116.

Figure 11B:
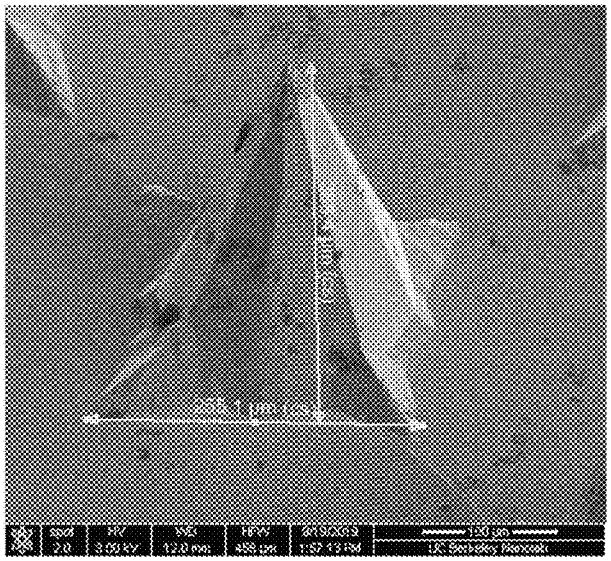
FIG. 11B is an image depicting a perspective view of an embodiment of the microneedle shown in FIG. 11A.

As shown in FIG. 11B, in some variations a microneedle 1100 having a pyramidal body portion 1112 may include a polygonal base, though the base may have any suitable shape (e.g., circular). The pyramidal body portion 1112 may include a plurality of planar facets each extending from a respective of the polygonal base of the microneedle. In some variations, the planar facets may include anisotropically etched <311> planar facets for increased mechanical strength (e.g., compressive strength and shear strength) of the microneedle 1110 and/or increased electrode surface area relative to a circular cone with a non-planar faceted surface. For example, the microneedle 1110 may have an octagonal base with anisotropically etched <311> planar facets that increase the mechanical strength and increase the metallization surface of the microneedle 110 for the electrode surface.

Figure 11C:
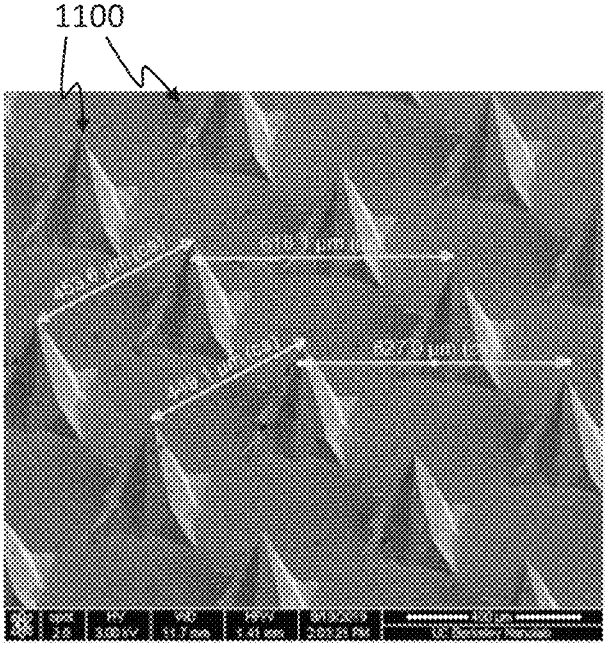
FIG. 11C is an image depicting an illustrative variation of a microneedle array including microneedles similar to that shown in FIG. 11B.

The microneedle 1100 may be formed at least in part by suitable MEMS fabrication techniques. For example, the microneedle pyramidal structure may be formed by a timed anisotropic wet etch of a silicon wafer substrate. To form the annular electrode surface, metal deposition on the tapered distal portion of the microneedle may be performed, such as using specialized lithographic techniques as described above with respect to electrode 720, without coating the distal apex 1116. However, compared to the process described above to form microneedle 700, much of the process to form microneedle 1100 does not involve expensive RIE techniques, which may thereby substantially reduce manufacturing costs. Furthermore, in some variations, instead of utilizing dry etch processes as described above with respect to microneedle 700, a process of forming the microneedle 1100 may include mechanical dicing, bulk micromachining, or other cutting techniques to shape the microneedle 1100 into having a pyramidal body. Furthermore, such techniques may be performed at a large scale, so as to form, for example, multiple microneedles 1110 arranged in an array as shown in FIG. 11C.

The microneedle 1100 may have any suitable dimensions. By way of illustration, the microneedle 1100 may, in some variations, have a height of between about 400 μm and about 600 μm, or about 500 μm. In some variations, the tapered distal portion 714 may have a tip angle between about 30 degrees and about 50 degrees, or about 40 degrees, which may provide a good balance between sharpness for skin penetration and lithography processability on the sloped surface on which the electrode 1120 is to be disposed.

Figure 12:
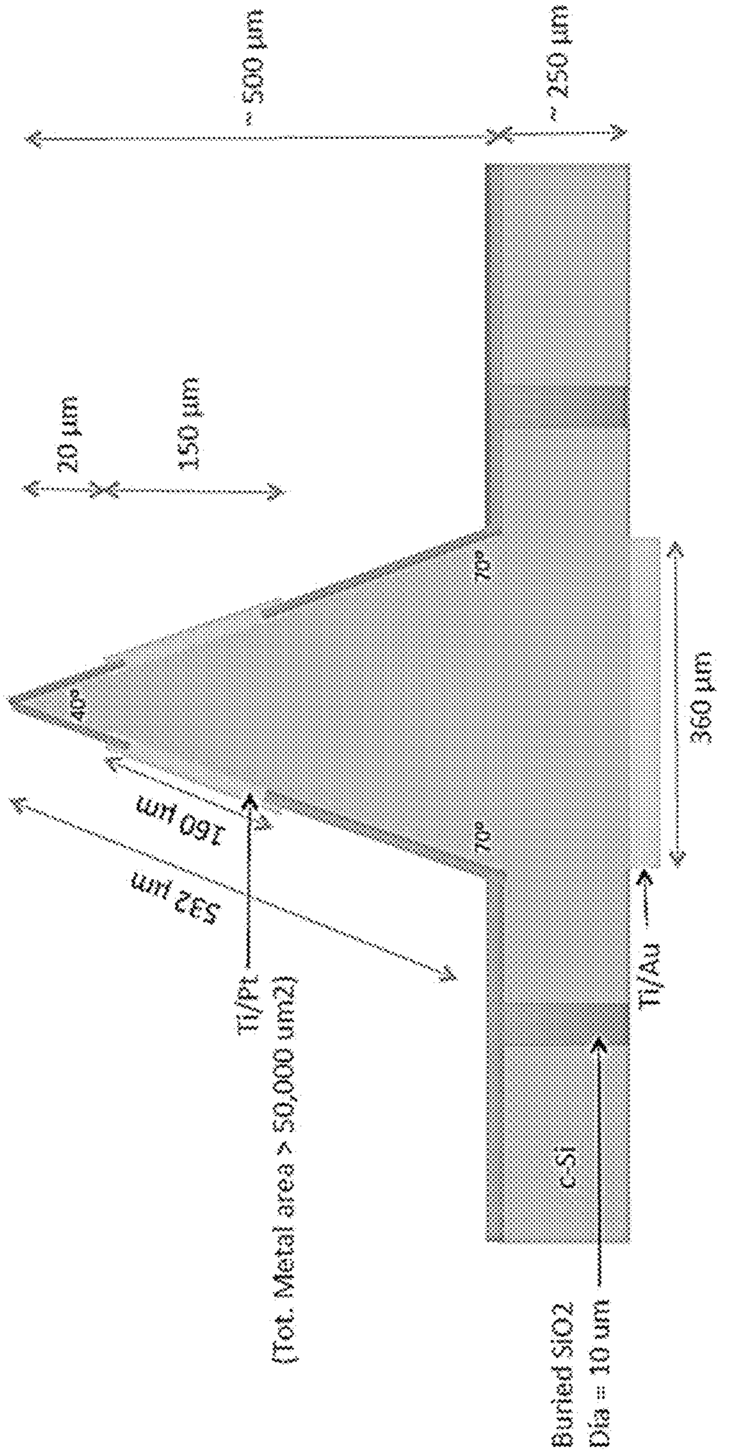
FIG. 12 depicts an illustrative schematic of a pyramidal microneedle having a tapered distal end.

FIG. 12 illustrates various dimensions of an example variation of a pyramidal microneedle with a tapered distal portion having planar facets and an electrode arranged on at least a portion of the planar facets. While in some variations the electrode may be annular or annular-like in that all of the planar facets on the pyramidal microneedle may include a metallization surface for the electrode, it should be understood that alternatively, in some variations only a portion of the planar facets on the pyramidal microneedle may include a metallization surface (e.g., one, two, three, four, five, six, or seven planar facets of a pyramidal microneedle having an octagonal base and eight planar facets extending distally from the octagonal base).

Figure 13A:
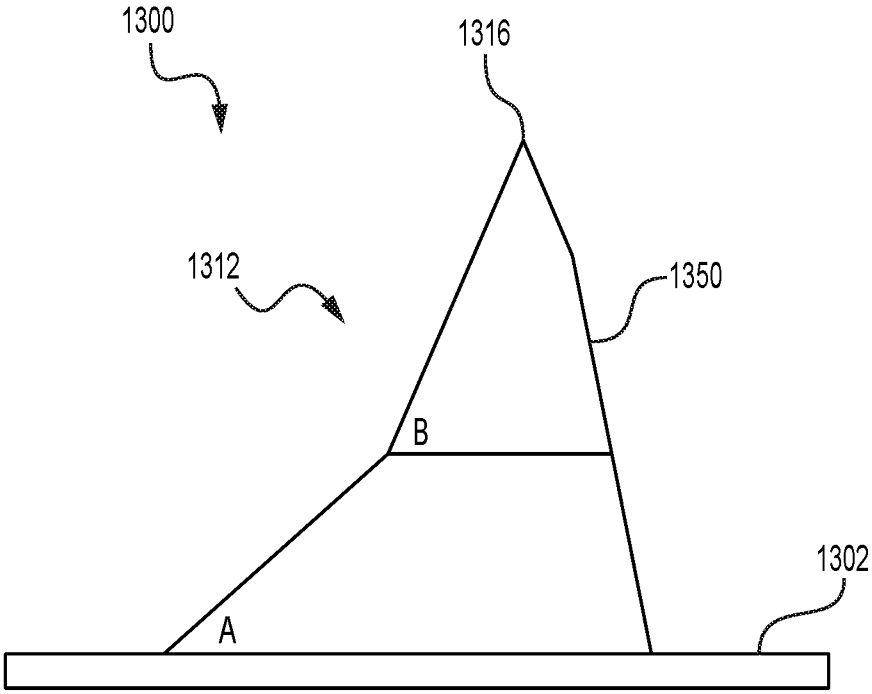
FIG. 13A depicts an illustrative schematic of a pyramidal microneedle having a tapered distal end and asymmetric cut surface.
Figure 13B:
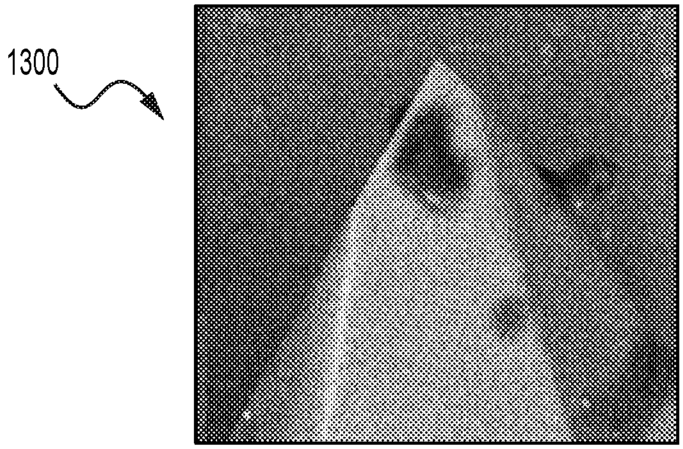
FIG. 13B is an image depicting an illustrative variation of the microneedle shown in FIG. 13A.

In some variations, a pyramidal microneedle may be similar to that described above with respect to FIG. 11A, except that the microneedle may have an asymmetrical shape as shown in FIGS. 13A and 13B. For example, in some variations as shown in FIG. 13A, a microneedle 1300 may have a non-circular or polygonal (e.g., square, octagonal) base, but may taper in a radially asymmetric manner. For example, the microneedle 1300 may include at least one cut surface 1350 (e.g., planar surface) that is offset from the distal apex 1316 of the microneedle (that is, not extending through a central z-axis defined as passing from the base of the microneedle 1300 to the distal apex 1316. The insulated distal apex 1316 may be kept intact so as to not compromise surface area for metallization for the electrode. In some variations, the cut surface 1350 may be angled at a non-orthogonal angle relative to the base of the microneedle (and/or surface of the substrate 1302), as shown in FIG. 13A. For example, in some variations the cut surface may configured to produce a sharpened asymmetrical distal tip at distal apex 1316 that is less than about 50 degrees, less than 40 degrees, less than about 30 degrees, or less than about 20 degrees. Alternatively, in some variations the cut surface 1350 may be angled normal to or orthogonal to the base of the microneedle (and/or surface of the substrate 1302).

Additionally or alternatively, as shown in FIG. 13A, an example variation of an asymmetric microneedle 1300 may have a polygonal (e.g., octagonal) base, but include various sloped surfaces that taper at different angles. As shown in FIG. 13A, a body portion 1312 of the microneedle 1300 may have a first taper angle (A) and a second taper angle (B) measured relative to a base of the body portion (and/or surface of the substrate 1302). The second taper angle (B) may be greater than the first taper angle (A) such that the microneedle has a sharper penetrating tip extending from a stable, mechanically strong base. For example, in some variations, the first taper angle (A) may be between about 10 degrees and about 30 degrees, between about 15 degrees and about 25 degrees, or about 20 degrees. Additionally, in some variations, the second taper angle (B) may be between about 60 degrees and about 80 degrees, between about 65 degrees and about 75 degrees, or about 70 degrees.

Figure 13C:
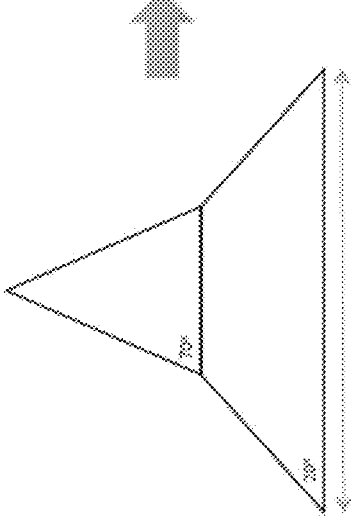
FIGS. 13C-13E illustrate a process for forming the pyramidal microneedle shown in FIG. 13A.
Figure 13D:
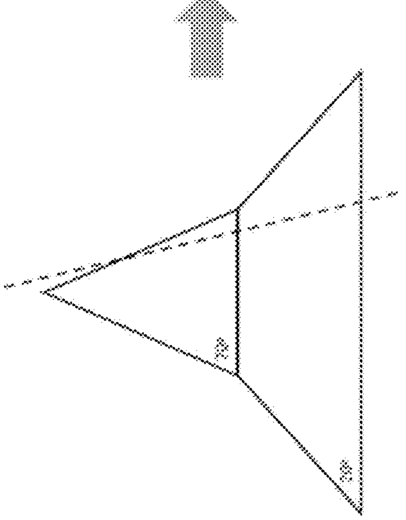
Figure 13E:
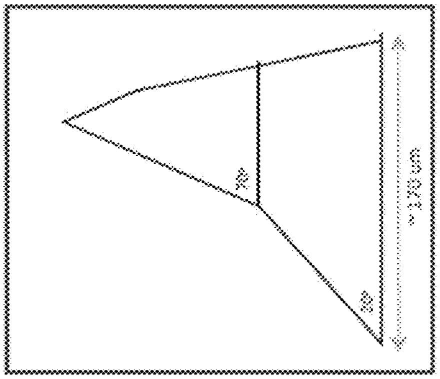

FIGS. 13C-13E depict a series of steps in an example variation of forming a pyramidal microneedle with an asymmetric cut surface. As shown in FIG. 13C, a symmetric pyramidal microneedle with two taper angles may be formed through an anisotropic wet etch process. The two taper angles of the microneedle may include, for example, a first taper angle of about 20 degrees located near the base of the microneedle, and a second taper angle of about 70 degrees located distal to the first tape angle, thereby forming progressively sloping surfaces (e.g., along planar facets of the pyramidal microneedle). As shown in FIG. 13D, a dicing blade may be applied at an angle offset from the distal apex of the microneedle, so as to form a cut surface similar to cut surface 1350 described above. The cut surface may leave a reduced microneedle base diameter (e.g., between about 150 μm and about 190 μm, or about 170 μm) so as to result in low tissue trauma. As shown in FIG. 13E, the resulting microneedle (with its offset cut surface) is asymmetric but has an intact, sharp distal apex.

Like the pyramidal microneedle 1100 described above with respect to FIG. 11A, the microneedle 1300 may derive its mechanical strength at least in part from anisotropically etched <311> planes and the pyramidal shape. However, an asymmetric pyramidal microneedle with a asymmetric cut surface may be advantageous in that it may reduce the longitudinal shear forces compared to a symmetric microneedle having similar dimensions but lacking the asymmetric cut. Furthermore, a sharper (e.g., more acute angle) distal microneedle tip may be achieved with such an asymmetric cut surface. Although the cut surface 1350 is shown in FIG. 13A as positioned at a non-orthogonal angle relative to the base of the microneedle, alternatively as described above, in some variations the cut surface 1350 may be generally orthogonal or normal to the base of the microneedle (and/or surface of the substrate 1302), which may further reduce the longitudinal shear forces in the microneedle.

Figure 14A:
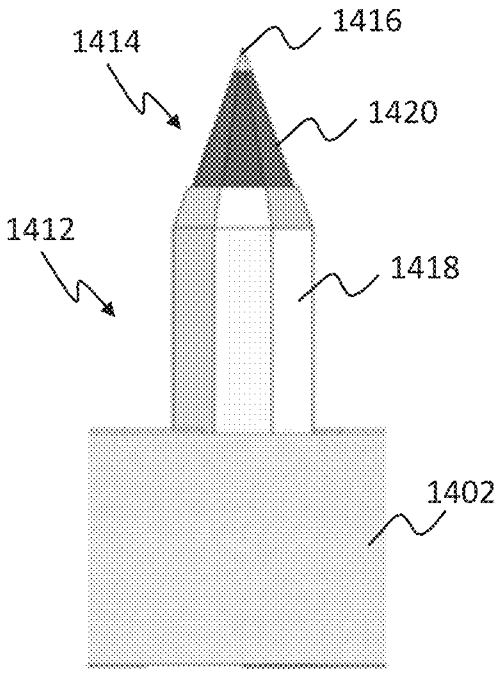
FIG. 14A depicts an illustrative schematic of a columnar-pyramidal microneedle having a tapered distal end.
Figure 14B:
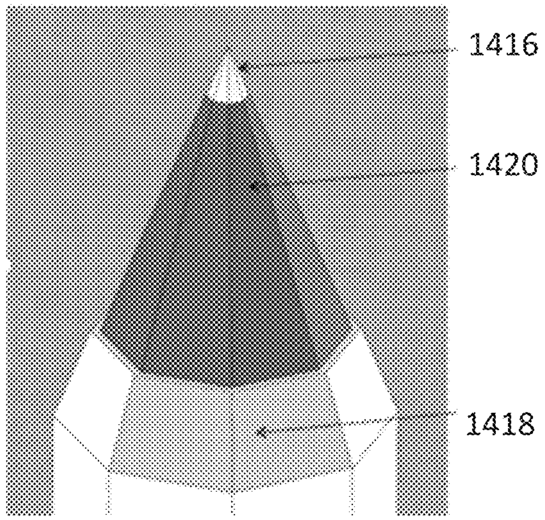
FIG. 14B depicts a detailed view of the distal portion of the microneedle depicted in FIG. 14A.

In some variations, a microneedle may be similar to those described above, except that the microneedle may include a columnar body portion and a pyramidal distal portion. For example, as shown in FIG. 14A, a columnar-pyramidal microneedle 1400 may include a columnar body portion 1412 that may extend from a polygonal (e.g., octagonal) base out of a non-electrically conductive substrate 1402 such as intrinsic (undoped) silicon. Additionally, the columnar-pyramidal microneedle 1400 may include a tapered distal portion 1414 having a pyramidal shape with a plurality of planar facets. For example, the columnar-pyramidal microneedle 1400 may include a tapered distal portion 1414 having a pyramidal shape with eight facets extending from the octagonal columnar body portion 1412. However, the pyramidal shape may have any suitable number of planar facets (e.g., one, two, three, four, five, six, seven, nine, or more). An annular electrode 1420 may be formed on all the planar facets of the pyramidal distal portion 1414, or on only a portion of the planar facets (e.g., on one, two, three, four, five, six, seven facets) may include a metallization surface for the electrode. Similar to that described above, the columnar body portion 1412 may include a conductive core including an electrically conductive material functioning as a conductive pathway for signals to and from the electrode 1420. The columnar body portion 1412 may further include an insulation material 1418 may extend along the body portion 1412 and up to (or slightly overlapping) a proximal edge of the electrode 1420. The distal apex 1416 may or may not be covered by similar insulation material.

In some variations, the tapered distal portion 1414 may be similar to that described above with respect to FIGS. 11A-11C, 12, and/or 13A-13E. For example, the tapered distal portion 1414 may be formed using anisotropic wet etching techniques. The electrode 1420 may be formed on the tapered distal portion 1414 by lithography, electrodeposition or other suitable technique. The tapered distal portion 1414 may then be protected by an etch resistant material while the body portion 1412 is formed out of the substrate by dry etching (e.g., DRIE) or other suitable process(es).

The combination of columnar and pyramidal aspects of the microneedle 1400 has a number of advantages. Similar to that described above, the tapered distal portion 1414 and apex 1416 have high mechanical strength due to the <311> wet etched planes and the pyramidal shape. Additionally, because the substrate is formed from a non-conductive material, an insulation "moat" as described above may not be required to electrically isolate the microneedle, thereby simplifying and reducing cost of fabrication. The absence of the insulation moat also permits material continuity in the substrate, which may lead to better mechanical integrity of the overall microneedle array structure.

Although the columnar-pyramidal microneedle 1400 is described above as including a non-conductive substrate, it should be understood alternatively, in some variations a columnar-pyramidal microneedle may include a conductive core extending from a conductive substrate (e.g., doped silicon). For example, in some variations the columnar body portion 1412 may be similar to that described above with respect to FIGS. 7A-7C, and 8-10 (e.g., may include an insulation moat to electrically isolate the microneedle, etc.).

Figure 15A:
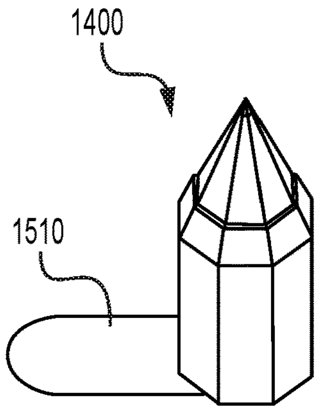
FIGS. 15A-15D depict illustrative schematics of formation of conductive pathways within a microneedle array.
Figure 15B:
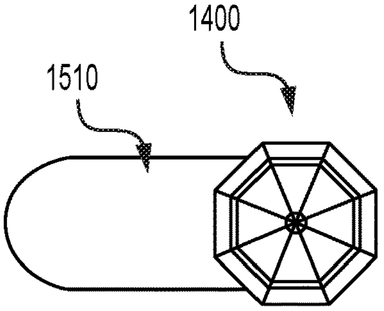
Figure 15C:
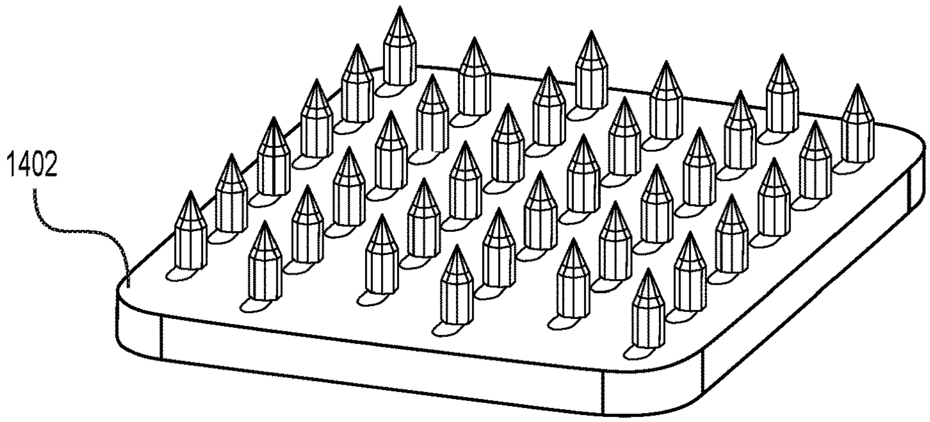
Figure 15D:
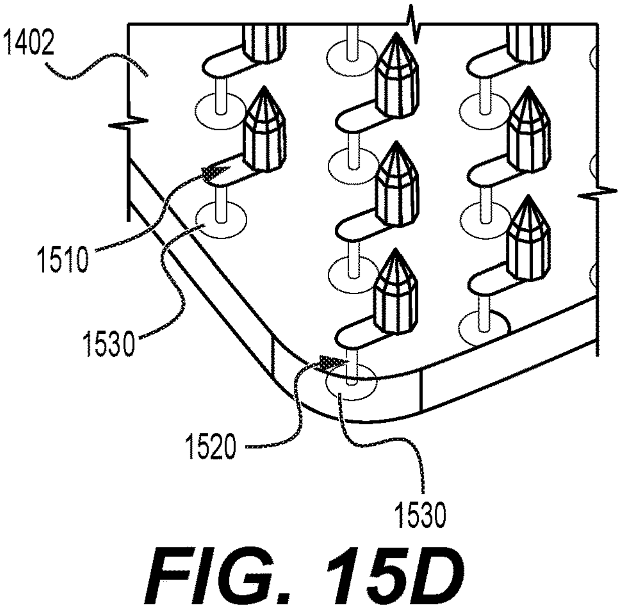

In some variations of microneedle arrays including one or more microneedles 1400, conductive pathways may be formed in the non-conductive substrate to facilitate communication with the electrode(s) 1420. For example, as described above, the body portion 1412 of each microneedle may include a conductive core including a conductive material. Such conductive material may extend between the electrode 1420 to the substrate 1402. As shown in FIG. 15D, the microneedle array may include one or more connectors 1510 made of a conductive material (e.g., gold, aluminum) that is each in turn coupled to a backside electrical contact 1530 for further sensor communication. In some variations, as shown FIGS. 15A-15D, the one or more connectors 1510 may extend laterally along the surface of the substrate and then connect to the backside electrical contact 1530 with a conductive via 1520 within the substrate.

Additional details of example variations of microneedle array configurations are described in further detail below.

Electrodes

As described above, each microneedle in the microneedle array may include an electrode. In some variations, multiple distinct types of electrodes may be included among the microneedles in the microneedle array. For example, in some variations the microneedle array may function as an electrochemical cell operable in an electrolytic manner with three types of electrodes. In other words, the microneedle array may include at least one working electrode, at least one counter electrode, and at least one reference electrode. Thus, the microneedle array may include three distinct electrode types, though one or more of each electrode type may form a complete system (e.g., the system might include multiple distinct working electrodes). Furthermore, multiple distinct microneedles may be electrically joined to form an effective electrode type (e.g., a single working electrode may be formed from two or more connected microneedles with working electrode sites). Each of these electrode types may include a metallization layer and may include one or more coatings or layers over the metallization layer that help facilitate the function of that electrode.

Generally, the working electrode is the electrode at which oxidation and/or reduction reaction of interest occurs for detection of an analyte of interest. The counter electrode functions to source (provide) or sink (accumulate) the electrons, via an electrical current, that are required to sustain the electrochemical reaction at the working electrode. The reference electrode functions to provide a reference potential for the system; that is, the electrical potential at which the working electrode is biased is referenced to the reference electrode. A fixed, time-varying, or at least controlled potential relationship is established between the working and reference electrodes, and within practical limits no current is sourced from or sinked to the reference electrode. Additionally, to implement such a three-electrode system, the analyte monitoring device may include a suitable potentiostat or electrochemical analog front end to maintain a fixed potential relationship between the working electrode and reference electrode contingents within the electrochemical system (via an electronic feedback mechanism), while permitting the counter electrode to dynamically swing to potentials required to sustain the redox reaction of interest.

Working Electrode

As described above, the working electrode is the electrode at which the oxidation and/or reduction reaction of interest occurs. In some variations, sensing may be performed at the interface of the working electrode and interstitial fluid located within the body (e.g., on an outer surface of the overall microneedle). In some variations, a working electrode may include an electrode material and a biorecognition layer in which a biorecognition element (e.g., enzyme) is immobilized on the working electrode to facilitate selective analyte quantification. In some variations, the biorecognition layer may also function as an interference-blocking layer and may help prevent endogenous and/or exogenous species from directly oxidizing (or reducing) at the electrode.

A redox current detected at the working electrode may be correlated to a detected concentration of an analyte of interest. This is because assuming a steady-state, diffusion-limited system, the redox current detected at the working electrode follows the Cottrell relation below:

$$i(t) = \frac{nFA\sqrt{D}C}{\sqrt{\pi t}}$$

where n is the stoichiometric number of electrons mitigating a redox reaction, F is Faraday's constant, A is electrode surface area, D is the diffusion coefficient of the analyte of interest, C is the concentration of the analyte of interest, and t is the duration of time that the system is biased with an electrical potential. Thus, the detected current at the working electrode scales linearly with the analyte concentration.

Moreover, because the detected current is a direct function of electrode surface area A, the surface area of the electrode may be increased to enhance the sensitivity (e.g., amperes per molar of analyte) of the sensor. For example, multiple singular working electrodes may be grouped into arrays of two or more constituents to increase total effective sensing surface area. Additionally or alternatively, to obtain redundancy, multiple working electrodes may be operated as parallelized sensors to obtain a plurality of independent measures of the concentration of an analyte of interest. The working electrode can either be operated as the anode (such that an analyte is oxidized at its surface), or as the cathode (such that an analyte is reduced at its surface).

Figure 16A:
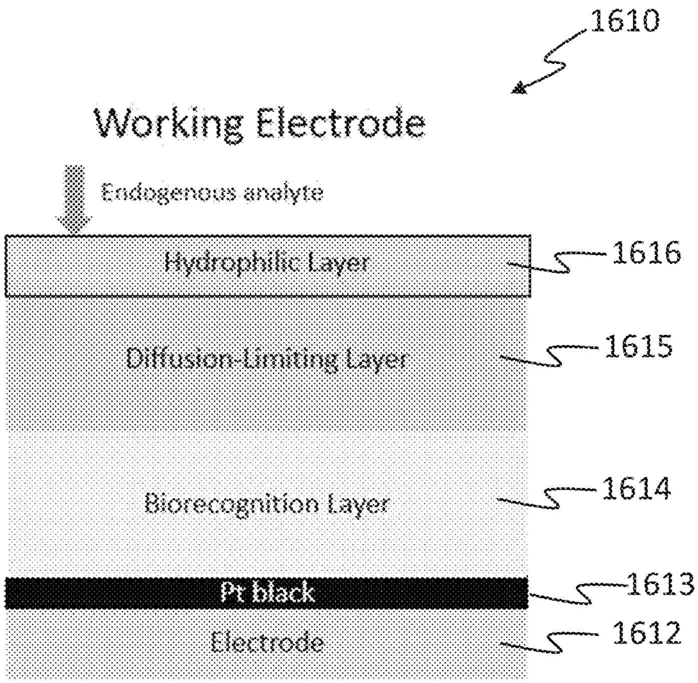
FIGS. 16A-16C depict illustrative schematics of layered structures of a working electrode, a counter electrode, and a reference electrode, respectively.

FIG. 16A depicts a schematic of an exemplary set of layers for a working electrode 1610. For example, as described above, in some variations the working electrode 1610 may include an electrode material 1612 and a biorecognition layer including a biorecognition element. The electrode material 1612 functions to encourage the electrocatalytic detection of an analyte or the product of the reaction of the analyte and the biorecognition element. The electrode material 1612 also provides ohmic contact and routes an electrical signal from the electrocatalytic reaction to processing circuitry. In some variations, the electrode material 1612 may include platinum as shown in FIG. 16A. However, the electrode material 1612 may alternatively include, for example, palladium, iridium, rhodium, gold, ruthenium, titanium, nickel, carbon, doped diamond, or other suitable catalytic and inert material.

In some variations, the electrode material 1612 may be coated with a highly porous electrocatalytic layer, such as a platinum black layer 1613, which may augment the electrode surface area for enhanced sensitivity. Additionally or alternatively, the platinum black layer 1613 may enable the electrocatalytic oxidation or reduction of the product of the biorecognition reaction facilitated by the biorecognition layer 1614. However, in some variations the platinum black layer 1613 may be omitted (as shown in FIGS. 16D and 16G, for example). The electrode may enable the electrocatalytic oxidation or reduction of the product of the biorecognition reaction if the platinum black layer 1613 is not present.

The biorecognition layer 1614 may be arranged over the electrode material 1612 (or platinum black layer 1613 if it is present) and functions to immobilize and stabilize the biorecognition element which facilitates selective analyte quantification for extended time periods. In some variations, the biorecognition element may include an enzyme, such as an oxidase. As an exemplary variation for use in a glucose monitoring system, the biorecognition element may include glucose oxidase, which converts glucose, in the presence of oxygen, to an electroactive product (i.e., hydrogen peroxide) that can be detected at the electrode surface. Specifically, the redox equation associated with this exemplary variation is Glucose+Oxygen→Hydrogen Peroxide+Gluconolactone (mediated by glucose oxidase); Hydrogen Peroxide→Water+Oxygen (mediated by applying an oxidizing potential at the working electrode).

However, in other variations the biorecognition element may additionally or alternatively comprise another suitable oxidase or oxidoreductase enzyme such as lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and/or xanthine oxidase.

In some variations, the biorecognition element may be cross-linked with an amine-condensing carbonyl chemical species that may help stabilize the biorecognition element within the biorecognition layer 1614. As further described below, in some variations, the cross-linking of the biorecognition element may result in the microneedle array being compatible with ethylene oxide (EO) sterilization, which permits exposure of the entire analyte monitoring device (including sensing elements and electronics) to the same sterilization cycle, thereby simplifying the sterilization process and lowering manufacture costs. For example, the biorecognition element may be cross-linked with glutaraldehyde, formaldehyde, glyoxal, malonaldehyde, succinaldehyde, and/or other suitable species. In some variations, the biorecognition element may be cross-linked with such an amine-condensing carbonyl chemical species to form cross-linked biorecognition element aggregates. Cross-linked biorecognition element aggregates that have at least a threshold molecular weight may then be embedded in a conducting polymer. By embedding only those aggregates that have a threshold molecular weight, any uncross-linked enzymes may be screened out and not incorporated into the biorecogntion layer. Accordingly, only aggregates having a desired molecular weight may be selected for use in the conducting polymer, to help ensure that only sufficiently stabilized, cross-linked enzyme entities are included in the biorecognition layer, thereby contributing to a biorecognition layer that is overall better suited for EO sterilization without loss in sensing performance. In some variations, only cross-linked aggregates that have a molecular weight that is at least twice that of glucose oxidase may be embedded in the conducting polymer.

In some variations, the conducting polymer may be permselective to contribute to the biorecognition layer's robustness against circulating androgynous electroactive species (e.g., ascorbic acid, vitamin C, etc.), fluctuations of which may adversely affect the sensitivity of the sensor. Such a permselective conducting polymer in the biorecognition layer may further be more robust against pharmacological interferences (e.g., acetaminophen) in the interstitial fluid that may affect sensor accuracy. Conducting polymers may be made permselective by, for example, removing excess charge carriers by an oxidative electropolymerization process or by neutralizing these charge carriers with a counter-ion dopant, thereby transforming the conducting polymer into a non-conducting form. These oxidatively-polymerized conducting polymers exhibit permselectivity and are hence able to reject ions of similar charge polarity to the dopant ion (net positive or negative) or by via size exclusion due to the dense and compact form of the conducting polymers.

Furthermore, in some variations the conducting polymer may exhibit self-sealing and/or self-healing properties. For example, the conducting polymer may undergo oxidative electropolymerization, during which the conducting polymer may lose its conductivity as the thickness of the deposited conducting polymer on the electrode increases, until the lack of sufficient conductivity causes the deposition of additional conducting polymer to diminish. In the event that the conducting polymer has succumbed to minor physical damage (e.g., during use), the polymeric backbone may re-assemble to neutralize free charge and thereby lower overall surface energy of the molecular structure, which may manifest as self-sealing and/or self-healing properties.

In some variations, the working electrode may further include a diffusion-limiting layer 1615 arranged over the biorecognition layer 1614. The diffusion-limiting layer 1615 may function to limit the flux of the analyte of interest in order to reduce the sensitivity of the sensor to endogenous oxygen fluctuations. For example, the diffusion-limiting layer 1615 may attenuate the concentration of the analyte of interest so that it becomes the limiting reactant to an aerobic enzyme. However, in some variation (e.g., if the biorecognition element is not aerobic), the diffusion-limiting layer 1615 may be omitted.

The working electrode may further include, in some variations, a hydrophilic layer 1616 that provides for a biocompatible interface to, for example, reduce the foreign body response. However, in some variations the hydrophilic layer 1616 may be omitted (e.g., if the diffusion-limiting layer expresses hydrophilic moieties to serve this purpose), as shown in FIGS. 16D and 16G, for example.

Counter Electrode

As described above, the counter electrode is the electrode that is sourcing or sinking electrons (via an electrical current) required to sustain the electrochemical reaction at the working electrode. The number of counter electrode constituents can be augmented in the form of a counter electrode array to enhance surface area such that the current-carrying capacity of the counter electrode does not limit the redox reaction of the working electrode. It thus may be desirable to have an excess of counter electrode area versus the working electrode area to circumvent the current-carrying capacity limitation. If the working electrode is operated as an anode, the counter electrode will serve as the cathode and vice versa. Similarly, if an oxidation reaction occurs at the working electrode, a reduction reaction occurs at the counter electrode and vice versa. Unlike the working or reference electrodes, the counter electrode is permitted to dynamically swing to electrical potentials required to sustain the redox reaction of interest on the working electrode.

Figure 16B:
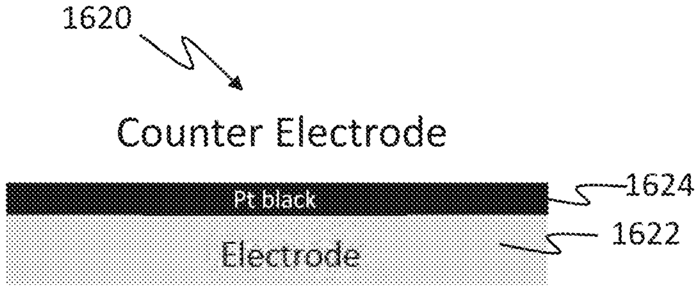

As shown in FIG. 16B, a counter electrode 1620 may include an electrode material 1622, similar to electrode material 1612. For example, like the electrode material 1612, the electrode material 1622 in the counter electrode 1620 may include a noble metal such as gold, platinum, palladium, iridium, carbon, doped diamond, and/or other suitable catalytic and inert material.

In some variations, the counter electrode 1620 may have few or no additional layers over the electrode material 1632. However, in some variations the counter electrode 1620 may benefit from increase surface area to increase the amount of current it can support. For example, the counter electrode material 1632 may be textured or otherwise roughened in such a way to augment the surface area of the electrode material 1632 for enhanced current sourcing or sinking ability. Additionally or alternatively, the counter electrode 1620 may include a layer of platinum black 1624, which may augment electrode surface as described above with respect to some variations of the working electrode. However, in some variations of the counter electrode, the layer of platinum black may be omitted (e.g., as shown in FIG. 16E). In some variations, the counter electrode may further include, a hydrophilic layer that provides for a biocompatible interface to, for example, reduce the foreign body response.

Figure 16C:
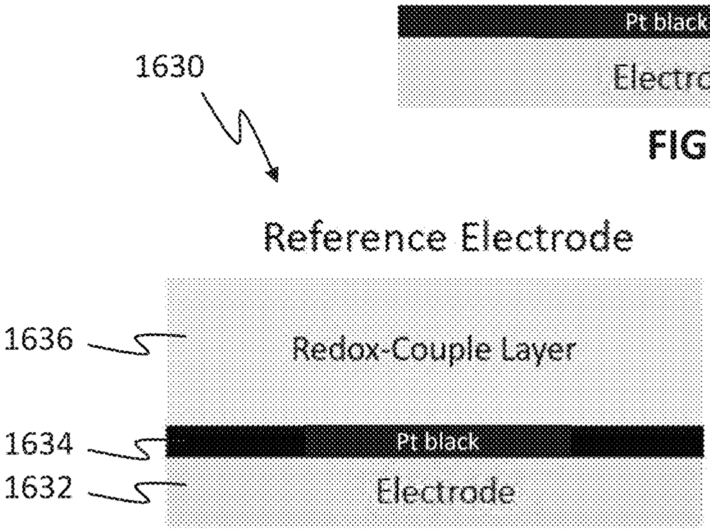
Figure 16D:
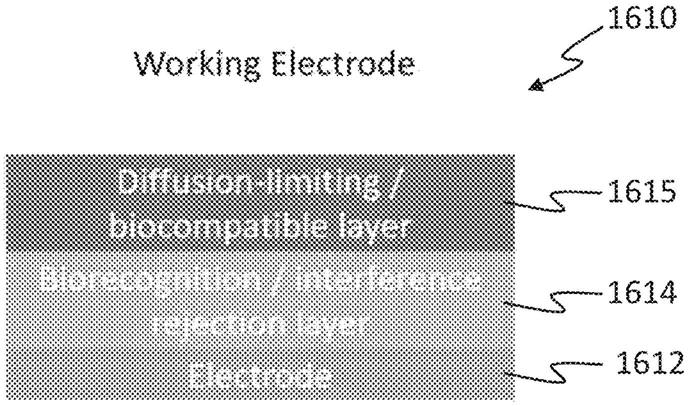
FIGS. 16D-16F depict illustrative schematics of layered structures of a working electrode, a counter electrode, and a reference electrode, respectively.
Figure 16E:
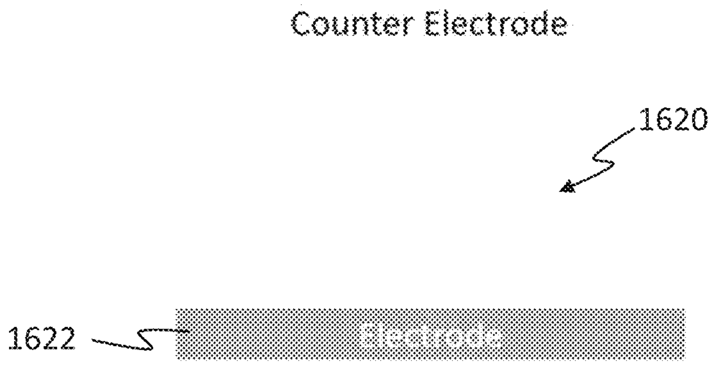
Figure 16F:
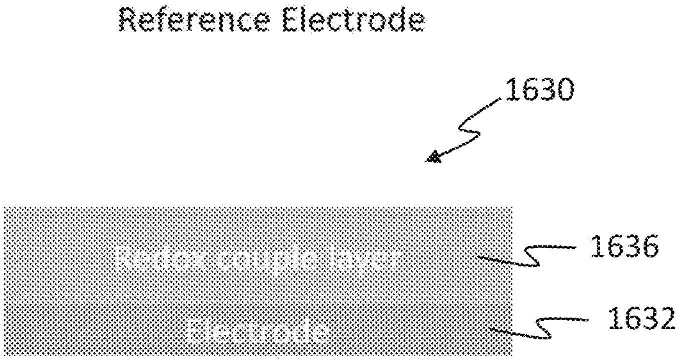
Figure 16G:
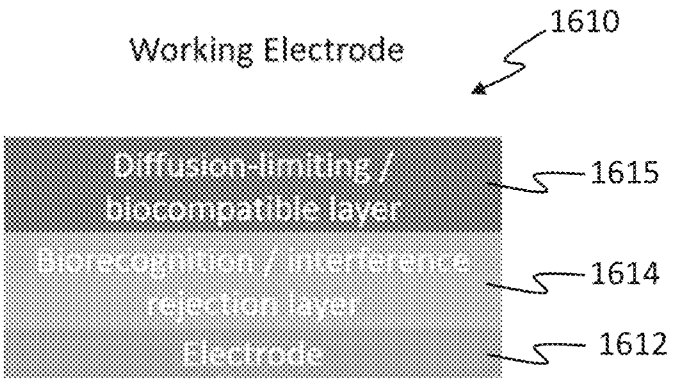
FIGS. 16G-16I depict illustrative schematics of layered structures of a working electrode, a counter electrode, and a reference electrode, respectively.
Figure 16H:
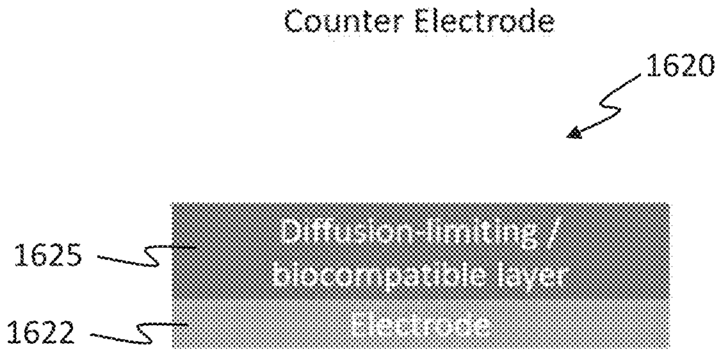

Additionally or alternatively, in some variations as shown in FIG. 16H, the counter electrode 1620 may include a diffusion-limiting layer 1625 (e.g., arranged over the electrode). The diffusion-limiting layer 1625 may, for example, be similar to the diffusion-limiting layer 1615 described above with respect to FIG. 16A.

Reference Electrode

As described above, the reference electrode functions to provide a reference potential for the system; that is, the electrical potential at which the working electrode is biased is referenced to the reference electrode. A fixed or at least controlled potential relationship may be established between the working and reference electrodes, and within practical limits no current is sourced from or sinked to the reference electrode.

As shown in FIG. 16C, a reference electrode 1630 may include an electrode material 1632, similar to electrode material 1612. In some variations, like the electrode material 1612, the electrode material 1632 in the reference electrode 1630 may include a metal salt or metal oxide, which serves as a stable redox coupled with a well-known electrode potential. For example, the metal salt may, for example, include silver-silver chloride (Ag/AgCl) and the metal oxide may include iridium oxide ($IrOx/Ir_2O_3/IrO_2$). In other variations, noble and inert metal surfaces may function as quasi-reference electrodes and include gold, platinum, palladium, iridium, carbon, doped diamond, and/or other suitable catalytic and inert material. Furthermore, in some variations the reference electrode 1630 may be textured or otherwise roughened in such a way to enhance adhesion with any subsequent layers. Such subsequent layers on the electrode material 1632 may include a platinum black layer 1634. However, in some variations, the platinum black layer may be omitted (e.g., as shown in FIGS. 16F and 16I).

The reference electrode 1630 may, in some variations, further include a redox-couple layer 1636, which main contain a surface-immobilized, solid-state redox couple with a stable thermodynamic potential. For example, the reference electrode may operate at a stable standard thermodynamic potential with respect to a standard hydrogen electrode (SHE). The high stability of the electrode potential may be attained by employing a redox system with constant (e.g., buffered or saturated) concentrations of each participant of the redox reaction. For example, the reference electrode may include saturated Ag/AgCl (E=+0.197V vs. SHE) or IrOx (E=+0.177 vs. SHE, pH=7.00) in the redox-couple layer 1636. Other examples of redox-couple layers 1636 may include a suitable conducting polymer with a dopant molecule such as that described in U.S. Patent Pub.

No. 2019/0309433, which is incorporated in its entirety herein by this reference. In some variations, the reference electrode may be used as a half-cell to construct a complete electrochemical cell.

Figure 16I:
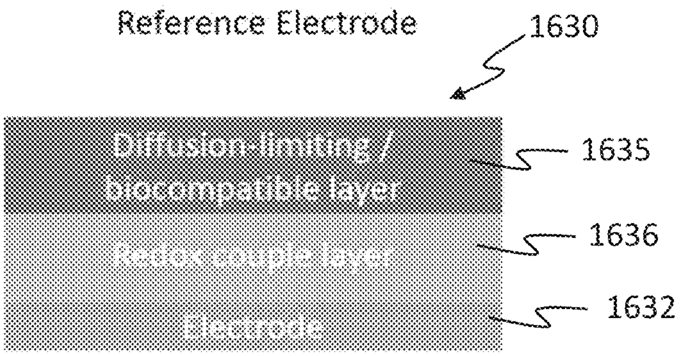

Additionally or alternatively, in some variations as shown in FIG. 16I, the reference electrode 1630 may include a diffusion-limiting layer 1635 (e.g., arranged over the electrode and/or the redox-couple layer). The diffusion-limiting layer 1635 may, for example, be similar to the diffusion-limiting layer 1615 described above with respect to FIG. 16A.

Exemplary Electrode Layer Formation

Various layers of the working electrode, counter electrode, and reference electrode may be applied to the microneedle array and/or functionalized, etc. using suitable processes such as those described below.

In a pre-processing step for the microneedle array, the microneedle array may be plasma cleaned in an inert gas (e.g., RF-generated inert gas such as argon) plasma environment to render the surface of the material, including the electrode material (e.g., electrode material 1612, 1622, and 1632 as described above), to be more hydrophilic and chemically reactive. This pre-processing functions to not only physically remove organic debris and contaminants, but also to clean and prepare the electrode surface to enhance adhesion of subsequently deposited films on its surface.

Working Electrode

Anodization: To configure the working electrode after the pre-processing step, the electrode material 1612 may undergo an anodization treatment using an amperometry approach in which the electrode constituent(s) assigned for the working electrode function is (are) subject to a fixed high anodic potential (e.g., between +1.0-+1.3 V vs. Ag/AgCl reference electrode) for a suitable amount of time (e.g., between about 30 sec and about 10 min) in a moderate-strength acid solution (e.g., 0.1-3M $H_2SO_4$). In this process, a thin, yet stable native oxide layer may be generated on the electrode surface. Owing to the low pH arising at the electrode surface, any trace contaminants may be removed as well.

In an alternative embodiment using a coulometry approach, anodization can proceed until a specified amount of charge has passed (measured in Coulombs). The anodic potential may be applied as described above; however, the duration of this might vary until the specified amount of charge has passed.

Activation: Following the anodization process, the working electrode constituents may be subjected to a cyclically-scanned potential waveform in an activation process using cyclic voltammetry. In the activation process, which may occur in a moderate-strength acid solution (e.g. 0.1-3M $H_2SO_4$), the potential applied may time-varying in a suitable function (e.g., sawtooth function). For example, the voltage may be linearly scanned between a cathodic value (e.g., between −0.3-−0.2 V vs. Ag/AgCl reference electrode) and an anodic value (e.g., between +1.0-+1.3 V vs. Ag/AgCl reference electrode) in an alternating function (e.g., 15-50 linear sweep segments). The scan rate of this waveform can take on a value between 1-1000 mV/sec. It should be noted that a current peak arising during the anodic sweep (sweep to positive extreme) corresponds to the oxidation of a chemical species, while the current peak arising during the ensuing cathodic sweep (sweep to negative extreme) corresponds to the reduction of said chemical species.

Functionalization of the biorecognition layer: Following the activation process, the working electrode constituents may be functionalized with the biorecognition layer 1614 such as that described above. Assuming that the working electrode contingent of the microneedle array has undergone the aforementioned steps, the potential applied may be time-varying in a sawtooth function. For example, a voltage may be linearly scanned between a cathodic value (e.g., between 0.0 V vs. Ag/AgCl reference electrode) and an anodic value (e.g., between +1.0 V vs Ag/AgCl reference electrode) in an alternating function (e.g., 10 linear sweep segments). In an example variation, the scan rate of this waveform can take on a value between about 1 mV/sec and about 10 mV/sec in an aqueous solution comprised of a monomeric precursor to the entrapment conducting polymer and a cross-linked biorecognition element (e.g., enzyme, such as glucose oxidase). In this process, a thin film (e.g., between about 10 nm and about 1000 nm) of biorecognition layer comprising of polymer with a dispersed cross-linked biorecognition element may be generated (e.g., electrodeposited or electropolymerized) on the working electrode surface. In some variations, the conducting polymer may include one or more of aniline, pyrrole, acetylene, phenylene, phenylene vinylene, phenylene diamine, thiophene, 3,4-ethylenedioxythiophene, and aminophenylboronic acid. The biorecognition layer imparts a selective sensing capability towards an analyte of interest, as described above.

In some variations, the working electrode surface may be electrochemically roughened in order to enhance adhesion of the biorecognition layer to the electrode material 1612 surface (and/or Pt black layer). The roughening process may involve a cathodization treatment (e.g., cathodic deposition, a subset of amperometry) wherein the electrode is subject to a fixed cathodic potential (e.g., between −0.4-+0.2 V vs. Ag/AgCl reference electrode) for a certain amount of time (e.g., 5 sec-10 min) in an acid solution containing the desired metal cation dissolved therein (e.g., 0.01-100 mM $H_2PtCl_6$). Alternatively, the electrode is subject to a fixed cathodic potential (e.g., between about −0.4 to about +0.2 V vs. Ag/AgCl reference electrode) until a certain amount of charge has passed (e.g., 0.1 mC-100 mC) in an acid solution containing the desired metal cation dissolved therein (e.g., 0.01-100 mM $H_2PtCl_6$). In this process, a thin, yet highly porous layer of the metal may be generated on the electrode surface, thereby augmenting the electrode surface area dramatically. Additionally or alternatively, in some variations as described above, elemental platinum metal may deposited on the electrode to form or deposit a platinum black layer 1613.

Functionalization of the diffusion-limiting layer: Following the functionalization of the biorecognition layer, the working electrode constituents may, in some variations, be functionalized with the diffusion-limiting layer. Assuming that the working electrode contingent of the microneedle array has undergone the aforementioned steps, one or more of the following methods may be employed to apply the diffusion-limiting layer, which may be a thin film of thickness between about 100 nm to about 10,000 nm.

In some variations, a diffusion-limiting layer may applied by a spray coating method in which an aerosolized polymer formulation (dispersed in water or a solvent) is applied to the microneedle array device with a specified spray pattern and duration in a controlled-environment setting. This creates a thin film with the desired thickness and porosity required to restrict the diffusion of an analyte of interest to the biorecognition layer.

In some variations, a diffusion-limiting layer may be applied by a plasma-induced polymerization method in which a plasma source generates a gas discharge that provides energy to activate a cross-linking reaction within a gaseous, aerosolized, or liquid monomeric precursor (e.g., vinylpyridine). This converts the monomeric precursor to a polymeric coating that may be deposited on the microneedle array to a specified thickness, thereby creating a thin film with the desired thickness and porosity required to restrict the diffusion of an analyte of interest to the biorecognition layer 1614.

Furthermore, in some variations, a diffusion-limiting layer may applied by electrophoretic or dielectrophoretic deposition, such as example techniques described in U.S. Pat. No. 10,092,207, which is incorporated herein in its entirety by this reference.

Counter Electrode

Anodization: In some variations, the counter electrode material may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the counter electrode may alternatively use a coulometry approach as described above.

Activation: In some variations, following the anodization process, the counter electrode constituents may be subjected to a cyclically-scanned potential waveform in an activation process using cyclic voltammetry. In some variations, the activation process may be similar to that described above for the working electrode.

Roughening: Furthermore, in some variations, the counter electrode surface may be electrochemically roughened in order to enhance the current-sinking or current-sourcing capacity of this electrode contingent. The electrochemical roughening process may be similar to that described above for the working electrode. Additionally or alternatively, in some variations as described above, elemental platinum metal may deposited on the electrode to form or deposit a platinum black layer 1623.

Reference Electrode

Anodization: Like the working and counter electrodes as described above, the reference electrode may undergo an anodization treatment using an amperometry approach in which the electrode constituent(s) assigned for the counter electrode function is subject to a fixed high anodic potential or a suitable amount of time in a moderate-strength acid solution. Exemplary parameters and other specifics of the anodization process for the counter electrode may be similar to that described above for the working electrode. Similarly, anodization for the counter electrode may Activation: Following the anodization process, the reference electrode constituents may be subjected to a cyclically-scanned potential waveform in an activation process using cyclic voltammetry. In some variations, the activation process may be similar to that described above for the working electrode.

Functionalization: Following the activation process, the reference electrode constituents may be functionalized. Assuming that the reference electrode contingent of the microneedle array has undergone the aforementioned steps, a fixed anodic potential (e.g., between +0.4-+1.0 V vs. Ag/AgCl reference electrode) may be applied for a certain suitable duration (e.g., between about 10 sec and about 10 min) in an aqueous solution. Alternatively, the reference electrode is subject to a fixed anodic potential (e.g., between about +0.4 to about +1.0 V vs. Ag/AgCl reference electrode) until a certain amount of charge has passed (e.g., 0.01 mC-10 mC) in an aqueous solution. In some variations, the aqueous solution may include a monomeric precursor to a conducting polymer and a charged dopant counter ion or material (e.g., poly(styrene sulfonate)) carrying an opposing charge. In this process, a thin film (e.g., between about 10 nm and about 10,000 nm) of a conducting polymer with a dispersed counter ion or material may be generated on the reference electrode surface. This creates a surface-immobilized, solid-state redox couple with a stable thermodynamic potential. In some variations, the conducting polymer may include one or more of aniline, pyrrole, acetylene, phenylene, phenylene vinylene, phenylene diamine, thiophene, 3,4-ethylenedioxythiophene, and aminophenylboronic acid.

In some alternative embodiments, a native iridium oxide film (e.g., $IrO_2$ or $Ir_2O_3$ or $IrO_4$) may be electrochemically grown on an iridium electrode surface in an oxidative process. This also creates a stable redox couple, as discussed above.

Furthermore, in some variations the reference electrode surface may be electrochemically roughened in order to enhance adhesion of the surface-immobilized redox couple. The electrochemical roughening process may be similar to that described above for the working electrode. Additionally or alternatively, in some variations as described above, elemental platinum metal may deposited on the electrode to form or deposit a platinum black layer 1633.

Other features and techniques for forming the reference electrode may be similar to that described in, for example, U.S. Patent Pub. No. 2019/0309433, which was incorporated above by reference.

Microneedle Array Configurations

Multiple microneedles (e.g., any of the microneedle variations described herein, each of which may have a working electrode, counter electrode, or reference electrode as described above) may be arranged in a microneedle array. Considerations of how to configure the microneedles include factors such as desired insertion force for penetrating skin with the microneedle array, optimization of electrode signal levels and other performance aspects, manufacturing costs and complexity, etc.

For example, the microneedle array may include multiple microneedles that are spaced apart at a predefined pitch (distance between the center of one microneedle to the center of its nearest neighboring microneedle). In some variations, the microneedles may be spaced apart with a sufficient pitch so as to distribute force (e.g., avoid a "bed of nails" effect) that is applied to the skin of the user to cause the microneedle array to penetrate the skin. As pitch increases, force required to insert the microneedle array tends to decrease and depth of penetration tends to increase. However, it has been found that pitch only begins to affect insertion force at low values (e.g., less than about 150 μm). Accordingly, in some variations the microneedles in a microneedle array may have a pitch of at least 200 μm, at least 300 μm, at least 400 μm, at least 500 μm, at least 600 μm, at least 700 μm, or at least 750 μm. For example, the pitch may be between about 200 μm and about 800 μm, between about 300 μm and about 700 μm, or between about 400 μm and about 600 μm. In some variations, the microneedles may be arranged in a periodic grid, and the pitch may be uniform in all directions and across all regions of the microneedle array. Alternatively, the pitch may be different as measured along different axes (e.g., X, Y directions) and/or some regions of the microneedle array may include a smaller pitch while other may include a larger pitch.

Figure 17:
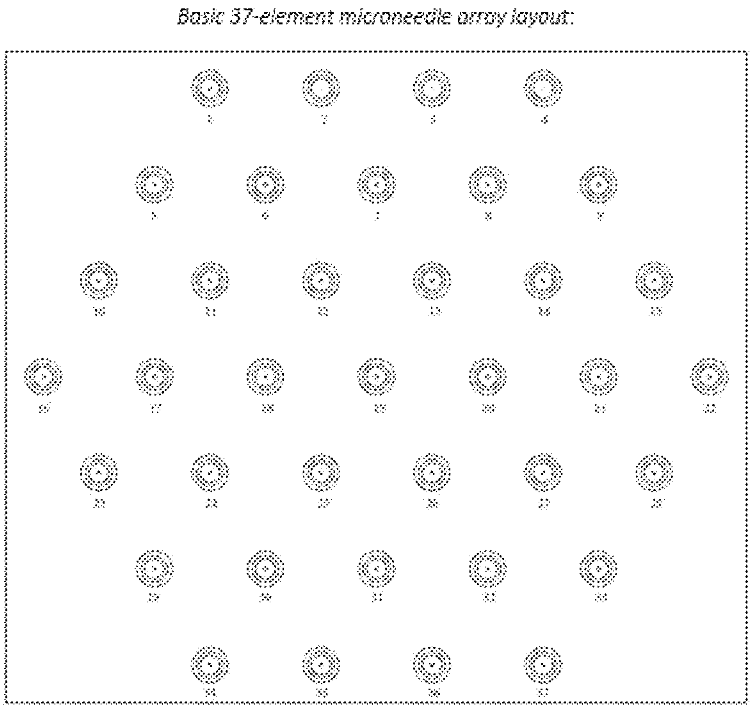
FIG. 17 depicts an illustrative schematic of a microneedle array configuration.
Figure 29A:
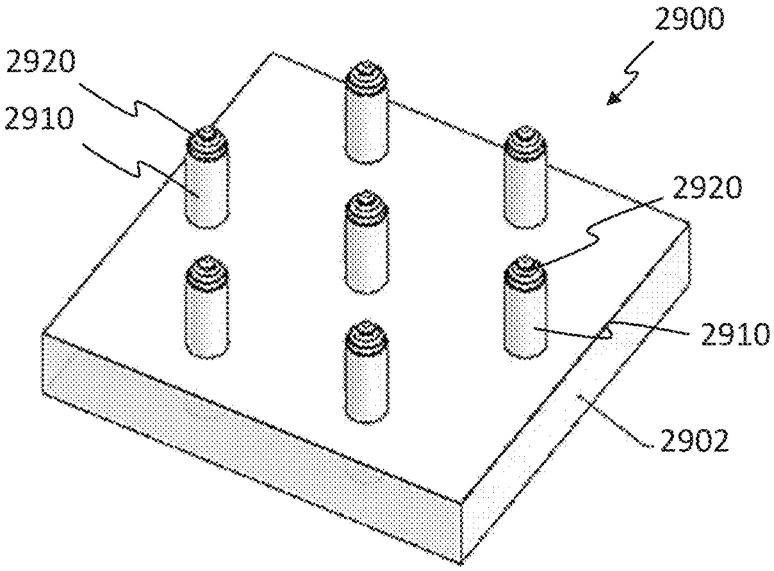
FIGS. 29A and 29B depict illustrative schematics of a microneedle array configuration.
Figure 29B:
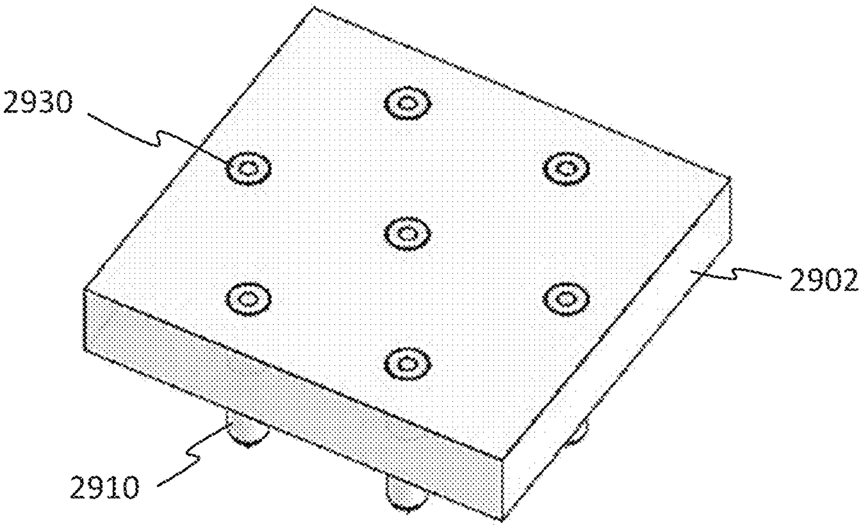

Furthermore, for more consistent penetration, microneedles may be spaced equidistant from one another (e.g., same pitch in all directions). To that end, in some variations, the microneedles in a microneedle array may be arranged in a hexagonal configuration as shown in FIG. 17. Alternatively, the microneedles in a microneedle array may arranged in a rectangular array (e.g., square array), or in another suitable symmetrical manner Another consideration for determining configuration of a microneedle array is overall signal level provided by the microneedles. Generally, signal level at each microneedle is invariant of the total number of microneedle elements in an array. However, signal levels can be enhanced by electrically interconnecting multiple microneedles together in an array. For example, an array with a large number of electrically connected microneedles is expected to produce a greater signal intensity (and hence increased accuracy) than one with fewer microneedles. However, a higher number of microneedles on a die will increase die cost (given a constant pitch) and will also require greater force and/or velocity to insert into skin. In contrast, a lower number of microneedles on a die may reduce die cost and enable insertion into the skin with reduced application force and/or velocity. Furthermore, in some variations a lower number of microneedles on a die may reduce the overall footprint area of the die, which may lead to less unwanted localized edema and/or erythema. Accordingly, in some variations, a balance among these factors may be achieved with a microneedle array including 37 microneedles as shown in FIG. 17 or a microneedle array including 7 microneedles are shown in FIGS. 29A and 29B. However, in other variations there may be fewer microneedles in an array (e.g., between about 5 and about 35, between about 5 and about 30, between about 5 and about 25, between about 5 and about 20, between about 5 and about 15, between about 5 and about 100, between about 10 and about 30, between about 15 and about 25, etc.) or more microneedles in an array (e.g., more than 37, more than 40, more than 45, etc.).

Additionally, as described in further detail below, in some variations only a subset of the microneedles in a microneedle array may be active during operation of the analyte monitoring device. For example, a portion of the microneedles in a microneedle array may be inactive (e.g., no signals read from electrodes of inactive microneedles). In some variations, a portion of the microneedles in a microneedle array may be activated at a certain time during operation and remain active for the remainder of the operating lifetime of the device. Furthermore, in some variations, a portion of the microneedles in a microneedle array may additionally or alternatively be deactivated at a certain time during operation and remain inactive for the remainder of the operating lifetime of the device.

In considering characteristics of a die for a microneedle array, die size is a function of the number of microneedles in the microneedle array and the pitch of the microneedles. Manufacturing costs are also a consideration, as a smaller die size will contribute to lower cost since the number of dies that can be formed from a single wafer of a given area will increase. Furthermore, a smaller die size will also be less susceptible to brittle fracture due to the relative fragility of the substrate.

Furthermore, in some variations, microneedles at the periphery of the microneedle array (e.g., near the edge or boundary of the die, near the edge or boundary of the housing, near the edge or boundary of an adhesive layer on the housing, along the outer border of the microneedle array, etc.) may be found to have better performance (e.g., sensitivity) due to better penetration compared to microneedles in the center of the microneedle array or die. Accordingly, in some variations, working electrodes may be arranged largely or entirely on microneedles located at the periphery of the microneedle array, to obtain more accurate and/or precise analyte measurements.

Figure 18A:
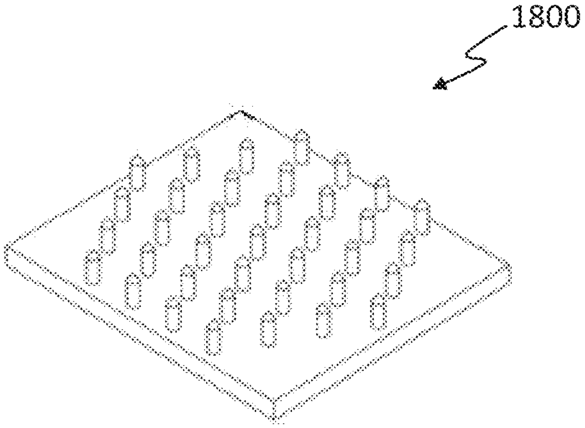
FIGS. 18A and 18B depict perspective and orthogonal views, respectively, of an illustrative variation of a die including a microneedle array.
Figure 18B:
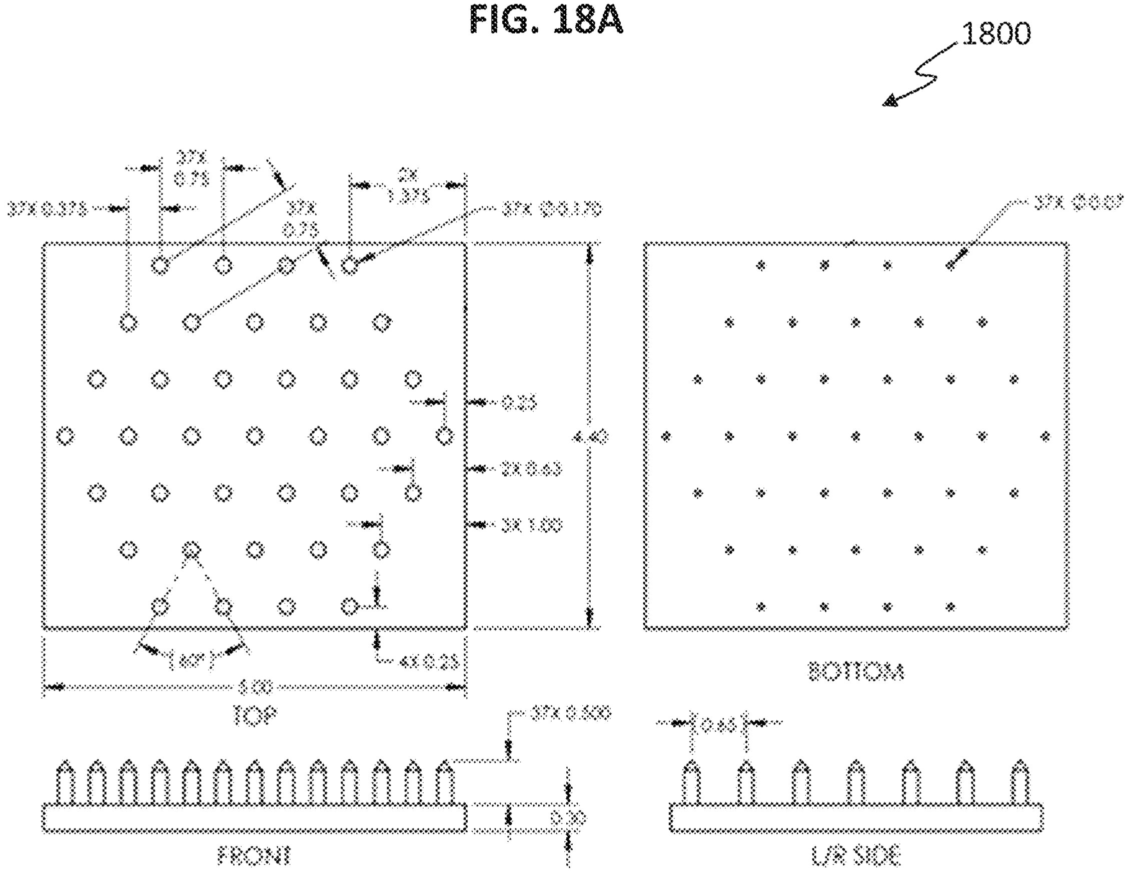

FIG. 17 depicts an illustrative schematic of 37 microneedles arranged in an example variation of a microneedle array. The 37 microneedles may, for example, be arranged in a hexagonal array with an inter-needle center-to-center pitch of about 750 μm (or between about 700 μm and about 800 μm, or between about 725 μm and about 775 μm) between the center of each microneedle and the center of its immediate neighbor in any direction. FIG. 18A depicts an illustrative schematic of an example variation of a die 1800 including the microneedle arrangement shown in FIG. 17. Example dimensions of the die 1800 (e.g., about 4.4 mm by about 5.0 mm) and the microneedle array are shown in FIG. 18B.

Figure 30A:
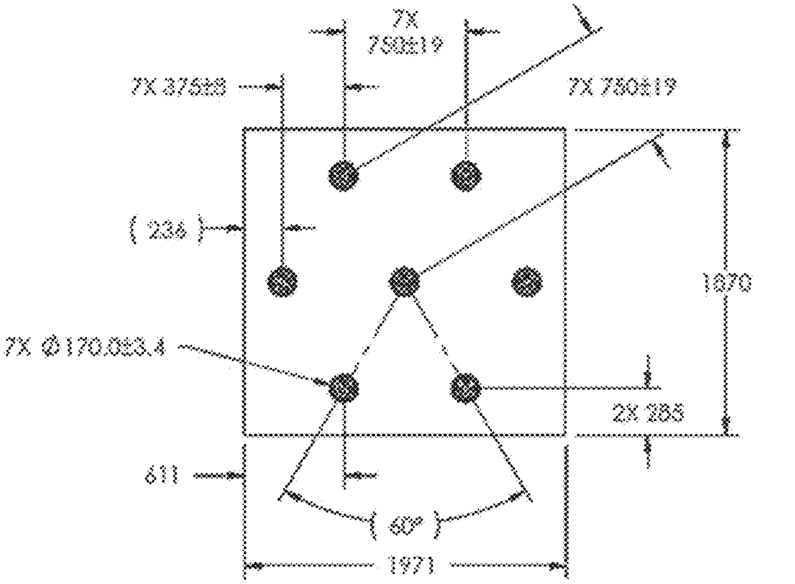
FIGS. 30A and 30B depict illustrative schematics of a microneedle array configuration.
Figure 30B:
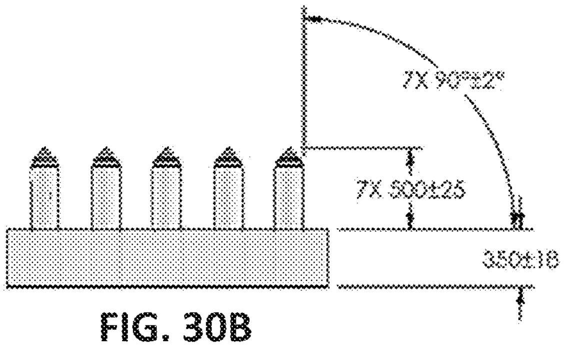

FIGS. 29A and 29B depict perspective views of an illustrative schematic of seven microneedles 2910 arranged in an example variation of a microneedle array 2900. The seven microneedles 2910 are arranged in a hexagonal array on a substrate 2902. As shown in FIG. 29A, the electrodes 2920 are arranged on distal portions of the microneedles 2910 extending from a first surface of the substrate 2902. As shown in FIG. 29B, proximal portions of the microneedles 2910 are conductively connected to respective backside electrical contacts 2930 on a second surface of the substrate 2902 opposite the first surface of the substrate 2902. FIGS. 30A and 30B depict plan and side views of an illustrative schematic of a microneedle array similar to microneedle array 2900. As shown in FIGS. 30A and 30B, the seven microneedles are arranged in a hexagonal array with an inter-needle center-to-center pitch of about 750 μm between the center of each microneedle and the center of its immediate neighbor in any direction. In other variations the inter-needle center-to-center pitch may be, for example, between about 700 μm and about 800 μm, or between about 725 μm and about 775 μm. The microneedles may have an approximate outer shaft diameter of about 170 μm (or between about 150 μm and about 190 μm, or between about 125 μm and about 200 μm) and a height of about 500 μm (or between about 475 μm and about 525 μm, or between about 450 μm and about 550 μm).

Furthermore, the microneedle arrays described herein may have a high degree of configurability concerning where the working electrode(s), counter electrode(s), and reference electrode(s) are located within the microneedle array. This configurability may be facilitated by the electronics system.

Figure 19A:
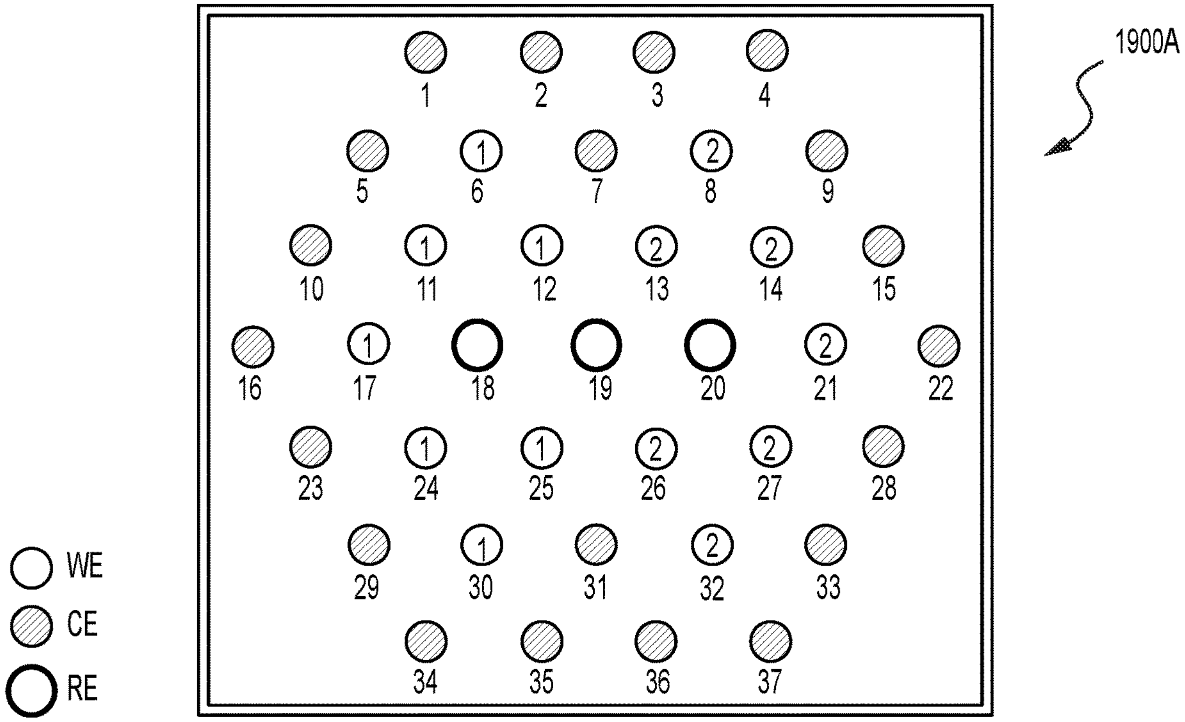
FIGS. 19A-19J depict illustrative schematics of different variations of microneedle array configurations.

In some variations, a microneedle array may include electrodes distributed in two or more groups in a symmetrical or non-symmetrical manner in the microneedle array, with each group featuring the same or differing number of electrode constituents depending on requirements for signal sensitivity and/or redundancy. For example, electrodes of the same type (e.g., working electrodes) may be distributed in a bilaterally or radially symmetrical manner in the microneedle array. For example, FIG. 19A depicts a variation of a microneedle array 1900A including two symmetrical groups of seven working electrodes (WE), with the two working electrode groups labeled “1” and “2”. In this variation, the two working electrode groups are distributed in a bilaterally symmetrical manner within the microneedle array. The working electrodes are generally arranged between a central region of three reference electrodes (RE) and an outer perimeter region of twenty counter electrodes (CE). In some variations, each of the two working electrode groups may include seven working electrodes that are electrically connected amongst themselves (e.g., to enhance sensor signal). Alternatively, only a portion of one or both of the working electrode groups may include multiple electrodes that are electrically connected amongst themselves. As yet another alternative, the working electrode groups may include working electrodes that are standalone and not electrically connected to other working electrodes. Furthermore, in some variations the working electrode groups may be distributed in the microneedle array in a non-symmetrical or random configuration.

Figure 19B:
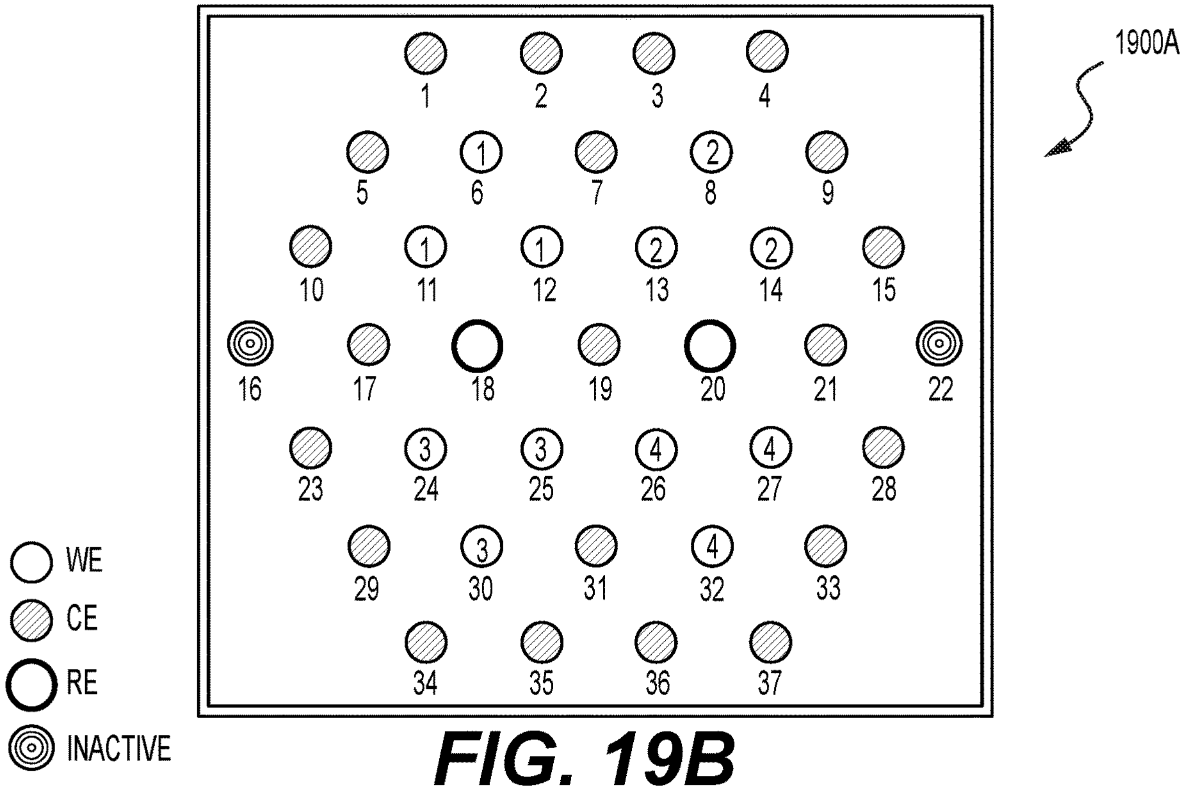

As another example, FIG. 19B depicts a variation of a microneedle array 1900B including four symmetrical groups of three working electrodes (WE), with the four working electrode groups labeled "1", "2", "3", and "4." In this variation, the four working electrode groups are distributed in a radially symmetrical manner in the microneedle array. Each working electrode group is adjacent to one of two reference electrode (RE) constituents in the microneedle array and arranged in a symmetrical manner. The microneedle array also includes counter electrodes (CE) arranged around the perimeter of the microneedle array, except for two electrodes on vertices of the hexagon that are inactive or may be used for other features or modes of operation.

In some variations, only a portion of microneedle array may include active electrodes. For example, FIG. 19C depicts a variation of a microneedle array 1900C with 37 microneedles and a reduced number of active electrodes, including four working electrodes (labeled "1", "2", "3", and "4") in a bilaterally symmetrical arrangement, twenty-two counter electrodes, and three reference electrodes. The remaining eight electrodes in the microneedle array are inactive. In the microneedle array shown in FIG. 19C, each of the working electrodes is surrounded by a group of counter electrodes. Two groups of such clusters of working electrodes and counter electrodes are separated by a row of the three reference electrodes.

Figure 19D:
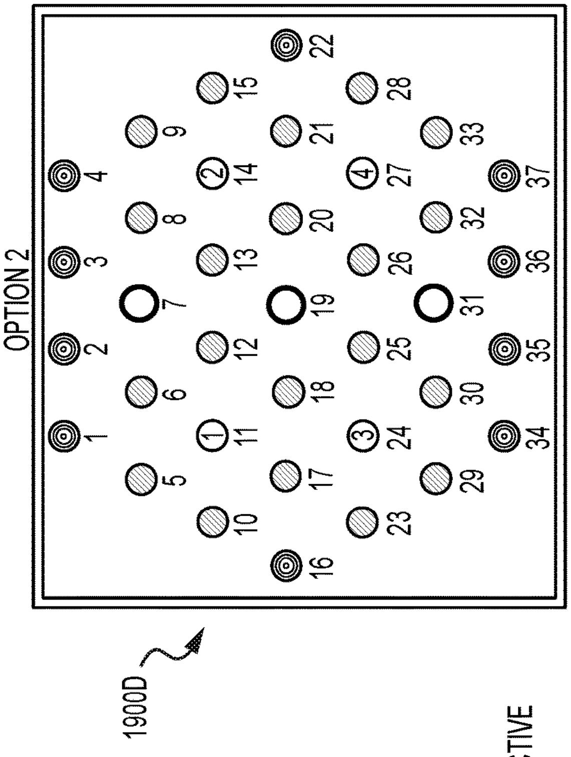
Figure 19C:
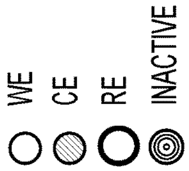
Figure 19C:
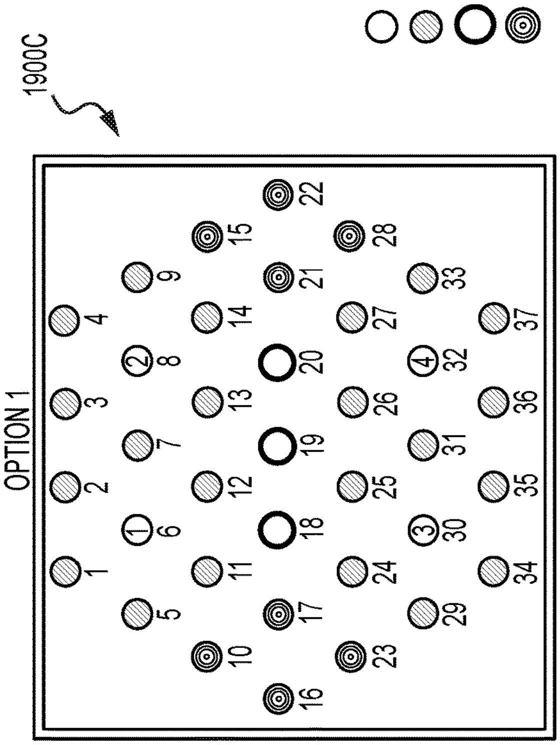

As another example, FIG. 19D depicts a variation of a microneedle array 1900D with 37 microneedles and a reduced number of active electrodes, including four working electrodes (labeled "1", "2", "3", and "4") in a bilaterally symmetrical arrangement, twenty counter electrodes, and three reference electrodes, where the remaining ten electrodes in the microneedle array are inactive.

Figure 19E:
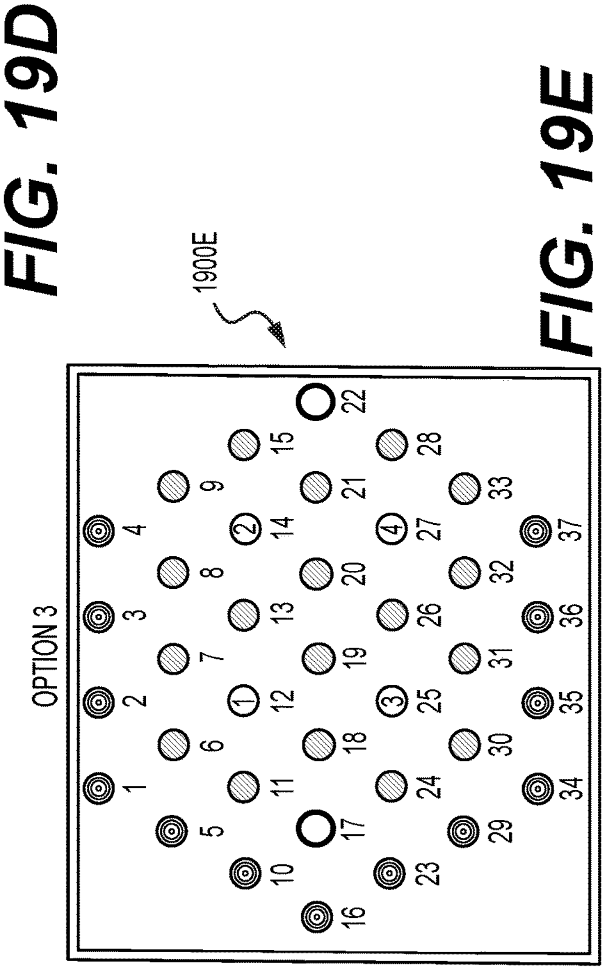

As another example, FIG. 19E depicts a variation of a microneedle array 1900E with 37 microneedles and a reduced number of active electrodes, including four working electrodes (labeled "1", "2", "3", and "4"), eighteen counter electrodes, and two reference electrodes. The remaining thirteen electrodes in the microneedle array are inactive. The inactive electrodes are along a partial perimeter of the overall microneedle array, thereby reducing the effective size and shape of the active microneedle arrangement to a smaller hexagonal array. Within the active microneedle arrangement, the four working electrodes are generally in a radially symmetrical arrangement, and each of the working electrodes is surrounded by a group of counter electrodes.

Figure 19F:
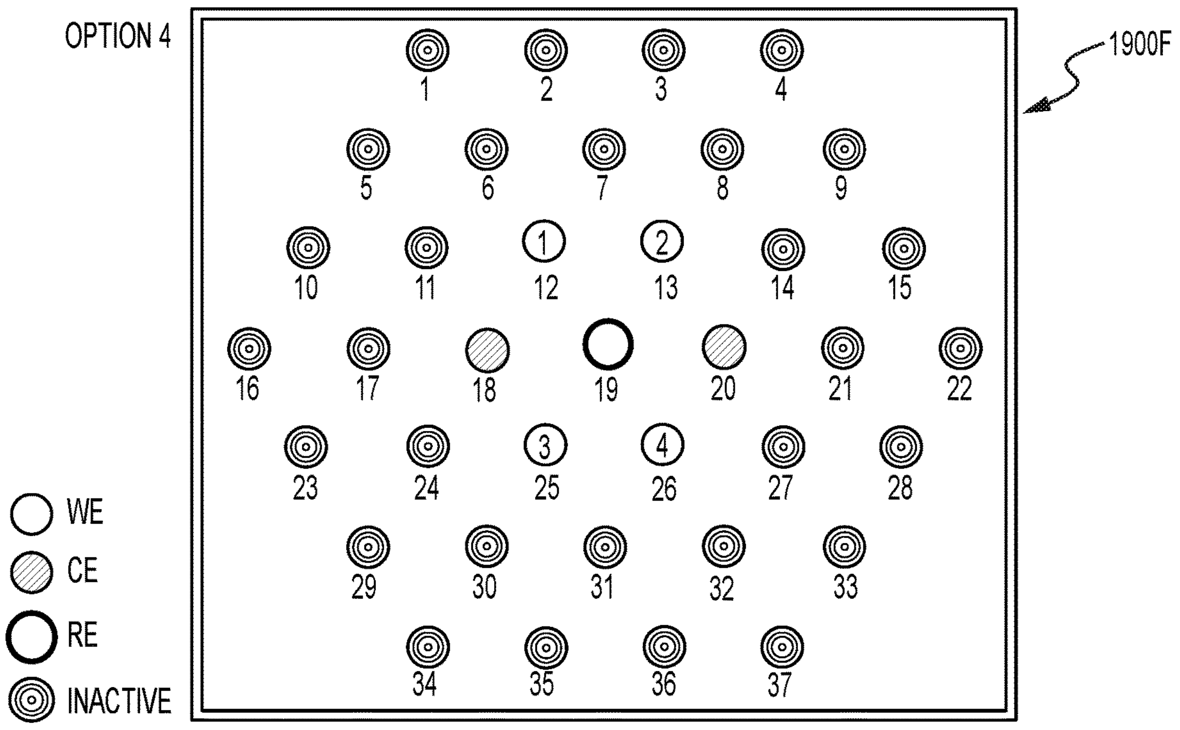

FIG. 19F depicts another example variation of a microneedle array 1900F with 37 microneedles and a reduced number of active electrodes, including four working electrodes (labeled "1", "2", "3", and "4"), two counter electrodes, and one reference electrode. The remaining thirty electrodes in the microneedle array are inactive. The inactive electrodes are arranged in two layers around the perimeter of the overall microneedle array, thereby reducing the effective size and shape of the active microneedle arrangement to a smaller hexagonal array centered around the reference electrode. Within the active microneedle arrangement, the four working electrodes are in a bilaterally symmetrical arrangement and the counter electrodes are equidistant from the central reference electrode.

Figure 19G:
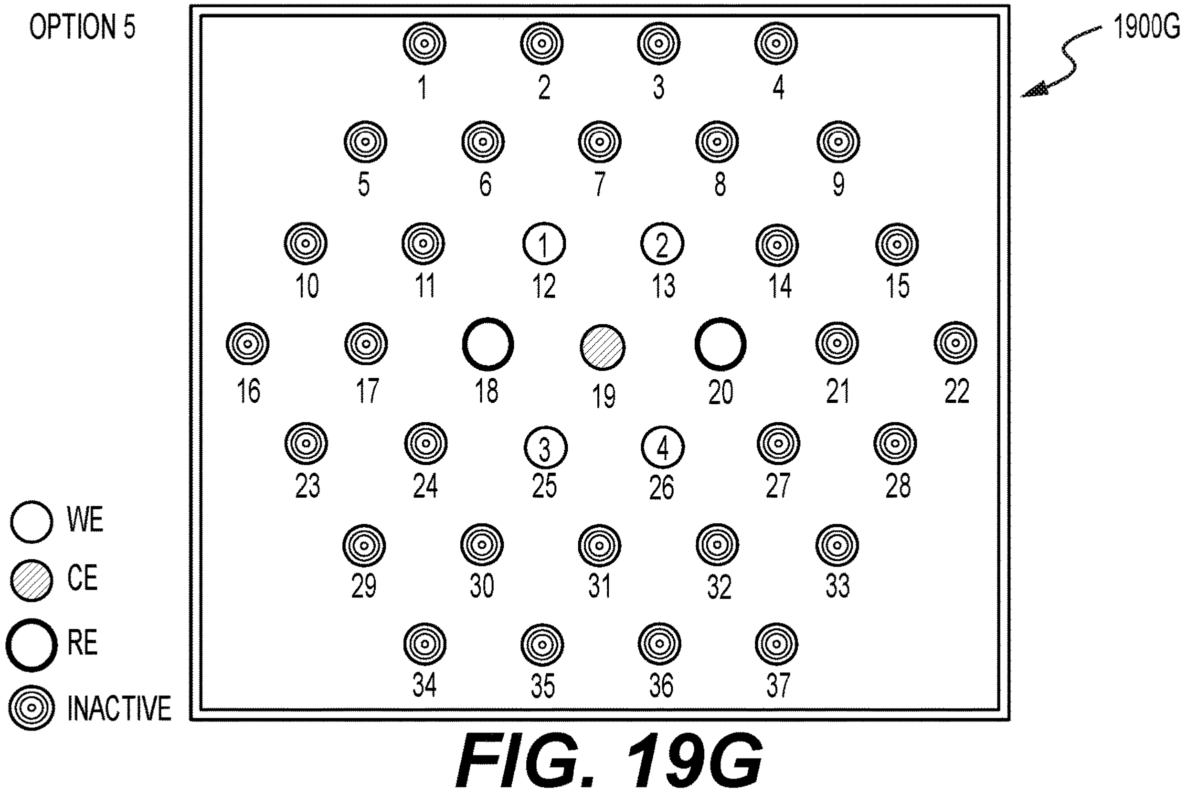

FIG. 19G depicts another example variation of a microneedle array 1900G with 37 microneedles and a reduced number of active electrodes. The active electrodes in microneedle array 1900G are arranged in a similar manner as that in microneedle array 1900F shown in FIG. 19F, except that the microneedle array 1900G includes one counter electrode and two reference electrodes, and the smaller hexagonal array of active microneedles is centered around the counter electrode. Within the active microneedle arrangement, the four working electrodes are in a bilaterally symmetrical arrangement and the reference electrodes are equidistant from the central counter electrode.

Figure 19J:
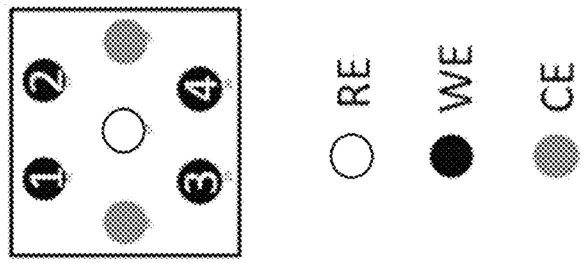
Figure 19I:
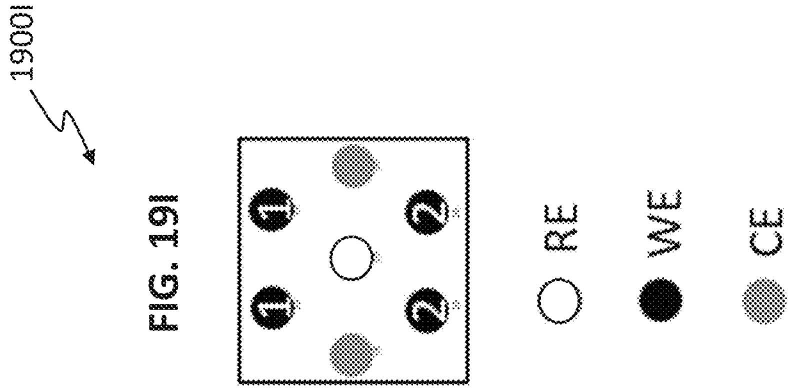
Figure 19H:
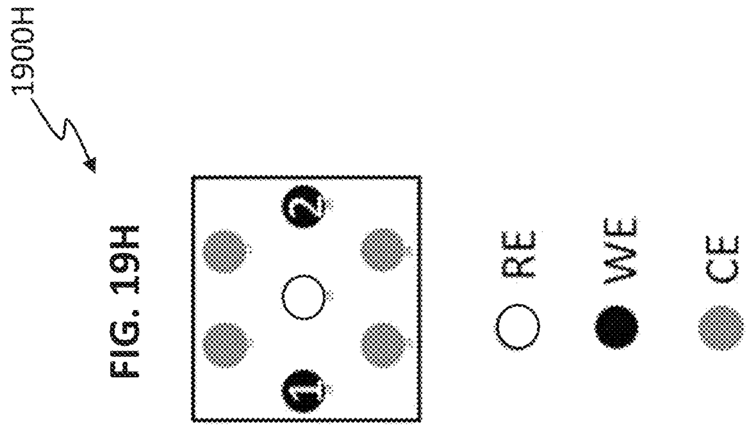

FIG. 19H depicts another example variation of a microneedle array 1900H with 7 microneedles. The microneedle arrangement contains two microneedles assigned as independent working electrodes (1 and 2), a counter electrode contingent comprised of 4 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 19I depicts another example variation of a microneedle array 1900I with 7 microneedles. The microneedle arrangement contains four microneedles assigned as two independent groupings (1 and 2) of two working electrodes each, a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

FIG. 19J depicts another example variation of a microneedle array 1900J with 7 microneedles. The microneedle arrangement contains four microneedles assigned as independent working electrodes (1, 2, 3, and 4), a counter electrode contingent comprised of 2 microneedles, and a single reference electrode. There is bilateral symmetry in the arrangement of working and counter electrodes, which are equidistant from the central reference electrode. Additionally, the working electrodes are arranged as far as possible from the center of the microneedle array (e.g., at the periphery of the die or array) to take advantage of a location where the working electrodes are expected to have greater sensitivity and overall performance.

While FIGS. 19A-19J illustrate example variations of microneedle array configurations, it should be understood that these figures are not limiting and other microneedle configurations (including different numbers and/or distributions of working electrodes, counter electrodes, and reference electrodes, and different numbers and/or distributions of active electrodes and inactive electrodes, etc.) may be suitable in other variations of microneedle arrays.

Warm-Up

Many implanted electrochemical sensors require a “warm-up” time, or time for the sensor to attain a stable signal value following implantation. This process has origins in both physiology and sensor dynamics. However, various aspects of analyte monitoring devices described herein are configured to mitigate factors contributing to warm-up time, thereby allowing the analyte monitoring devices described herein to have significantly shorter warm-up times compared to traditional CGM systems. For example, the analyte monitoring devices described herein may have a warm-up time of about 30 minutes or less (e.g., between about 10 minutes and about 30 minutes, between about 15 minutes and about 30 minutes, between about 20 minutes and about 30 minutes, between about 25 minutes and about 30 minutes), about 45 minutes or less, about 60 minutes or less, about 90 minutes or less, or about 120 minutes or less. In some variations, following a warm-up period, the analyte monitoring device may calibration during a calibration period.

Wound response: For example, the implantation of a sensor creates a wound response due to the localization disruption, displacement, and destruction of tissue. The larger the sensor, or the deeper the implant, the more prolific the wound response. Accordingly, there is a compelling rationale to miniaturize the sensor to elicit an attenuated wound response, which would result in more rapid warm-up.

Protein adsorption: Additionally, following implantation of a sensor, the foreign body response is immediately instigated. The foreign body response includes a complex biochemical cascade that aims to encapsulate the foreign material with cellular matter. Hydrophobic surfaces tend to be subject to adsorption of endogenous proteins very rapidly following implant; this is referred to as biofouling. Hydrophilic surfaces, on the other hand, resist biofouling due to high water content. Human serum albumin (HSA) is the predominant protein in the dermal interstitial fluid, constituting about 60% of total protein, and maintains a negative charge at physiological pH. When the sensor is polarized with a positive potential (as in some variation of the analyte monitoring device), endogenous HSA is subject to electric drift and charge attraction to the positive (working) electrode of the sensor. This can give rise to an increased propensity for the sensor surface to biofoul. This is the rationale behind the implementation of either a hydrophilic diffusion limiting layer or outer biocompatible layer to effectively conceal the sensor from being recognized as a foreign body, as described in further detail above.

As described herein, the analyte monitoring device reduces the influence of the above physiological factors on warm-up time due to, for example, the shallow nature of the implant, the minimal volume of tissue displaced (e.g., up to about two orders of magnitude lower than current CGM systems, such as between about 100 and about 1000 times less tissue displaced, or between about 200 and about 600 times less tissue displaced compared to current CGM systems), the minimal amount of trauma to said tissue during implantation, and the lack of permeation of the vasculature deeper in the reticular dermis, which, when perturbed, can instigate a more prolific wound response that will engender an accelerated effort to encapsulate the implant, as is the case with competing wire-implanted CGM systems.

Attainment of equilibrium: One example of the effect of sensor dynamics on warm-up time relates to the attainment of equilibrium. An electrochemical sensor requires a finite amount of time to achieve equilibrium when used in a new environment. This is typically associated with the establishment of thermodynamic equilibrium due to an adsorbed surface layer of ions at the electrodes. As the reference electrode in most implantable electrochemical sensors does not employ an internal filling solution with a redox couple that is sealed from the rest of the electrochemical cell, this reference electrode must attain equilibrium with its surroundings in order to establish a stable reference potential.

Hydration of sensor layers: The electrode sensor layers must be immersed in an aqueous environment to function properly. The resulting hydration process may activate the electrode’s polymer layer(s) and biorecognition element(s) and allows them to rearrange and return to their native active tertiary structure, which is primarily responsible for their activity or unique properties. This process is often known as sensor ‘wetting’ and allows the medium in which the sensing operation occurs to intercalate the sensor layers to a sufficient extent. Decaying of the non-Faradaic response: The biasing (application of a voltage) of an electrochemical sensor will cause a double layer of ions to form at the electrode surface. This process requires a finite amount of time due to the charging of the adsorbed species on the electrode surface. This gives rise to a double layer capacitance. The non-Faradaic time constant is equal to the product of the said double layer capacitance and the solution resistance. Oftentimes, the non-Faradic response (electrical current) decays to negligible levels more rapidly than other physical phenomena and it is often not the rate-limiting step in the warm-up process. Once the non-Faradaic response decays to negligible levels, the Faradaic response ensues, which is reflective of the electrochemical/redox reaction of interest As described herein, the analyte monitoring device may reduce the influence of sensor dynamics on warm-up time due to, for example, the implementation thin membrane layers (on the order of 10 nm-5000 nm), which allow the layers to hydrate more rapidly than competing implantable CGM systems. Moreover and owing to the diminutive dimensions of the electrodes described herein (e.g., geometric surface area of the working electrode(s)), the non-Faradaic response transpires for shorter durations (due to reduced double layer capacitance and hence charging of the double layer). In some variations, a high-potential (e.g., >0.75V) bias for a limited period of time following application of the device to skin may further expedite burn-in or warm-up of the sensor to achieve equilibrium and stable signal levels.

Signal Latency

Typically, implanted electrochemical sensors also experience a delay, or signal latency, in attaining a stable signal value following changes in analyte levels. This signal latency is a function of various factors. At a high level, latency is a function of 3 distinct effects: (1) diffusional lag (amount of time that is required for a molecule of analyte to diffuse from the capillary (source) to the sensor surface, (2) diffusional limitation imposed by the sensor membrane/layer architecture on the sensors, and (3) algorithmic processing of data (averaging, filtering, signal denoising, and other signal processing measures), which often results in a group delay. However, various aspects of the analyte monitoring devices described herein minimize these factors contributing to signal latency, thereby resulting in a faster response time for analyte measurements.

As described above, one significant advantage of the analyte monitoring devices described herein is that location of sensor placement. Because the electrode surface is implanted at a location in such close proximity (e.g., within a few hundred micrometers or less) to the dense and well-perfused capillary bed of the reticular dermis, the diffusional lag is negligible. This is a significant advantage over conventional analyte sensors, which reside in the very poorly vascularized adipose tissue beneath the dermis and hence the diffusion distance, and resulting diffusional latency, from the vasculature in the dermis is substantial (e.g., typically 5-20 minutes).

Additionally, as the films deposited on the electrode sensor surface use electrodeposition methods, the precise thickness of said films can be controlled to a highly precise degree. For example, the electrodeposition methods of forming the sensor surface enable consistent, controlled creation of thin film layers that may reduce diffusional lag. Moreover, the spatial localization of the thin film layers to the sensing electrode allows the realization of thinner and less diffusionally resistive films, which further reduce latency due to diffusion of the analyte from the other film surface to the biorecognition layer.

Furthermore, the high level of redundancy (parallel channels of analyte measurement) afforded by the microneedle array allows for higher fidelity measurement and less reliance on the algorithm to interpolate sensor readings, which imparts greater reduced delay or latency.

Electronics System

As shown in the schematic of FIG. 2A of an analyte monitoring device 110, the electronics system 120 may be integrated within the housing 112, such that the electronics system 120 may be combined with sensing elements (e.g., microneedle array) as part of a single unit, in contrast to traditional CGM systems, which typically incorporate components in multiple physically distinct units. Further details of an example variation of an electronics system 120 are described below.

PCBs

In some variations, the analyte monitoring device may include one or more PCBs. For example, the analyte monitoring device may include at least one PCB in the sensor assembly 320 that includes the microneedle array, and at least one device PCB 350 as shown in FIG. 3E.

For example, as shown in FIGS. 3F-3I, a sensor assembly 320 may include a sensor standoff PCB 322 coupled to a connecting PCB 324. The microneedle array 330 may be attached to the sensor standoff PCB 322 (e.g., FR-4, PTFE, Rogers 4350B), such as through a soldering process combined with an epoxy underfill for mechanical strength. In some variations, an epoxy skirt may be deposited along the edges of the silicon microneedle array 330 to relieve the sharp edges from the silicon dicing processes described above. The epoxy may also provide a transition from the edge of the silicon substrate of the microneedle array silicon to the edge of the PCB 322. Alternatively, this epoxy may be replaced or supplemented by a rubber gasket or the like.

Figure 3H:
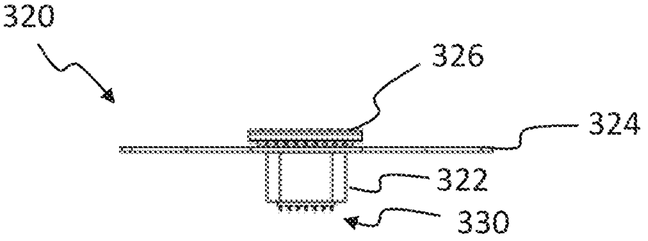
Figure 3I:
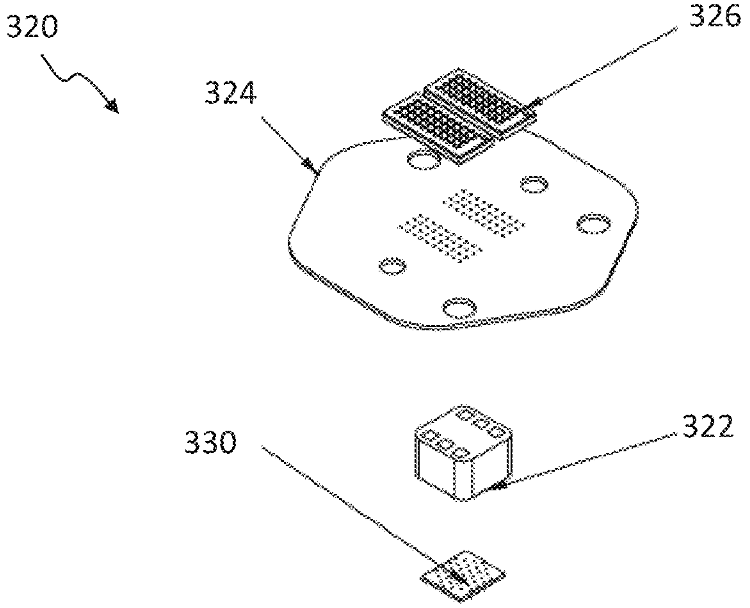
Figure 3J:
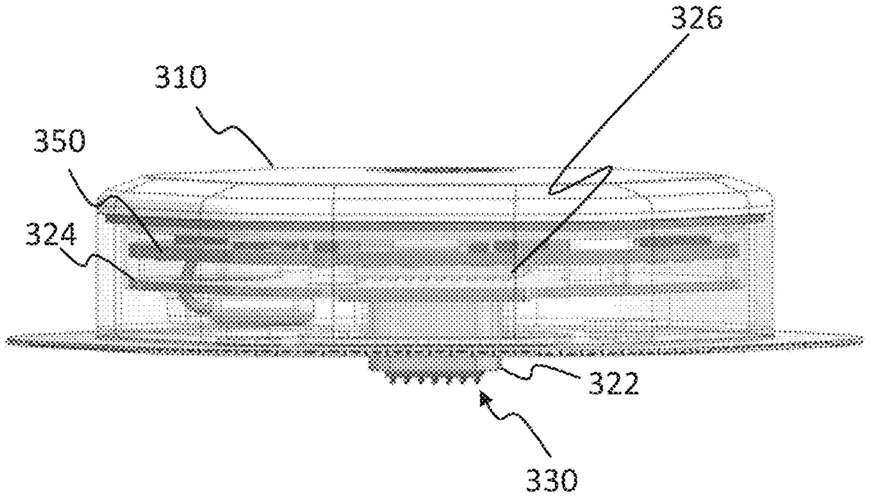
FIG. 3J depicts a transparent side view of a sensor assembly in an analyte monitoring device.

As shown in FIG. 3J, the sensor standoff PCB 322 may function as a standoff that at least in part determines the desired distance to which the microneedle array 330 protrudes from the housing 310. Accordingly, the standoff height of the sensor standoff PCB 322 may be selected to help ensure that the microneedle array 330 is inserted properly into a user's skin. During needle insertion, the bottom surface of the housing 310 will act as a stop for needle insertion. If the sensor standoff PCB 322 has a reduced height and its lower surface is flush or nearly flush with the bottom surface of the housing, then the housing 310 may prevent the microneedle array 330 from being fully inserted into the skin. However, increasing the standoff height may lead to more pressure of the microneedle array on the skin during microneedle insertion, which can lead to dermatological irritation and/or erythema (redness of the skin).

The sensor standoff PCB 322 may be secured to the housing 310 and/or secured within the stack up inside the housing, such as with suitable fasteners or the like. For example, as shown in FIGS. 3H-3J, the sensor standoff PCB 322 (with the microneedle array 330) may be coupled to a first side of the connecting PCB 324, while a second opposite side of the connecting PCB 324 may in turn be coupled to an interposer PCB connector 326. As shown in FIG. 3J, the interposer PCB connector 326 may be communicatively coupled to the device PCB 350, such as for signal processing as described below. Accordingly, signals from the microneedle array 330 may be communicated through the sensor standoff PCB 322 and to the device PCB via the sensor standoff PCB 322, connecting PCB 324, and interposer PCB connector 326. However, in some variations the analyte monitoring device may include fewer PCBs. For example, in some variations, the sensor assembly 320 may omit the sensor standoff PCB 322, such that the microneedle array 330 may directly communicate electrically to the connecting PCB 324 (or directly to the device PCB 350).

Additionally or alternatively, in some variations at least one of the PCBs in the sensor assembly 320 may include or be coupled to one or more additional sensors in combination with the microneedle array 330. For example, the sensor assembly 320 may include a temperature sensor (e.g., thermistor, resistance temperature detector, thermocouple, bandgap reference, non-contact temperature sensor, etc.). In some variations, temperature measurement may additionally or alternatively be performed by one or more analyte-insensitive electrodes in the microneedle array.

In some variations, the sensor standoff PCB 322 may be between about 0.05 inches and about 0.15 inches, or between about 0.093 inches and about 0.127 inches in thickness. The sensor standoff PCB 322, in some variations, may include one or a plurality of conductive through-substrate vias configured to route electrical signals from an anterior surface of the PCB to a posterior surface of the PCB. In some variations, the sensor standoff PCB 322 may comprise a semiconductor (e.g., silicon) with conductive through-substrate vias configured to route electrical signals from an anterior surface of the semiconductor to a posterior surface of the semiconductor. In yet other variations, the microneedle array 330 may be mounted directly to the PCB 324, without the sensor standoff PCB 322.

Analog Front End

In some variations, the electronics system of the analyte monitoring device may include an analog front end. The analog front end may include sensor circuitry (e.g., sensor circuitry 124 as shown in FIG. 2A) that converts analog current measurements to digital values that can be processed by the microcontroller. The analog front end may, for example, include a programmable analog front end that is suitable for use with electrochemical sensors. For example, the analog front end may include a MAX30131, MAX30132, or MAX30134 component (which have 1, 2, and 4 channel, respectively), available from Maxim Integrated (San Jose, CA), which are ultra-low power programmable analog front ends for use with electrochemical sensors. The analog front end may also include an AD5940 or AD5941 component, available from Analog Devices (Norwood, MA), which are high precision, impedance and electrochemical front ends. Similarly, the analog front end may also include an LMP91000, available from Texas Instruments (Dallas, TX), which is a configurable analog front end potentiostat for low-power chemical sensing applications. The analog front end may provide biasing and a complete measurement path, including the analog to digital converters (ADCs). Ultra-low power may allow for the continuous biasing of the sensor to maintain accuracy and fast response when measurement is required for an extended duration (e.g. 7 days) using a body-worn, battery-operated device.

In some variations, the analog front end device may be compatible with both two and three terminal electrochemical sensors, such as to enable both DC current measurement, AC current measurement, and electrochemical impedance spectroscopy (EIS) measurement capabilities. Furthermore, the analog front end may include an internal temperature sensor and programmable voltage reference, support external temperature monitoring and an external reference source and integrate voltage monitoring of bias and supply voltages for safety and compliance.

In some variations, the analog front end may include a multi-channel potentiostat to multiplex sensor inputs and handle multiple signal channels. For example, the analog front end may include a multi-channel potentiostat such as that described in U.S. Pat. No. 9,933,387, which is incorporated herein in its entirety by this reference.

In some variations, the analog front end and peripheral electronics may be integrated into an application-specific integrated circuit (ASIC), which may help reduce cost, for example. This integrated solution may include the microcontroller described below, in some variations.

Microcontroller

In some variations, the electronics system of the analyte monitoring device may include at least one microcontroller (e.g., controller 122 as shown in FIG. 2A). The microcontroller may include, for example, a processor with integrated flash memory. In some variations, the microcontroller in the analyte monitoring device may be configured to perform analysis to correlate sensor signals to an analyte measurement (e.g., glucose measurement). For example, the microcontroller may execute a programmed routine in firmware to interpret the digital signal (e.g., from the analog front end), perform any relevant algorithms and/or other analysis, and route processed data to and/or from the communication module. Keeping the analysis on-board the analyte monitoring device may, for example, enable the analyte monitoring device to broadcast analyte measurement(s) to multiple devices (e.g., mobile computing devices such as a smartphone or smartwatch, therapeutic delivery systems such as insulin pens or pumps, etc.) in parallel, while ensuring that each connected device has the same information.

In some variations, the microcontroller may be configured to activate and/or inactivate the analyte monitoring device on one or more detected conditions. For example, the device may be configured to power on the analyte monitoring device upon insertion of the microneedle array into skin. This may, for example, enable a power-saving feature in which the battery is disconnected until the microneedle array is placed in skin, at which time the device may begin broadcasting sensor data. Such a feature may, for example, help improve the shelf life of the analyte monitoring device and/or simplify the analyte monitoring device-external device pairing process for the user.

Figure 25:
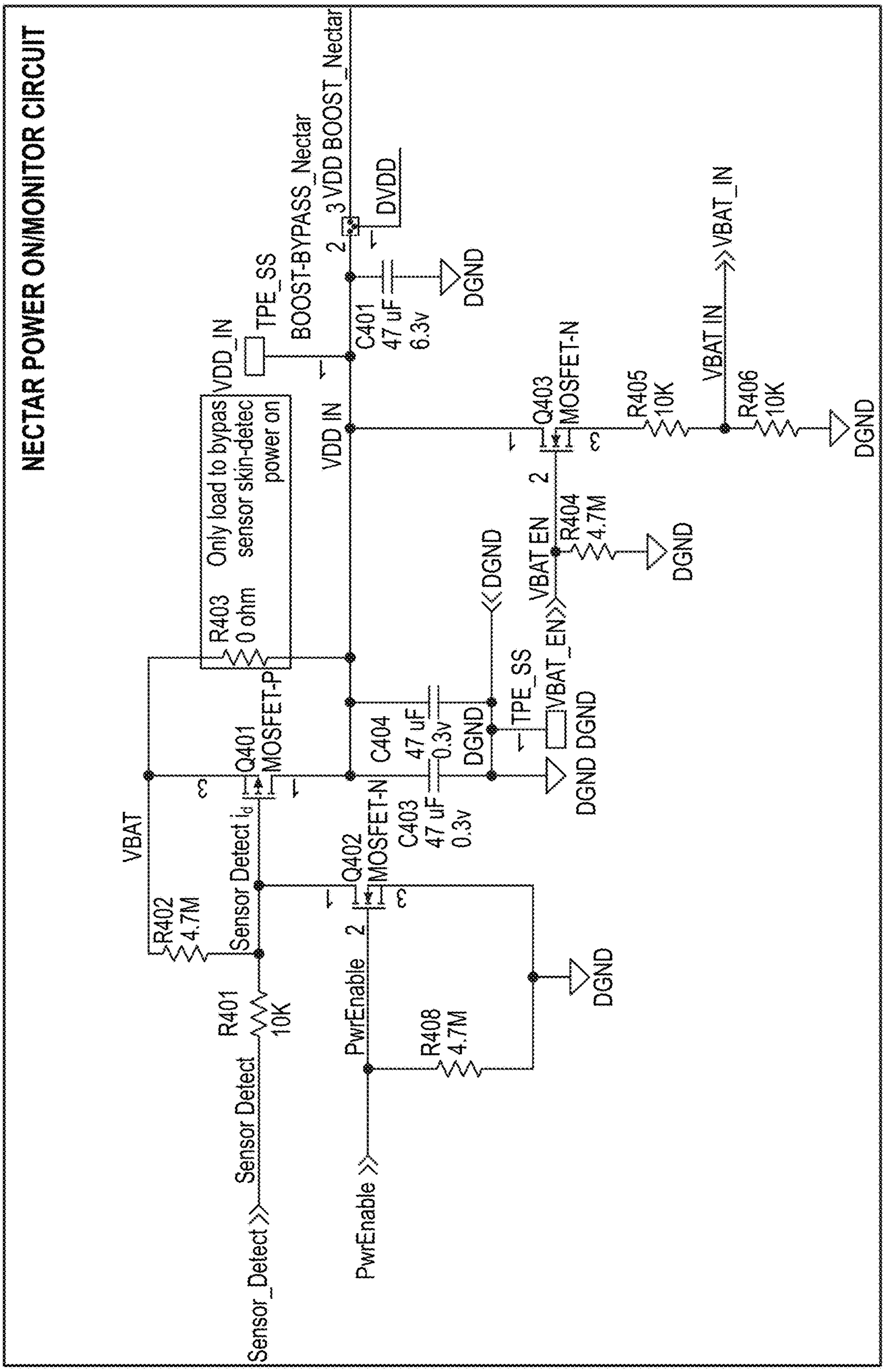
FIG. 25 is an illustrative schematic of electronic circuitry enabling activation of an analyte monitoring device upon insertion of the microneedle array in skin.

FIG. 25 illustrates a schematic of an example variation of circuitry enabling the above-described activation of the analyte monitoring device upon insertion. Generally, upon penetration of the stratum corneum of the skin and positioning of the electrode at the distal tip of the microneedle constituents in the highly electrolytic dermal interstitial fluid, the resistance of "Sensor Detect" reduces to a significant extent, thereby activating the p-channel MOSFET Q401. Once Q401 is turned on, the battery voltage VBAT flows to VDD_IN and that provides power for the device. When the microcontroller powers on, the first routine it executes is to set "PwrEnable" high, hence keeping the device the device powered by pulling the gate of Q401 low through Q402. This is performed in order to mitigate a scenario wherein the microneedles are not keeping contact with the skin. If the device has been subject to a false start, a high resistance on "Sensor_Detect" should be present and the microprocessor can take "PwrEnable" low, thereby removing power to the device (and inactivating the device). Other example variations of structures and methods for activating and/or inactivating an analyte monitoring device are described in further detail in U.S. patent application Ser. No. 16/051,398, which is incorporated herein in its entirety by this reference.

Additionally or alternatively, the microcontroller may be configured to actively confirm the insertion of the microneedle array into skin based on sensor measurements performed with the microneedle array. For example, after two or more microneedles in the microneedle array are presumed to have been inserted into skin, a fixed or time-varying electrical potential or current may be applied to those microneedles. A measurement result (e.g., electrical potential or current value) of a signal generated between the electrodes of the inserted microneedles is measured, and then compared to a known reference value to corroborate successful insertion of the microneedle array into the skin. The reference value may, for example, include a voltage, a current, a resistant, a conductance, a capacitance, an inductance and/or an impedance. Other example variations of structures and methods for activating and/or inactivating an analyte monitoring device are described in further detail in U.S. patent application Ser. No. 16/051,398 which was incorporated above by reference.

In some variations, the microcontroller may utilize an 8-bit, 16-bit, 32-bit, or 64-bit data structure. Suitable microcontroller architectures include ARM® and RISC® architectures, and flash memory may be embedded or external to the microcontroller for suitable data storage. In some variations the microcontroller may be a single core microcontroller, while in some variations the microcontroller may be a multi-core (e.g., dual core) microcontroller which may enable flexible architectures for optimizing power and/or performance within the system. For example, the cores in the microcontroller may include similar or differing architectures. For example, in an example variation, the microcontroller may be a dual core microcontroller including a first core with a high performance and high power architecture, and a second core with a low performance and low power architecture. The first core may function as a "workhorse" in that it may be used to process higher performance functions (e.g., sensor measurements, algorithmic calculations, etc.), while the second core may be used to perform lower performance functions (e.g., background routines, data transmission, etc.). Accordingly, the different cores of the microcontroller may be run at different duty cycles (e.g., the second core for lower performance functions may be run at a higher duty cycles) optimized for their respective functions, thereby improving overall power efficiency. Additionally or alternatively, in some variations the microcontroller may include embedded analog circuitry, such as for interfacing with additional sensor(s) and/or the microneedle array. In some variations, the microcontroller may be configured to operate using a 0.8V-5V power source, such as a 1.2V-3V power source.

Communication Module

In some variations, the electronics system of the analyte monitoring device may include at least one communication module (e.g., communication module 126 as shown in FIG. 2A), such as a wireless communication module to communicate with one or more devices. For example, the communication module may include a wireless transceiver that is integrated into the microcontroller device. However, the electronics system may additionally or alternatively include a communication module that is separate from the microcontroller device. In some variations, the communication module may communicate via wireless network (e.g., through Bluetooth, NFC, WiFi, RFID, or any type of data transmission that is not connected by cables). For example, devices may directly communicate with each other in pairwise connection (1:1 relationship, i.e. unicasting), or in a hub-spoke or broadcasting connection ("one to many" or 1:m relationship, i.e. multicasting). As another example, the devices may communicate with each other through mesh networking connections (e.g., "many to many", or m:m relationships, or ad-hoc), such as through Bluetooth mesh networking. Wireless communication may use any of a plurality of communication standards, protocols, and technologies, including but not limited to, Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (WiFi) (e.g., IEEE 802.11a, IEEE 802.11b, IEEE 802.11g, IEEE 802.11n, and the like), or any other suitable communication protocol. Some wireless network deployments may combine networks from multiple cellular networks or use a mix of cellular, Wi-Fi, and satellite communication. In an example variation, the communication module may include a wireless transceiver integrated into the microcontroller and including a Bluetooth Low Energy compatible radio that complies with the Bluetooth Special Interest Group 5.0 specification.

The communication module may further include or be coupled to one or more antennas (e.g., antenna 128 as shown in FIG. 2A). For example, the electronics system may include a chip antenna mounted on the PCB, or an antenna implemented directly onto the PCB, which may provide better range while reducing cost and complexity. In some variations, a user wearing the analyte monitoring device 110 may function as an antenna (e.g., antenna 128). For example, the antenna input/output 128 of the communication module 126 may be electrically connected to a single microneedle or plurality of microneedles, which are inserted into the wearer's skin (e.g., similar to microneedle array 140 shown in FIG. 2B). This may increase the effective cross-sectional area of the antenna, provide for an adequate impedance match between the antenna input/output of the communication module and free space, and/or help improve operational metrics such as antenna gain, antenna diversity, omnidirectionality, and communication module receiver sensitivity/transmitter efficiency.

Devices can come in and out of range from the communication module to connect and reconnect so that the user is able to seamlessly connect and transfer information between devices. In some variations, the microcontroller on each analyte monitoring device may have a unique serial number, which enables tracking of specific analyte monitoring devices during production and/or field use.

Additional Sensors

As described above, in some variations, the analyte monitoring device may include one or more sensors in addition the microneedle array. For example, the analyte monitoring device may include one or more temperature sensors configured to measure skin temperature, thereby enabling temperature compensation for the analyte sensor(s). For example, in some variations, a temperature sensor (e.g., thermistor, RTD, semiconductor junction, bimetallic sensor, thermopile sensor) may be coupled to the device PCB within the housing such that the temperature sensor is arranged near a skin-facing portion or bottom portion of the housing 112. The housing may be thinned to reduce thermal resistance and improve heat transfer and hence measurement accuracy. Additionally or alternatively, a thermally conductive material may thermally couple a surface-mount temperature sensor to the user's skin. In variations in which the temperature sensor is coupled to the device PCB near the microneedle array die substrate, the thermally conductive material may, for example, be molded as a skirt to relieve the sharp edges of the die and wrap along the edges of the die and along the surface of the main PCB.

In some variations, the temperature sensor may be employed to develop a glucose interpolation characteristic based on measured current and an a priori sensitivity (e.g., nA/mM or pA/mg/dL). In the temperature-invariant case, the electrical current characteristic can be modeled by the following relation: $y=m_G[G]$ where y is the measured current, $m_G$ is the glucose sensitivity, and [G] is the interpolated glucose concentration. In some cases, such as the incorporation of an analyte insensitive channel b, the background signal may be incorporated into the equation above: $y=m_G[G]+b$. Incorporating the measurements from a temperature sensor, the electrical current characteristic can be represented by the following relation: $y=m_G[G]+m_T[T]+b$ where $m_T$ is the temperature sensitivity (e.g., pA/° C.), T is the measured temperature, and b is the background signal (e.g., pA). In other operating scenarios, the electrical current characteristic is modeled by the following relation: $y=m_1[G][T]+b$ where $m_1$ is a weighting factor determined a priori. In other operating scenarios, the electrical current characteristic can be modeled as a convolution of temperature and glucose: $y=\{m_T[T]+m_2\}[G]+b$ where $m_2$ is a weighting factor determined a priori. In yet other operating scenarios, the electrical current characteristic is provided by the following relation: $y=\{m_G[G]+m_2\}[T][G]+b$. In yet other operating scenarios, the electrical current characteristic is given by the following nonlinear relation: $y=\{m_{G2}[G]^2+m_G[G]\}[T]+b$ where $m_{G2}$ is a nonlinear weighting factor. In yet other operating scenarios, the electrical current characteristic is given by the following Gaussian relation: $y=m_G[G]\exp\{-([T]-[T_{OPT}])^2/(2\sigma^2)\}+b$ where $T_{OPT}$ is the optimal temperature for maximal catalytic turnover of the enzyme and $\sigma$ is the operating temperature range of the enzyme.

In some variations, the analyte monitoring device may include at least one microneedle with an electrode configured to function as an analyte insensitive channel (e.g., glucose insensitive channel) having a known temperature sensitivity, where such a known temperature sensitivity may be used to compensate for temperature. For example, one advantage of using a glucose insensitive channel includes proximity to the glucose sensor (e.g., resulting in less error from thermal gradients) and cost (e.g., by reducing external components and specialized processes to thermally couple the sensor to the skin). In some variations, the analyte monitoring device may include both an analyte insensitive channel along with a thermistor, with an algorithm that utilizes information from both. Additionally or alternatively, the analyte monitoring device may include an additional sensor(s) that measures ambient temperature, which may also be useful in the temperature compensation algorithm.

In some variations, the analyte insensitive channel may be used to perform differential measurements and/or subtract background noise levels from the analyte-sensitive channel(s) to improve signal fidelity and/or signal-to-noise ratio. The analyte insensitive channel may be sensitive to common mode signals that also arise on the analyte-sensitive channel(s) (e.g., endogenous and pharmacologic interference, pressure attenuations, etc.).

Additionally or alternatively, in some variations, the analyte monitoring device may include at least one kinetic sensor. The kinetic sensor may, for example, comprise an accelerometer, gyroscope, and/or inertial measurement unit to capture positional, displacement, trajectory, velocity, acceleration, and/or device orientation values. For example, such measurements may be used to infer the wearer's physical activity (e.g., steps, intense exercise) over a finite duration. Additionally or alternatively, in some variations, the kinetic sensor(s) may be employed to enable detection of wearer interactions with the analyte monitoring device such as touch or tapping. For example, touch or tap detection can be employed to silence or snooze notifications, alerts, and alarms, control a wirelessly connected mobile computing device, or to activate/deactivate a user interface on the analyte monitoring device (e.g., an embedded display or indicator light). Touching or tapping may be performed in a defined sequence and/or for a predetermined duration (e.g., at least 3 seconds, at least 5 seconds) to elicit certain actions (e.g., display or indicator light deactivation/activation). Additionally or alternatively, in some variations, the analyte monitoring device may enter into a power saving mode upon detection of limited motion or activity (e.g., absence of significant acceleration) for at least a predetermined period of time (e.g., 15 minutes, 30 minutes, 45 minutes, 1 hour, or other suitable of time), as measured by the kinetic sensor(s).

Additionally, or alternatively, in some variations, the analyte monitoring device may include at least one real-time clock (RTC). The real-time clock may be employed to track absolute time (e.g., Coordinated Universal Time, UTC, or local time) when the analyte monitoring device is in storage or during use. In some variations, synchronization to absolute time may be performed following manufacturing of the analyte monitoring device. The real-time clock may be employed to time-stamp analyte measurements (e.g., glucose measurements) during operation of the analyte monitoring device in order to create a time-series data set that is communicated to a connected peripheral device (e.g., mobile computing device), cloud storage, or other suitable data storage device, such as for later review by the user (e.g., wearer of the analyte monitoring device), their support network, or their healthcare provider, etc.

Power Source(s)

As shown in FIG. 2A, the analyte monitoring device may include one or more power sources 130 (e.g., battery) in the housing 112 configured to provide power to other components. For example, the analyte monitoring device may include an AgO battery, which has a high energy density and is more environmentally friendly than lithium batteries. In some variations, a primary (e.g., non-rechargeable) battery may be used. Furthermore, in some variations, a secondary (e.g., rechargeable) battery may be used. However, any suitable power source may be used, including a lithium-based battery.

Figure 20:
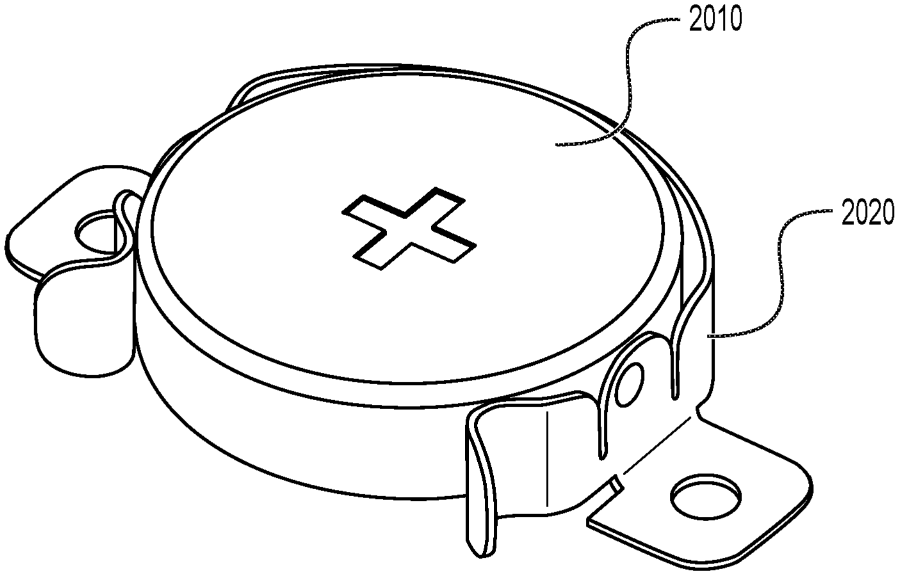
FIG. 20 depicts an illustrative schematic of a low profile battery holder.

In some variations, the power source may be coupled to the device PCB using a low profile holder or mount that reduces the overall height of the electronics, thereby minimizing the height or profile of the analyte monitoring device. For example, whereas traditional battery holders apply force to the topside of the battery using a conductive metal with a spring force, in some variations a lateral mounted battery holder may contact the sides of the battery to complete the electrical circuit. For example, as shown in FIG. 20, a lateral mounted battery holder 2020 may include an arcuate clip that clamps or otherwise contacts the sides of a battery 2010 without increasing vertical bulk. The battery holder 2020 may further include one or more mounting holes to couple to the device PCB via one or more suitable fasteners (and/or may couple to the device PCB in any suitable manner). In some variations, the housing may be sized and/or shaped with suitable tolerances so as to apply vertical or downward force on the battery 2010 toward the device PCB, in order to keep the battery 2010 in contact with the PCB.

Applicator

In some variations, the analyte monitoring device may be applied manually. For example, a user may remove a protective film on the adhesive layer, and manually press the device onto his or her skin on a desired wear site. Additionally or alternatively, as illustrated in FIG. 1, in some variations the analyte monitoring device may be applied to the skin using a suitable applicator 160. The applicator 160 may, for example, be configured to urge the analyte monitoring device 110 toward the skin of the user such that the microneedle array 140 of the analyte monitoring device 110 may be inserted into the skin (e.g., to the desired target depth).

Kits

In some variations, some or all components of the analyte monitoring system may be provided in a kit (e.g., to a user, to a clinician, etc.). For example, a kit may include at least one analyte monitoring device 110 and/or at least one applicator 160. In some variations, a kit may include multiple analyte monitoring devices 110, which may form a supply of analyte monitoring devices sufficient that is for a predetermined period of time (e.g., a week, two weeks, three weeks, a month, two months, three months, six months, a year, etc.). The kit may include any suitable ratio of applicators to analyte monitoring devices (e.g., 1:1, lower than 1:1, greater than 1:1). For example, the kit may include the same number of applicators as analyte monitoring devices, such as if each applicator is single-use and is configured to be disposed after its use in applying a respective analyte monitoring device to the user. As another example, the kit may include a number of applicators that is lower than the number of analyte monitoring devices in the kit (e.g., one applicator per two or three analyte monitoring devices), such as if an applicator is intended to be reused for applying multiple analyte monitoring devices or if multiple analyte monitoring devices are loaded into a single applicator for repeated applications. As another example, the kit may include a number of applicators that is higher than the number of analyte monitoring devices in the kit (e.g., two applicators per analyte monitoring device), such as to provide extra or redundant applicators in case of applicator loss or breakage, etc.

In some variations, the kit may further include user instructions for operating the analyte monitoring device and/or applicator (e.g., instructions for applying the analyte monitoring device manually or with the applicator, instructions for pairing the analyte monitoring device with one or more peripheral devices (e.g., computing devices such as a mobile phone), etc.).

Sterilization of Analyte Monitoring Device

As described above, the analyte monitoring devices 110 such as those described herein are differentiated from other CGM devices at least in that the sensing elements (e.g., microneedle array) and electronics are integrated into one unit. One benefit to this integration is that the user is not required to perform any assembly of the analyte monitoring device 110. However, there are sterilization-related challenges to enabling such integration Traditional CGM devices and similar electrochemical sensors are typically sterilized through processes that are incompatible with electronics. For example, conventional electrochemical sensor sterilization use gamma radiation or electron beam radiation to sterilize the sensing elements. However, the bosonic or fermionic particles associated with these sterilization processes interfere with electronics operation. Thus, typically the electronic component(s) must either be sterilized separately and require the end user to perform some assembly of the device, or the electronic component(s) are simply not sterilized, which may lead to contamination issues.

In contrast, the sensor technologies described above are configured to be compatible with a form of sterilization that is suitable for both the sensing elements and the electronics. In some variations, as described above, the working electrodes in the microneedle array may include a biorecognition layer including a cross-linked biorecognition element. For example, the biorecognition element may be cross-linked with an amine-condensing carbonyl chemical species, which helps to bridge amine groups and thus help stabilize the biorecognition element within the biorecognition layer. For example, the biorecognition element may include an enzyme (e.g., glucose oxidase) that is cross-linked with glutaraldehyde, formaldehyde, glyoxal, malonaldehyde, succinaldehyde, and/or other suitable species and then embedded in a conducting polymer as described above.

A result of the above-described cross-linked structure is that the enzyme is sufficiently stabilized so that it may undergo gaseous methods of sterilization, such as ethylene oxide (EO) sterilization, with surprisingly only minimal impact on sensing elements in terms of sensing performance. Thus, since electronics may undergo EO sterilization, in some variations the analyte monitoring devices 110 are uniquely and advantageously configured to survive an "all in one" sterilization procedure with their electronics and sensing elements fully integrated and simultaneously sterilized in a single unit, without damaging either set of components.

Accordingly, in some variations, a method of sterilizing an analyte monitoring device may include exposing the analyte monitoring device to a sterilant gas, where the analyte monitoring device includes a housing (e.g., wearable housing), a microneedle array extending from the housing and including an analyte sensor, and an electronics system arranged in the housing and electrically coupled to the microneedle array. The analyte monitoring device is exposed to the sterilant gas for a dwell time sufficient to sterilize the analyte monitoring device. In some variations, the analyte monitoring device may be sterilized to a Sterility Assurance Level (SAL) of $10^{-6}$ (i.e., having a probability that not more than 1 viable microorganism among 1,000,000 sterilized devices).

Figure 21:
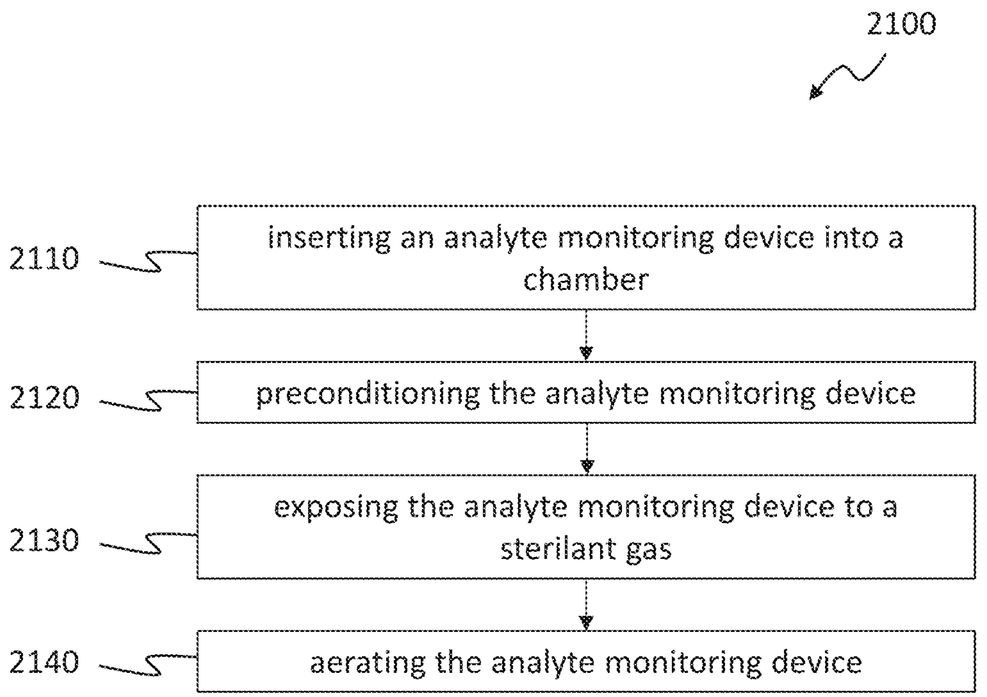
FIG. 21 depicts an illustrative flowchart of a method for sterilizing an analyte monitoring device.

FIG. 21 illustrates an example variation of a method 2100 for sterilizing an analyte monitoring device. Method 2100 may include, for example, inserting an analyte monitoring device into a chamber 2110 suitable for sterilization, preconditioning the analyte monitoring device 2120, exposing the analyte monitoring device to a sterilant gas 2130, and aerating the analyte monitoring device 2140.

Figure 22:
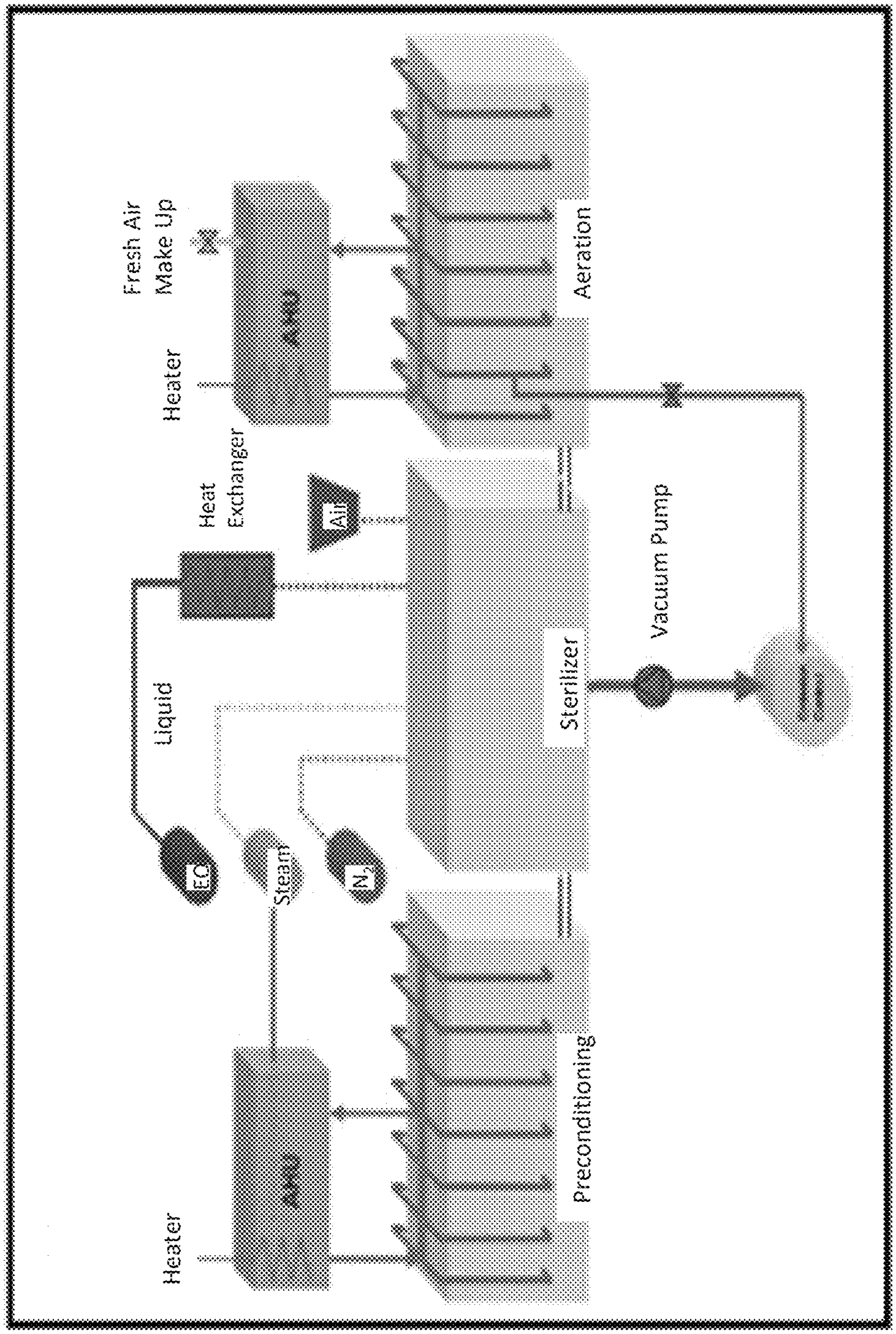
FIG. 22 depicts an illustrative schematic of a sterilization setup usable for ethylene oxide sterilization.

FIG. 22 depicts a schematic of an example variation of a sterilization system including a chamber (or series of chambers) suitable for use in sterilizing an analyte monitoring device. For example, the sterilization system may include at least one chamber for executing a preconditioning process, at least one chamber for a sterilizing process, and/or at least one chamber for an aerating process. In some variations, the same chamber may be utilized for two or more these processes of method 2100.

Thus, for example, an analyte monitoring device may be placed within a preconditioning chamber for the preconditioning process 2120. As described above, the analyte monitoring device may be placed in the chamber as an integrated device, including both electrochemical sensing elements and electronic components.

Figure 23:
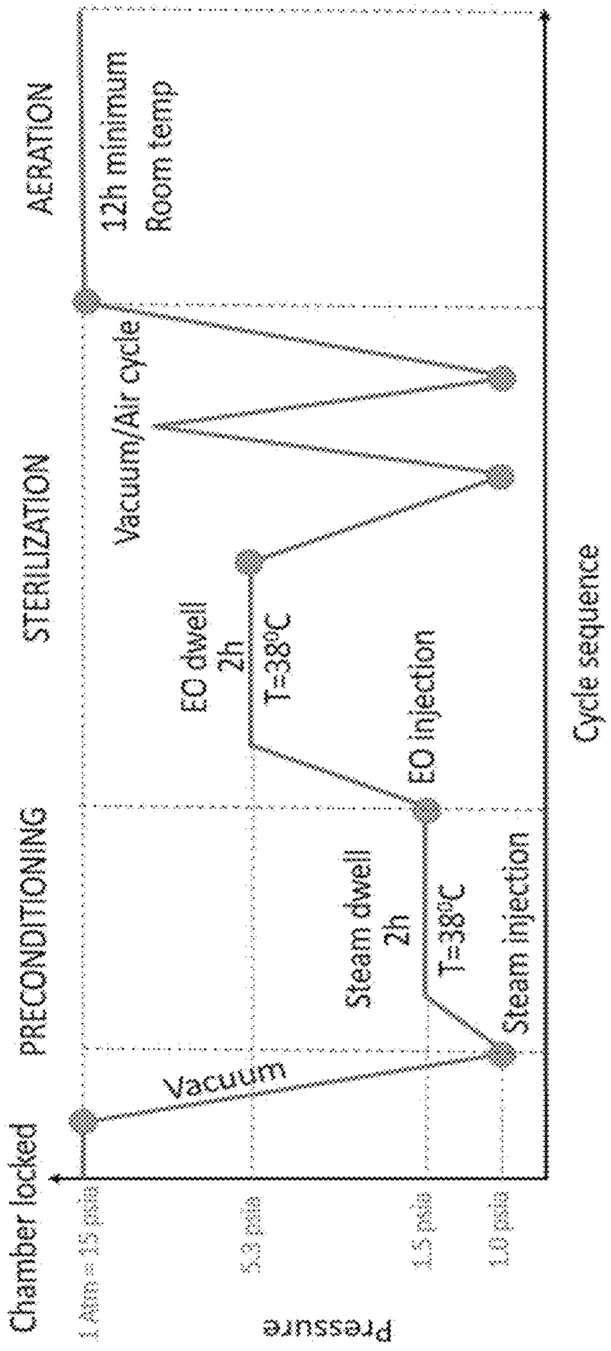
FIG. 23 depicts an illustrative variation of an ethylene oxide sterilization protocol.

Preconditioning may function to heat and humidify the analyte monitoring device to a stable temperature and moisture content prior to entering the sterilization chamber, which may help ensure consistency and reliability of the sterilization process, regardless of environmental conditions. As shown in FIG. 23, preconditioning the analyte monitoring device may include reducing the pressure in the chamber to a vacuum set point (e.g., 1.0 psia). The vacuum may be established gradually, such as at a rate of about 2 psia/minute or other suitable rate. Furthermore, preconditioning may include setting other environmental conditions to various set points for a predetermined dwell time. For example, as shown in FIG. 23, after reducing the pressure to the vacuum set point, steam may be injected into the chamber so as to establish the temperature, relative humidity, and/or humidity at predetermined set points. For example in one implementation, temperature inside the chamber may be set to between about 35 degrees Celsius to about 40 degrees Celsius, or about 38 degrees Celsius, which may be suitable so as to avoid denaturing the biorecognition element (e.g., enzyme) from higher heat during preconditioning. As another example, relative humidity may be set to between about 45% to about 55% (or about 51%). The temperature, relative humidity, and vacuum set points may be maintained for a predetermined dwell time, such as between about 90 minutes and about 180 minutes, between about 100 minutes and about 100 minutes and about 160 minutes, between about 110 minutes and about 140 minutes, or about 120 minutes, or other suitable period of time. After the dwell time has passed, the chamber may be evacuated and/or the conditioned analyte monitoring device may be removed and placed in a sterilization chamber.

As shown in FIG. 21, after preconditioning the analyte monitoring device, the method may include exposing the analyte monitoring device to a sterilant gas 2130, such as ethylene oxide (EO). In some variations, the EO may be introduced into the sterilization chamber at a gas concentration of between about 425 mg/L and about 475 mg/L, or about 450 mg/L. As shown in FIG. 23, during the sterilization process the pressure in the chamber may be set to a sterilant set point of between about 5 psia and about 6 psia, or about 5.3 psia. In some variations, at least about 97% of the air must be evacuated from the chamber prior to delivering EO gas into the chamber. Additionally or alternatively, a series of partial vacuums may be established in the chamber followed by a series of nitrogen ($N_2$) injections to purge a sufficient amount of air from the chamber. Similar to the temperature during preconditioning, temperature of the chamber during sterilization may be set to between about 35 degrees Celsius to about 40 degrees Celsius, or about 38 degrees Celsius. Temperature may be increased to the temperature set point as EO is introduced. After introducing EO gas into the chamber, the analyte monitoring device may remain exposed to the EO gas for a suitable sterilant dwell time or exposure time. Suitable sterilant dwell times may, for example, range between about 90 minutes and about 180 minutes, between about 100 minutes and about 100 minutes and about 160 minutes, between about 110 minutes and about 140 minutes, or about 120 minutes, or other suitable period of time sufficient for sterilizing the analyte monitoring device. It should be understood that in some variations, an increase in temperature during EO exposure will reduce the necessary EO dwell time (e.g., as a rule of thumb every 10 degrees Celsius increase in temperature may reduce the EO dwell time by about half). Following the sterilant dwell time, the chamber may undergo a vacuum/air cycle to purge the EO from the chamber.

As shown in FIG. 21, the method 2100 may include aerating the analyte monitoring device 2140. Aeration of the analyte monitoring device may allow for the additional removal of any residual gases from the device (e.g., prior to packaging and storage), as EO is flammable and any residual EO on the device post-sterilization can be extremely toxic. In some variations, aeration may occur at room temperature. As shown in FIG. 23, the aeration may last for a predetermined period of time sufficient to permit thorough outgassing. For example, the aeration process may last between at least about 4 hours and 24 hours, such as about 12 hours. In other variations, the aeration process may last at least about 12 hours, at least about 15 hours, or at least 24 hours, etc.

EXAMPLE

An EO sterilization cycle was evaluated for feasibility to sterilize an analyte monitoring device such as those described herein. Briefly, the preconditioning was done for two hours at a temperature of 38 degrees Celsius. This was followed by exposure to EO gas for two hours at 38 degrees Celsius. After EO exposure, the samples were aerated to vent out the EO gas at ambient temperatures for a minimum of 12 hours. Details of the EO exposure protocol are shown in Table 1:

TABLE 1

Example EO Exposure Protocol

| | |
|---|---|
| Sterilization Set Points | |
| EO Gas Concentration | 450 mg/L (100% EO) |
| Temperature | 38° C. |
| Relative Humidity | 51% |
| Initial Vacuum | 1.0 psia |
| EO Gas Dwell Time | 120 minutes |
| Steam Dwell Time | 120 minutes |
| Aeration Set Points | |
| Temperature | Ambient |
| Time | 12 hours (minimum) |
| Post-Vacuum | 3.5 psia |

TABLE 1-continued

Example EO Exposure Protocol

| | |
|---|---|
| DETOX A | |
| Initial Steam Flush | 3.7 psia |
| Initial Steam Flush Dwell Time | 0 min |
| Steam Pulse | 3.7 psia |
| Steam Pulse Dwell Time | 5 min |
| Vacuum | 3.5 psia |
| Steam Flush | 3.7 psia |
| Steam Flush Dwell Time | 0 |
| DETOX B | |
| Steam Pulse | 3.7 psia |
| Steam Pulse Dwell Time | 5 minutes |
| Vacuum | 3.5 psia |
| Steam Flush | 3.7 psia |
| Steam Flush Dwell Time | 0 min |
| Air Washes | 11.0-2.0 psia (5 total) |

Figure 24A:
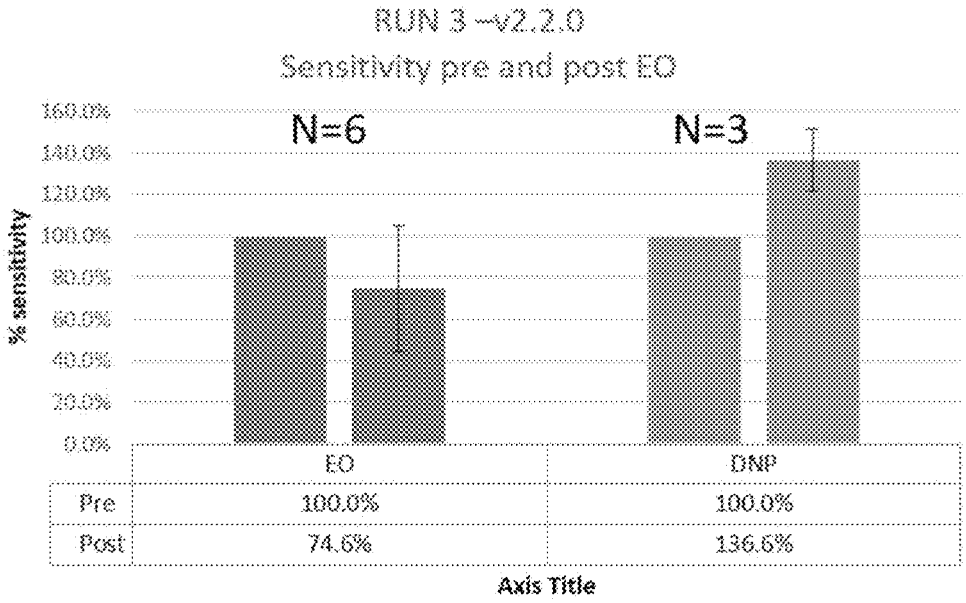
FIGS. 24A-24C depict exemplary data suggesting feasibility of ethylene oxide sterilization for an analyte monitoring device.

To test the stability of sensing chemistry following exposure to EO, six functionalized microneedle sensors were subject to an EO sterilization cycle. In this example, sensor chemistry using amide cross-linking of glucose oxidase was evaluated in this feasibility study. FIG. 24 shows the retained sensitivity for the six sensors after exposure to EO (EO), as well as for three sensors functioning as a negative control (do not process (DNP)). Overall, all six sensors that were exposed to EO remained sensitive to glucose post processing. The average percentage sensitivity retained was 75%.

Figure 24B:
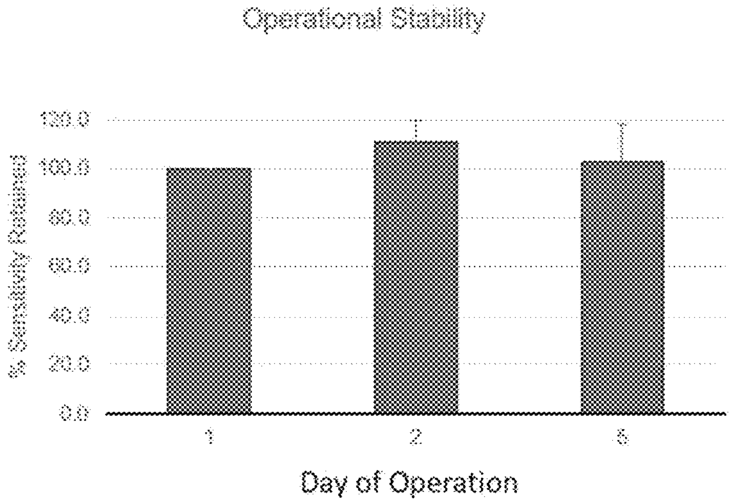

Three of the sensors that were exposed to EO were also subsequently tested for operational stability in PBS with 6 mM glucose over seven days. Sensors were kept in solution and sensitivity was measured by calibrating the sensors once per day. The summary results from the operational stability testing are shown in FIG. 24B. It is seen that the sensors remained stable over the course of the test. No data was obtained for days five and six due to instrument error. This trend is similar to that observed for sensors sterilized with gamma irradiation.

Figure 24C:
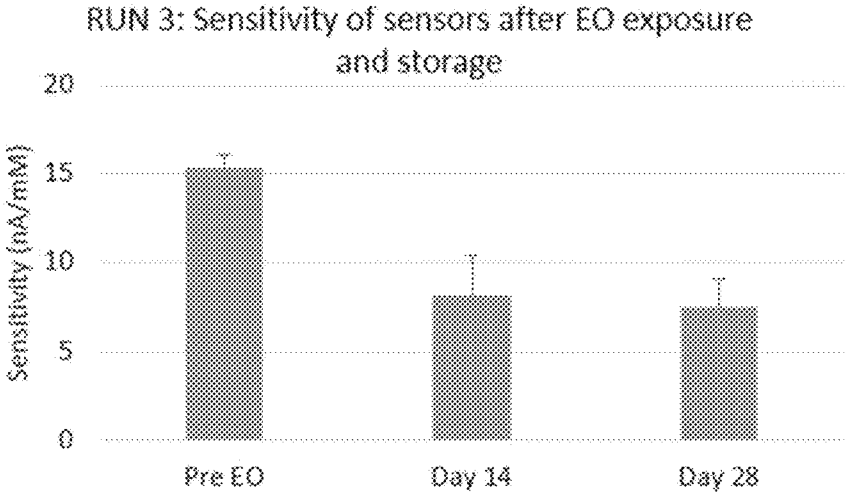

Additionally, three sensors exposed to EO were used to test the storage stability. FIG. 24C shows the average sensitivity on Day 0 (Pre EO exposure), Day 14, and Day 28. The sensors were stored dry between day 14 and 28 at 37 degrees C. The average sensitivity retained from Day 14 to Day 28 of dry storage was 92%. This shows the potential to be able to sterilize using EO and store the sensors after exposure to EO.

Thus, the cross-linked sensor chemistry was found to be sufficiently stable to EO exposure, indicating that using EO process is feasible to sterilize an analyte monitoring device with sensing elements including the cross-linked sensor chemistry. Additionally, the chemistry after EO exposure was stable over seven days of active operation and also during dry storage.

In some variations, the sensor may be decoupled from the electronics and undergo other suitable methods of sterilization, including those based on irradiation by means of gamma rays/particles or with an electron beam of sufficient acceleration potential. Dosage of sterilization (e.g., duration and particle energy) may be controlled in to achieve a satisfactory level of sterility, including a sterility assurance level (SAL) of less than 1E-6. In some variations, the electronics do not require sterilization as they do not contact breached or compromised skin surfaces. In such variations, the electronics may be coupled to the sensor prior to the application of the entire system to the user's skin.

Use of Analyte Monitoring System

Described below is an overview of various aspects of a method of use and operation of the analyte monitoring system, including the analyte monitoring device and peripheral devices, etc.

Application of Analyte Monitoring Device

As described above, the analyte monitoring device is applied to the skin of a user such that the microneedle array in the device penetrates the skin and the microneedle array's electrodes are positioned in the upper dermis for access to dermal interstitial fluid. For example, in some variations, the microneedle array may be geometrically configured to penetrate the outer layer of the skin, the stratum corneum, bore through the epidermis, and come to rest within the papillary or upper reticular dermis. The sensing region, confined to the electrode at the distal extent of each microneedle constituent of the array (as described above) may be configured to rest and remain seated in the papillary or upper reticular dermis following application in order to ensure adequate exposure to circulating dermal interstitial fluid (ISF) without the risk of bleeding or undue influence with nerve endings.

In some variations, the analyte monitoring device may include a wearable housing or patch with an adhesive layer configured to adhere to the skin and fix the microneedle array in position. While the analyte monitoring device may be applied manually (e.g., removing a protective film on the adhesive layer, and manually pressing the patch onto the skin on a desired wear site), in some variations the analyte monitoring device may be applied to the skin using a suitable applicator.

The analyte monitoring device may be applied in any suitable location, though in some variations it may be desirable to avoid anatomical areas of thick or calloused skin (e.g., palmar and plantar regions), or areas undergoing significant flexion (e.g., olecranon or patella). Suitable wear sites may include, for example, on the arm (e.g., upper arm, lower arm), shoulder (e.g., over the deltoid), back of hands, neck, face, scalp, torso (e.g., on the back such as in the thoracic region, lumbar region, sacral region, etc. or on the chest or abdomen), buttocks, legs (e.g., upper legs, lower legs, etc.), and/or top of feet, etc.

As described above, in some variations the analyte monitoring device may be configured to automatically activate upon insertion, and/or confirm correct insertion into skin. Details of these features are described in further detail above. In some variations, methods for performing such activation and/or confirmation may be similar to that described in U.S. patent application Ser. No. 16/051,398, which was incorporated by reference above.

Pairing to Peripheral Device

In some variations, the analyte monitoring device may be paired to at least one peripheral device such that the peripheral device receives broadcasted or otherwise transmitted data from the analyte monitoring device, including measurement data. Suitable peripheral devices include, for example a mobile computing device (e.g., smartphone, smartwatch) which may be executing a mobile application.

Additionally alternatively, an analyte monitoring device may be paired (or otherwise combined) with a therapeutic delivery device (e.g., insulin pen or pump). For example, an analyte monitoring device may be combined with a therapeutic delivery device in a manner similar to that described in U.S. Patent App. Nos. 62/823,628 and 62/862,658, each of which is incorporated herein in its entirety by this reference. Studies have shown that users with insulin delivery devices that have smart algorithms controlling dosing are in euglycemic range (i.e. healthy blood glucose levels) >95% of the time when CGM is available. The ability of the analyte monitoring device to communicate directly with insulin delivery devices (i.e. no intermediary smartphone required) allows users to achieve increased time in range significantly by eliminating the time when CGM is not available (during warmup or swap in of analyte monitoring devices). This feature may also enable users to wear multiple analyte monitoring devices that detect different analytes simultaneously and input data into the same mobile application.

As described above, the pairing may be accomplished through suitable wireless communication modules (e.g., implementing Bluetooth). In some variations, the pairing may occur after the analyte monitoring device is applied and inserted into the skin of a user (e.g., after the analyte monitoring device is activated). Additionally or alternatively, the pairing may occur prior to the analyte monitoring device being applied and inserted into the skin of a user.

Thus, the paired mobile or other device may receive the broadcasted or transmitted data from the analyte monitoring device. The peripheral device may display, store, and/or transmit the measurement data to the user and/or healthcare provider and/or support network. Furthermore, in some variations, the said paired mobile or wearable device performs algorithmic treatment to the data to improve the signal fidelity, accuracy, and/or calibration, etc. In some variations, measurement data and/or other user info may additionally or alternatively be communicated and/or stored via network (e.g., cloud network).

By way of illustration, in some variations a mobile computing device or other computing device (e.g., smartphones, smartwatches, tablets, etc.) may be configured to execute a mobile application that provides an interface to display estimated glucose values, trend information and historical data, etc. Although the below description refers specifically to glucose as a target analyte, it should be understood that the features and processes described below with respect to glucose may be similarly applied to applications relating to other kinds of analytes.

Figure 26:
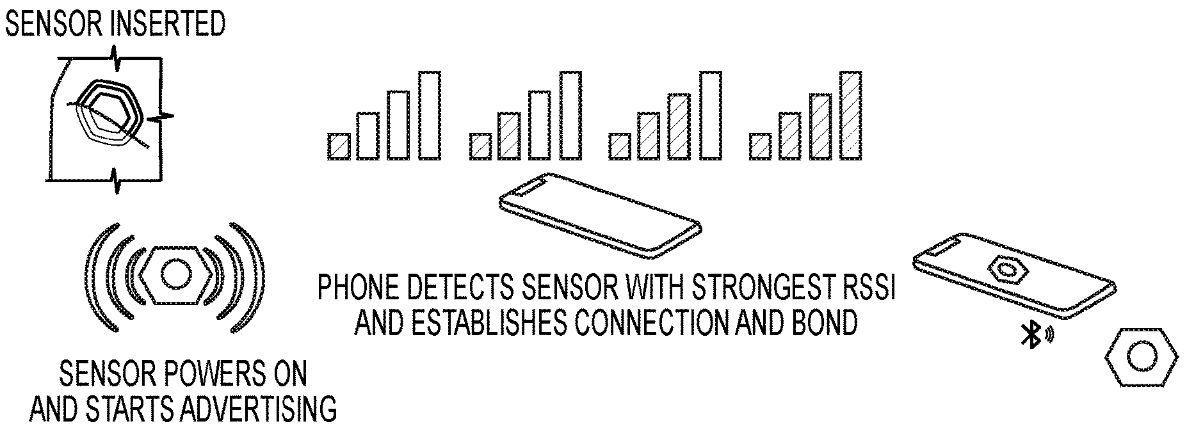
FIG. 26 is an illustrative schematic of pairing between an analyte monitoring device and a mobile computing device executing a mobile application.

In some variations, the mobile application may use the mobile computing device's Bluetooth framework to scan for the analyte monitoring device. As shown in FIG. 26, the analyte monitoring device may power on or initialize as soon as it is applied to the skin, and the analyte monitoring device may begin the advertising process. The mobile application may then connect to the analyte monitoring device and begin priming the sensor for measurement. In case the mobile application detects multiple analyte monitoring devices, the mobile application may detect the analyte monitoring device that is closest in proximity to itself and/or may request the user (e.g., via the user interface on the mobile device) to confirm disambiguation. In some variations, the mobile application may also be capable of connecting to multiple analyte monitoring devices simultaneously. This may be useful, for example, to replace sensors that are reaching the end of their lifetime.

In some variations, the Bluetooth® Low Energy™ (BLE) protocol may be used for connectivity. For example, the sensor implements a custom BLE peripheral profile for the analyte monitoring system. Data may be exchanged after establishing a standard secure BLE connection between the analyte monitoring device and the smartphone, smartwatch, or tablet running the mobile application. The BLE connection may be maintained permanently for the life of the sensor. If the connection is broken due to any reasons (e.g., weak signal) the analyte monitoring device may start advertising itself again and the mobile application may re-establish the connection at the earliest opportunity (i.e. when in range/physical proximity).

In some variations, there may be one or more additional layers of security implemented on top of the BLE connection to ensure authorized access consisting of a combination of one or more techniques such as passcode-protection, shared-secrets, encryption and multi-factor authentication.

The mobile application may guide the user through initiating a new analyte monitoring device. Once this process completes, the mobile application is not be required for the analyte monitoring device to operate and record measurements. In some variations, a smart insulin delivery device that is connected to the analyte monitoring device can be authorized from the mobile application to receive glucose readings from the sensor directly. Additionally or alternatively, a secondary display device like a smartwatch can be authorized from the mobile application to receive glucose readings from the sensor directly.

Furthermore, in some variations the mobile application may additionally or alternatively help calibrate the analyte monitoring device. For example, the analyte monitoring device may indicate a request for calibration to the mobile application, and the mobile application may request calibration input from the user to calibrate the sensor.

Sensor Measurements

Once the analyte monitoring device is inserted and warm-up and any calibration has completed, the analyte monitoring device may be ready for providing sensor measurements of a target analyte. The target analyte (and any requisite co-factor(s)) diffuses from the biological milieu, through the biocompatible and diffusion-limiting layers on the working electrode, and to the biorecognition layer including the biorecognition element. In the presence of a co-factor (if present), the biorecognition element may convert the target analyte to an electroactive product.

A bias potential may be applied between the working and reference electrodes of the analyte monitoring device, and an electrical current may flow from the counter electrode to maintain the fixed potential relationship between the working and reference electrodes. This causes the oxidation or reduction of the electroactive product, causing a current to flow between the working electrodes and counter electrodes. The current value is proportional to the rate of the redox reaction at the working electrode and, specifically, to the concentration of the analyte of interest according to the Cottrell relation as described in further detail above.

The electrical current may be converted to a voltage signal by a transimpedance amplifier and quantized to a digital bitstream by means of an analog-to-digital converter (ADC). Alternatively, the electrical current may be directly quantized to a digital bitstream by means of a current-mode ADC. The digital representation of the electrical current may be processed in the embedded microcontroller(s) in the analyte monitoring device and relayed to the wireless communication module for broadcast or transmission (e.g., to one or more peripheral devices). In some variations, the microcontroller may perform additional algorithmic treatment to the data to improve the signal fidelity, accuracy, and/or calibration, etc.

In some variations, the digital representation of the electrical current, or sensor signal, may be correlated to an analyte measurement (e.g., glucose measurement) by the analyte monitoring device. For example, the microcontroller may execute a programmed routine in firmware to interpret the digital signal and perform any relevant algorithms and/or other analysis. Keeping the analysis on-board the analyte monitoring device may, for example, enable the analyte monitoring device to broadcast analyte measurement(s) to multiple devices in parallel, while ensuring that each connected device has the same information. Thus, generally, the user's target analyte (e.g., glucose) values may be estimated and stored in the analyte monitoring device and communicated to one or more peripheral devices.

Data exchange can be initiated by either the mobile application or by the analyte monitoring device. For example, the analyte monitoring device may notify the mobile application of new analyte data as it becomes available. The frequency of updates may vary, for example, between about 5 seconds and about 5 minutes, and may depend on the type of data. Additionally or alternatively, the mobile application may request data from the analyte monitoring device (e.g., if the mobile application identifies gaps in the data it has collected, such as due to disconnections).

If the mobile application is not connected to the analyte monitoring device, the mobile application may not receive data from the sensor electronics. However, the electronics in the analyte monitoring device may store each actual and/or estimated analyte data point. When the mobile application is reconnected to the analyte monitoring device, it may request data that it has missed during the period of disconnection and the electronics on the analyte monitoring device may transmit that set of data as well (e.g., backfill).

Generally, the mobile application may be configured to provide display of real-time or near real-time analyte measurement data, such as on the display of the mobile computing device executing the mobile application. In some variations, the mobile application may communicate through a user interface regarding analysis of the analyte measurement, such as alerts, alarms, insights on trends, etc. such as to notify the user of analyte measurements requiring attention or follow-up action (e.g., high analyte values, low analyte values, high rates of change, analyte values outside of a pre-set range, etc.). In some variations, the mobile application may additionally or alternatively facilitate communication of the measurement data to the cloud for storage and/or archive for later retrieval.

Interpreting Analyte Monitoring Device User Interface

In some variations, information relating to analyte measurement data and/or the analyte monitoring device may be communicated via a user interface of the analyte monitoring device. In some variations, the user interface of the analyte monitoring device may be used to communicate information to a user in addition to, or as an alternative to, communicating such information via a peripheral device such as through a mobile application on a computing device. Accordingly, a user and/or those around the user may easily and intuitively view the analyte monitoring device itself for an assessment of analyte measurement data (e.g., analyte measurement status such as current and/or trending analyte measurement levels) and/or device status, without the need to view a separate device (e.g., peripheral device or other device remote from, and in communication with, the analyte monitoring device). Availability of such information directly on the analyte monitoring device itself may also enable a user and/or those around the user to more promptly be alerted of any concerns (e.g., analyte measurements that are above or below target range, and/or analyte measurements that are increasing or decreasing at an alarming rate), thereby enabling a user to take appropriate corrective action more quickly.

Figure 32A:
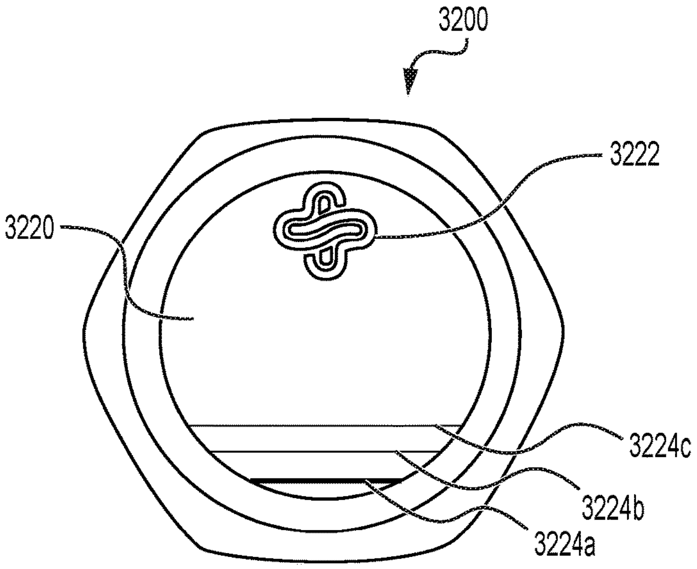
FIGS. 32A-32C depict illustrative schematics of illumination modes in an analyte monitoring device for indicating analyte measurement data.
Figure 32B:
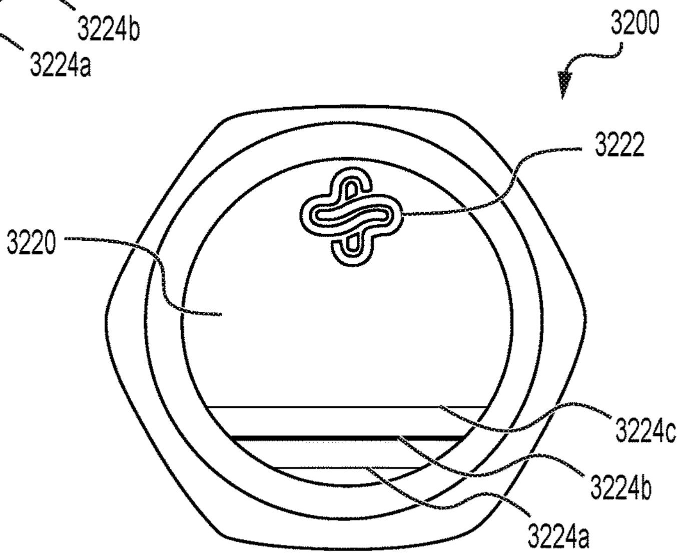
Figure 32C:
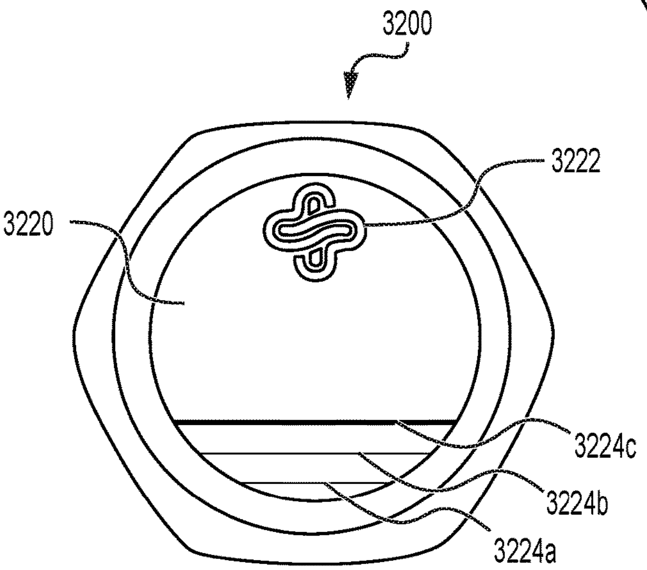

For example, FIGS. 32A-32C depict an example variation of an analyte measurement device 3200 including a user interface 3220 with multiple indicator lights, including indicator lights 3224*a*-3224*c*, which may be selectively illuminated to communicate a user status (e.g., information relating to analyte measurement in the user). The user interface 3220 may be similar, for example, to user interface 3120 described above with respect to FIG. 31A and/or FIG. 31B. Although the user interface 3220 includes three indicator lights 3224*a*-3224*c*, it should be understood that in some variations, the user interface 3220 may include any suitable number of lights, including fewer than three (e.g., one, two) or more than three (e.g., four, five, six, or more).

The indicator lights 3224*a*-3224*c* may be arranged in a sequential manner such that their relative positions help a user to intuitively understand information communicated collectively by the user interface. For example, the three indicator lights 3224*a*-3224*c* may be illuminated to generally indicate three progressive levels (or ranges) of analyte measurements: the lowest indicator light 3224*a* may be illuminated to generally indicate an analyte measurement that is lowest of the three levels, the middle indicator light 3224*b* may be illuminated to generally indicate an analyte measurement that is in the middle of the three levels, and the highest indicator light 3224*c* may be illuminated to generally indicate an analyte measurement that is highest of the three levels. In one example variation, the lowest indicator light 3224*a* may be illuminated to indicate an analyte measurement that is in a target range (FIG. 32A), the middle indicator light 3224*b* may be illuminated to indicate an analyte measurement that is above a target range (FIG. 32B), and the highest indicator light 3224*c* may be illuminated to indicate an analyte measurement that is significantly above a target range (FIG. 32C). In another example variation, the lowest indicator light 3224*a* may be illuminated to indicate an analyte measurement that is below a target range, the middle indicator light 3224*b* may be illuminated to indicate an analyte measurement that is within the target range, and the highest indicator light 3224*c* may be illuminated to indicate an analyte measurement that is above a target range.

The threshold values for a target range may be any suitable values. For example, in some variations in which glucose monitoring is being performed, analyte measurements may be considered within a target range if they are between about 70 mg/dL and about 180 mg/dl (or between about 80 mg/dL or about 60 mg/dL and about 170 mg/dL or about 190 mg/dL, etc.), and may be considered below a target range if they are below about 70 mg/dL (or below about 80 mg/dL, or below about 60 mg/dL, etc.). The different thresholds for "above" a target range and "significantly" above a target range may have any suitable value. For example, in some variations, analyte measurements may be considered "above" a target range if it is above a first predetermined threshold (e.g., above a threshold value of about 180 mg/dL for hyperglycemia determination in glucose monitoring, or above a threshold value that is between about 170 mg/dL and about 200 mg/dL for hyperglycemia determination in glucose monitoring) and analyte measurement may be considered "significantly above" a target range if it is a predetermined amount (e.g., percentage) above the first predetermined threshold, such as at least 33% above the first predetermined threshold (e.g., >240 mg/dL for extreme hyperglycemia determination in glucose monitoring), or at least about 25% above the first predetermined threshold, at least about 30% above the first predetermined threshold, at least 35% above the first predetermined threshold, or at least 40% above the first predetermined threshold, or other suitable second predetermined threshold.

Furthermore, the thresholds for considering analyte measurements within target range, or below target range, or "above" target range or "significantly above" target range (or other characterization of the analyte measurements) may be static or dynamic, and/or may vary based on user information such as historical measurements and/or trends or other historical data (e.g., relative to an average or expected analyte measurement for the user at particular times or average or expected rate of change). Furthermore, it should be understood that while the user interface 3220 includes three sequential indicator lights, in other variations a user interface on the housing of an analyte monitoring device may include fewer (e.g., two) or more (e.g., four, five, six, or more) that may be similarly illuminated individually to indicate an analyte measurement (e.g., each corresponding to a general relative level of analyte measurement).

In some variations, different illumination colors and/or timing for one or more of the indicator lights 3224*a*-3224*c* may additionally or alternatively enable a user to easily distinguish between each analyte measurement level. For example, when an analyte measurement is within a target range, the appropriate indicator light(s) may be illuminated in a first color (e.g., blue), while when the analyte measurement is outside the target range, the appropriate indicator light(s) may be illuminated in another color (e.g., white for below target range, orange for above target range). As another example, when the analyte measurement is within a target range, the appropriate indicator light(s) may be illuminated in a first temporal pattern (e.g., long, gentle pulse of illumination "on" time), while when the analyte measurement is outside the target range, the appropriate indicator light(s) may be illuminated in another temporal pattern (e.g., short, flash-like pulse of illumination "on" time). Shorter pulses of illumination "on" time may, for example, be helpful to better attract user attention and/or more intuitively communicate an alert when the analyte measurement is below a target range, above a target range, or significantly above a target range. Higher frequency illumination may, in some variations, correlate to greater alert level (e.g., significantly below the target range or significantly above the target range).

FIGS. 33A-33D and Table 2 illustrate different illuminating modes used in an example method of operating the user interface 3220 of an analyte monitoring device. The exact parameter values of these illumination modes are non-limiting and are included for an example variation for illustrative purposes only. For example, in the "below target range" illumination mode, the illumination color may be any suitable color, and/or the illumination "on" time may be between about 0.1 seconds and 1 second, between about 0.2 seconds and 0.5 seconds, or about 0.3 seconds, and/or the illumination "off" time may be between about 0.5 seconds and about 5 seconds, or between about 1 second and about 4 seconds, or between about 2 seconds and about 4 seconds, or about 3 seconds; and/or the ratio between the illumination "on" and illumination "off" times may be about 0.1, about 0.2, about 0.3, about 0.4, about 0.5, and/or other suitable illumination parameters. As another example, in the "in target range" illumination mode and/or the "above target range illumination mode, the illumination color may be any suitable color, and/or the illumination "on" time may be between about 0.1 seconds and about 3 seconds, between about 0.5 seconds and about 2 seconds, or about 1 second, and/or the illumination "off" mode may be between about 0.5 seconds and about 5 seconds, or between about 1 second and about 4 seconds, or between about 2 seconds and about 4 seconds, or about 3 seconds, and/or the ratio between the illumination "on" and illumination "off" times may be about 0.1, about 0.2, about 0.3, about 0.4, about 0.5, and/or other suitable illumination parameters. As another example, in the "significantly above target range", the illumination color may be any suitable color, and/or the illumination "on" time may be between about 0.2 seconds and 2 seconds, between about 0.5 seconds and about 1.5 seconds, or about 0.8 seconds, and/or the illumination "off" time may be between about 0.5 seconds and about 5 seconds, or between about 1 second and about 4 seconds, or between about 2 seconds and about 4 seconds, or about 3 seconds and/or other suitable illumination parameters. Furthermore, fewer or more illumination modes for indicating analyte measurement level may be possible in other variations.

TABLE 2

Example illumination modes for indicating analyte measurement

Figure 33A:
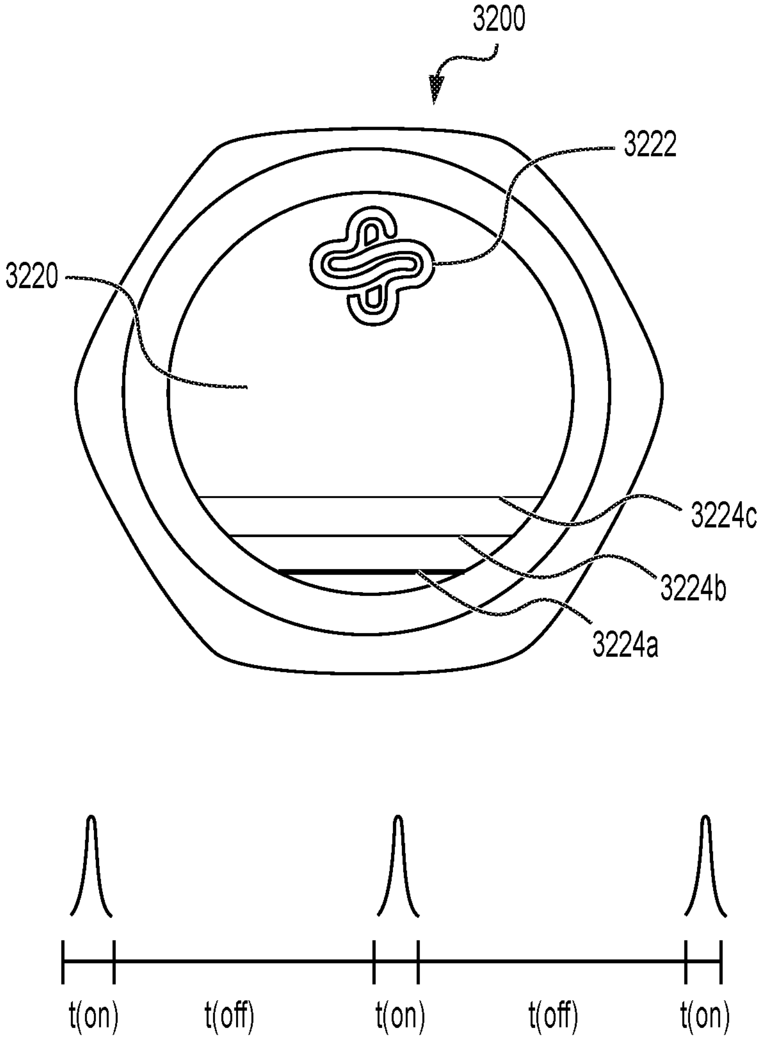
FIGS. 33A-33D depict illustrative schematics of illumination modes in an analyte monitoring device for indicating analyte measurement data.
Figure 33B:
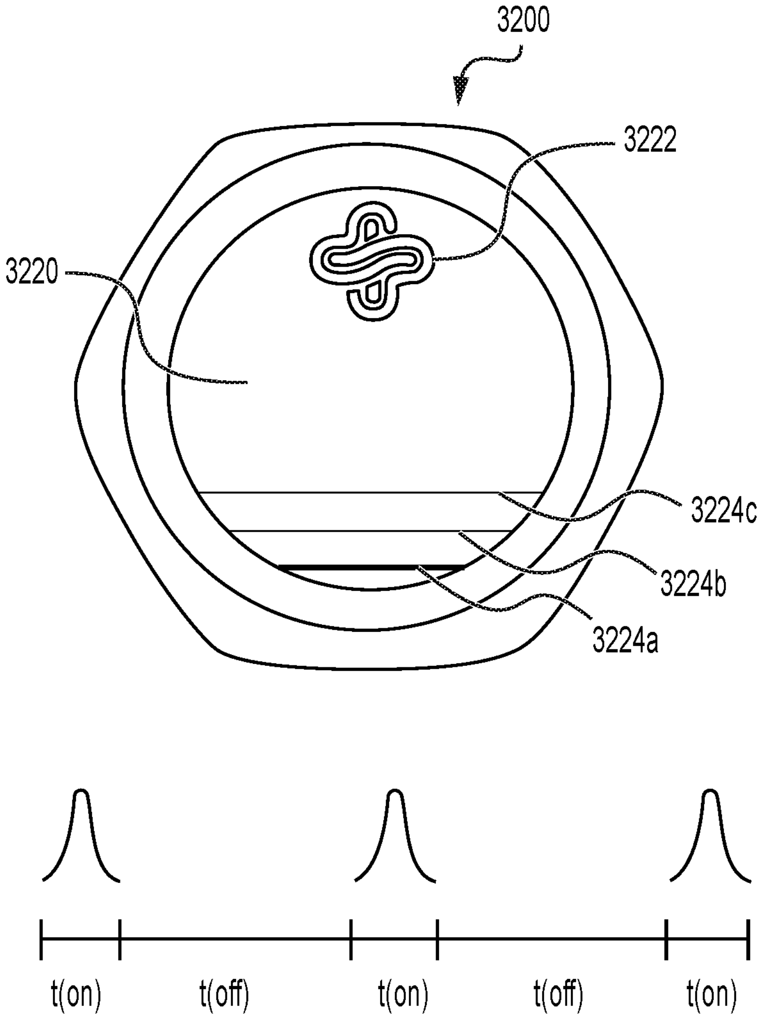
Figure 33C:
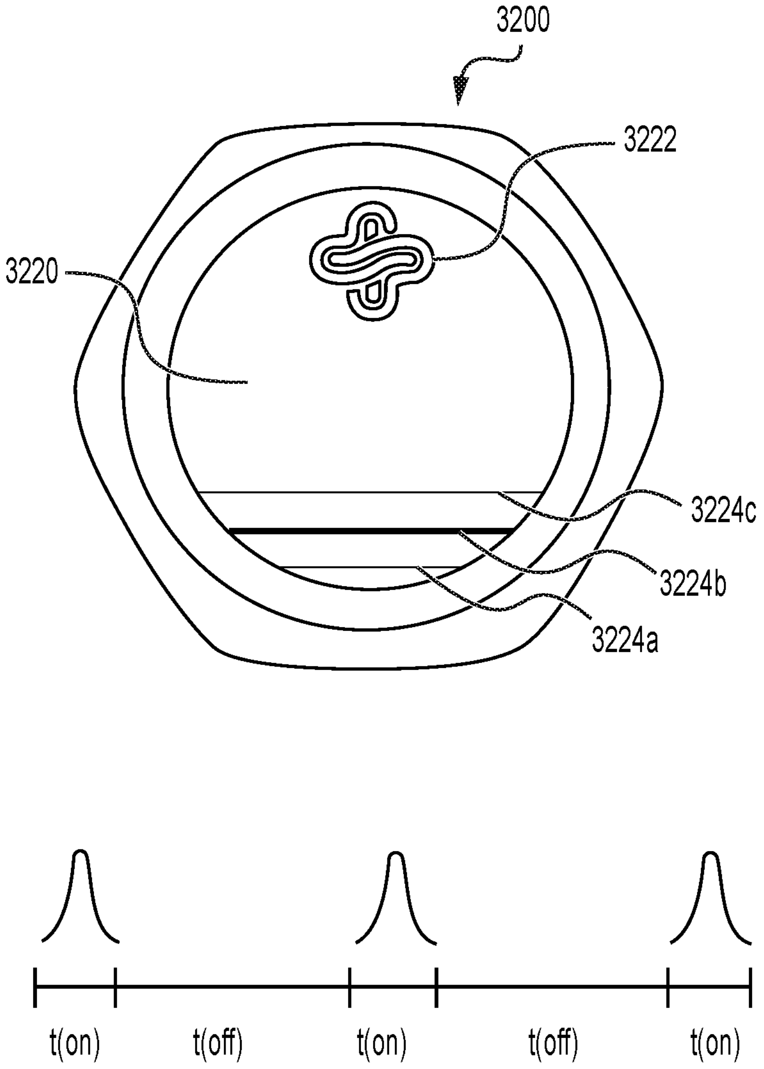
Figure 33D:
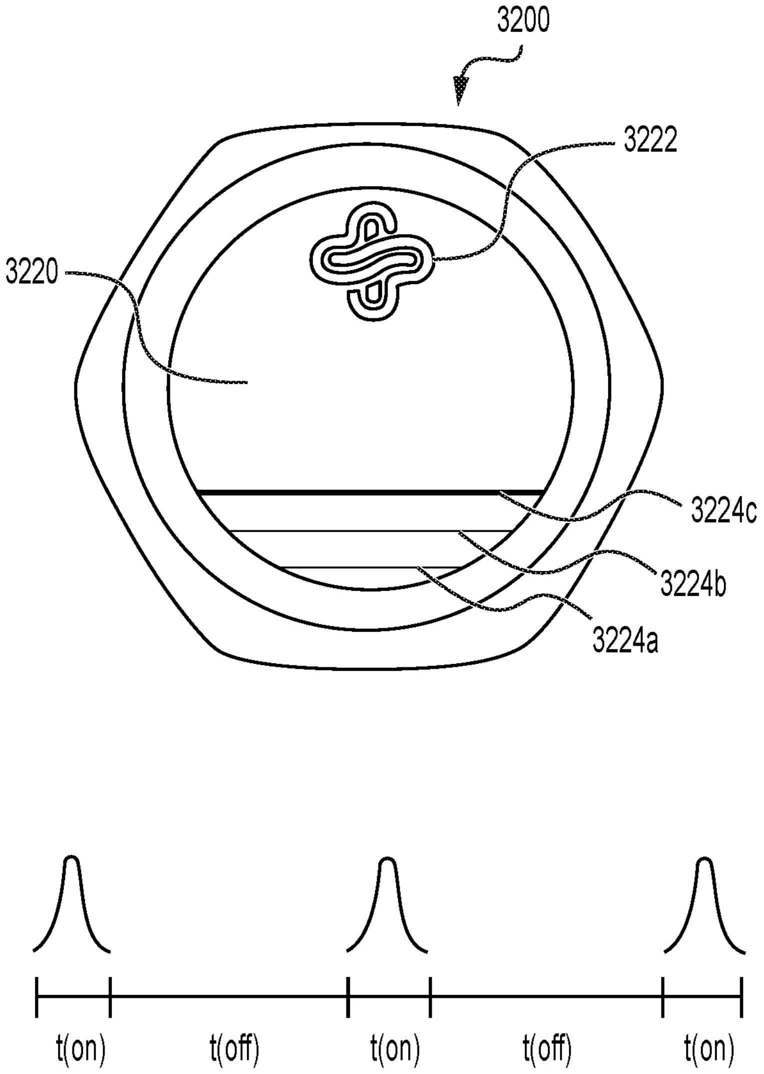

| Analyte measurement level | Figure | Indicator light illuminated | Illumination color | Illumination "on" time t(on) | Illumination "off" time t(off) |
|---|---|---|---|---|---|
| Below target range | FIG. 33A | Lowest | White | 0.3 sec | 3 sec |
| In target range | FIG. 33B | Lowest | Blue | 1 sec | 3 sec |
| Above target range | FIG. 33C | Middle | Orange | 1 sec | 3 sec |
| Significantly above target range | FIG. 33D | Highest | Orange | 0.8 sec | 3 sec |

Figure 34A:
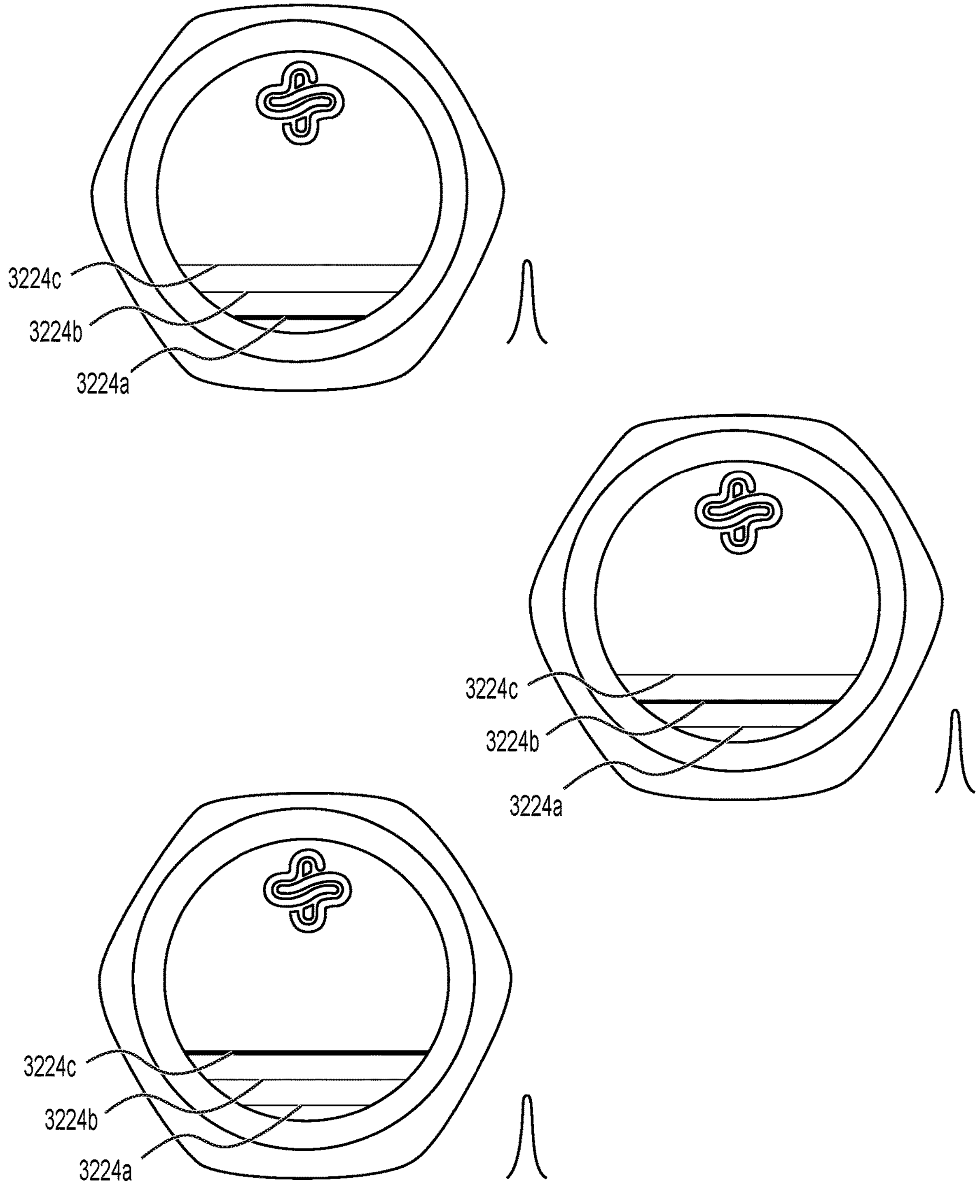
FIGS. 34A-34C depict illustrative schematics of illumination modes in an analyte monitoring device for indicating analyte measurement data.
Figure 34B:
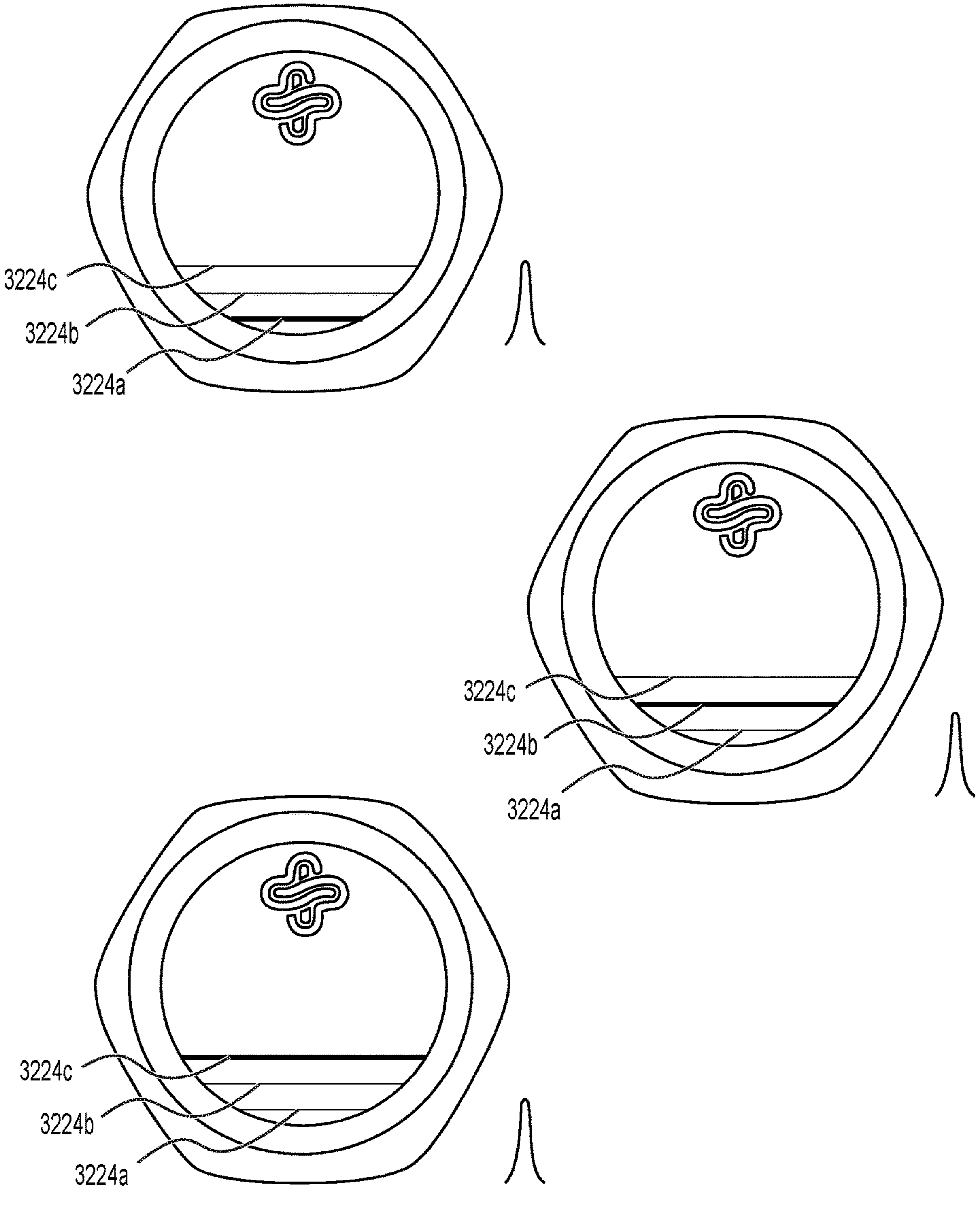

Additionally or alternatively, in some variations, the indicator lights 3224*a*-3224*c* may be illuminated in a progressive sequence to indicate trend information of analyte measurements over time. For example, as shown in FIG. 34A, a progressive sequence of illumination of the indicator lights 3224*a*-3224*c* in a first direction from lower indicator light(s) to higher indicator light(s) (e.g., indicator light 3224*a* followed by indicator light 3244*b*, followed by indicator light 3224*c*) may intuitively indicate a trend of increasing analyte measurements. In some variations, the progressive sequence of illumination could have any suitable illumination color. In some variations, such rising sequential illumination of indicator lights may be in a suitable color to indicate either that the current analyte measurement is within a target range and rising, or that the current analyte measurement is above a target range and rising. For example, FIG. 34A illustrates rising progressive illumination in a first color (e.g., blue) to indicate that current analyte measurement is within the target range and rising, whereas FIG. 34B illustrates rising progressive illumination in a second color (e.g., orange) to indicate that the current analyte measurement is above (or significantly above) the target range and rising. As yet another example, a rising progressive illumination in a third color (e.g., white) may indicate that the current analyte measurement is below (or significantly below) the target range and rising.

Figure 34C:
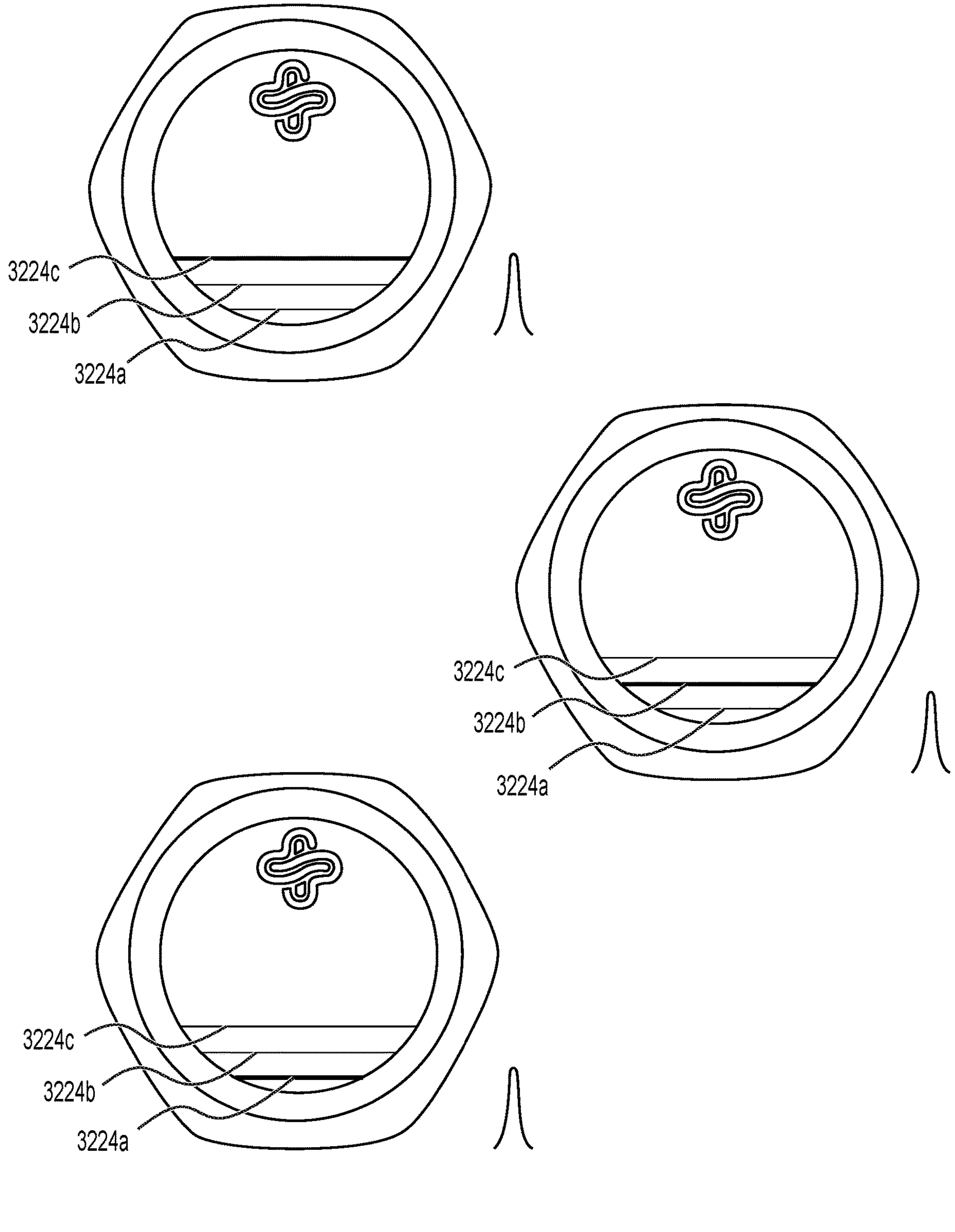

As another example, as shown in FIG. 34C, a progressive sequence of illumination of the indicator lights 3224*a*-3224*c* in a second direction (e.g., opposite direction of the first direction) from higher indicator light(s) to lower indicator light(s) (e.g., indicator light 3224*c* followed by indicator light 3244*b*, followed by indicator light 3224*a*) may intuitively indicate a trend of decreasing analyte measurements. Similar to that described above with respect to FIGS. 34A and 34B, such a falling progressive sequence of illumination of indicator lights may be a suitable color to indicate the status of the current analyte measurement that is falling (e.g., falling progressive illumination in a first color (e.g., blue) to indicate that current analyte measurement is within the target range and falling, falling progressive illumination in a second color (e.g., orange) to indicate the current analyte measurement is above (or significantly above) the target range and falling, or falling progressive illumination in a third color (e.g., white) may indicate that the current analyte measurement is below (or significantly below) the target range and falling.

It should be understood that other variations of progressive sequences of illumination may be used to similarly indicate analyte measurement trends. For example, a 1-dimensional array of indicator lights (e.g., arranged in a row, a column, an arc, etc.) may be illuminated in a progressive sequence from a first end of the array to a second end of the array to indicate a rising analyte measurement trend, and illuminated in a progressive sequence from a second end of the array to a first end of the array to indicate a falling analyte measurement trend. For example, progressive sequences of illumination may be characterized as left-to-right, right-to-left, top-to-bottom, bottom-to-top, clockwise, counter-clockwise, etc. Furthermore, it should be understood that while the user interface 3220 includes three sequential indicator lights, in other variations a user interface on the housing of an analyte monitoring device may include fewer (e.g., two) or more (e.g., four, five, six, or more) that may be similarly illuminated in a progressive sequence to indicate rising and/or falling analyte measurement trends.

In some variations, within each rising or falling sequence of illumination across the indicator lights, the illumination of adjacent indicator lights may be interspersed by an illumination "off" period. Furthermore, in some variations, the pace at which the illumination transitions between indicator lights may indicate rate of change of analyte measurements. For example, the faster the illumination transitions from lower to higher indicator lights, the faster the rate of change (and potentially the greater urgency or need for user attention to the trend). Additionally or alternatively, each rising or falling sequence of illumination across the indicator lights may be separated by a sequence end illumination "off" time in order to help distinguish between a rising sequence and a falling sequence. The sequence end illumination "off" time may be longer than the illumination "off" period within each sequence. In some variations, the start or end of each rising or falling sequence of illumination may additionally or alternatively be demarcated in any suitable manner (e.g., illuminating all lights simultaneously at the start or end of a rising or falling sequence).

Table 3 illustrates different illumination modes used in an example method of operating the user interface 3220 of an analyte monitoring device to indicate analyte measurement trends. The exact parameter values of these illumination modes are non-limiting and are included for an example variation for illustrative purposes only. For example, in a progressive sequence of illumination (e.g., for any one of more suitable illumination modes), the illumination color may be any suitable color, and/or the illumination "on" time may be between about 0.1 seconds and 1 second, between about 0.2 seconds and 0.5 seconds, or about 0.3 seconds, and/or the illumination "off" time between illumination of adjacent indicator lights may be between about 0.05 seconds and about 1 second, between about 0.1 seconds and about 0.5 seconds, or about 0.18 seconds, and/or the ratio between the illumination "on" time and illumination "off" time may be about 1, about 1.5, or about 2, and/or the sequence end may be designated by illumination "off" for between about 2 seconds and about 5 seconds, or about 3 seconds. Furthermore, fewer or more illumination modes for indicating analyte measurement trends may be possible in other variations.

TABLE 3

Example illumination modes for indicating analyte measurement trends

| Analyte measurement trend | FIG. | Indicator lights illumination sequence | Illumination color | Illumination "on" time | Illumination "off" time | Sequence end |
|---|---|---|---|---|---|---|
| In target range, rising | FIG. 34A | Lower → Higher | Blue | 0.3 sec | 0.18 sec | 3 sec illumination "off" |
| Above target range, rising | FIG. 34B | Lower → Higher | Orange | 0.3 sec | 0.18 sec | 3 sec illumination "off" |
| Above (and/or significantly above) target range, dropping | FIG. 34C | Higher → Lower | Orange | 0.3 sec | 0.18 sec | 3 sec illumination "off" |

Figure 35A:
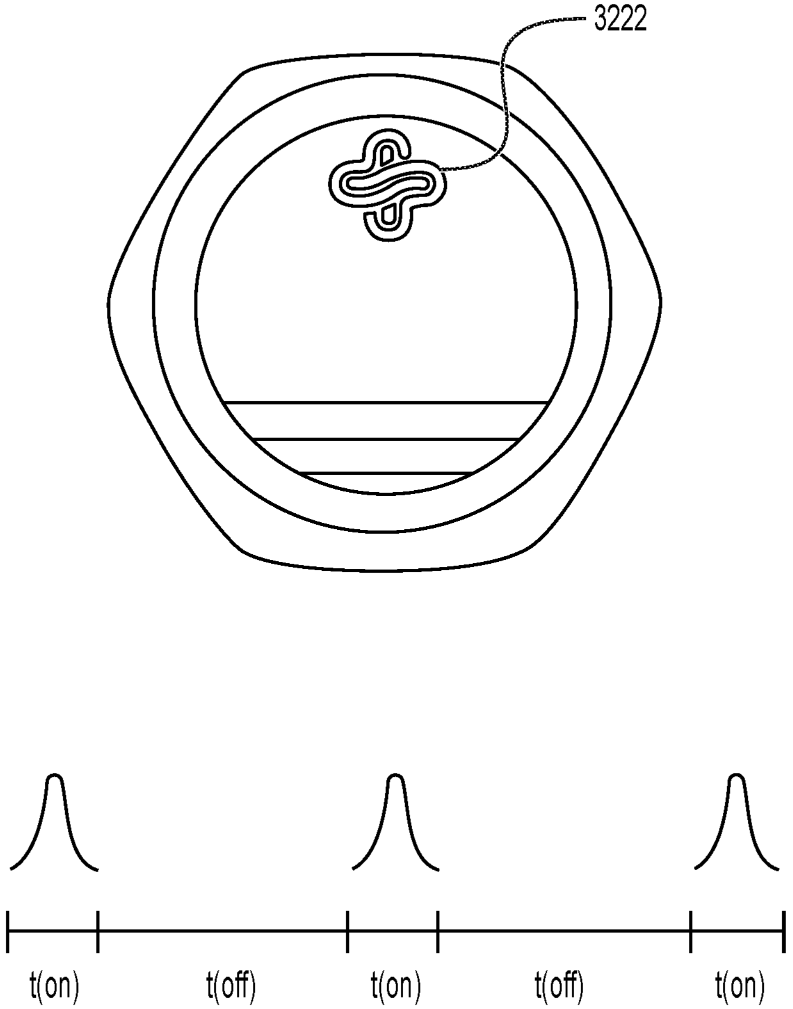
FIGS. 35A and 35B depict illustrative schematics of illumination modes in an analyte monitoring device for indicating device information (e.g., operational status, and/or fault modes).
Figure 35B:
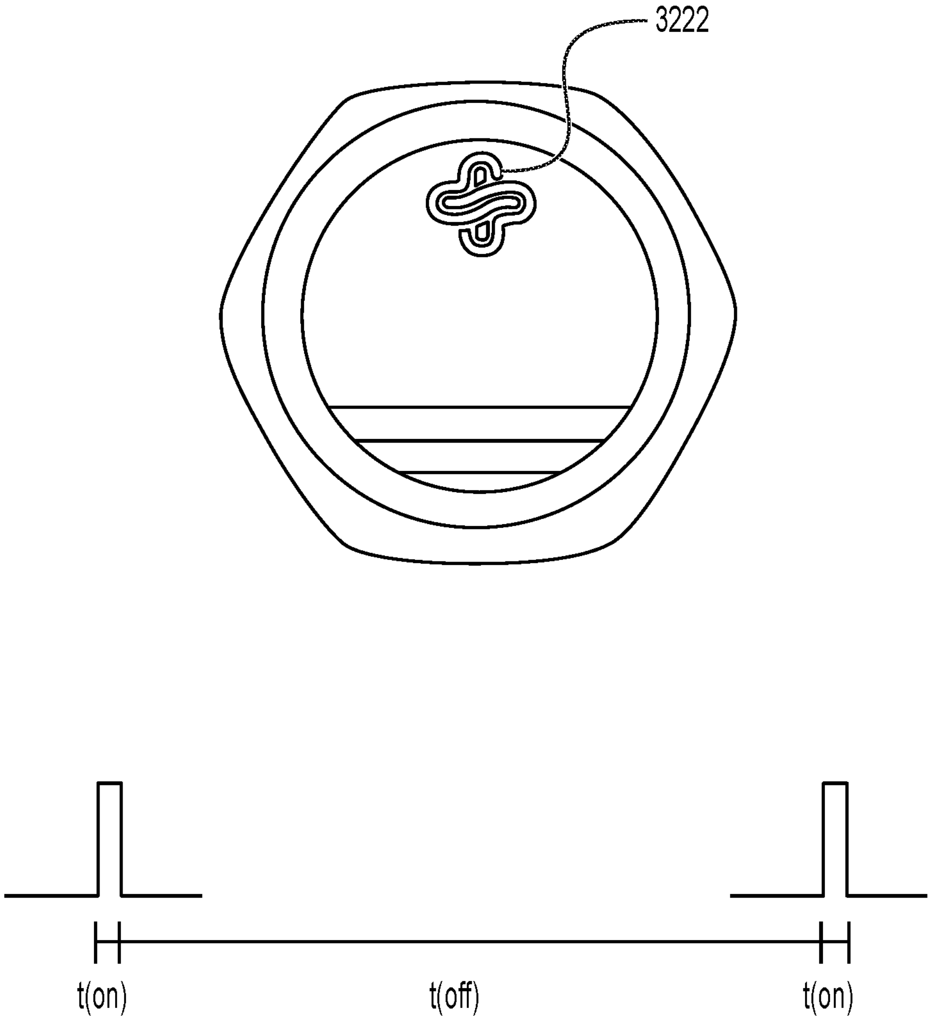

Additionally or alternatively, an indicator light 3222 may be selectively illuminated to communicate a device status. Similar to that described above, color and/or timing of illumination may be varied in a predetermined manner to indicate different device statuses. Status may, for example, include a warm-up period notification, an end-of-life notification, a sensor fault state notification, a sensor failure mode (e.g., improper insertion) notification, a low battery notification, and/or a device error notification. Furthermore, any suitable number of indicators lights may be illuminated individually and/or collectively (e.g., in sequence or simultaneously) to indicate different device statuses. For example, as shown in FIG. 35A, a user interface including an indicator light 3222 may be illuminated in a first illumination mode (e.g., first illumination color such as white and/or first temporal illumination pattern) to indicate a device "wait" mode. The wait mode may, for example, correspond to a device warmup period (as described elsewhere herein), detection of a temporary error (e.g., detection of pressure-induced sensor attenuation). As another example, as shown in FIG. 35B, a user interface including an indicator light 3222 may be illuminated in a second illumination mode (e.g., second illumination color such as red and/or second temporal illumination pattern) to indicate a device "end of life" mode (e.g., determination of an end of a predetermined wear period such as that described below, detection of a permanent error, etc.).

Table 4 illustrates different illumination modes used in an example method of operating the user interface of an analyte monitoring device to indicate device status. The exact parameter values of these illumination modes are non-limiting and are included for an example variation for illustrative purposes only. For example, in the "wait" illumination mode, the illumination color may be any suitable color, and/or the illumination "on" time may be between about. 1 seconds and about 3 seconds, between about 0.5 seconds and about 2 seconds, or about 1 second, and/or the illumination "off" mode may be between about 0.5 seconds and about 5 seconds, or between about 1 second and about 4 seconds, or between about 2 seconds and about 4 seconds, or about 3 seconds, and/or the ratio between the illumination "on" and illumination "off" times may be about 0.1, about 0.2, about 0.3, about 0.4, about 0.5, and/or other suitable illumination parameters. As another example, in the "end of life" illumination mode, the illumination color may be any suitable color, and/or the illumination "on" time may be between about 0.01 seconds and about 1 second, between about 0.01 seconds and about 0.5 seconds, between about 0.01 seconds and about 0.3 seconds, between about 0.01 seconds and about 0.1 seconds, or about 0.04 seconds, and/or the illumination "off" time may be between about 1 second and about 10 seconds, between about 3 seconds and about 8 seconds, or about 6 seconds, and/or the ratio between the illumination "on" and illumination "off" times may be about 0.3, about 0.2, about 0.1, about 0.05, about 0.01, or less than about 0.01, and/or other suitable illumination parameters. Although only two illumination modes are shown, in some variations an analyte monitoring device may have fewer or more illumination modes, such as for each of the above statuses (e.g., first illumination mode for a device warmup period, a second illumination mode for detection of a temporary error, a third illumination mode for determination of an end of device lifetime, a fourth illumination mode for detection of a permanent error, etc.).

TABLE 4

Example illumination modes for indicating device status

| Device status | Figure | Illumination color | Illumination "on" time t(on) | Illumination "off" time t(off) |
|---|---|---|---|---|
| Wait | FIG. 35A | White | 1 sec | 3 sec |
| End of life | FIG. 35B | Red | 0.04 sec | 6 sec |

In some variations, a photodiode, phototransistor, photodetector, or other suitable ambient light sensor may be employed to measure the illumination level in the device's immediate environment. The ambient light measurement may, for example, be used to trigger an adjustment (e.g., dimming) of the brightness of the user interface (e.g., display, indicator light(s), etc.) to conserve battery charge in a power saving mode, to improve contrast under various illumination scenarios, and/or to reduce device visibility to other individuals. For example, the analyte monitoring device may enter the power saving mode in response to measurements from the ambient light sensor indicating general absence of ambient light (e.g., sufficient darkness for at least a predetermined period of time) such as when the device is placed under the clothing of a wearer or when the wearer is asleep in a dark environment. In these scenarios, the power saving mode may be practical because the indicator lights may have limited utility when concealed and out of view of the wearer (e.g., under clothing) or otherwise may be perceived as an annoyance (e.g., during slumber), etc. In response to measurements from the ambient light sensor indicating exposure to ambient light (e.g., sufficient brightness for at least a predetermined period of time), the analyte monitoring device may then exit the power saving mode and increase the brightness of the user interface accordingly.

Additional System Functions

In some variations, the mobile application may help a user manage the lifetimes and replacement of analyte monitoring devices. For example, the mobile application may terminate data display when the wear period of the analyte monitoring device has elapsed. In some variations, the analyte monitoring device may have enhanced longevity compared to conventional CGM devices. For example, the analyte monitoring devices described herein may have a wear period (e.g., intended lifetime) of at least 3 days, at least 5 days, at least 6 days, at least 7 days, at least 10 days, or at least 12 days, between 5 days and between 10 days, between 10 days and 14 days, etc. without material loss in performance.

Additionally or alternatively, mobile application may provide configurable alerts to the user that the wear period is about to elapse, which permits users to apply a new analyte monitoring device when the current analyte monitoring device is still active but close to expiry. Additionally, the new analyte monitoring device can warm up (typically between about 30 minutes and about 2 hours) while the old unit is still delivering analyte measurements. The old analyte monitoring device can then be removed upon expiry. The new analyte monitoring device may then become the primary sensor delivering analyte measurements to the mobile application. This may provide for an uninterrupted coverage for analyte measurements. Additionally, the readings from the old analyte monitoring device may be used to calibrate or algorithmically improve the accuracy of the new analyte monitoring device.

In some variations, an analyte monitoring device may have a unique serial number contained within the microcontroller (e.g., located in the electronics system). This serial number may enable sensors to be tracked from manufacturing and throughout the use of the product. For example, sensor device history records including manufacturing and customer use may be transmitted and stored in the cloud database. This enables tracking and inferences to be made on various parameters such as sensor performance metrics and improvement for individual users as well as sensor lots, tracking defective sensor lots back from field data to manufacturing or supplier issues very rapidly, personalized health monitoring features for individual users, etc.

In some variations, the system may be able to track inventory of analyte monitoring devices from warehousing to purchasing transactions to product use, which may enable the system to assist users in fulfillment of timely orders (e.g., to ensure that users don't run out of analyte monitoring devices). Additionally or alternatively, fulfillment can be executed automatically as monitoring device utilization is tracked, and timely delivery can be made to the user's residence to help ensure that sensor supply never depletes (e.g. 'just-in-time' delivery). This can interface with virtual or e-pharmacies, logistics centers, and/or web-based sales portals, such as Amazon™.

Through web portals, the cloud infrastructure may also allow users to view their real-time and historical glucose data/trends and share the said data with caregivers, their healthcare provider(s), support network, and/or other suitable persons.

ENUMERATED EMBODIMENTS

Embodiment I-1. A microneedle array for use in sensing an analyte, comprising:

a plurality of solid microneedles, wherein at least one microneedle comprises:

a tapered distal portion having an insulated distal apex; and an electrode on a surface of the tapered distal portion, wherein the electrode is located proximal to the insulated distal apex.

Embodiment I-2. The microneedle array of embodiment I-1, wherein the electrode is a working electrode configured to sense at least one analyte and the at least one microneedle comprises a biorecognition layer arranged over the working electrode, wherein the biorecognition layer comprises a biorecognition element.

Embodiment I-3. The microneedle array of embodiment I-2, wherein the biorecognition element comprises an enzyme.

Embodiment I-4. The microneedle array of embodiment I-3, wherein the enzyme is an oxidoreductase.

Embodiment I-5. The microneedle array of embodiment I-4, wherein the oxidoreductase is at least one of lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and xanthine oxidase.

Embodiment I-6. The microneedle array of embodiment I-4, wherein the oxidoreductase is glucose oxidase.

Embodiment I-7. The microneedle array of embodiment I-2, wherein the biorecognition element is cross-linked with an amine-condensing carbonyl chemical species.

Embodiment I-8. The microneedle array of embodiment I-7, wherein the amine-condensing carbonyl chemical species is at least one of formaldehyde, glyoxal, malonaldehyde, and succinaldehyde.

Embodiment I-9. The microneedle array of embodiment I-7, wherein the amine-condensing carbonyl chemical species is glutaraldehyde.

Embodiment I-10. The microneedle array of embodiment I-2, wherein the at least one microneedle comprises at least one of a diffusion-limiting layer and a hydrophilic layer arranged over the biorecognition layer.

Embodiment I-11. The microneedle array of embodiment I-2, wherein the microneedle array comprises at least one microneedle comprising a counter electrode configured to source or sink current to sustain an electrochemical reaction on the working electrode.

Embodiment I-12. The microneedle array of embodiment I-2, wherein the microneedle array comprises at least one microneedle comprising a reference electrode configured to provide a reference potential for the working electrode.

Embodiment I-13. The microneedle array of embodiment I-12, further comprising a conducting polymer arranged over the reference electrode.

Embodiment I-14. The microneedle array of embodiment I-13, wherein the conducting polymer comprises a dopant.

Embodiment I-15. The microneedle array of embodiment I-13, wherein the reference electrode comprises a metal oxide with a stable electrode potential.

Embodiment I-16. The microneedle array of embodiment I-15, wherein the metal oxide comprises iridium oxide.

Embodiment I-17. The microneedle array of embodiment I-13, wherein the reference electrode comprises a metal salt with a stable electrode potential.

Embodiment I-18. The microneedle array of embodiment I-17, wherein the metal salt comprises silver chloride.

Embodiment I-19. The microneedle array of embodiment I-1, wherein the entirety of the electrode is on the tapered distal portion of the at least one microneedle.

Embodiment I-20. The microneedle array of embodiment I-1, wherein the electrode comprises a catalytic surface.

Embodiment I-21. The microneedle array of embodiment I-20, wherein the catalytic surface comprises at least one of platinum, palladium, iridium, rhodium, gold, ruthenium, titanium, nickel, carbon, and doped diamond.

Embodiment I-22. The microneedle array of embodiment I-20, wherein the at least one microneedle comprises platinum black arranged over the electrode.

Embodiment I-23. The microneedle array of embodiment I-1, wherein a distal end of the electrode is offset from the distal apex by an offset distance of at least about 10 μm, wherein the offset distance is measured along a longitudinal axis of the at least one microneedle.

Embodiment I-24. The microneedle array of embodiment I-1, wherein the electrode is annular.

Embodiment I-25. The microneedle array of embodiment I-1, wherein a portion of the working electrode is recessed into the tapered distal portion.

Embodiment I-26. The microneedle array of embodiment I-1, wherein the electrode is on only a segment of the tapered distal portion.

Embodiment I-27. The microneedle array of embodiment I-1, further comprising an electrical contact, wherein the at least one microneedle comprises a body portion providing a conductive pathway between the electrical contact and the electrode.

Embodiment I-28. The microneedle array of embodiment I-27, wherein the body portion is formed from a conductive material.

Embodiment I-29. The microneedle array of embodiment I-27, wherein the body portion comprises an embedded pathway.

Embodiment I-30. The microneedle array of embodiment I-27, wherein the body portion is insulated.

Embodiment I-31. The microneedle array of embodiment I-27, wherein the body portion has a circular, square, or an octagonal base.

Embodiment I-32. The microneedle array of embodiment I-27, wherein at least a segment of the body portion is columnar.

Embodiment I-33. The microneedle array of embodiment I-27, wherein at least a segment of the body portion is pyramidal.

Embodiment I-34. The microneedle array of embodiment I-33, wherein at least a portion of the body portion has a first taper angle measured relative to a base of the body portion and the distal apex has a second taper angle measured relative to the base, wherein the second taper angle is greater than the first taper angle.

Embodiment I-35. The microneedle array of embodiment I-34, wherein at least one of the body portion and the distal portion of the microneedle is radially asymmetric.

Embodiment I-36. The microneedle array of embodiment I-35, wherein the tapered distal portion comprises a planar surface that is offset from the distal apex of the at least one microneedle.

Embodiment I-37. The microneedle array of embodiment I-1, wherein each of the microneedles in the plurality of microneedles comprises a

- a tapered distal portion having an insulated distal apex; and
- an electrode on a surface of the tapered distal portion, wherein the electrode is located proximal to the insulated distal apex.

Embodiment I-38. The microneedle array of embodiment I-1, wherein the microneedles of the plurality of microneedles are electrically insulated from one another.

Embodiment I-39. The microneedle array of embodiment I-38, wherein the microneedle array is configured to detect multiple analytes.

Embodiment I-40. The microneedle array of embodiment I-1, wherein the microneedles of the plurality of microneedles are arranged in a periodic grid.

Embodiment I-41. The microneedle array of embodiment I-40, wherein the periodic grid comprises a rectangular array.

Embodiment I-42. The microneedle array of embodiment I-40, wherein the periodic grid comprises a hexagonal array.

Embodiment I-43. The microneedle array of embodiment I-40, wherein the microneedles in the periodic grid are spaced apart by a distance between about 200 μm and about 800 μm.

Embodiment I-44. The microneedle array of embodiment I-40, wherein the microneedles in the periodic grid are uniformly spaced apart.

Embodiment I-45. The microneedle array of embodiment I-1, wherein the plurality of microneedles comprises at least one delivery microneedle with a lumen.

Embodiment I-46. The microneedle array of embodiment I-1, wherein the at least one microneedle is configured to puncture skin of a user and sense an analyte in interstitial fluid in a dermal layer of the user.

Embodiment I-47. An analyte monitoring system comprising the microneedle array of embodiment I-1 and a wearable housing, wherein the microneedle array extends outwardly from the housing.

Embodiment I-48. The system of embodiment I-47, wherein the at least one microneedle extends from the housing such that a distal end of the electrode is located less than about 5 mm from the housing.

Embodiment I-49. The system of embodiment I-48, wherein the at least one microneedle extends from the housing such that the distal end of the electrode is located less than about 1 mm from the housing.

Embodiment I-50. The system of embodiment I-47, wherein the housing encloses an electronics system comprising at least one of a processor and a wireless communication module.

Embodiment I-51. The system of embodiment I-50, wherein the electronics system comprises a wireless communication module and the system further comprises a software application executable on a mobile computing device to be paired with the wireless communication module.

Embodiment I-52. The system of embodiment I-47, wherein the housing comprises one or more indicator lights configured to communicate status information.

Embodiment I-53. The system of embodiment I-52, wherein at least one of the indicator lights is configured to be selectively illuminated in accordance with an illumination mode corresponding to an analyte measurement status.

Embodiment I-54. The system of embodiment I-53, wherein at least one of the indicator lights is configured to be selectively illuminated to communicate a current analyte measurement level.

Embodiment I-55. The system of embodiment I-53, wherein the user interface comprises a plurality of indicator lights configured to be selectively illuminated in a progressive sequence to communicate an analyte measurement trend.

Embodiment I-56. The system of embodiment I-55, wherein the plurality of indicator lights is configured to be selectively illuminated in a first progressive sequence in a first direction to communicate a rising analyte measurement trend, and is further configured to be selectively illuminated in a second progressive sequence in a second direction to communicate a falling analyte measurement trend.

Embodiment I-57. The system of embodiment I-52, wherein the user interface is further configured to communicate information indicative of a status of the analyte monitoring device.

Embodiment I-58. The system of embodiment I-47, further comprising an adhesive configured to couple the housing to the skin of a user.

Embodiment I-59. The system of embodiment I-47, further comprising an applicator configured to apply the at least a portion of the analyte monitoring system to the skin of a user.

Embodiment I-60. The system of embodiment I-47, wherein the analyte monitoring system is a skin-adhered patch.

Embodiment I-61. The system of embodiment I-47, wherein the plurality of microneedles comprises at least one delivery microneedle with a lumen.

Embodiment I-62. The system of embodiment I-47, wherein the plurality of microneedles comprises at least one solid microneedle comprising a coating comprising a therapeutic substance.

Embodiment I-63. The system of embodiment I-62, wherein the therapeutic substance comprises at least one of insulin, glucagon, metformin, acetaminophen, acetylsalicylic acid, isobutylphenylpropionic acid, levodopa, a statin, a hydrocodone, an opioid, a non-steroidal anti-inflammatory, an anesthetic, an analgesic, an anticonvulsant, an antidepressant, an antipsychotic, a sedative, a relaxant, a hormonal agent, an antibacterial agent, and an antiviral agent.

Embodiment I-64. A method for monitoring a user, comprising:

- accessing a body fluid of the user with an analyte monitoring device; and
- quantifying one or more analytes in the body fluid using the analyte monitoring device,
- wherein the analyte monitoring device comprises a plurality of solid microneedles, wherein at least one microneedle comprises:
  - a tapered distal portion having an insulated distal apex; and
  - an electrode on a surface of the tapered distal portion, wherein the electrode is located proximal to the insulated distal apex.

Embodiment I-65. The method of embodiment I-64, wherein the body fluid comprises a dermal interstitial fluid of the user.

Embodiment I-66. The method of embodiment I-64, wherein the one or more analytes comprises glucose.

Embodiment I-67. A microneedle array for use in sensing an analyte, comprising:

- a plurality of solid microneedles, wherein at least one microneedle comprises:
- a tapered distal portion having an insulated distal apex; and
- an electrode on a surface of the tapered distal portion, wherein a distal end of the electrode is offset from the distal apex.

Embodiment I-68. The microneedle array of embodiment I-67, wherein the electrode is a working electrode configured to sense at least one analyte and the at least one microneedle comprises a biorecognition layer arranged over the working electrode, wherein the biorecognition layer comprises a biorecognition element.

Embodiment I-69. The microneedle array of embodiment I-68, wherein the biorecognition element comprises glucose oxidase.

Embodiment I-70. The microneedle array of embodiment I-67, wherein the distal end of the electrode is offset from the distal apex by an offset distance of at least about 10 μm, wherein the offset distance is measured along a longitudinal axis of the at least one microneedle.

Embodiment I-71. The microneedle array of embodiment I-67, wherein the electrode is annular.

Embodiment I-72. The microneedle array of embodiment I-67, wherein in at least one microneedle, a portion of the working electrode is recessed into the tapered distal portion.

Embodiment I-73. The microneedle array of embodiment I-67, wherein the electrode is on only a segment of the tapered distal portion.

Embodiment I-74. The microneedle array of embodiment I-67, further comprising an electrical contact, wherein the at least one microneedle comprises a body portion providing a conductive pathway between the electrical contact and the electrode.

Embodiment I-75. The microneedle array of embodiment I-67, wherein each of the microneedles in the plurality of microneedles comprises a

- a tapered distal portion having an insulated distal apex; and
- an electrode on a surface of the tapered distal portion, wherein the electrode is located proximal to the insulated distal apex.

Embodiment I-76. The microneedle array of embodiment I-67, wherein the microneedle array comprises a plurality of working electrodes, wherein each working electrode is individually addressable and electrically isolated from every other working electrode in the analyte monitoring device.

Embodiment I-77. The microneedle array of embodiment I-76, wherein the microneedle array is configured to detect multiple analytes.

Embodiment I-78. The microneedle array of embodiment I-67, wherein the microneedles of the plurality of microneedles are arranged in a hexagonal array.

Embodiment I-79. The microneedle array of embodiment I-67, wherein the at least one microneedle is configured to puncture skin of a user and sense an analyte in interstitial fluid in a dermal layer of the user.

Embodiment I-80. An analyte monitoring system comprising the microneedle array of embodiment I-67 and a wearable housing, wherein the microneedle array extends outwardly from the housing.

Embodiment I-81. The system of embodiment I-80, wherein the at least one microneedle extends from the housing such that the distal end of the electrode is located less than about 5 mm from the housing.

Embodiment I-82. The system of embodiment I-80, wherein the housing encloses an electronics system comprising a wireless communication module and the system further comprises a software application executable on a mobile computing device to be paired with the wireless communication module.

Embodiment I-83. The system of embodiment I-80, wherein the housing comprises a user interface comprising one or more indicator lights configured to communicate status information.

Embodiment I-84. The system of embodiment I-83, wherein at least one of the indicator lights is configured to be selectively illuminated in accordance with an illumination mode corresponding to an analyte measurement status.

Embodiment I-85. The system of embodiment I-83, wherein the analyte monitoring system comprises a skin-adhered patch.

Embodiment I-86. A method of sterilizing an analyte monitoring device, the method comprising:

exposing the analyte monitoring device to a sterilant gas, wherein the analyte monitoring device comprises a wearable housing, a microneedle array extending from the housing and comprising an analyte sensor, and an electronics system arranged in the housing and electrically coupled to the microneedle array, wherein the analyte monitoring device is exposed to the sterilant gas for a dwell time sufficient to sterilize the analyte monitoring device.

Embodiment I-87. The method of embodiment I-86, wherein the sterilant gas is suitable for oxidative sterilization.

Embodiment I-88. The method of embodiment I-87, wherein the sterilant gas comprises ethylene oxide.

Embodiment I-89. The method of embodiment I-86, wherein the analyte sensor comprises an electrode.

Embodiment I-90. The method of embodiment I-89, wherein the analyte sensor comprises a biorecognition layer arranged over the electrode, wherein the biorecognition layer comprises a biorecognition element.

Embodiment I-91. The method of embodiment I-90, wherein the biorecognition element comprises an enzyme.

Embodiment I-92. The method of embodiment I-91, wherein the enzyme is an oxidoreductase.

Embodiment I-93. The method of embodiment I-92, wherein the oxidoreductase is at least one of lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and xanthine oxidase.

Embodiment I-94. The method of embodiment I-92, wherein the oxidoreductase is glucose oxidase.

Embodiment I-95. The method of embodiment I-90, wherein the biorecognition element is cross-linked with an amine-condensing carbonyl chemical species.

Embodiment I-96. The method of embodiment I-95, wherein the amine-condensing carbonyl chemical species is at least one of formaldehyde, glyoxal, malonaldehyde, and succinaldehyde.

Embodiment I-97. The method of embodiment I-95, wherein the amine-condensing carbonyl chemical species is glutaraldehyde.

Embodiment I-98. The method of embodiment I-90, wherein the biorecognition layer is formed at least in part by cross-linking the biorecognition element to form cross-linked biorecognition element aggregates, and embedding the cross-linked biorecognition element aggregates in a conducting polymer.

Embodiment I-99. The method of embodiment I-98, wherein embedding the cross-linked biorecognition element aggregates comprises embedding only cross-linked biorecognition element aggregates having at least a threshold molecular weight.

Embodiment I-100. The method of embodiment I-86, wherein exposing the analyte monitoring device to the sterilant gas comprises injecting the sterilant gas into a compartment containing the analyte monitoring device, and heating the compartment to a sterilization temperature.

Embodiment I-101. The method of embodiment I-100, wherein the sterilization temperature is below about 45 degrees Celsius and the dwell time is at least about 2 hours.

Embodiment I-102. The method of embodiment I-86, further comprising preconditioning the analyte monitoring device prior to exposing the analyte monitoring device to the sterilant gas, wherein preconditioning the analyte comprises exposing the analyte monitoring device to steam.

Embodiment I-103. A microneedle array for an analyte monitoring device, the microneedle array comprising:

a plurality of solid sensing microneedles, wherein each sensing microneedle comprises:

a tapered distal portion comprising a working electrode configured to sense an analyte; and a body portion providing a conductive connection to the working electrode, wherein the body portion of each sensing microneedle is insulated such that each working electrode is individually addressable and electrically isolated from every other working electrode in the microneedle array.

Embodiment I-104. The microneedle array of embodiment I-103, wherein at least one sensing microneedle comprises a biorecognition layer arranged over the working electrode, wherein the biorecognition layer comprises a biorecognition element.

Embodiment I-105. The microneedle array of embodiment I-104, wherein the biorecognition element comprises an enzyme.

Embodiment I-106. The microneedle array of embodiment I-105, wherein the enzyme is an oxidoreductase.

Embodiment I-107. The microneedle array of embodiment I-106, wherein the oxidoreductase is at least one of lactate oxidase, alcohol oxidase, beta-hydroxybutyrate dehydrogenase, tyrosinase, catalase, ascorbate oxidase, cholesterol oxidase, choline oxidase, pyruvate oxidase, urate oxidase, urease, and xanthine oxidase.

Embodiment I-108. The microneedle array of embodiment I-106, wherein the oxidoreductase is glucose oxidase.

Embodiment I-109. The microneedle array of embodiment I-104, wherein the biorecognition element is cross-linked with an amine-condensing carbonyl chemical species.

Embodiment I-110. The microneedle array of embodiment I-109, wherein the amine-condensing carbonyl chemical species is at least one of formaldehyde, glyoxal, malonaldehyde, and succinaldehyde.

Embodiment I-111. The microneedle array of embodiment I-109, wherein the amine-condensing carbonyl chemical species is glutaraldehyde.

Embodiment I-112. The microneedle array of embodiment I-104, wherein the at least one sensing microneedle comprises at least one of a diffusion-limiting layer and a hydrophilic layer arranged over the biorecognition layer.

Embodiment I-113. The microneedle array of embodiment I-103, wherein the microneedle array further comprises at least one microneedle comprising a counter electrode configured to source or sink current to sustain an electrochemical reaction on the working electrode of at least one sensing microneedle.

Embodiment I-114. The microneedle array of embodiment I-103, wherein the plurality of microneedles comprises at least one microneedle comprising a reference electrode configured to provide a reference potential for the working electrode.

Embodiment I-115. The microneedle array of embodiment I-114, further comprising a conducting polymer arranged over the reference electrode.

Embodiment I-116. The microneedle array of embodiment I-115, wherein the conducting polymer comprises a dopant.

Embodiment I-117. The microneedle array of embodiment I-114, wherein the reference electrode comprises a metal oxide with a stable electrode potential.

Embodiment I-118. The microneedle array of embodiment I-117, wherein the metal oxide comprises iridium oxide.

Embodiment I-119. The microneedle array of embodiment I-114, wherein the reference electrode comprises a metal salt with a stable electrode potential.

Embodiment I-120. The microneedle array of embodiment I-119, wherein the metal salt comprises silver chloride.

Embodiment I-121. The microneedle array of embodiment I-103, wherein in at least one sensing microneedle, the tapered distal portion comprises an insulated distal apex and the working electrode is proximal to the insulated distal apex.

Embodiment I-122. The microneedle array of embodiment I-121, wherein a distal end of the working electrode is offset from the distal apex by an offset distance of at least about 10 μm, wherein the offset distance is measured along a longitudinal axis of the at least one sensing microneedle.

Embodiment I-123. The microneedle array of embodiment I-103, wherein in at least one sensing microneedle, a portion of the working electrode is recessed into the tapered distal portion.

Embodiment I-124. An analyte monitoring device comprising the microneedle array of embodiment I-103 and a wearable housing, wherein the microneedle array extends outwardly from the housing.

Embodiment I-125. The analyte monitoring device of embodiment I-124, wherein the housing comprises one or more indicator lights configured to communicate status information.

Embodiment I-126. The analyte monitoring device of embodiment I-124, wherein the housing encloses an electronics system comprising at least one of a processor and a wireless communication module.

Embodiment I-127. The analyte monitoring device of embodiment I-126, wherein the analyte monitoring device is a skin-adhered patch.

Embodiment I-128. A microneedle array for a body-worn analyte monitoring device, wherein the microneedle array comprises:

at least one microneedle comprising:

a pyramidal body portion having a non-circular base; and a tapered distal portion extending from the body portion and comprising an electrode, wherein the distal portion comprises a planar surface that is offset from a distal apex of the at least one microneedle.

Embodiment I-129. The microneedle array of embodiment I-128, wherein at least a portion of the body portion has a first taper angle measured relative to the base and the distal apex has a second taper angle measured relative to the base, wherein the second taper angle is greater than the first taper angle.

Embodiment I-130. The microneedle array of embodiment I-128, wherein the second taper is between about 65 degrees and about 75 degrees.

Embodiment I-131. The microneedle array of embodiment I-130, wherein the first taper is between about 15 degrees and about 25 degrees.

Embodiment I-132. The microneedle array of embodiment I-128, wherein the planar surface is angled between about 75 degrees and 85 degrees measured relative to the base.

Embodiment I-133. The microneedle array of embodiment I-128, wherein the tapered distal portion comprises an insulated distal apex.

Embodiment I-134. An analyte monitoring device comprising the microneedle array of embodiment I-128 and a wearable housing, wherein the microneedle array is configurable to extend outwardly from the housing.

Embodiment I-135. The analyte monitoring device of embodiment I-134, wherein the analyte monitoring device is a patch.

Embodiment I-136. A method for monitoring a user, comprising:

accessing a dermal interstitial fluid of the user at a plurality of sensor locations with an integrated analyte monitoring device comprising a single microneedle array;

quantifying one or more analytes in the dermal interstitial fluid using a plurality of working electrodes in the microneedle array, wherein each working electrode is individually addressable and electrically isolated from every other working electrode in the analyte monitoring device.

Embodiment I-137. The method of embodiment I-136, wherein quantifying one or more analytes comprises quantifying a plurality of analytes in the dermal interstitial fluid using the plurality of working electrodes.

Embodiment I-138. The method of embodiment I-136, wherein the microneedle array comprises a plurality of sensing microneedles, each sensing microneedle comprising a respective working electrode.

Embodiment I-139. The method of embodiment I-138, wherein at least one sensing microneedle comprises a biorecognition layer arranged over the working electrode, wherein the biorecognition layer comprises an enzyme.

Embodiment I-140. The method of embodiment I-139, wherein the at least one microneedle comprises at least one of a diffusion-limiting layer and a hydrophilic layer arranged over the biorecognition layer.

Embodiment I-141. The method of embodiment I-136, wherein the microneedle array comprises at least one microneedle comprising a counter electrode configured to source or sink current to sustain an electrochemical reaction on at least one working electrode.

Embodiment I-142. The method of embodiment I-136, wherein the plurality of microneedles comprises at least one microneedle comprising a reference electrode configured to provide a reference potential for at least one working electrode.

Embodiment I-143. The method of embodiment I-142, further comprising a conducting polymer arranged over the reference electrode.

Embodiment I-144. The method of embodiment I-143, wherein the conducting polymer comprises a dopant.

Embodiment I-145. The method of embodiment I-142, wherein the reference electrode comprises a metal oxide with a stable electrode potential.

Embodiment I-146. The method of embodiment I-145, wherein the metal oxide comprises iridium oxide.

Embodiment I-147. The method of embodiment I-142, wherein the reference electrode comprises a metal salt with a stable electrode potential.

Embodiment I-148. The method of embodiment I-147, wherein the metal salt comprises silver chloride.

Embodiment I-149. The method of embodiment I-136, further comprising communicating status information indicative of the quantification of the one or more analytes.

Embodiment I-150. The method of embodiment I-149, wherein the microneedle array extends outwardly from a wearable housing and communicating status information comprises communicating status information via a user interface on the housing.

Embodiment I-151. The method of embodiment I-150, wherein communicating status information comprises selectively illuminating one or more indicator lights on the housing in accordance with an illumination mode corresponding to an analyte measurement status or a status of the integrated analyte monitoring device.

Embodiment I-152. The method of embodiment I-150, wherein communicating status information comprises activating a display corresponding to an analyte measurement status or a status of the integrated analyte monitoring device.

Embodiment I-153. A body-worn analyte monitoring device, comprising:

- a wearable housing; and
- a microneedle array extending outwardly from the housing and comprising at least one microneedle configured to measure one or more analytes in a user wearing the housing,
- wherein the housing comprises a user interface configured to communicate information indicative of the measurement of the one or more analytes.

Embodiment I-154. The device of embodiment I-153, wherein the user interface comprises one or more indicator lights configured to be selectively illuminated in accordance with an illumination mode corresponding to an analyte measurement status or a status of an integrated analyte monitoring device.

Embodiment I-155. The device of embodiment I-154, wherein at least one of the indicator lights is configured to be selectively illuminated to communicate a current analyte measurement level.

Embodiment I-156. The device of embodiment I-154, wherein the user interface comprises a plurality of indicator lights configured to be selectively illuminated in a progressive sequence to communicate an analyte measurement trend.

Embodiment I-157. The device of embodiment I-156, wherein the plurality of indicator lights is configured to be selectively illuminated in a first progressive sequence in a first direction to communicate a rising analyte measurement trend.

Embodiment I-158. The device of embodiment I-156, wherein the plurality of indicator lights is configured to be selectively illuminated in a second progressive sequence in a second direction to communicate a falling analyte measurement trend.

Embodiment I-159. The device of embodiment I-153, wherein the user interface is further configured to communicate information indicative of a status of the analyte monitoring device.

Embodiment I-160. The device of embodiment I-153, wherein the user interface comprises a display screen.

Embodiment I-161. The device of embodiment I-153, wherein the analyte monitoring device is a skin-adhered patch.

Embodiment I-162. The device of embodiment I-153, wherein the at least one microneedle comprises a tapered distal portion with an insulated distal apex, and an electrode on a surface of the tapered distal portion, wherein the electrode is located proximal to the insulated distal apex.

Embodiment I-163. The device of embodiment I-153, wherein the microneedle array comprises a plurality of working electrodes, wherein each working electrode is individually addressable and electrically isolated from every other working electrode in the analyte monitoring device.

Embodiment I-164. A method for monitoring a user, comprising:

- measuring one or more analytes in the user using a body-worn analyte monitoring device comprising a wearable housing and one or more analyte sensors;
- communicating information indicative of the measurement of the one or more analytes through a user interface on the housing.

Embodiment I-165. The method of embodiment I-164, wherein communicating information comprises illuminating one or more indicator lights on the housing in accordance with an illumination mode corresponding to an analyte measurement status.

Embodiment I-166. The method of embodiment I-165, wherein communicating information comprises selectively illuminating at least one of the indicator lights to communicate a current analyte measurement level.

Embodiment I-167. The method of embodiment I-166, wherein communicating information comprises communicating the current analyte measurement level based on color of the illuminated indicator light, location of the illuminated indicator light, or both.

Embodiment I-168. The method of embodiment I-165, wherein communicating information comprises selectively illuminating a plurality of indicator lights on the housing in a progressive sequence to communicate an analyte measurement trend.

Embodiment I-169. The method of embodiment I-168, wherein communicating information comprises selectively illuminating the plurality of indicator lights in a first progressive sequence in a first direction to communicate a rising analyte measurement trend.

Embodiment I-170. The method of embodiment I-168, wherein communicating information comprises selectively illuminating the plurality of indicator lights in a second progressive sequence in a second direction to communicate a falling analyte measurement trend.

Embodiment I-171. The method of embodiment I-164, further comprising communicating information indicative of a status of the analyte monitoring device through the user interface.

Embodiment I-172. The method of embodiment I-164, further comprising accessing a dermal interstitial fluid of the user at a plurality of sensor locations with the analyte monitoring device, wherein quantifying one of more analytes comprises quantifying one or more analytes in the dermal interstitial fluid.

Embodiment I-173. The method of embodiment I-164, wherein the analyte monitoring device comprises a microneedle array comprising a plurality of working electrodes, wherein each working electrode is individually addressable and electrically isolated from every other working electrode in the analyte monitoring device.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to explain the principles of the invention and its practical applications, they thereby enable others skilled in the art to utilize the invention and various embodiments with various modifications as are suited to the particular use contemplated. It is intended that the following claims and their equivalents define the scope of the invention.

The invention claimed is:

1. A microneedle array for use in sensing an analyte, comprising:

a first microneedle comprising a working electrode, wherein the working electrode comprises platinum and a biorecognition layer comprising a biorecognition element configured to react with the analyte, wherein the platinum comprises an electrochemically roughened surface that increases adhesion with the biorecognition layer;

a second microneedle comprising a counter electrode, wherein the counter electrode comprises a counter electrode material; and a third microneedle comprising a reference electrode, wherein the reference electrode comprises a reference electrode material and a redox-couple layer, wherein a redox reaction occurs between the working electrode on the first microneedle and the counter electrode on the second microneedle.

2. The microneedle array of claim 1, wherein the working electrode further comprises an electrocatalytic layer between the electrochemically roughened surface of the platinum and the biorecognition layer.

3. The microneedle array of claim 1, wherein the counter electrode material comprises a roughened surface.

4. The microneedle array of claim 3, wherein the counter electrode comprises an electrocatalytic layer on the roughened surface of the counter electrode material.

5. The microneedle array of claim 1, wherein the reference electrode material comprises a roughened surface.

6. The microneedle array of claim 1, wherein the counter electrode material comprises platinum.

7. The microneedle array of claim 1, wherein the counter electrode comprises an electrocatalytic layer on the counter electrode material.

8. A microneedle array for use in sensing an analyte, comprising:

a first microneedle comprising a first working electrode, wherein the first working electrode comprises platinum and a first biorecognition layer comprising a first biorecognition element configured to react with the analyte;

a second microneedle comprising a second working electrode, wherein the second working electrode comprises platinum and a second biorecognition layer comprising a second biorecognition element configured to react with the analyte; and a third microneedle comprising a counter electrode, wherein the counter electrode comprises a counter electrode material, wherein a first redox reaction occurs between the first working electrode on the first microneedle and the counter electrode on the third microneedle, and a second redox reaction occurs between the second working electrode on the second microneedle and the counter electrode on the third microneedle, wherein the platinum of the first working electrode and the platinum of the second working electrode each comprise an electrochemically roughened surface that increases adhesion with the first biorecognition layer and the second biorecognition layer, respectively.

9. The microneedle array of claim 8, wherein one or more of the first working electrode, the second working electrode, or the counter electrode further comprises an electrocatalytic layer on a respective one of the electrochemically roughened surface of the platinum of the first working electrode, the electrochemically roughened surface of the platinum of the second working electrode, or the counter electrode material.

10. The microneedle array of claim 8, further comprising:

a fourth microneedle comprising a second counter electrode, wherein the second counter electrode comprises a second counter electrode material.

11. The microneedle array of claim 8, further comprising:

a fifth microneedle comprising a reference electrode, wherein the reference electrode comprises a reference electrode material and a redox-couple layer.

12. The microneedle array of claim 8, wherein the counter electrode material comprises platinum.

13. A method for sensing an analyte via a microneedle array, comprising:

applying a bias potential between a working electrode of a first microneedle of the microneedle array and a reference electrode of a second microneedle of the microneedle array, the working electrode comprising platinum and a biorecognition layer comprising a biorecognition element configured to react with the analyte, the reference electrode comprising a reference electrode material and a redox couple layer, wherein the platinum comprises an electrochemically roughened surface that increases adhesion with the biorecognition layer; and measuring a current value between the working electrode and a counter electrode of a third microneedle of the microneedle array, the counter electrode comprising a counter electrode material, the current value being proportional to a concentration of the analyte, wherein a redox reaction occurs between the working electrode and the counter electrode.

14. The method of claim 13, wherein the working electrode further comprises an electrocatalytic layer between the electrochemically roughened surface of the platinum and the biorecognition layer.

15. The method of claim 13, wherein the counter electrode material comprises a roughened surface.

16. The method of claim 15, wherein the counter electrode comprises an electrocatalytic layer on the roughened surface of the counter electrode material.

17. The method of claim 13, wherein the reference electrode material comprises a roughened surface.

18. The method of claim 13, wherein the counter electrode material comprises platinum.

19. The method of claim 13, wherein the counter electrode comprises an electrocatalytic layer on the counter electrode material.

20. A method for sensing an analyte via a microneedle array, comprising:

applying a first bias potential between a first working electrode of a first microneedle of the microneedle array and a reference electrode of a second microneedle of the microneedle array, the first working electrode comprising platinum and a first biorecognition layer comprising a first biorecognition element configured to react with the analyte, the reference electrode comprising a reference electrode material and a redox-couple layer;

applying a second bias potential between a second working electrode of a third microneedle of the microneedle array and the reference electrode, the second working electrode comprising platinum and a second biorecognition layer comprising a second biorecognition element configured to react with the analyte;

measuring a first current value between the first working electrode and a counter electrode of a fourth microneedle of the microneedle array, the counter electrode comprising a counter electrode material, the first current value being proportional to a concentration of the analyte; and measuring a second current value between the second working electrode and the counter electrode, the second current value being proportional to the concentration of the analyte, wherein a first redox reaction occurs between the first working electrode and the counter electrode, and a second redox reaction occurs between the second working electrode and the counter electrode, wherein the platinum of the first working electrode and the platinum of the second working electrode each comprise an electrochemically roughened surface that increases adhesion with the first biorecognition layer and the second biorecognition layer, respectively.

21. The method of claim 20, wherein one or more of the first working electrode or the second working electrode further comprises an electrocatalytic layer on a respective one of the electrochemically roughened surface of the platinum of the first working electrode or the electrochemically roughened surface of the platinum of the second working electrode.

22. The method of claim 20, wherein the microneedle array further comprises a fifth microneedle comprising a second counter electrode, wherein the second counter electrode comprises a second counter electrode material.

23. The method of claim 20, wherein the microneedle array further comprises a sixth microneedle comprising a second reference electrode, wherein the second reference electrode comprises a second reference electrode material and a redox-couple layer.

* * * * *